(12) United States Patent
Nishi et al.

(10) Patent No.: US 8,729,095 B2
(45) Date of Patent: May 20, 2014

(54) 3-(BIARYLOXY)PROPIONIC ACID DERIVATIVES FOR PREVENTION AND/OR TREATMENT OF THROMBOEMBOLIC DISEASES

(75) Inventors: Tatsuya Nishi, Tokyo (JP); Masashi Hasegawa, Tokyo (JP); Yumi Nakamoto, Tokyo (JP); Yuichi Ochiai, Tokyo (JP); Ryoko Kitazawa, Tokyo (JP); Hiroshi Susaki, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/393,018

(22) PCT Filed: Aug. 27, 2010

(86) PCT No.: PCT/JP2010/064551
§ 371 (c)(1),
(2), (4) Date: May 21, 2012

(87) PCT Pub. No.: WO2011/024933
PCT Pub. Date: Mar. 3, 2011

(65) Prior Publication Data
US 2012/0245152 A1    Sep. 27, 2012

(30) Foreign Application Priority Data
Aug. 28, 2009 (JP) .................. 2009-198598

(51) Int. Cl.
*A61K 31/44* (2006.01)
(52) U.S. Cl.
USPC ............ 514/300; 544/350; 546/245; 546/314
(58) Field of Classification Search
USPC .................... 514/300; 544/350; 546/245, 314
See application file for complete search history.

(56) References Cited

U.S. PATENT DOCUMENTS

| 5,225,402 | A | 7/1993 | Ogawa et al. |
| 5,356,904 | A | 10/1994 | Freidinger et al. |
| 5,436,254 | A | 7/1995 | Ogawa et al. |
| 5,652,247 | A | 7/1997 | Ogawa et al. |
| 5,665,719 | A | 9/1997 | Bock et al. |
| 2006/0229336 | A1 | 10/2006 | Kazmierski et al. |
| 2009/0048238 | A1 | 2/2009 | Aebi et al. |
| 2010/0113391 | A1 | 5/2010 | Koga et al. |

FOREIGN PATENT DOCUMENTS

| JP | 03-173870 | 7/1991 |
| JP | 09-500134 | 1/1997 |
| JP | 2006-511554 | 4/2006 |
| WO | WO 99/02542 | 1/1999 |
| WO | WO 02/098856 | 12/2002 |
| WO | WO 03/022214 | 3/2003 |
| WO | WO 2006/100591 | 9/2006 |
| WO | WO 2006/114774 | 11/2006 |
| WO | WO 2007/056167 | 5/2007 |
| WO | WO 2007/140333 | 12/2007 |
| WO | WO 2008/002247 | 1/2008 |
| WO | WO 2008/062770 | 5/2008 |
| WO | WO 2007/105751 | 10/2008 |
| WO | WO 2008/128647 | 10/2008 |
| WO | WO 2008/133155 | 11/2008 |

OTHER PUBLICATIONS

Jordan, V. C. Nature Reviews: Drug Discovery, 2, 2003, 205.*
Hackam, et al. JAMA, 296(14), 2006, 1731-1732.*
C. P. Decicco et al., "Asymmetric Synthesis of 2,3-Disubstituted Succinates via Chiral Oxazolidinone Controlled Displacement of α-Trifluoromethanesulfonate Substituted Esters," Journal of Organic Chemistry, 1995, 60, 4782-4785.
V. Koch, et al., "Chemistry of 3-Hydroxypyridine Part 2: Synthesis of 5,6-Dihalo-3-hydroxypyridines" Synthesis; 1990: 499-501.
M. Ihara, et al., "Asymmetric total synthesis of tacamonine (pseudovincamone I) via radical cyclization," The Journal of Organic Chemistry, 1994, 59(18), 5317-5323.
E.C. Taylor, et al., "Synthesis of 10-(Hydroxymethyl)-5,10-dideaza-5,6,7,8-tetrahydrofolic Acid, a Potent New Analog of DDATHF (Lometrexol)," The Journal of Organic Chemistry, 1994, 59(23), 7096-7098.
A.K. Ghosh, et al., "Synthesis of Enantiomerically Pure Anti-Aldols: A Highly Stereoselective Ester-Derived Titanium Enolate Aldol Reaction," Journal of the American Chemical Society, 1996, 118, 2527-2528.

(Continued)

*Primary Examiner* — Douglas M Willis
(74) *Attorney, Agent, or Firm* — Locke Lord, LLP

(57) ABSTRACT

A compound of the general formula (I):

[Chemical 1]

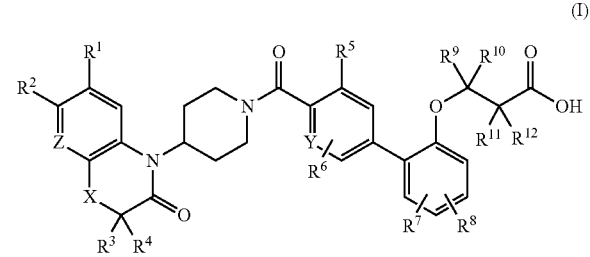

(I)

[wherein, $R^1$ represents a halogen atom, or the like, $R^2$ represents a hydrogen atom, or the like, $R^3$ and $R^4$, each independently, represent a hydrogen atom, a $C_{1-4}$ alkyl group, or the like, $R^5$ represents a hydrogen atom, a halogen atom, or the like, $R^6$ represents a hydrogen atom, a halogen atom, or the like, $R^7$ and $R^8$, each independently, represent a hydrogen atom, a halogen atom, or the like, $R^9$ and $R^{10}$, each independently, represent a hydrogen atom, a $C_{1-4}$ alkyl group, $R^{11}$ and $R^{12}$, each independently, represent a hydrogen atom, a $C_{1-4}$ alkyl group, or the like, X represents an oxygen atom, a group —$CH_2$—, or the like, Y represents a nitrogen atom, a group =CH—, or the like, and Z represents a nitrogen atom, or the like] or a pharmacologically acceptable salt thereof, which has an excellent suppressive action on platelet aggregation, and is useful for prevention and/or treatment of thromboembolism.

24 Claims, No Drawings

(56) References Cited

OTHER PUBLICATIONS

S.D. Kuduk, et al., "Tetrabutylammonium salt induced denitration of nitropyridines: synthesis of fluoro-, hydroxy-, and methoxypyridines," Organic Letters, 2005, 7(4), 577-579.

F. Jin, et al., "Palladium-catalyzed cyanation reactions of aryl chlorides," Tetrahedron Letters, 2000, 41(18), 3271-3273.

S. Chandrasekhar, et al., "Total synthesis of 6-epiprelactone-V via a syn-selective oxygen tethered intramolecular Michael reaction," Tetrahedron Letters, 2006, 47(7), 1213-1215.

C. Liechti, et al., "Salicylanilides as inhibitors of the protein tyrosine kinase epidermal growth factor receptor," European Journal of Medicinal Chemistry, 2004, 39(1), 11-26.

G.A. Kraus, et al., "The reaction of aryl triflates and aryl pivalates with electrophiles. The triflate as a meta-directing group," Tetrahedron Letters, 2002, 43(39), 7077-7078.

S. Caron, et al., "Efficient Synthesis of [6-Chloro-2-(4-chlorobenzoyl)-1H-indol-3-yl]-acetic Acid, a Novel COX-2 Inhibitor," Journal of Organic Chemistry, 2003, 68(10), 4104-4107.

C. Mugnaini, et al., "Dihydro-alkylthio-benzyl-oxopyrimidine Inhibitor of Reverse Transcriptase: Rationalization Biol Data on Both WT & Clinical Mutant," Journal of Medicinal Chemistry, 2007, 50(26), 6580-6595.

T.W. Greene, et al., "Protective Groups in Organic Synthesis", 3rd Edition, John Wiley & Sons, Inc. (1999).

Written Opinion of the International Searching Authority as issued in PCT/JP2010/064551, mailed Oct. 26, 2010.

International Preliminary Report on Patentability as issued in PCT/JP2010/064551, mailed Mar. 13, 2012.

International Search Report as issued in PCT/JP2010/064551, mailed Oct. 26, 2010.

\* cited by examiner

3-(BIARYLOXY)PROPIONIC ACID DERIVATIVES FOR PREVENTION AND/OR TREATMENT OF THROMBOEMBOLIC DISEASES

This application is a national phase entry under 35 U.S.C. §371 of International Application Number PCT/JP2010/064551, filed on Aug. 27, 2010, entitled "3-(BIARYLOXY) PROPIONIC ACID DERIVATIVE", which claims the benefit of Japanese Patent Application Number JP 2009-198598, filed on Aug. 28, 2009, all of which are hereby incorporated by reference.

BACKGROUND OF THE INVENTION

1. Field of the Invention

The present invention relates to a 3-(biaryloxy)propionic acid derivative or a pharmacologically acceptable salt thereof which is useful as a medicament. More particularly, the present invention relates to a 3-(biaryloxy)propionic acid derivative or a pharmacologically acceptable salt thereof having a suppressive action on platelet aggregation.

2. Description of Related Art

Recently, there has been a remarkable increase in cardiovascular diseases associated with aging of population as well as changes in eating habits and lifestyles. Among these, thrombotic diseases such as cerebral infarction, myocardial infarction, and peripheral circulatory disturbances not only have high mortality rates, but also impose a lot of individual or social burdens on a patient such as poor prognosis and limitations on life. As direct causes of the onset of these diseases, there are known angiostenosis resulting from thrombus generated by activation of platelets (such as adhesion to a vascular injury site, release of physiologically active substances, and formation of clumps), and ischemia associated with angiostenosis. Drugs having a suppressive action on platelet aggregation which suppress the activation of platelets play an important role in prevention of onset, prevention of reoccurrence or treatment of these diseases, and it is considered that they will be more and more important in the future, along with increased thrombotic diseases.

Examples of in vivo substances involved in platelet aggregation include adenosine 5'-diphosphate (ADP), thromboxane $A_2$(TXA$_2$), collagen, serotonin (5-hydroxytryptamine, 5-HT), or the like. Among these, a P2Y$_1$ receptor and a P2Y$_{12}$ receptor have been found as receptors of ADP, and some existing antithrombotic agents demonstrate an effect by these receptor antagonistic actions. Examples of such antithrombotic agents include ticlopidine and clopidogrel. These compounds are known to have a thienopyridine structure in common, but there has been a demand for a drug having higher safety and more excellent drug efficacy.

On the other hand, as antagonist drugs to ADP receptors, having a non-thienopyridine structure, there are known an ADP derivative (see Patent Documents 1, 2), a nicotinic acid ester derivative (see Patent Document 3), a thienopyrimidine derivative (see Patent Documents 4, 5), a sulfonyl urea derivative (see Patent Document 6), a piperazine derivative (see Patent Documents 7, 8), a quinoline derivative (see Patent Document 9), a quinolone derivative (see Patent Documents 10, 11), a quinazolinedione derivative (see Patent Document 12), and the like.

PRIOR ART DOCUMENTS

Patent Documents

[Patent Document 1] International Publication No. WO 1999/002542
[Patent Document 2] International Publication No. WO 2007/140333
[Patent Document 3] International Publication No. WO 2008/002247
[Patent Document 4] International Publication No. WO 2003/022214
[Patent Document 5] International Publication No. WO 2006/100591
[Patent Document 6] International Publication No. WO 2007/056167
[Patent Document 7] International Publication No. WO 2002/098856
[Patent Document 8] International Publication No. WO 2006/114774
[Patent Document 9] International Publication No. WO 2008/128647
[Patent Document 10] International Publication No. WO 2008/062770
[Patent Document 11] International Publication No. WO 2007/105751
[Patent Document 12] International Publication No. WO 2008/133155

BRIEF SUMMARY OF THE INVENTION

Problems to be Solved by the Invention

The present inventors have sought a compound having higher safety and more excellent suppressive action on platelet aggregation in order to develop a new antithrombotic agent, and as a result have found that a compound having the general formula (I), or a pharmacologically acceptable salt thereof according to the present invention has an excellent suppressive action on platelet aggregation, and have completed the present invention.

Means for Solving the Problems

The present invention relates to the following:
(1) a compound of the general formula (I):

[Chemical 1]

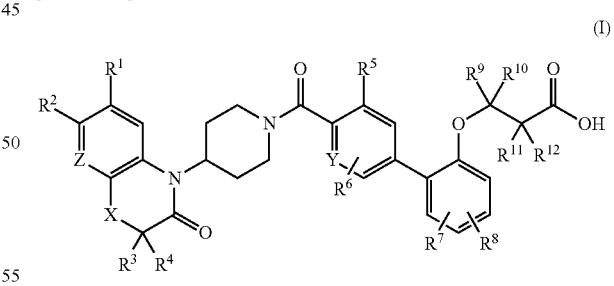

(I)

[wherein,
$R^1$ represents a halogen atom, a cyano group, an amino group, a $C_{1-4}$ alkyl group, a halogenated $C_{1-4}$ alkyl group or a $C_{1-4}$ alkoxy group,
$R^2$ represents a hydrogen atom, a halogen atom, a cyano group, or a $C_{1-4}$ alkyl group,
$R^3$ and $R^4$, each independently, represent a hydrogen atom, a $C_{1-4}$ alkyl group, a halogenated $C_{1-4}$ alkyl group, a $C_{1-4}$ alkoxy $C_{1-4}$ alkyl group, or a hydroxy $C_{1-4}$ alkyl group, or $R^3$ and $R^4$, together with the carbon atom to which they are attached, represent a group forming $C_{3-5}$ cycloalkyl, R⁵ represents a hydrogen atom, a halogen atom, a hydroxyl group, a nitro group, a $C_{1-4}$ alkyl group, or an amino group, R⁶ represents a hydrogen atom, a halogen atom, or a $C_{1-4}$ alkyl group, R⁷ and R⁸, each independently, represent a hydrogen atom, a halogen atom, or a $C_{1-4}$ alkyl group, R⁹ and R¹⁰, each independently, represent a hydrogen atom, or a $C_{1-4}$ alkyl group, R¹¹ and R¹², each independently, represent a hydrogen atom, or a $C_{1-4}$ alkyl group, or R¹¹ and R¹², together with the carbon atom to which they are attached, represent a group forming $C_{3-5}$ cycloalkyl, X represents an oxygen atom, a sulfur atom, or a group represented by —CH(Rc)—, Rc represents a hydrogen atom, or a hydroxyl group, Y represents a nitrogen atom, or a group represented by =C(Ra)—, Ra represents a hydrogen atom, a halogen atom, or a $C_{1-4}$ alkyl group, and Z represents a nitrogen atom, or a group represented by =CH—] or a pharmacologically acceptable salt thereof;

(2) the compound or pharmacologically acceptable salt thereof described in (1) above, wherein R¹ represents a fluorine atom, a chlorine atom, a cyano group, a methyl group, an ethyl group, or a trifluoromethyl group;

(3) the compound or pharmacologically acceptable salt thereof described in (1) above, wherein R¹ represents a chlorine atom;

(4) the compound or pharmacologically acceptable salt thereof described in any one of (1) to (3) above, wherein R² represents a hydrogen atom, a chlorine atom, or a methyl group;

(5) the compound or pharmacologically acceptable salt thereof described in any one of (1) to (3) above, wherein R² represents a hydrogen atom;

(6) the compound or pharmacologically acceptable salt thereof described in any one of (1) to (5) above, wherein R³ and R⁴, each independently, represent a hydrogen atom, or a methyl group, or R³ and R⁴, together with the carbon atom to which they are attached, represent a group forming cyclopropyl;

(7) the compound or pharmacologically acceptable salt thereof described in any one of (1) to (5) above, wherein R³ represents a methyl group, and R⁴ represents a hydrogen atom or a methyl group;

(8) the compound or pharmacologically acceptable salt thereof described in any one of (1) to (7) above, wherein R⁵ represents a hydrogen atom, a chlorine atom, a fluorine atom, a hydroxyl group, a nitro group, a methyl group, or an amino group;

(9) the compound or pharmacologically acceptable salt thereof described in any one of (1) to (7) above, wherein R⁵ represents a fluorine atom, a methyl group, or an amino group;

(10) the compound or pharmacologically acceptable salt thereof described in any one of (1) to (9) above, wherein R⁶ represents a hydrogen atom, a fluorine atom, a chlorine atom, or a methyl group;

(11) the compound or pharmacologically acceptable salt thereof described in any one of (1) to (9) above, wherein R⁶ represents a hydrogen atom, or a fluorine atom;

(12) the compound or pharmacologically acceptable salt thereof described in any one of (1) to (11) above, wherein R⁷ and R⁸, each independently, represent a hydrogen atom, a fluorine atom, a chlorine atom, or a methyl group;

(13) the compound or pharmacologically acceptable salt thereof described in any one of (1) to (11) above, wherein R⁷ and R⁸, each independently, represent a hydrogen atom, or a fluorine atom;

(14) the compound or pharmacologically acceptable salt thereof described in any one of (1) to (13) above, wherein R⁹ and R¹⁰, each independently, represent a hydrogen atom, a methyl group, an ethyl group, or an n-propyl group;

(15) the compound or pharmacologically acceptable salt thereof described in any one of (1) to (13) above, wherein R⁹ represents a hydrogen atom, and R¹⁰ represents a hydrogen atom, a methyl group, or an ethyl group;

(16) the compound or pharmacologically acceptable salt thereof described in any one of (1) to (15) above, wherein R¹¹ and R¹², each independently, represent a hydrogen atom, a methyl group, or an ethyl group, or R¹¹ and R¹², together with the carbon atom to which they are attached, represent a group forming cyclopropyl;

(17) the compound or pharmacologically acceptable salt thereof described in any one of (1) to (16) above, wherein X represents an oxygen atom;

(18) the compound or pharmacologically acceptable salt thereof described in any one of (1) to (16) above, wherein X represents a group represented by —CH₂—;

(19) the compound or pharmacologically acceptable salt thereof described in any one of (1) to (18) above, wherein Y represents a nitrogen atom, or a group represented by =C(Ra)—, and Ra represents a hydrogen atom;

(20) the compound or pharmacologically acceptable salt thereof described in any one of (1) to (19) above, wherein Z represents a nitrogen atom;

(21) the compound or pharmacologically acceptable salt thereof described in (1) above, selected from the following: 3-{[4'-({4-[(3S)-7-chloro-3-methyl-2-oxo-2,3-dihydro-1H-pyrido[2,3-b][1,4]oxazin-1-yl]piperidin-1-yl}carbonyl)-3'-fluorobiphenyl-2-yl]oxy}-2,2-dimethylpropanoic acid, (3R)-3-[(4'-{[4-(7-chloro-3,3-dimethyl-2-oxo-3,4-dihydro-1,5-naphthyridin-1(2H)-yl)piperidin-1-yl]carbonyl}-3'-fluorobiphenyl-2-yl)oxy]butanoic acid, (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]butanoic acid, (2R,3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]-2-methylbutanoic acid, (2S)-2-{[(4'-{[4-(7-chloro-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]methyl}butanoic acid, (2S)-3-[(4'-{[4-(7-chloro-3,3-dimethyl-2-oxo-3,4-dihydro-1,5-naphthyridin-1(2H)-yl)piperidin-1-yl]carbonyl}-3'-fluorobiphenyl-2-yl)oxy]-2-methylpropanoic acid, (3R)-3-[(4'-{4-(7-chloro-3,3-dimethyl-2-oxo-2,3-dihydro-1H-pyrido[2,3-b][1,4]oxazin-1-yl)piperidin-1-yl]carbonyl}-3',5-difluorobiphenyl-2-yl)oxy]butanoic acid, (3R)-3-[(4'-{[4-(7-chloro-3,3-dimethyl-2-oxo-3,4-dihydro-1,5-naphthyridin-1(2H)-yl)piperidin-1-yl]carbonyl}-3',5-difluorobiphenyl-2-yl)oxy]butanoic acid, (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3'-methylbiphenyl-2-yl)oxy]butanoic acid, (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-5-fluoro-3'-methylbiphenyl-2-yl)oxy]butanoic acid, (3R)-3-[(3'-chloro-4'-{[4-(7-chloro-3,3-dimethyl-2-oxo-2,3-dihydro-1H-pyrido[2,3-b][1,4]oxazin-1-yl)piperidin-1-yl]carbonyl}biphenyl-2-yl)oxy]butanoic acid, (2S)-3-{[4'-({4-[(3S)-7-chloro-3-methyl-2-oxo-2,3-dihydro-1H-pyrido[2,3- b][1,4]oxazin-1-yl]piperidin-1-yl}carbonyl)-3'-fluorobiphenyl-2-yl]oxy}-2-methylpropanoic acid, (2S)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]-2-methylpropanoic acid, (2S)-3-{[4'-({4-[(3S)-7-chloro-3-methyl-2-oxo-2,3-dihydro-1H-pyrido[2,3-b][1,4]oxazin-1-yl]piperidin-1-yl}carbonyl)-3',5-difluorobiphenyl-2-yl]oxy}-2-methylpropanoic acid, (2S)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3',5-difluorobiphenyl-2-yl)oxy]-2-methylpropanoic acid, (3R)-3-{[4'-({4-[(3S)-7-chloro-3-methyl-2-oxo-2,3-dihydro-1H-pyrido[2,3-b][1,4]oxazin-1-yl]piperidin-1-yl}carbonyl)-3'-fluorobiphenyl-2-yl]oxy}butanoic acid, (3R)-3-{[4'-({4-[(3S)-7-chloro-3-methyl-2-oxo-2,3-dihydro-1H-pyrido[2,3-b][1,4]oxazin-1-yl]piperidin-1-yl}carbonyl)-3',5-difluorobiphenyl-2-yl]oxy}butanoic acid, (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-2',5'-difluorobiphenyl-2-yl)oxy]butanoic acid, (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3',4-difluorobiphenyl-2-yl)oxy]butanoic acid, (3R)-3-[(4'-{[4-(7-chloro-3,3-dimethyl-2-oxo-3,4-dihydro-1,5-naphthyridin-1(2H)-yl)piperidin-1-yl]carbonyl}-3'-methylbiphenyl-2-yl)oxy]butanoic acid, (3R)-3-[2-(6-{[4-(7-chloro-3,3-dimethyl-2-oxo-3,4-dihydro-1,5-naphthyridin-1(2H)-yl)piperidin-1-yl]carbonyl}-5-fluoropyridin-3-yl)phenoxy]butanoic acid, (3R)-3-[2-(6-{[4-(7-chloro-3,3-dimethyl-2-oxo-2,3-dihydro-1H-pyrido[2,3-b][1,4]oxazin-1-yl)piperidin-1-yl]carbonyl}-5-fluoropyridin-3-yl)phenoxy]pentanoic acid, (3R)-3-[2-(6-{[4-(7-chloro-3,3-dimethyl-2-oxo-2,3-dihydro-1H-pyrido[2,3-b][1,4]oxazin-1-yl)piperidin-1-yl]carbonyl}-5-fluoropyridin-3-yl)-4-fluorophenoxy]butanoic acid, (3R)-3-[2-(6-{[4-(7-chloro-3,3-dimethyl-2-oxo-3,4-dihydro-1,5-naphthyridin-1(2H)-yl)piperidin-1-yl]carbonyl}-5-fluoropyridin-3-yl)-4-fluorophenoxy]butanoic acid, (3R)-3-[(4'-{[4-(7-chloro-3,3-dimethyl-2-oxo-3,4-dihydro-1,5-naphthyridin-1(2H)-yl)piperidin-1-yl]carbonyl}-5-fluoro-3'-methylbiphenyl-2-yl)oxy]butanoic acid, (2S)-3-[2-(6-{[4-(7-chloro-3,3-dimethyl-2-oxo-3,4-dihydro-1,5-naphthyridin-1(2H)-yl)piperidin-1-yl]carbonyl}-5-fluoropyridin-3-yl)phenoxy]-2-methylpropanoic acid, (3R)-3-[(3'-amino-4'-{[4-(7-chloro-3,3-dimethyl-2-oxo-2,3-dihydro-1H-pyrido[2,3-b][1,4]oxazin-1-yl)piperidin-1-yl]carbonyl}biphenyl-2-yl)oxy]butanoic acid, (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3',5'-difluorobiphenyl-2-yl)oxy]butanoic acid, (3R)-3-[(4'-{[4-(7-cyano-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]butanoic acid, (3R)-3-[(4'-{[4-(7-ethyl-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]butanoic acid, and (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3'-fluoro-4-methylbiphenyl-2-yl)oxy]butanoic acid;

(22) (3R)-3-[(4'-{[4-(7-chloro-3,3-dimethyl-2-oxo-3,4-dihydro-1,5-naphthyridin-1(2H)-yl)piperidin-1-yl]carbonyl}-3'-fluorobiphenyl-2-yl)oxy]butanoic acid or a pharmacologically acceptable salt thereof;

(23) (3R)-3-[(4'-{[4-(7-chloro-3,3-dimethyl-2-oxo-3,4-dihydro-1,5-naphthyridin-1(2H)-yl)piperidin-1-yl]carbonyl}-3',5-difluorobiphenyl-2-yl)oxy]butanoic acid or a pharmacologically acceptable salt thereof;

(24) (3R)-3-{[4'-({4-[(3S)-7-chloro-3-methyl-2-oxo-2,3-dihydro-1H-pyrido[2,3-b][1,4]oxazin-1-yl]piperidin-1-yl}carbonyl)-3'-fluorobiphenyl-2-yl]oxy}butanoic acid or a pharmacologically acceptable salt thereof;

(25) (3R)-3-{[4'-({4-[(3S)-7-chloro-3-methyl-2-oxo-2,3-dihydro-1H-pyrido[2,3-b][1,4]oxazin-1-yl]piperidin-1-yl}carbonyl)-3',5-difluorobiphenyl-2-yl]oxy}butanoic acid or a pharmacologically acceptable salt thereof;

(26) (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3',4-difluorobiphenyl-2-yl)oxy]butanoic acid or a pharmacologically acceptable salt thereof;

(27) (3R)-3-[(4'-{[4-(7-cyano-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]butanoic acid or a pharmacologically acceptable salt thereof;

(28) a medicament comprising as an active ingredient the compound or pharmacologically acceptable salt thereof described in any one of (1) to (27) above;

(29) an antiplatelet agent comprising as an active ingredient the compound or pharmacologically acceptable salt thereof described in any one of (1) to (27) above;

(30) a medicament for prevention and/or treatment of thromboembolic diseases, comprising as an active ingredient the compound or pharmacologically acceptable salt thereof described in any one of (1) to (27) above;

(31) a medicament for prevention and/or treatment of ischemic cerebrovascular diseases, acute coronary syndrome, or restenosis or reocclusion in cases of acute coronary syndrome where coronary artery bypass graft (CABG) or percutaneous coronary intervention (PCI) has been applied, comprising as an active ingredient the compound or pharmacologically acceptable salt thereof described in any one of (1) to (27) above;

(32) use of the compound or pharmacologically acceptable salt thereof described in any one of (1) to (27) above, for producing a medicament,

(33) the use described in (32) above, wherein the medicament is a medicament for prevention and/or treatment of thromboembolic diseases;

(34) the use described in (33) above, wherein the thromboembolic disease is ischemic cerebrovascular diseases, acute coronary syndrome, or restenosis or reocclusion in cases of acute coronary syndrome where coronary artery bypass graft (CABG) or percutaneous coronary intervention (PCI) has been applied;

(35) a method for prevention and/or treatment of thromboembolic diseases, comprising administering to a mammal an effective amount of the compound or pharmacologically acceptable salt thereof described in any one of (1) to (27) above;

(36) a method for prevention and/or treatment of thromboembolic diseases, comprising administering to a human an effective amount of the compound or pharmacologically acceptable salt thereof described in any one of (1) to (27) above;

(37) the compound or pharmacologically acceptable salt thereof described in any one of (1) to (27) above, for use in prevention and/or treatment of thromboembolic diseases; and

(38) the compound or pharmacologically acceptable salt thereof described in (37) above, wherein the thromboembolic disease is ischemic cerebrovascular diseases, acute coronary syndrome, or restenosis or reocclusion in cases of acute coronary syndrome where coronary artery bypass graft (CABG) or percutaneous coronary intervention (PCI) has been applied.

Further, the present invention relates to a method for prevention and/or treatment of ischemic cerebrovascular diseases, acute coronary syndrome, restenosis or reocclusion in cases of acute coronary syndrome where coronary artery bypass graft (CABG) or percutaneous coronary intervention (PCI) has been applied, thromboembolism associated with vascular surgery and blood extracorporeal circulation, or chronic arterial occlusion, comprising orally or parenterally administering to a mammal (preferably, a human) an effective amount of the compound or pharmacologically acceptable salt thereof described in any one of (1) to (27) above.

DETAILED DESCRIPTION OF THE INVENTION

Hereinafter, the definition of substituents in the compound (I) of the present invention will be explained.

In the compound (I) of the present invention, "halogen atom" in the definition of $R^1$, $R^2$, $R^5$ to $R^8$, and Ra represents a fluorine atom, a chlorine atom, a bromine atom, or an iodine atom.

In the compound (I) of the present invention, "$C_{1-4}$ alkyl group" in the definition of $R^1$ to $R^{12}$, and Ra represents a linear or branched alkyl group having 1 to 4 carbon atoms. Examples include a methyl group, an ethyl group, an n-propyl group, an isopropyl group, an n-butyl group, a sec-butyl group, a tert-butyl group, and the like.

In the compound (I) of the present invention, "$R^3$ and $R^4$, together with the carbon atom to which they are attached, represent a group forming $C_{3-5}$ cycloalkyl" in the definition of $R^3$ and $R^4$ represents a group forming (spiro)cycloalkyl having 3 to 5 carbon atoms together with the carbon atom which is attached to $R^3$ and $R^4$. Specific examples include a (spiro)cyclopropyl group, a (spiro)cyclobutyl group, and a (spiro)cyclopentyl group.

"$R^{11}$ and $R^{12}$, together with the carbon atom to which they are attached, represent a group forming $C_{3-5}$ cycloalkyl" in the definition of $R^{11}$ and $R^{12}$ represents a group forming (spiro)cycloalkyl having 3 to 5 carbon atoms together with the carbon atom which is attached to $R^{11}$ and $R^{12}$. Specific examples include a (spiro)cyclopropyl group, a (spiro)cyclobutyl group, and a (spiro)cyclopentyl group.

In the compound (I) of the present invention, "a halogenated $C_{1-4}$ alkyl group" in the definition of $R^1$, $R^3$, and $R^4$ represents a group in which 1 or 2 or more hydrogen atoms in the aforementioned "$C_{1-4}$ alkyl group" are substituted by the aforementioned "halogen atom". Examples include a fluoromethyl group, a chloromethyl group, a bromomethyl group, a difluoromethyl group, a dichloromethyl group, dibromomethyl group, a trifluoromethyl group, a trichloromethyl group, a 2,2,2-trifluoroethyl group, and the like.

In the compound (I) of the present invention, "$C_{1-4}$ alkoxy group" in the definition of $R^1$ represents a group in which an oxygen atom is attached to the aforementioned "$C_{1-4}$ alkyl group". Examples include a methoxy group, an ethoxy group, a propoxy group, an isopropoxy group, a butoxy group, a sec-butoxy group, a tert-butoxy group, and the like.

In the compound (I) of the present invention, "$C_{1-4}$ alkoxy $C_{1-4}$ alkyl group" in the definition of $R^3$ and $R^4$ represents a group in which the aforementioned "$C_{1-4}$ alkoxy group" is attached to the aforementioned "$C_{1-4}$ alkyl group". Examples include a methoxymethyl group, a methoxyethyl group, a methoxypropyl group, a methoxybutyl group, an ethoxymethyl group, an ethoxyethyl group, and the like.

In the compound (I) of the present invention, "hydroxy $C_{1-4}$ alkyl group" in the definition of $R^3$ and $R^4$ represents a group in which 1 hydrogen atom of the aforementioned "$C_{1-4}$ alkyl group" is substituted by a hydroxyl group. Examples include a hydroxymethyl group, a 1-hydroxyethyl group, a 2-hydroxyethyl group, and the like.

$R^1$ in the compound (I) of the present invention preferably represents a fluorine atom, a chlorine atom, a cyano group, a methyl group, an ethyl group, or a trifluoromethyl group, more preferably $R^1$ represents a chlorine atom, or a cyano group, and even more preferably $R^1$ represents a chlorine atom.

$R^2$ in the compound (I) of the present invention preferably represents a hydrogen atom, a chlorine atom, or a methyl group, and more preferably $R^2$ represents a hydrogen atom.

$R^3$ and $R^4$ in the compound of the present invention, each independently, preferably represent a hydrogen atom, or a methyl group, or $R^3$ and $R^4$, together with the carbon atom to which they are attached, represent a group forming cyclopropyl, more preferably, $R^3$ and $R^4$, each independently, represent a hydrogen atom, or a methyl group, and even more preferably, $R^3$ represents a methyl group, and $R^4$ represents a hydrogen atom, or a methyl group.

Furthermore, when X represents an oxygen atom, $R^3$ represents a methyl group, and $R^4$ represents a hydrogen atom, then the carbon atom to which $R^3$ and $R^4$ are attached is an asymmetric carbon atom, and the configuration of $R^3$ and $R^4$ preferably assumes the following configuration (S configuration):

[Chemical 2]

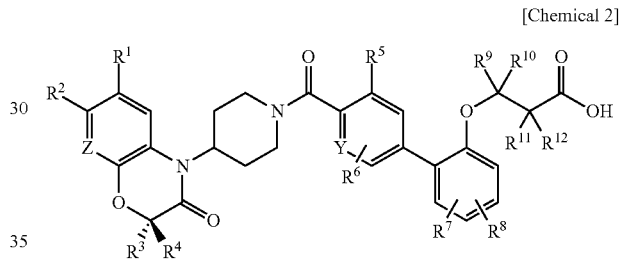

$R^5$ in the compound (I) of the present invention preferably represents a hydrogen atom, a chlorine atom, a fluorine atom, a hydroxyl group, a nitro group, a methyl group, or an amino group, more preferably $R^5$ represents a fluorine atom, a methyl group, or an amino group, and even more preferably $R^5$ represents a fluorine atom.

$R^6$ in the compound (I) of the present invention preferably represents a hydrogen atom, a fluorine atom, a chlorine atom, or a methyl group, and more preferably $R^6$ represents a hydrogen atom, or a fluorine atom. Furthermore, $R^6$ is preferably substituted at the following position:

[Chemical 3]

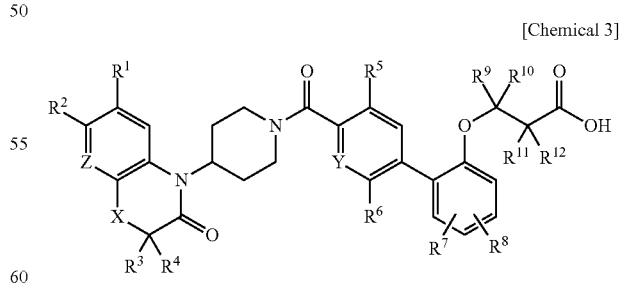

$R^7$ and $R^8$ in the compound (I) of the present invention, each independently, preferably represent a hydrogen atom, a fluorine atom, a chlorine atom, or a methyl group, and more preferably $R^7$ and $R^8$, each independently, represent a hydrogen atom, or a fluorine atom. Furthermore, $R^7$ and $R^8$ are preferably substituted at the following positions:

[Chemical 4]

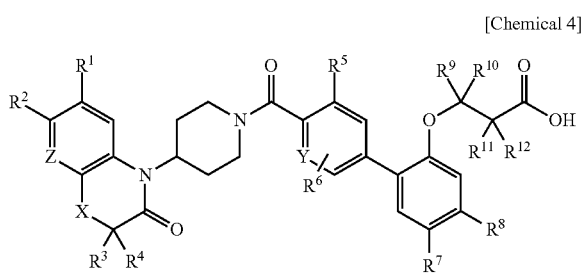

$R^9$ and $R^{10}$ in the compound (I) of the present invention, each independently, preferably represent a hydrogen atom, a methyl group, an ethyl group, or an n-propyl group, more preferably $R^9$ represents a hydrogen atom, $R^{10}$ represents a hydrogen atom, a methyl group, or an ethyl group, and even more preferably $R^9$ represents a hydrogen atom, $R^{10}$ represents a methyl group. Furthermore, when $R^9$ represents a hydrogen atom, and $R^{10}$ represents a methyl group or an ethyl group, then the carbon atom to which $R^9$ and $R^{10}$ are attached is an asymmetric carbon atom, and the configuration of $R^9$ and $R^{10}$ preferably assumes the following configuration (R configuration).

[Chemical 5]

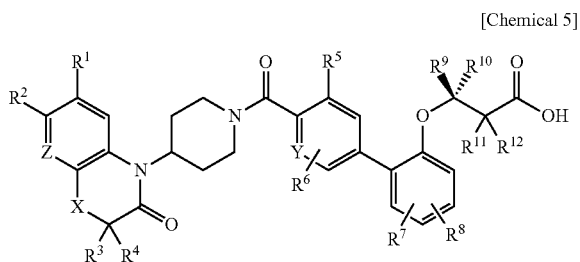

$R^{11}$ and $R^{12}$ in the compound (I) of the present invention, each independently, preferably represent a hydrogen atom, a methyl group, or an ethyl group, or $R^{11}$ and $R^{12}$, together with the carbon atom to which they are attached, represent a group forming cyclopropyl.

X in the compound (I) of the present invention preferably represents an oxygen atom, or a group represented by —$CH_2$—.

Y in the compound (I) of the present invention preferably represents a nitrogen atom, or a group represented by =C(Ra)—, and Ra represents a hydrogen atom, and more preferably Y represents a group represented by =C(Ra)—, and Ra represents a hydrogen atom.

Z in the compound (I) of the present invention preferably represents a nitrogen atom.

In the compound (I) of the present invention, preferably $R^1$ represents a fluorine atom, a chlorine atom, a cyano group, a methyl group, an ethyl group, or a trifluoromethyl group, $R^2$ represents a hydrogen atom, a chlorine atom, or a methyl group, $R^3$ and $R^4$, each independently, represent a hydrogen atom, or a methyl group, or $R^3$ and $R^4$, together with the carbon atom to which they are attached, represent a group forming cyclopropyl, $R^5$ represents a hydrogen atom, a chlorine atom, a fluorine atom, a hydroxyl group, a nitro group, a methyl group, or an amino group, $R^6$ represents a hydrogen atom, a fluorine atom, a chlorine atom, or a methyl group, $R^7$ and $R^8$, each independently, represent a hydrogen atom, a fluorine atom, a chlorine atom, or a methyl group, $R^9$ and $R^{10}$, each independently, represent a hydrogen atom, a methyl group, an ethyl group, or an n-propyl group, $R^{11}$ and $R^{12}$, each independently, represent a hydrogen atom, a methyl group, or an ethyl group, or $R^{11}$ and $R^{12}$, together with the carbon atom to which they are attached, represent a group forming cyclopropyl, X represents an oxygen atom, Y represents a nitrogen atom, or a group represented by =C(Ra)—, Ra represents a hydrogen atom, and Z represents a nitrogen atom; or $R^1$ represents a fluorine atom, a chlorine atom, a cyano group, a methyl group, an ethyl group, or a trifluoromethyl group, $R^2$ represents a hydrogen atom, a chlorine atom, or a methyl group, $R^3$ and $R^4$, each independently, represent a hydrogen atom, or a methyl group, or $R^3$ and $R^4$, together with the carbon atom to which they are attached, represent a group forming cyclopropyl, $R^5$ represents a hydrogen atom, a chlorine atom, a fluorine atom, a hydroxyl group, a nitro group, a methyl group, or an amino group, $R^6$ represents a hydrogen atom, a fluorine atom, a chlorine atom, or a methyl group, $R^7$ and $R^8$, each independently, represent a hydrogen atom, a fluorine atom, a chlorine atom, or a methyl group, $R^9$ and $R^{10}$, each independently, represent a hydrogen atom, a methyl group, an ethyl group, or an n-propyl group, $R^{11}$ and $R^{12}$, each independently, represent a hydrogen atom, a methyl group, or an ethyl group, or $R^{11}$ and $R^{12}$, together with the carbon atom to which they are attached, represent a group forming cyclopropyl, X represents a group represented by —$CH_2$—, Y represents a nitrogen atom, or a group represented by =C(Ra)—, Ra represents a hydrogen atom, and Z represents a nitrogen atom; and more preferably $R^1$ represents a chlorine atom, $R^2$ represents a hydrogen atom, $R^3$ represents a methyl group, $R^4$ represents a hydrogen atom, or a methyl group, $R^5$ represents a fluorine atom, a methyl group, or an amino group, $R^6$ represents a hydrogen atom, or a fluorine atom, $R^7$ and $R^8$, each independently, represent a hydrogen atom, or a fluorine atom, $R^9$ represents a hydrogen atom, $R^{10}$ represents a hydrogen atom, a methyl group, or an ethyl group, $R^{11}$ and $R^{12}$, each independently, represent a hydrogen atom, a methyl group, or an ethyl group, or $R^{11}$ and $R^{12}$, together with the carbon atom to which they are attached, represent a group forming cyclopropyl, X represents an oxygen atom, Y represents a nitrogen atom, or a group represented by =C(Ra)—, Ra represents a hydrogen atom, and Z represents a nitrogen atom; or $R^1$ represents a chlorine atom, $R^2$ represents a hydrogen atom, $R^3$ represents a methyl group, $R^4$ represents a hydrogen atom, or a methyl group, $R^5$ represents a fluorine atom, a methyl group, or an amino group, $R^6$ represents a hydrogen atom, or a fluorine atom, $R^7$ and $R^8$, each independently, represent a hydrogen atom, or a fluorine atom, $R^9$ represents a hydrogen atom, $R^{10}$ represents a hydrogen atom, a methyl group, or an ethyl group, $R^{11}$ and $R^{12}$, each independently, represent a hydrogen atom, a methyl group, or an ethyl group, or $R^{11}$ and $R^{12}$, together with the carbon atom to which they are attached, represent a group forming cyclopropyl, X represents a group represented by —$CH_2$—, Y represents a nitrogen atom, or a group represented by =C(Ra)—, Ra represents a hydrogen atom, and Z represents a nitrogen atom.

"Pharmacologically acceptable salt thereof" in the present invention represents a salt which can be obtained by reacting the compound (I) of the present invention, when having a basic group such as an amino group, with an acid, or by reacting it, when having an acidic group such as a carboxyl group, with a base.

Examples of the salt based on a basic group include hydrohalides such as hydrofluoride, hydrochloride, hydrobromide, and hydroiodide; inorganic acid salts such as nitrates, perchlorates, sulfates, and phosphates; lower alkanesulfonates such as methanesulfonates, trifluoromethanesulfonates, and ethanesulfonates; aryl sulfonates such as benzenesulfonates, and p-toluenesulfonates; organic acid salts such as acetates, malates, fumarates, succinates, citrates, ascorbates, tartrates, oxalates, and maleates; and amino acid salts such as glycine salts, lysine salts, arginine salts, ornithine salts, glutamates and aspartates, with methanesulfonates being preferred.

On the other hand, examples of the salt based on an acidic group include alkali metal salts such as sodium salts, potassium salts, and lithium salts; alkaline earth metal salts such as calcium salts, and magnesium salts; metal salts such as aluminum salts, and iron salts; inorganic salts such as ammonium salts; amine salts including organic salts such as tert-octylamine salts, dibenzyl salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzylphenethylamine salts, piperazine salts, tetramethylammonium salts, and tris(hydroxymethyl)aminomethane salts; and amino acid salts such as glycine salts, lysine salts, arginine salts, ornithine salts, glutamates, and aspartates, with sodium salts or potassium salts being preferred.

There are cases where the compounds (1) or pharmacologically acceptable salts thereof of the present invention are left in the atmosphere to absorb moisture and become hydrates, and such hydrates are also embraced in the present invention.

Further, there are cases where the compounds (1) or pharmacologically acceptable salts thereof of the present invention are left in a solvent to become solvates, and such solvates are also embraced in the present invention.

There are cases where optical isomers based on an asymmetric center in a molecule are present in the compound (I) of the present invention. In the compound of the present invention, all of these isomers and mixtures thereof are represented by a single formula, i.e., the general formula (I). Accordingly, the present invention will also include all of these isomers and mixtures of these isomers.

There are cases where atropisomers are present in the compound (I) of the present invention, depending on the types of substituents of a benzene ring, which isomers are derived from axis asymmetry resulting from limitation, by steric hindrance, of the rotation of the bond between two benzene rings of a biphenyl group. The present invention will also include these isomers and mixtures of these isomers.

Further, the compound (I) of the present invention may also contain a non-natural ratio of atomic isotopes in one or more atoms constituting a compound. Examples of atomic isotopes include deuterium ($^2H$), tritium ($^3H$), iodine-125 ($^{125}I$), carbon-14 ($^{14}C$), or the like. Further, said compound may be radiolabeled with radioisotopes such as, for example, tritium ($^3H$), iodine-125 ($^{125}I$), or carbon-14 ($^{14}C$). A radiolabeled compound is useful as a therapeutic or preventive agent, a research agent, for example, an assay reagent, and a diagnostic agent, for example, an in vivo diagnostic imaging agent. All the isotope variants of the compound of the present invention will be embraced in the scope of the present invention, regardless of whether or not they are radioactive.

Among the compounds of the general formula (I) of the present invention, examples of representative compounds include, but are not limited to, the following compounds: 3-{[4'-({4-[(3S)-7-chloro-3-methyl-2-oxo-2,3-dihydro-1H-pyrido[2,3-b][1,4]oxazin-1-yl]piperidin-1-yl}carbonyl)-3'-fluorobiphenyl-2-yl]oxy}-2,2-dimethylpropanoic acid, (3R)-3-[(4'-{[4-(7-chloro-3,3-dimethyl-2-oxo-3,4-dihydro-1,5-naphthyridin-1(2H)-yl)piperidin-1-yl]carbonyl}-3'-fluorobiphenyl-2-yl)oxy]butanoic acid, (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]butanoic acid, (2R,3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]-2-methylbutanoic acid, ((2S)-2-{[(4'-{[4-(7-chloro-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]methyl}butanoic acid, (2S)-3-[(4'-{[4-(7-chloro-3,3-dimethyl-2-oxo-3,4-dihydro-1,5-naphthyridin-1(2H)-yl)piperidin-1-yl]carbonyl}-3'-fluorobiphenyl-2-yl)oxy]-2-methylpropanoic acid, (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3',5-difluorobiphenyl-2-yl)oxy]butanoic acid, (3R)-3-[(4'-{[4-(7-chloro-3,3-dimethyl-2-oxo-3,4-dihydro-1,5-naphthyridin-1(2H)-yl)piperidin-1-yl]carbonyl}-3',5-difluorobiphenyl-2-yl)oxy]butanoic acid, (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3'-methylbiphenyl-2-yl)oxy]butanoic acid, (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-5-fluoro-3'-methylbiphenyl-2-yl)oxy]butanoic acid, (3R)-3-[(3'-chloro-4'-{[4-(7-chloro-3,3-dimethyl-2-oxo-2,3-dihydro-1H-pyrido[2,3-b][1,4]oxazin-1-yl)piperidin-1-yl]carbonyl}biphenyl-2-yl)oxy]butanoic acid, (2S)-3-{[4'-({4-[(3S)-7-chloro-3-methyl-2-oxo-2,3-dihydro-1H-pyrido[2,3-b][1,4]oxazin-1-yl]piperidin-1-yl}carbonyl)-3'-fluorobiphenyl-2-yl]oxy}-2-methylpropanoic acid, (2S)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]-2-methylpropanoic acid, (2S)-3-{[4'-({4-[(3S)-7-chloro-3-methyl-2-oxo-2,3-dihydro-1H-pyrido[2,3-b][1,4]oxazin-1-yl]piperidin-1-yl}carbonyl)-3',5-difluorobiphenyl-2-yl]oxy}-2-methylpropanoic acid, (2S)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3',5-difluorobiphenyl-2-yl)oxy]-2-methylpropanoic acid, (3R)-3-{[4'-({4-[(3S)-7-chloro-3-methyl-2-oxo-2,3-dihydro-1H-pyrido[2,3-b][1,4]oxazin-1-yl]piperidin-1-yl}carbonyl)-3'-fluorobiphenyl-2-yl]oxy}butanoic acid, (3R)-3-{[4'-({4-[(3S)-7-chloro-3-methyl-2-oxo-2,3-dihydro-1H-pyrido[2,3-b][1,4]oxazin-1-yl]piperidin-1-yl}carbonyl)-3',5-difluorobiphenyl-2-yl]oxy}butanoic acid, (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-2',5'-difluorobiphenyl-2-yl)oxy]butanoic acid, (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3',4-difluorobiphenyl-2-yl)oxy]butanoic acid, (3R)-3-[(4'-{[4-(7-chloro-3,3-dimethyl-2-oxo-3,4-dihydro-1,5-naphthyridin-1(2H)-yl)piperidin-1-yl]carbonyl}-3'-methylbiphenyl-2-yl)oxy]butanoic acid, (3R)-3-[2-(6-{[4-(7-chloro-3,3-dimethyl-2-oxo-3,4-dihydro-1,5-naphthyridin-1(2H)-yl)piperidin-1-yl]carbonyl}-5-fluoropyridin-3-yl)phenoxy]butanoic acid, (3R)-3-[2-(6-{[4-(7-chloro-3,3-dimethyl-2-oxo-2,3-dihydro-1H-pyrido[2,3-b][1,4]oxazin-1-yl)piperidin-1-yl]carbonyl}-5-fluoropyridin-3-yl)phenoxy]pentanoic acid, (3R)-3-[2-(6-{[4-(7-chloro-3,3-dimethyl-2-oxo-2,3-dihydro-1H-pyrido[2,3-b][1,4]oxazin-1-yl)piperidin-1-yl]carbonyl}-5-fluoropyridin-3-yl)-4-fluorophenoxy]butanoic acid, (3R)-3-[2-(6-{[4-(7-chloro-3,3-dimethyl-2-oxo-3,4-dihydro-1,5-naphthyridin-1(2H)-yl)piperidin-1-yl]carbonyl}-5-fluoropyridin-3-yl)-4-fluorophenoxy]butanoic acid, (3R)-3-[(4'-{[4-(7-chloro-3,3-dimethyl-2-oxo-3,4-dihydro-1,5-naphthyridin-1(2H)-yl)piperidin-1-yl]carbonyl}-5-fluoro-3'- methylbiphenyl-2-yl)oxy]butanoic acid, (2S)-3-[2-(6-{[4-(7-chloro-3,3-dimethyl-2-oxo-3,4-dihydro-1,5-naphthyridin-1(2H)-yl)piperidin-1-yl]carbonyl}-5-fluoropyridin-3-yl)phenoxy]-2-methylpropanoic acid, (3R)-3-[(3'-amino-4'-{[4-(7-chloro-3,3-dimethyl-2-oxo-2,3-dihydro-1H-pyrido[2,3-b][1,4]oxazin-1-yl)piperidin-1-yl]carbonyl}biphenyl-2-yl)oxy]butanoic acid, (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3',5'-difluorobiphenyl-2-yl)oxy]butanoic acid, (3R)-3-[(4'-{[4-(7-cyano-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]butanoic acid, (3R)-3-[(4'-{[4-(7-ethyl-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]butanoic acid, and (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3'-fluoro-4-methylbiphenyl-2-yl)oxy]butanoic acid.

Preferable examples thereof include: (3R)-3-[(4'-{[4-(7-chloro-3,3-dimethyl-2-oxo-3,4-dihydro-1,5-naphthyridin-1(2H)-yl)piperidin-1-yl]carbonyl}-3'-fluorobiphenyl-2-yl)oxy]butanoic acid, (3R)-3-[(4'-{[4-(7-chloro-3,3-dimethyl-2-oxo-3,4-dihydro-1,5-naphthyridin-1(2H)-yl)piperidin-1-yl]carbonyl}-3',5-difluorobiphenyl-2-yl)oxy]butanoic acid, (3R)-3-{[4'-({4-[(3S)-7-chloro-3-methyl-2-oxo-2,3-dihydro-1H-pyrido[2,3-b][1,4]oxazin-1-yl]piperidin-1-yl}carbonyl)-3'-fluorobiphenyl-2-yl]oxy}butanoic acid, (3R)-3-{[4'-({4-[(3S)-7-chloro-3-methyl-2-oxo-2,3-dihydro-1H-pyrido[2,3-b][1,4]oxazin-1-yl]piperidin-1-yl}carbonyl)-3',5-difluorobiphenyl-2-yl]oxy}butanoic acid, (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3',4-difluorobiphenyl-2-yl)oxy]butanoic acid, or (3R)-3-[(4'-{[4-(7-cyano-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]butanoic acid.

Effect of the Invention

Since the compound of the general formula (I) or pharmacologically acceptable salt thereof of the present invention has an excellent suppressive action on platelet aggregation, it is useful as an active ingredient of a medicament, in particular, an antiplatelet agent, and is useful as an active ingredient of a preventive and/or therapeutic agent for thromboembolic diseases. The compound of the general formula (I) or pharmacologically acceptable salt thereof of the present invention is particularly useful as an active ingredient of a preventive and/or therapeutic agent for ischemic cerebrovascular diseases (transient cerebral ischemic attack (TIA), atherothrombotic brain infarction, lacunar infarction), of a preventive and/or therapeutic agent for acute coronary syndrome (unstable angina, acute myocardial infarction), and of a preventive agent for restenosis or reocclusion in cases of acute coronary syndrome where coronary artery bypass graft (CABG) or percutaneous coronary intervention (PCI) has been applied. Further, it is also available for treatment of thrombosis/embolism associated with vascular surgery and blood extracorporeal circulation as well as amelioration of blood circulation disorder, amelioration of various ischemic symptoms such as ulcer, pain and coldness associated with chronic artery occlusion, and amelioration of blood circulation disorder associated with cerebral vasospasm after subarachnoid hemorrhage.

DETAILED DESCRIPTION

A compound or a pharmacologically acceptable salt thereof of the present invention can be produced utilizing the basic skeleton thereof or features based on the types of substituents and applying various known synthesis methods. During the production, there are cases where it is effective in a production technique, depending on the type of a functional group, to substitute such functional group by a suitable protective group (a group capable of being easily converted to such functional group) at stages from starting materials to intermediates. Examples of such functional group include an amino group, a hydroxyl group, a carboxyl group, or the like, and their protective groups, for example, include protective groups, or the like set forth in Greene and Wuts, "Protective Groups in Organic Synthesis (3rd ed., 1999)", and an appropriate selection may be made for use depending on these reaction conditions. Such method enables one to obtain a desired compound by introducing such protective group and carrying out the reaction, and then by removing a protective group as needed.

Hereinafter, a compound (I) of the present invention and representative methods for producing a starting material compound to be used for the production of the compound (I) of the present invention will be explained. Furthermore, the production methods of the present invention are not limited to examples shown below, and the following methods, known methods, or modifications thereof can be used.

Production Method 1

Production method 1 is a method for producing a compound (I) of the present invention from compound (1).

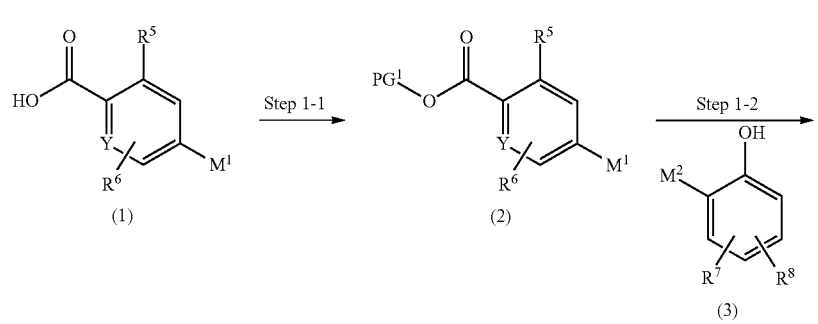

[Chemical 6]

-continued

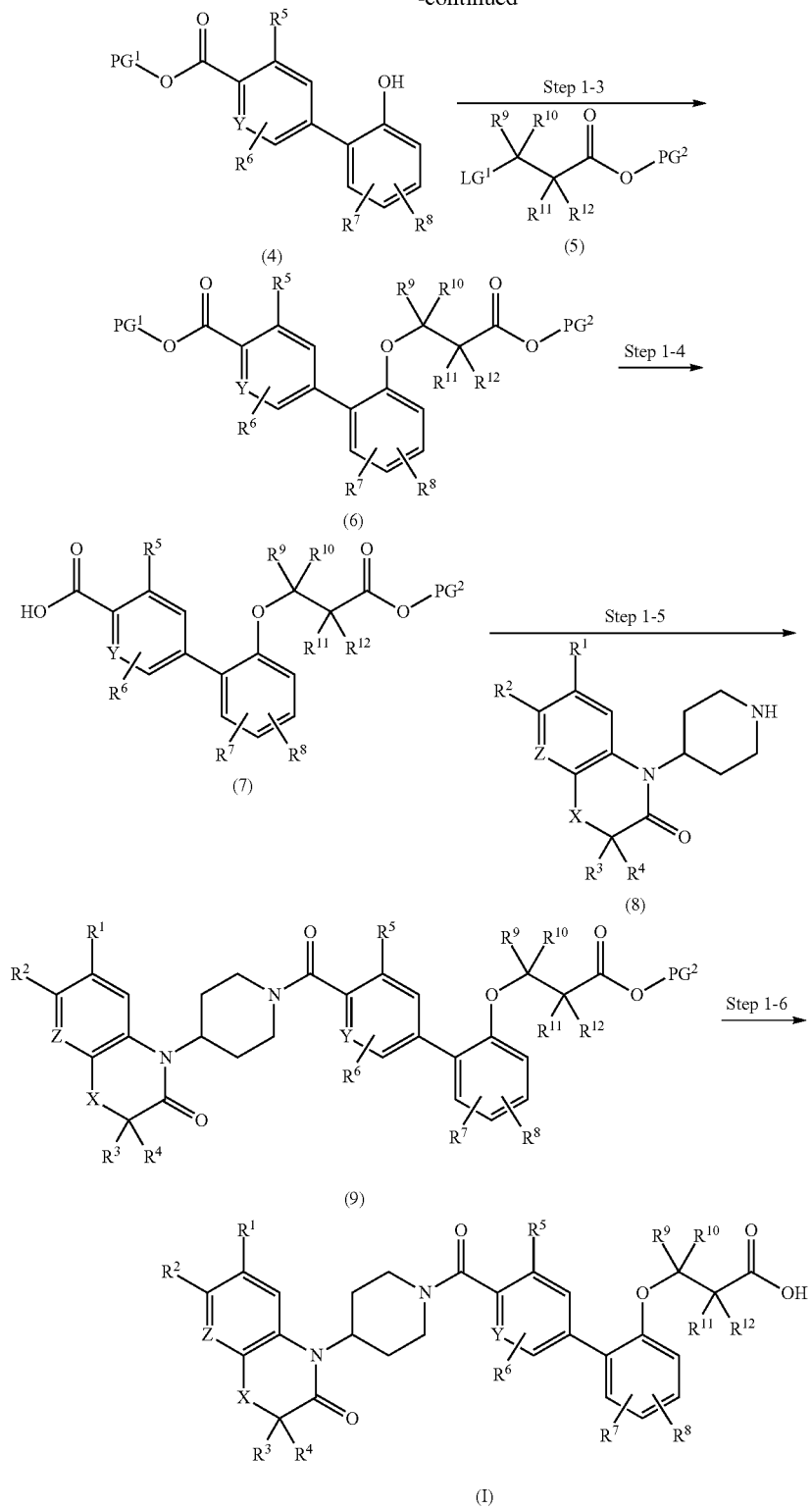

In the above formulae, $R^1$, $R^2$, $R^3$, $R^4$, $R^5$, $R^6$, $R^7$, $R^8$, $R^9$, $R^{10}$, $R^{11}$, $R^{12}$, X, Y, and Z have the same meanings as those mentioned above. $PG^1$ and $PG^2$ represent protective groups of carboxylic acid, and examples include protective groups, or the like set forth in Greene and Wuts, "Protective Groups in Organic Synthesis (3rd ed., 1999)". Preferably, $PG^1$ is a methyl group, an ethyl group, or a benzyl group, and $PG^2$ is a tert-butyl group or a 2-trimethylsilylethyl group. $M^1$ represents a chlorine atom, a bromine atom, an iodine atom, or a trifluoromethanesulfonyloxy group, and $M^2$ represents a boronic acid or a boronic acid ester. Alternatively, a reverse combination of $M^1$ and $M^2$ is also acceptable. $LG^1$ represents a leaving group such as a chlorine atom, a bromine atom, an iodine atom, a methanesulfonyloxy group, or a p-toluenesulfonyloxy group, or a hydroxyl group.

(Step 1-1)

The present step is a step for introducing a protective group of a carboxyl group. Compound (2) can be produced from compound (1) using an appropriate method out of the reactions (a), (b), (c), or (d) described below.

The reaction (a) is carried out by allowing a base and an alkyl halide to act on compound (1) in a solvent inactive to the reaction. Examples of the solvent include alcohols such as methanol, ethanol, n-propanol, isopropanol, n-butanol, isobutanol, tert-butanol, isoamyl alcohol, octanol, cyclohexanol, 2-methoxyethanol, diethyleneglycol, or glycerin, amides such as N,N-dimethylformamide, N,N-dimethylacetamide, N-methyl-2-pyrrolidinone, or hexamethylphosphorotriamide, nitriles such as acetonitrile, or ketones such as acetone, with N,N-dimethylformamide, acetonitrile, or acetone being preferred. Examples of the base include inorganic bases such as sodium carbonate, potassium carbonate, cesium carbonate, sodium tert-butoxide, or potassium tert-butoxide, or organic bases such as triethylamine, diisopropylethylamine, N-methylmorpholine, pyridine, or 2,6-lutidine, with potassium carbonate or cesium carbonate being preferred. Examples of the alkyl halide include methyl iodide, ethyl iodide, or benzyl bromide. Usually, the reaction temperature is 0° C. to 100° C., preferably 20° C. to 80° C. The reaction time is 1 hour to 24 hours, preferably 2 hours to 12 hours.

The reaction (b) is carried out by allowing an acid to act on compound (1) in an alcohol corresponding to $PG^1$. Examples of the alcohol include methanol, ethanol, or benzylalcohol. Examples of the acid include inorganic acids such as hydrochloric acid, hydrobromic acid, sulfuric acid, perchloric acid, or phosphoric acid, or organic acids such as acetic acid, formic acid, oxalic acid, methanesulfonic acid, p-toluenesulfonic acid, camphorsulfonic acid, trifluoroacetic acid, or trifluoromethanesulfonic acid, with hydrochloric acid or sulfuric acid being preferred. Usually, the reaction temperature is 20° C. to 150° C., preferably 50° C. to 100° C. The reaction time is 30 minutes to 48 hours, preferably 1 hour to 24 hours.

The reaction (c) is carried out by allowing thionyl chloride to act on compound (1) in an alcohol corresponding to $PG^1$. Examples of the alcohol include methanol, ethanol, or benzylalcohol. Usually, the reaction temperature is −20° C. to 100° C., preferably 0° C. to 50° C. The reaction time is 30 minutes to 48 hours, preferably 1 hour to 24 hours.

The reaction (d), in which $PG^1$ is used for the case of a methyl group, is carried out by allowing trimethylsilyldiazomethane to act on compound (1) in a mixed solvent of ethyl acetate, diethylether, or toluene with methanol. Usually, the reaction temperature is −20° C. to 50° C., preferably 0° C. to 30° C. The reaction time is 15 minutes to 24 hours, preferably 30 minutes to 12 hours.

(Step 1-2)

The present step is a Suzuki-Miyaura reaction. A base and a palladium catalyst can be allowed to act on compound (2) and compound (3) in a solvent inactive to the reaction to produce compound (4). Examples of the solvent include aromatic hydrocarbons such as benzene, toluene, or xylene, ethers such as diethylether, diisopropylether, tetrahydrofuran, dioxane, dimethoxyethane, or tert-butyl-methylether, amides such as N,N-dimethylformamide, N,N-dimethylacetamide, N-methyl-2-pyrrolidinone, or hexamethylphosphorotriamide, water, a mixed solvent thereof, or the like, with N,N-dimethylformamide, dioxane, or dimethoxyethane-water mixed solvent being preferred. Examples of the base include sodium carbonate, potassium carbonate, cesium carbonate, sodium acetate, tripotassium phosphate, sodium tert-butoxide, potassium tert-butoxide, or the like, with sodium carbonate, potassium carbonate, or tripotassium phosphate being preferred.

Examples of the palladium catalyst include tetrakis(triphenylphosphine)palladium, bis(dibenzylideneacetone)palladium, tris(dibenzylideneacetone)dipalladium, bis(triphenylphosphine)dichloropalladium, [1,1'-bis(diphenylphosphino)ferrocene]dichloropalladium, bis(2,4-pentanedionate)palladium, palladium acetate, or the like, with tetrakis(triphenylphosphine)palladium or [1,1'-bis(diphenylphosphino)ferrocene]dichloropalladium being preferred. There are cases where, in order to allow the reaction to proceed smoothly, it is useful to add as an additive triphenylphosphine, tri(2-tolyl)phosphine, 1,4-bis(diphenylphosphino)butane, 1,1'-bis(diphenylphosphino)ferrocene, 2,2'-bis(diphenylphosphino)-1,1'-binaphthyl, or the like. Usually, the reaction temperature is 20° C. to 150° C., preferably 80° C. to 100° C. The reaction time is 30 minutes to 24 hours, preferably 1 hour to 12 hours.

(Step 1-3)

The present step is a step for producing compound (6) by reacting compound (4) with compound (5), and (Step 1-3a) or (Step 1-3b) are to be mentioned. Compound (5) can be produced from a commercially available compound or a known compound in accordance with a known method, for example, a method set forth in Greene and Wuts, "Protective Groups in Organic Synthesis (3rd ed., 1999)", C. P. Decicco et al., "Journal of Organic Chemistry, 1995, 60, 4782-4785", or the like.

(Step 1-3a)

The present step is a substitution reaction in which $LG^1$ of compound (5) is a leaving group. A base can be allowed to act on compound (4) and compound (5) in a solvent inactive to the reaction to produce compound (6). Examples of the solvent include aromatic hydrocarbons such as benzene, toluene, or xylene, ethers such as diethylether, diisopropylether, tetrahydrofuran, dioxane, dimethoxyethane, or tert-butylmethylether, alcohols such as methanol, ethanol, n-propanol, isopropanol, n-butanol, isobutanol, tert-butanol, isoamyl alcohol, octanol, cyclohexanol, 2-methoxyethanol, diethyleneglycol, or glycerin, amides such as N,N-dimethylformamide, N,N-dimethylacetamide, N-methyl-2-pyrrolidinone, or hexamethylphosphorotriamide, sulfoxides such as dimethylsulfoxide or sulfolane, ketones such as acetone, nitriles such as acetonitrile, or a mixed solvent thereof, with N,N-dimethylformamide or acetonitrile being preferred. Examples of the base include inorganic bases such as sodium carbonate, potassium carbonate, cesium carbonate, sodium hydroxide, potassium hydroxide, sodium hydride, sodium tert-butoxide, or potassium tert-butoxide, or organic bases such as triethylamine, diisopropylethylamine, N-methylmorpholine, pyridine, or 2,6-lutidine, with cesium carbonate or potassium carbonate being preferred. Depending on the reaction, there are cases where, in order to allow the reaction to proceed smoothly, it is useful to use as an additive sodium iodide, potassium iodide, tetra n-butylammonium iodide, or the like. Usually, the reaction temperature is 0° C. to 150° C., preferably 50° C. to 100° C. The reaction time is 30 minutes to 100 hours, preferably 1 hour to 48 hours.

(Step 1-3b)

When $LG^1$ of compound (5) is a hydroxyl group, the present step is a Mitsunobu reaction. A reagent for use in the Mitsunobu reaction can be allowed to act on compound (4) and compound (5) in a solvent inactive to the reaction to produce compound (6). Examples of the solvent include aromatic hydrocarbons such as benzene, toluene, or xylene, halogenated hydrocarbons such as dichloromethane, chloroform, carbon tetrachloride, 1,2-dichloroethane, chlorobenzene, or dichlorobenzene, ethers such as diethylether, diisopropylether, tetrahydrofuran, dioxane, dimethoxyethane, or tert-butyl-methylether, or a mixed solvent thereof, with tetrahydrofuran being preferred. Examples of the reagent for use in the Mitsunobu reaction include a combination of an azodicarboxylic acid derivative such as diethyl azodicarboxylate, di-tert-butyl azodicarboxylate, or azodicarboxylic acid dipiperidinamide, and a phosphine compound such as triphenylphosphine, tri(2-tolyl)phosphine, or tri-n-butylphosphine, with a combination of di-tert-butyl azodicarboxylate and triphenylphosphine being preferred. Usually, the reaction temperature is 0° C. to 100° C., preferably 20° C. to 70° C. The reaction time is 30 minutes to 48 hours, preferably 1 hour to 24 hours.

(Step 1-4)

The present step is deprotection of $PG^1$ of compound (6). A base can be allowed to act on compound (6) in a solvent inactive to the reaction to produce compound (7). Examples of the solvent include ethers such as diethylether, diisopropylether, tetrahydrofuran, dioxane, dimethoxyethane, or tert-butyl methylether, alcohols such as methanol, ethanol, n-propanol, isopropanol, n-butanol, isobutanol, tert-butanol, isoamyl alcohol, octanol, cyclohexanol, 2-methoxyethanol, diethyleneglycol, or glycerin, water, a mixed solvent thereof, or the like, with tetrahydrofuran, ethanol, methanol, water, or a mixed solvent thereof being preferred. Although there are no particular limitations on the base that can be used, provided that it is used for the usual reaction, examples thereof include lithium hydroxide, sodium hydroxide, or potassium trimethylsilanolate. Usually, the reaction temperature is 0° C. to 100° C., preferably 20° C. to 60° C. The reaction time is 30 minutes to 24 hours, preferably 1 hour to 12 hours.

When $PG^1$ is a benzyl group, a hydrogenolysis reaction using a transition metal catalyst can also be used in a solvent inactive to the reaction to deprotect $PG^1$. Examples of the solvent include ethers such as diethylether, diisopropylether, tetrahydrofuran, dioxane, dimethoxyethane, or tert-butyl methylether, esters such as ethyl formate, ethyl acetate, propyl acetate, butyl acetate, or diethyl carbonate, alcohols such as methanol, ethanol, n-propanol, isopropanol, n-butanol, isobutanol, tert-butanol, isoamyl alcohol, octanol, cyclohexanol, 2-methoxyethanol, diethyleneglycol, or glycerin, amides such as N,N-dimethylformamide, N,N-dimethylacetamide, N-methyl-2-pyrrolidinone, or hexamethylphosphorotriamide, acetic acid, water, a mixed solvent thereof, or the like, with methanol, ethanol, tetrahydrofuran, water, or a mixed solvent thereof being preferred. Examples of the transition metal catalyst include platinum oxide, platinum carbon, platinum black, palladium carbon, palladium black, palladium hydroxide carbon, or Raney nickel, with palladium carbon or palladium hydroxide carbon being preferred. Usually, the reaction temperature is 10° C. to 60° C., preferably 20° C. to 35° C. The reaction pressure is, under a hydrogen atmosphere, normal pressure to increased pressure, preferably normal pressure. The reaction time is 1 hour to 48 hours, preferably 3 hours to 24 hours.

(Step 1-5)

The present step is an amidation reaction. A condensing agent can be allowed to act on compound (7) and compound (8) obtainable by a production method described later in a solvent inactive to the reaction to produce compound (9). Examples of the solvent include halogenated hydrocarbons such as dichloromethane, chloroform, carbon tetrachloride, 1,2-dichloroethane, chlorobenzene, or dichlorobenzene, ethers such as diethylether, diisopropylether, tetrahydrofuran, dioxane, dimethoxyethane, or tert-butyl methylether, alcohols such as methanol, ethanol, n-propanol, isopropanol, n-butanol, isobutanol, tert-butanol, isoamyl alcohol, octanol, cyclohexanol, 2-methoxyethanol, diethyleneglycol, or glycerin, amides such as N,N-dimethylformamide, N,N-dimethylacetamide, N-methyl-2-pyrrolidinone, or hexamethylphosphorotriamide, water, a mixed solvent thereof, or the like, with dichloromethane, tetrahydrofuran, methanol, N,N-dimethylformamide, or a mixed solvent thereof being preferred. Examples of the condensing agent include 1,1-carbonyldiimidazole, N,N'-diisopropylcarbodiimide, 1-ethyl-3-(3-dimethylaminopropyl)carbodiimide hydrochloride, 2-(1H-benzotriazol-1-yl)-1,1,3,3-tetramethyluronium hexafluorophosphate, (1H-benzotriazol-1-yloxy)tripyrrolidinophosphonium hexafluorophosphate, 4-(4,6-dimethoxy-1,3,5-triazin-2-yl)-4-methylmorpholinium chloride, or the like, with 1-ethyl-3-(3-dimethylaminopropyl)carbodiimide hydrochloride, 2-(1H-benzotriazol-1-yl)-1,1,3,3-tetramethyluronium hexafluorophosphate, or 4-(4,6-dimethoxy-1,3,5-triazin-2-yl)-4-methylmorpholinium chloride being preferred. Depending on the condensing agent, 1-hydroxybenzotriazole can be used simultaneously. Depending on the reaction, there are cases where, in order to allow the reaction to proceed smoothly, it is useful to carry out the reaction in the presence of a base. Examples of the base include organic bases such as triethylamine, diisopropylethylamine, N-methylmorpholine, pyridine, or 4-(N,N-dimethylamino)pyridine, or inorganic bases such as potassium carbonate, cesium carbonate, or sodium hydrogen carbonate, with diisopropylethylamine or N-methylmorpholine being preferred. Usually, the reaction temperature is 0° C. to 100° C., preferably 20° C. to 50° C. The reaction time is 2 hours to 48 hours, preferably 4 hours to 24 hours.

(Step 1-6)

The present step is deprotection of $PG^2$ of compound (9). An acid can be allowed to act on compound (9) in a solvent inactive to the reaction, or without using a solvent to produce the compound (I) of the present invention. Examples of the solvent include aromatic hydrocarbons such as benzene, toluene, or xylene, hydrocarbons such as pentane, hexane, or cyclohexane, halogenated hydrocarbons such as dichloromethane, chloroform, carbon tetrachloride, 1,2-dichloroethane, chlorobenzene, or dichlorobenzene, esters such as ethyl formate, ethyl acetate, propyl acetate, butyl acetate, or diethyl carbonate, ethers such as diethylether, diisopropylether, tetrahydrofuran, dioxane, dimethoxyethane, or tert-butyl methylether, alcohols such as methanol, ethanol, n-propanol, isopropanol, n-butanol, isobutanol, tert-butanol, isoamyl alcohol, octanol, cyclohexanol, 2-methoxyethanol, diethyleneglycol, or glycerin, water, a mixed solvent thereof, or the like, with dichloromethane being preferred. Examples of the acid include inorganic acids such as hydrochloric acid, hydrobromic acid, sulfuric acid, perchloric acid, or phosphoric acid, or organic acids such as acetic acid, formic acid, oxalic acid, methanesulfonic acid, p-toluenesulfonic acid, camphorsulfonic acid, trifluoroacetic acid, or trifluoromethanesulfonic acid, with trifluoroacetic acid being preferred. Usually, the reaction temperature is −50° C. to 100° C., preferably 0° C. to 50° C. The reaction time is 15 minutes to 48 hours, preferably 30 minutes to 24 hours.

Production Method 2

Production Method 2 is an alternative method for producing compound (I) of the present invention from compound (4) in Production Method 1.

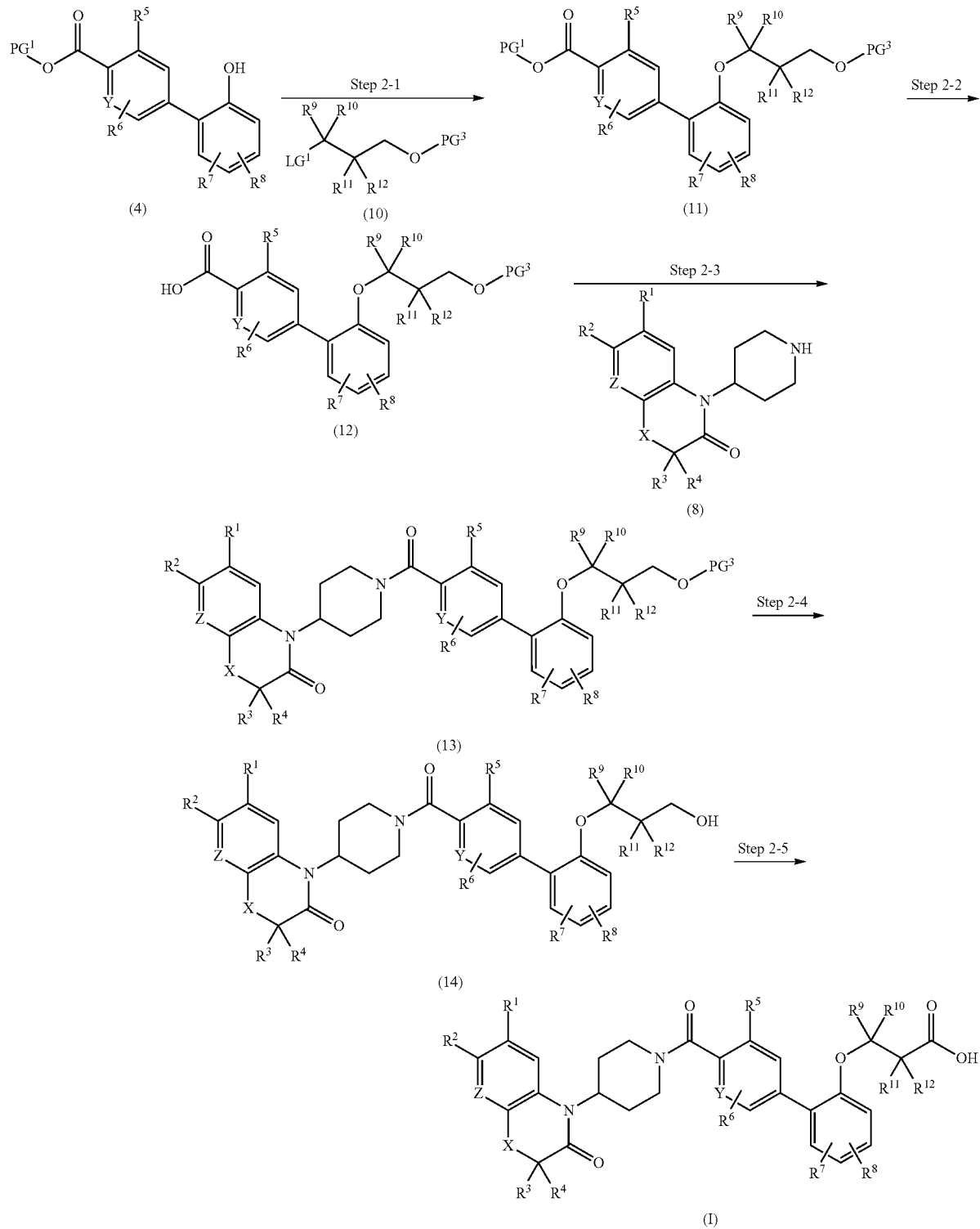

[Chemical 7]

In the formulae, $R^1$, $R^2$, $R^3$, $R^4$, $R^5$, $R^6$, $R^7$, $R^8$, $R^9$, $R^{10}$, $R^{11}$, $R^{12}$, X, Y, Z, $PG^1$, and $LG^1$ have the same meanings as those mentioned above. $PG^3$ represents a protective group of a hydroxyl group, and examples include silyl groups such as a tert-butyldimethylsilyl group, a tert-butyldiphenylsilyl group, or a triisopropylsilyl group, or cyclic ether groups such as a tetrahydropyranyl group or a tetrahydrofuranyl group, with a tert-butyldimethylsilyl group or a tert-butyldiphenylsilyl group, or a tetrahydropyranyl group being preferred.

(Step 2-1)

The present step is a substitution reaction in which $LG^1$ of compound (10) is a leaving group, and is a Mitsunobu reaction when $LG^1$ is a hydroxyl group. Analogously to Step 1-3a or 1-3b, compound (11) can be produced from compound (4). Compound (10) can be produced from a commercially available compound or a known compound in accordance with a known method, for example, a method set forth in Greene and Wuts, "Protective Groups in Organic Synthesis (3rd ed., 1999)", or the like.

(Step 2-2)

The present step is deprotection of $PG^1$ of compound (11). Analogously to Step 1-4, compound (12) can be produced from compound (11).

(Step 2-3)

The present step is an amidation reaction. Analogously to Step 1-5, compound (13) can be produced from compound (8) and compound (12).

(Step 2-4)

The present step is deprotection of $PG^3$ of compound (13). When $PG^3$ of compound (13) is a silyl group such as a tert-butyldimethylsilyl group or a tert-butyldiphenylsilyl group, a base can be allowed to act on compound (13) in a solvent inactive to the reaction to produce compound (14). Examples of the solvent include ethers such as diethylether, diisopropylether, tetrahydrofuran, dioxane, dimethoxyethane, or tert-butyl methylether, alcohols such as methanol, ethanol, n-propanol, isopropanol, n-butanol, isobutanol, tert-butanol, isoamyl alcohol, octanol, cyclohexanol, 2-methoxyethanol, diethyleneglycol, or glycerin, amides such as N,N-dimethylformamide, N,N-dimethylacetamide, N-methyl-2-pyrrolidinone, or hexamethylphosphorotriamide, nitriles such as acetonitrile, water, a mixed solvent thereof, or the like, with tetrahydrofuran being preferred. Examples of the base include tetra-n-butylammonium fluoride, tetraethylammonium fluoride, or pyridinium fluoride, with tetra-n-butylammonium fluoride being preferred. Depending on the compound, there are cases where it is useful to use acetic acid as an additive. Usually, the reaction temperature is 0° C. to 80° C., preferably 20° C. to 40° C. The reaction time is 30 minutes to 48 hours, preferably 3 hours to 24 hours.

When $PG^3$ of compound (13) is a cyclic ether group such as a tetrahydropyranyl group, an acid can be allowed to act on compound (13) in a solvent inactive to the reaction to produce compound (14). Examples of the solvent include ethers such as diethylether, diisopropylether, tetrahydrofuran, dioxane, dimethoxyethane, or tert-butyl methylether, alcohols such as methanol, ethanol, n-propanol, isopropanol, n-butanol, isobutanol, tert-butanol, isoamyl alcohol, octanol, cyclohexanol, 2-methoxyethanol, diethyleneglycol, or glycerin, water, a mixed solvent thereof, or the like, with methanol or ethanol being preferred. Examples of the acid include inorganic acids such as hydrochloric acid, hydrobromic acid, sulfuric acid, perchloric acid, or phosphoric acid, or organic acids such as acetic acid, formic acid, oxalic acid, methanesulfonic acid, p-toluenesulfonic acid, camphorsulfonic acid, trifluoroacetic acid, or trifluoromethanesulfonic acid, with p-toluenesulfonic acid being preferred. Usually, the reaction temperature is 0° C. to 70° C., preferably 20° C. to 40° C. The reaction time is 30 minutes to 12 hours, preferably 1 hour to 6 hours.

(Step 2-5)

The present step is an oxidation reaction of alcohols. An oxidizing agent can be allowed to act on compound (14) in a solvent inactive to the reaction to produce the compound (I) of the present invention. Examples of the solvent include aromatic hydrocarbons such as benzene, toluene, or xylene, hydrocarbons such as pentane, hexane, or cyclohexane, halogenated hydrocarbons such as dichloromethane, chloroform, carbon tetrachloride, 1,2-dichloroethane, chlorobenzene, or dichlorobenzene, esters such as ethyl formate, ethyl acetate, propyl acetate, butyl acetate, or diethyl carbonate, ethers such as diethylether, diisopropylether, tetrahydrofuran, dioxane, dimethoxyethane, or tert-butyl methylether, alcohols such as tert-butanol, nitriles such as acetonitrile, ketones such as acetone, water, a mixed solvent thereof, or the like, with acetonitrile or an ethyl acetate-water mixed solvent being preferred. Examples of the oxidizing agent include a combination of chromium(VI) oxide/sulfuric acid, a combination of ruthenium(III) chloride/orthoperiodic acid, a combination of 2,2,6,6-tetramethyl-1-piperidyloxy radical/sodium hypochlorite/sodium chlorite, or the like, with a combination of 2,2,6,6-tetramethyl-1-piperidyloxy radical/sodium hypochlorite/sodium chlorite being preferred. It is useful to use a neutral phosphate pH standard solution (pH maintained at 6.5-7.0) or potassium bromide/hydrochloric acid simultaneously, in order to allow the reaction to proceed smoothly. Usually, the reaction temperature is 0° C. to 80° C., preferably 20° C. to 60° C. The reaction time is 1 hour to 48 hours, preferably 4 hours to 24 hours.

Production Method 3

Production Method 3 is an alternative method for producing compound (14) from compound (11) in Production Method 2.

[Chemical 8]

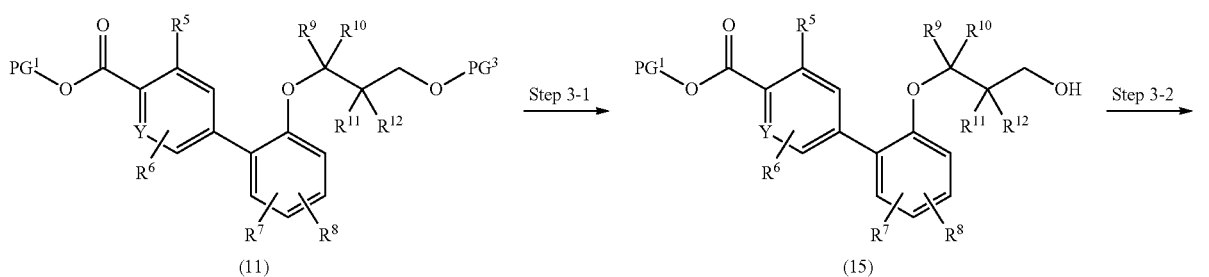

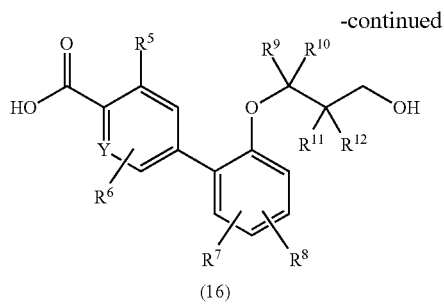

(16)

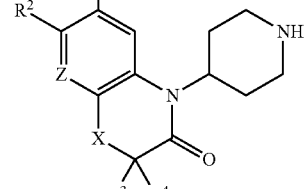

(8)

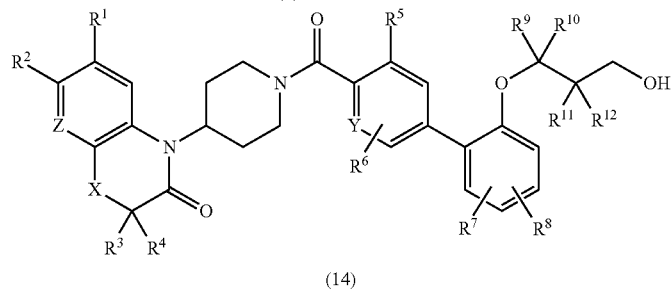

(14)

In the formulae, $R^1$, $R^2$, $R^3$, $R^4$, $R^5$, $R^6$, $R^7$, $R^8$, $R^9$, $R^{10}$, $R^{11}$, $R^{12}$, X, Y, Z, $PG^1$, and $PG^3$ have the same meanings as those mentioned above.

(Step 3-1)

The present step is deprotection of $PG^3$ of compound (11). Analogously to Step 2-4, compound (15) can be produced from compound (11).

(Step 3-2)

The present step is deprotection of $PG^1$ of compound (15). Analogously to Step 1-4, compound (16) can be produced from compound (15).

(Step 3-3)

The present step is an amidation reaction. Analogously to Step 1-5, compound (14) can be produced from compound (8) and compound (16).

Production Method 4

Production Method 4 is an alternative method for producing compound (4) in Production Method 1.

[Chemical 9]

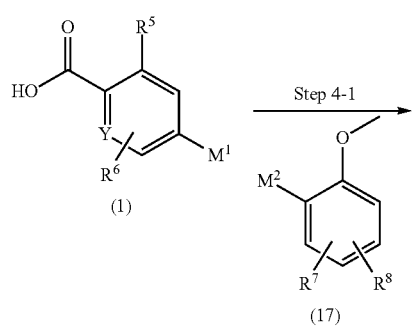

(1)

(17)

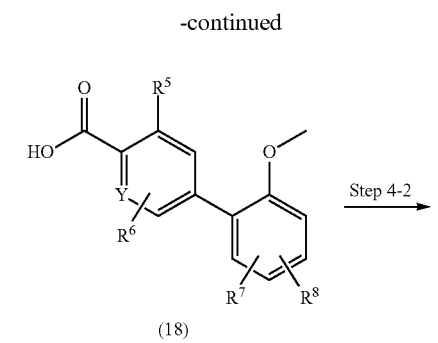

(18)

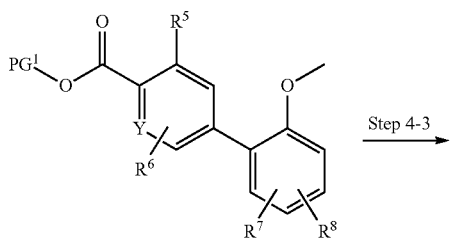

(19)

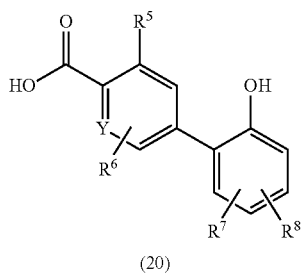

(20)

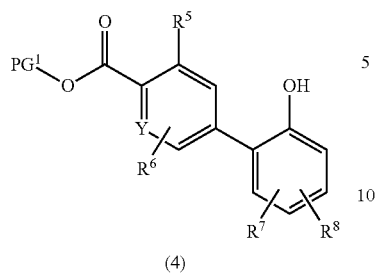

(4)

In the formulae, $R^5$, $R^6$, $R^7$, $R^8$, Y, $PG^1$, $M^1$, and $M^2$ have the same meanings as those mentioned above.

(Step 4-1)

The present step is a Suzuki-Miyaura reaction. Analogously to Step 1-2, compound (18) can be produced from compound (1) and compound (17).

(Step 4-2)

The present step is an esterification reaction. Analogously to Step 1-1, compound (19) can be produced from compound (18).

(Step 4-3)

The present step is deprotection of a methoxy group and $PG^1$ of compound (19). Lewis acid is allowed to act on compound (19) in a solvent inactive to the reaction to produce compound (20). Examples of the solvent include halogenated hydrocarbons such as dichloromethane, chloroform, carbon tetrachloride, 1,2-dichloroethane, chlorobenzene, or dichlorobenzene, nitriles such as acetonitrile, or the like, with dichloromethane being preferred. Examples of the Lewis acid include boron tribromide, boron trichloride, aluminum tribromide, or the like, with boron tribromide being preferred. Usually, the reaction temperature is −78° C. to 40° C., preferably −20° C. to 30° C. The reaction time is 6 hours to 48 hours, preferably 12 hours to 24 hours.

(Step 4-4)

The present step is an esterification reaction. Analogously to Step 1-1, compound (4) can be produced from compound (20).

Production Method 5

Production Method 5 is an alternative method for producing compound (20) in Production Method 4.

[Chemical 10]

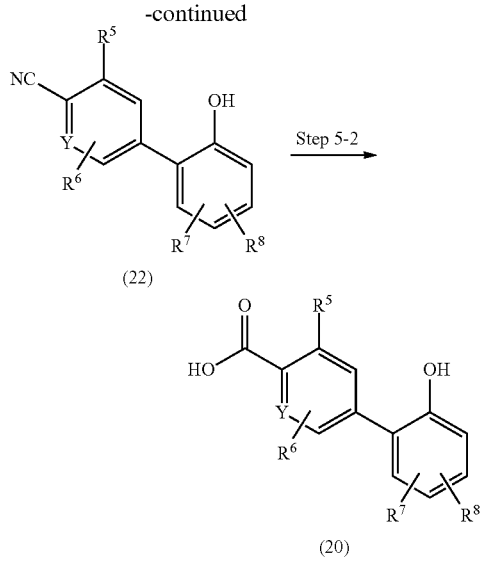

In the formulae, $R^5$, $R^6$, $R^7$, $R^8$, Y, $M^1$, and $M^2$ have the same meanings as those mentioned above.

(Step 5-1)

The present step is a Suzuki-Miyaura reaction. Analogously to Step 1-2, compound (22) can be produced from compound (3) and compound (21).

(Step 5-2)

The present step is a hydrolysis reaction of nitriles. An acid or a base can be allowed to act on compound (22) in water to produce compound (20). Examples of the acid include inorganic acids such as hydrochloric acid, hydrobromic acid, sulfuric acid, perchloric acid, or phosphoric acid, or organic acids such as acetic acid, formic acid, oxalic acid, methanesulfonic acid, p-toluenesulfonic acid, camphorsulfonic acid, trifluoroacetic acid, or trifluoromethanesulfonic acid, or examples of the base include inorganic bases such as sodium hydroxide, potassium hydroxide, lithium hydroxide, or the like. An inorganic acid is preferred, and sulfuric acid or hydrochloric acid is more preferred. Usually, the reaction temperature is 20° C. to 150° C., preferably 80° C. to 100° C. The reaction time is 1 hour to 24 hours, preferably 4 hours to 12 hours.

Production Method 6

Production Method 6 is a method for producing a compound in which $R^5$ is a fluorine atom, and Y is a nitrogen atom in compound (21).

[Chemical 11]

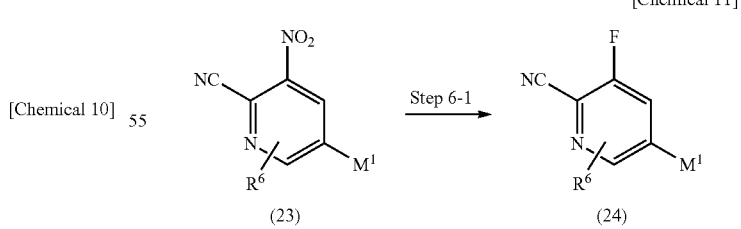

In the formulae, $R^6$, and $M^1$ have the same meanings as those mentioned above.

(Step 6-1)

The present step is a substitution reaction of a nitro group.

A compound (24) can be produced from compound (23) using a method set forth in Organic Letters, 2005, 7(4), 577-579. Production Method 7

Production Method 7 is a method for producing a compound in which X is an oxygen atom, and Z is a nitrogen atom in compound (8).

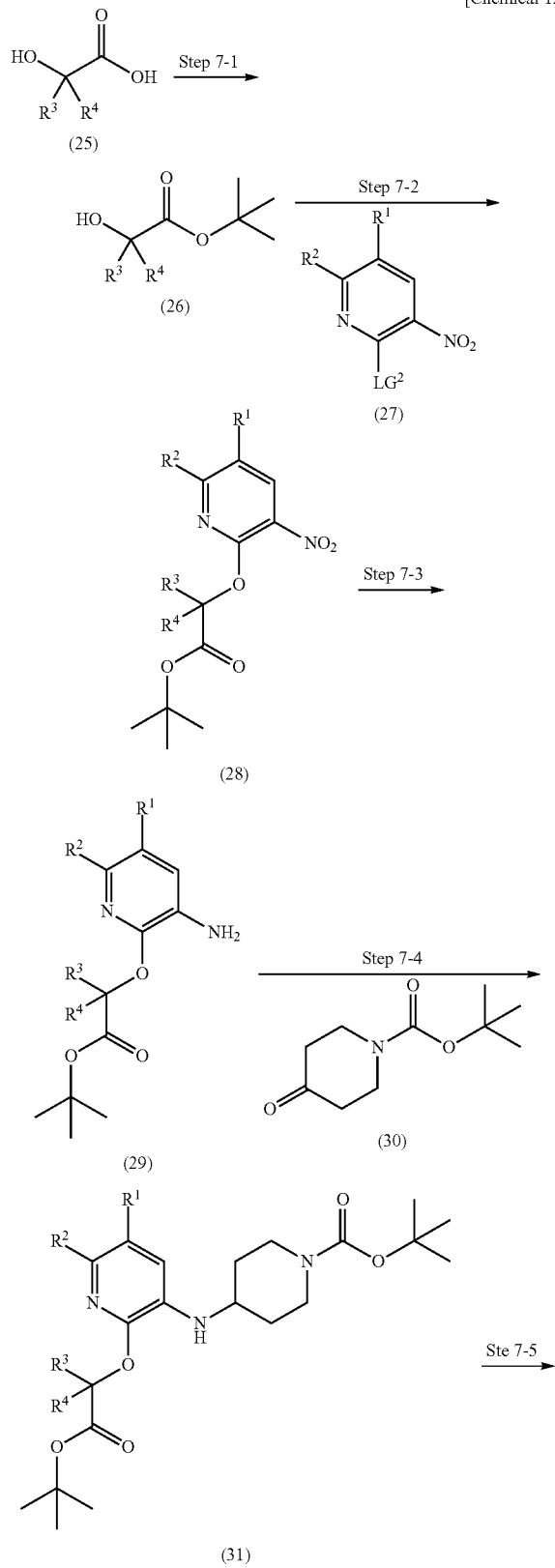

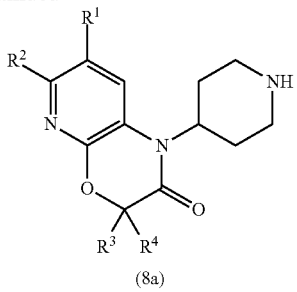

In the formulae, $R^1$, $R^2$, $R^3$, and $R^4$ have the same meanings as those mentioned above. Compound (8a) is a compound in which X is an oxygen atom, and Z is a nitrogen atom in compound (8), and a free amine or an acid addition salt thereof can be used for the next step. $LG^2$ represents a leaving group, such as a chlorine atom or a bromine atom.

(Step 7-1)

The present step is a tert-butyl esterification reaction. A method for allowing a tert-butylating reagent to act on compound (25) in a solvent inactive to the reaction can be used to produce compound (26). Examples of the solvent include aromatic hydrocarbons such as benzene, toluene, or xylene, hydrocarbons such as pentane, hexane, or cyclohexane, ethers such as diethylether, diisopropylether, tetrahydrofuran, dioxane, dimethoxyethane, or tert-butyl methylether, halogenated hydrocarbons such as dichloromethane, chloroform, carbon tetrachloride, 1,2-dichloroethane, chlorobenzene, or dichlorobenzene, or the like, with dichloromethane being preferred. Examples of the tert-butylating reagent include tert-butyl N,N'-diisopropylimidocarbamate, N,N-dimethylformamide di-tert-butyl acetal, or tert-butyl 2,2,2-trichloroacetimidate, with tert-butyl N,N'-diisopropylimidocarbamate being preferred. Usually, the reaction temperature is 0° C. to 40° C., preferably 20° C. to 35° C. The reaction time is 12 hours to 72 hours, preferably 18 hours to 48 hours.

(Step 7-2)

The present step is an etherification reaction. A base can be allowed to act on compound (26) and compound (27) in a solvent inactive to the reaction to produce compound (28). Examples of the solvent include aromatic hydrocarbons such as benzene, toluene, or xylene, hydrocarbons such as pentane, hexane, or cyclohexane, halogenated hydrocarbons such as dichloromethane, chloroform, carbon tetrachloride, 1,2-dichloroethane, chlorobenzene, or dichlorobenzene, ethers such as diethylether, diisopropylether, tetrahydrofuran, dioxane, dimethoxyethane, or tert-butyl methylether, amides such as N,N-dimethylformamide, N,N-dimethylacetamide, N-methyl-2-pyrrolidinone, or hexamethylphosphorotriamide, sulfoxides such as dimethylsulfoxide or sulfolane, nitriles such as acetonitrile, a mixed solvent thereof, or the like, with toluene, tetrahydrofuran, or N,N-dimethylformamide being preferred. Examples of the base include sodium hydride, potassium hydride, calcium hydride, sodium tert-butoxide, potassium tert-butoxide, or the like, with sodium hydride being preferred. Usually, the reaction temperature is −50° C. to 100° C., preferably 0° C. to 50° C. The reaction time is 30 minutes to 24 hours, preferably 1 hour to 12 hours.

(Step 7-3)

The present step is a reduction reaction of a nitro group. A metal catalyst can be allowed to act on compound (28) in a solvent inactive to the reaction to produce compound (29). Examples of the solvent include alcohols such as methanol, ethanol, n-propanol, isopropanol, n-butanol, isobutanol, tert-butanol, isoamyl alcohol, octanol, cyclohexanol, 2-methoxyethanol, diethyleneglycol, or glycerin, ethers such as diethylether, diisopropylether, tetrahydrofuran, dioxane, dimethoxyethane, or tert-butyl methylether, water, acetic acid, a mixed solvent thereof, or the like, with acetic acid or an ethanol-water mixed solvent being preferred. Examples of the metal catalyst include iron, zinc, aluminum, tin, indium, Raney nickel, or the like, with iron being preferred. When the reaction is carried out in an ethanol-water mixed solvent, it is useful to use ammonium chloride or calcium chloride simultaneously, in order to allow the reaction to proceed smoothly. Usually, the reaction temperature is 0° C. to 150° C., preferably 20° C. to 100° C. The reaction time is 30 minutes to 24 hours, preferably 1 hour to 12 hours.

(Step 7-4)

The present step is a reductive alkylation reaction. A reducing agent can be allowed to act on compound (29) and compound (30) in a solvent inactive to the reaction to produce compound (31). Examples of the solvent include aromatic hydrocarbons such as benzene, toluene, or xylene, hydrocarbons such as pentane, hexane, or cyclohexane, halogenated hydrocarbons such as dichloromethane, chloroform, carbon tetrachloride, 1,2-dichloroethane, chlorobenzene, or dichlorobenzene, ethers such as diethylether, diisopropylether, tetrahydrofuran, dioxane, dimethoxyethane, or tert-butyl methylether, alcohols such as methanol, ethanol, n-propanol, isopropanol, n-butanol, isobutanol, tert-butanol, isoamyl alcohol, octanol, cyclohexanol, 2-methoxyethanol, diethyleneglycol, or glycerin, a mixed solvent thereof, or the like, with dichloromethane, 1,2-dichloroethane, tetrahydrofuran, or a mixed solvent thereof being preferred. Examples of the reducing agent include sodium triacetoxyborohydride, sodium cyanoborohydride, or sodium borohydride, with sodium triacetoxyborohydride being preferred. Depending on the reaction, there are cases where it is useful to add acids such as acetic acid, trifluoroacetic acid, hydrochloric acid, or titanium tetraisopropoxide, or dehydrating agents such as molecular sieves, in order to allow the reaction to proceed smoothly. Usually, the reaction temperature is −50° C. to the temperature at heating under reflux, preferably room temperature to 80° C. The reaction time is 30 minutes to 48 hours, preferably 1 hour to 24 hours.

(Step 7-5)

The present step is deprotection of protective groups of an amine and carboxylic acid of compound (31), followed by an intramolecular cyclization reaction. An acid can be allowed to act on compound (31) without using a solvent to produce compound (8a). Examples of the acid include inorganic acids such as hydrochloric acid, hydrobromic acid, sulfuric acid, perchloric acid, or phosphoric acid, or organic acids such as acetic acid, formic acid, methanesulfonic acid, trifluoroacetic acid, or trifluoromethanesulfonic acid, with organic acids being preferred, and trifluoroacetic acid being more preferred. Usually, the reaction temperature is 0° C. to 100° C., preferably 20° C. to 75° C. The reaction time is 12 hours to 48 hours, preferably 24 hours to 36 hours.

Production Method 8

Production Method 8 is an alternative method for producing a compound in which X is an oxygen atom, and Z is a nitrogen atom in compound (8).

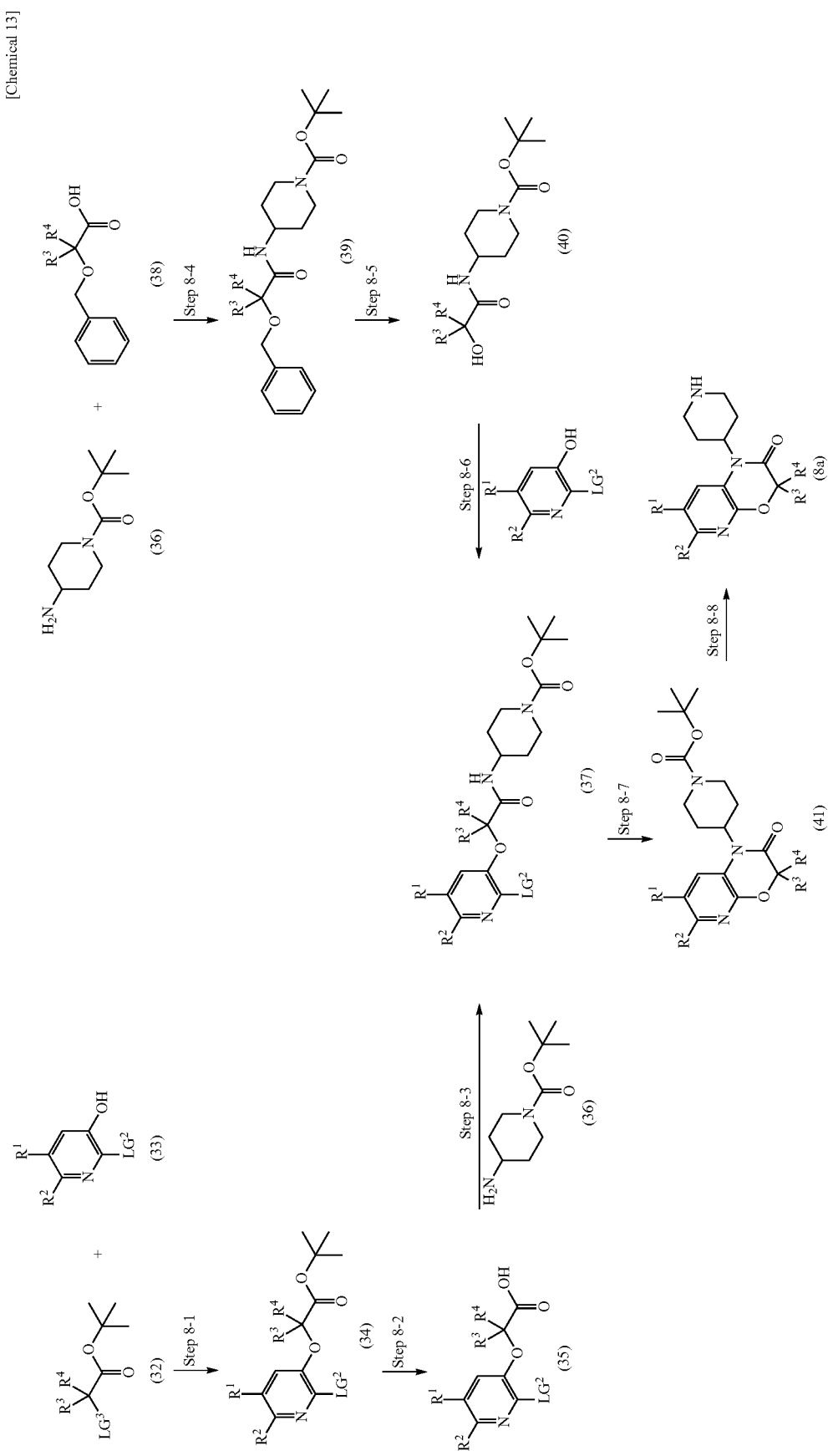

In the formulae, $R^1$, $R^2$, $R^3$, $R^4$, $LG^2$, and compound (8a) have the same meanings as those mentioned above. $LG^3$ represents a leaving group such as a chlorine atom, a bromine atom, an iodine atom, a methanesulfonyloxy group or a p-toluenesulfonyloxy group, or a hydroxyl group.

(Step 8-1)

The present step is a substitution reaction in which $LG^3$ of compound (32) is a leaving group, and is a Mitsunobu reaction when $LG^3$ is a hydroxyl group. Analogously to Step 1-3a or 1-3b, compound (34) can be produced from compound (33). Compound (32) can be produced from a commercially available compound or a known compound in accordance with a known method, for example, a method set forth in Greene and Wuts, "Protective Groups in Organic Synthesis (3rd ed., 1999)", C. P. Decicco et al., "Journal of Organic Chemistry, 1995, 60, 4782-4785", or the like.

(Step 8-2)

The present step is deprotection of a tert-butylester. Analogously to Step 1-6, compound (35) can be produced from compound (34).

(Step 8-3)

The present step is an amidation reaction. Analogously to Step 1-5, compound (37) can be produced from compound (35) and compound (36).

(Step 8-4)

The present step is an amidation reaction. Analogously to Step 1-5, compound (39) can be produced from compound (36) and compound (38).

(Step 8-5)

The present step is a hydrogenolysis reaction of benzylether. A transition metal catalyst can be allowed to act on compound (39) in a solvent inactive to the reaction under a hydrogen atmosphere to produce compound (40). Examples of the solvent include ethers such as diethylether, diisopropylether, tetrahydrofuran, dioxane, dimethoxyethane, or tert-butyl methylether, esters such as ethyl formate, ethyl acetate, propyl acetate, butyl acetate, or diethyl carbonate, alcohols such as methanol, ethanol, n-propanol, isopropanol, n-butanol, isobutanol, tert-butanol, isoamyl alcohol, octanol, cyclohexanol, 2-methoxyethanol, diethyleneglycol, or glycerin, amides such as N,N-dimethylformamide, N,N-dimethylacetamide, N-methyl-2-pyrrolidinone, or hexamethylphosphorotriamide, acetic acid, water, a mixed solvent thereof, or the like, with methanol, ethanol, tetrahydrofuran, water, or a mixed solvent thereof being preferred. Examples of the transition metal catalyst include platinum oxide, platinum carbon, platinum black, palladium carbon, palladium black, palladium hydroxide carbon, or Raney nickel, with palladium carbon or palladium hydroxide carbon being preferred. Usually, the reaction temperature is 0° C. to 80° C., preferably 20° C. to 60° C. The reaction pressure is, under a hydrogen atmosphere, normal pressure to increased pressure, preferably normal pressure. The reaction time is 1 hour to 48 hours, preferably 3 hours to 24 hours.

(Step 8-6)

The present step is a Mitsunobu reaction. Analogously to Step 1-3b, compound (37) can be produced from compound (33) and compound (40).

(Step 8-7)

The present step is a Smiles rearrangement reaction, followed by an intramolecular cyclization reaction. A base can be allowed to act on compound (37) in a solvent inactive to the reaction to produce compound (41). Examples of the solvent include ethers such as diethylether, diisopropylether, tetrahydrofuran, dioxane, dimethoxyethane, or tert-butyl methylether, amides such as N,N-dimethylformamide, N,N-dimethylacetamide, N-methyl-2-pyrrolidinone, or hexamethylphosphorotriamide, nitriles such as acetonitrile, a mixed solvent thereof, or the like, with tetrahydrofuran or N,N-dimethylformamide being preferred. Examples of the base include inorganic bases such as sodium hydride, potassium hydride, sodium carbonate, potassium carbonate, cesium carbonate, or sodium hydrogen carbonate, with sodium hydride or cesium carbonate being preferred. Usually, the reaction temperature is 0° C. to 150° C., preferably 10° C. to 100° C. The reaction time is 30 minutes to 24 hours, preferably 1 hour to 12 hours.

(Step 8-8)

The present step is deprotection of a tert-butyloxycarbonyl group which is a protective group of an amine. An acid can be allowed to act on compound (41) in a solvent inactive to the reaction or without using a solvent to produce compound (8a). Examples of the solvent include aromatic hydrocarbons such as benzene, toluene, or xylene, hydrocarbons such as pentane, hexane, or cyclohexane, halogenated hydrocarbons such as dichloromethane, chloroform, carbon tetrachloride, 1,2-dichloroethane, chlorobenzene, or dichlorobenzene, esters such as ethyl formate, ethyl acetate, propyl acetate, butyl acetate, or diethyl carbonate, ethers such as diethylether, diisopropylether, tetrahydrofuran, dioxane, dimethoxyethane, or tert-butyl methylether, alcohols such as methanol, ethanol, n-propanol, isopropanol, n-butanol, isobutanol, tert-butanol, isoamyl alcohol, octanol, cyclohexanol, 2-methoxyethanol, diethyleneglycol, or glycerin, water, a mixed solvent thereof, or the like, with dichloromethane being preferred. Examples of the acid include inorganic acids such as hydrochloric acid, hydrobromic acid, sulfuric acid, perchloric acid, or phosphoric acid, or organic acids such as acetic acid, formic acid, oxalic acid, methanesulfonic acid, p-toluenesulfonic acid, camphorsulfonic acid, trifluoroacetic acid, or trifluoromethanesulfonic acid, with trifluoroacetic acid being preferred. Usually, the reaction temperature is −50° C. to 100° C., preferably 0° C. to 50° C. The reaction time is 15 minutes to 48 hours, preferably 30 minutes to 24 hours.

Production Method 9

Production Method 9 is an alternative method for producing compound (41) in Production Method 8.

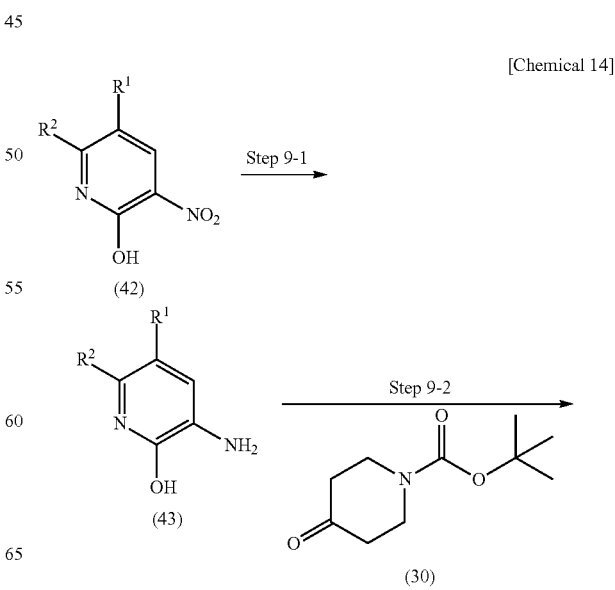

[Chemical 14]

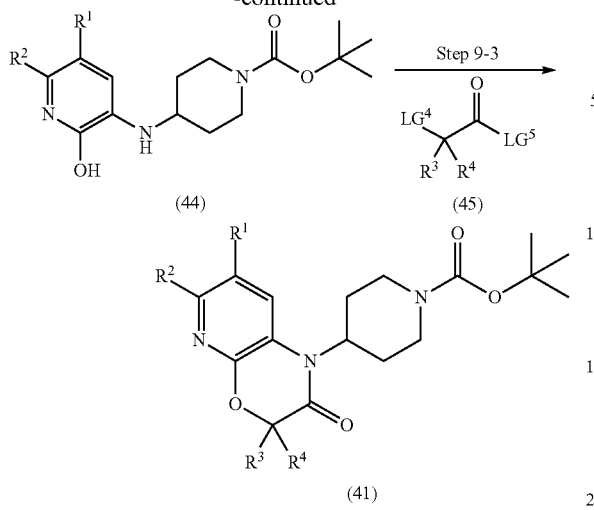

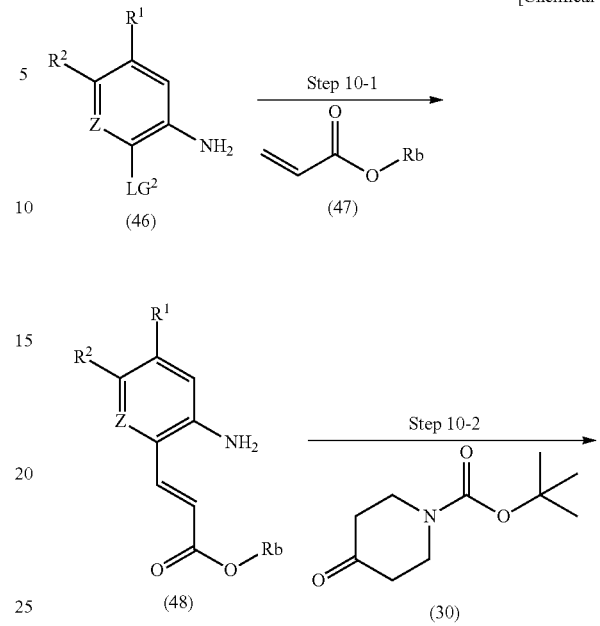

In the formulae, $R^1$, $R^2$, $R^3$, and $R^4$ have the same meanings as those mentioned above. $LG^4$ and $LG^5$ represent a leaving group, each independently being a chlorine atom or a bromine atom.

(Step 9-1)

The present step is a reduction reaction of a nitro group. Analogously to Step 7-3 or 8-5, compound (43) can be produced from compound (42).

(Step 9-2)

The present step is a reductive alkylation reaction. Analogously to Step 7-4, compound (44) can be produced from compound (30) and compound (43).

(Step 9-3)

The present step is an intermolecular cyclization reaction. A base can be allowed to act on compound (44) and compound (45) in a solvent inactive to the reaction to produce compound (41). Examples of the solvent include aromatic hydrocarbons such as benzene, toluene, or xylene, hydrocarbons such as pentane, hexane, or cyclohexane, halogenated hydrocarbons such as dichloromethane, chloroform, carbon tetrachloride, 1,2-dichloroethane, chlorobenzene, or dichlorobenzene, ethers such as diethylether, diisopropylether, tetrahydrofuran, dioxane, dimethoxyethane, or tert-butyl methylether, amides such as N,N-dimethylformamide, N,N-dimethylacetamide, N-methyl-2-pyrrolidinone, or hexamethylphosphorotriamide, sulfoxides such as dimethylsulfoxide or sulfolane, nitriles such as acetonitrile, a mixed solvent thereof, or the like, with N,N-dimethylformamide, dichloromethane, or a mixed solvent thereof being preferred. Examples of the base include inorganic bases such as sodium carbonate, potassium carbonate, cesium carbonate, sodium tert-butoxide, or potassium tert-butoxide, or organic bases such as triethylamine, diisopropylethylamine, N-methylmorpholine, pyridine, or 2,6-lutidine, with potassium carbonate or 2,6-lutidine being preferred. Usually, the reaction temperature is 0° C. to 200° C., preferably 20° C. to 150° C. The reaction time is 30 minutes to 48 hours, preferably 1 hour to 24 hours.

Production Method 10

Production Method 10 is a method for producing a compound in which X is a group represented by —$CH_2$— in compound (8).

[Chemical 15]

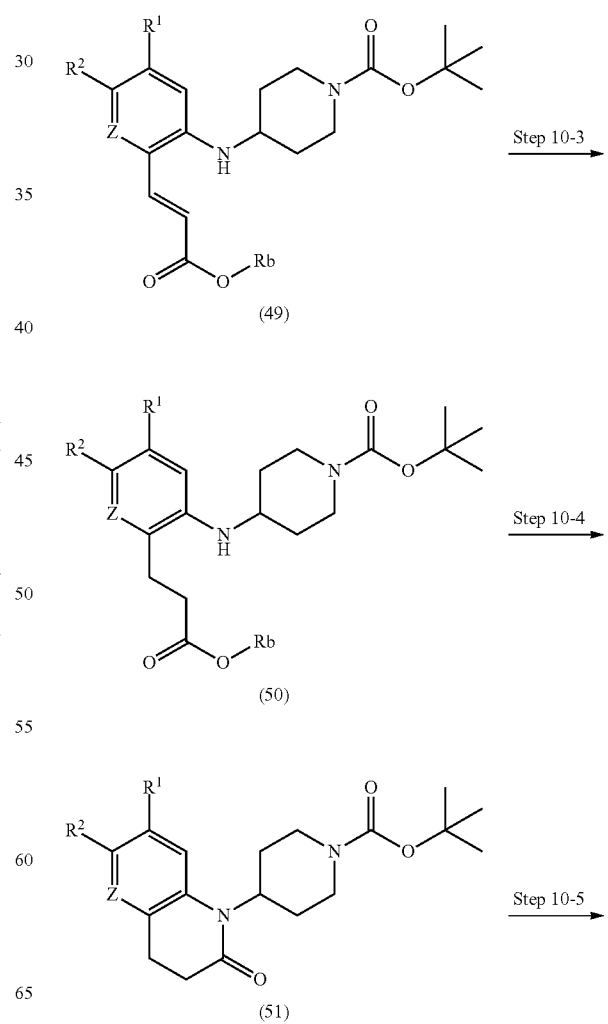

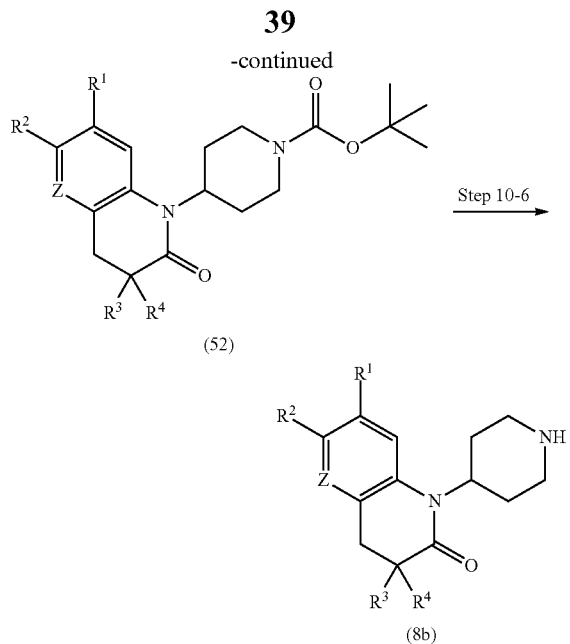

In the formulae, $R^1$, $R^2$, $R^3$, $R^4$, Z, and $LG^2$ have the same meanings as those mentioned above. Compound (8b) is a compound in which X of compound (8) is represented by —$CH_2$—, and a free amine or an acid addition salt thereof can be used for the next step. Rb is a methyl group or an ethyl group.

(Step 10-1)

The present step is Heck reaction. A base and a palladium catalyst can be allowed to act on compound (46) and compound (47) in a solvent inactive to the reaction to produce compound (48). Examples of the solvent include aromatic hydrocarbons such as benzene, toluene, or xylene, ethers such as diethylether, diisopropylether, tetrahydrofuran, dioxane, dimethoxyethane, or tert-butyl methylether, amides such as N,N-dimethylformamide, N,N-dimethylacetamide, N-methyl-2-pyrrolidinone, or hexamethylphosphorotriamide, water, a mixed solvent thereof, or the like, with N,N-dimethylformamide, N,N-dimethylacetamide, or N-methyl-2-pyrrolidinone being preferred. Examples of the base include inorganic bases such as sodium carbonate, potassium carbonate, cesium carbonate, sodium acetate, potassium acetate, or tripotassium phosphate, or organic bases such as triethylamine, diisopropylethylamine, tri-n-butylamine, or 1,4-diazabicyclo[2,2,2]octane, with organic bases being preferred, and diisopropylethylamine or triethylamine being more preferred. Examples of the palladium catalyst include bis(dibenzylideneacetone)palladium, tris(dibenzylideneacetone)dipalladium, bis(triphenylphosphine)dichloropalladium, palladium acetate, palladium trifluoroacetate, palladium carbon, or the like, with palladium acetate being preferred. It is useful to add as an additive 1,4-bis(diphenylphosphino)butane and tetra-n-butylammonium bromide, in order to allow the reaction to proceed smoothly. Usually, the reaction temperature is 60° C. to 200° C., preferably 100° C. to 140° C. The reaction time is 12 hours to 48 hours, preferably 20 hours to 30 hours.

(Step 10-2)

The present step is a reductive alkylation reaction. Analogously to Step 7-4, compound (49) can be produced from compound (30) and compound (48).

(Step 10-3)

The present step is a reduction reaction of an olefin. A transition metal catalyst can be allowed to act on compound (49) in a solvent inactive to the reaction under a hydrogen atmosphere to produce compound (50). Examples of the solvent include halogenated hydrocarbons such as dichloromethane, chloroform, carbon tetrachloride, 1,2-dichloroethane, chlorobenzene, or dichlorobenzene, ethers such as diethylether, diisopropylether, tetrahydrofuran, dioxane, dimethoxyethane, or tert-butyl methylether, esters such as ethyl formate, ethyl acetate, propyl acetate, butyl acetate, or diethyl carbonate, alcohols such as methanol, ethanol, n-propanol, isopropanol, n-butanol, isobutanol, tert-butanol, isoamyl alcohol, octanol, cyclohexanol, 2-methoxyethanol, diethyleneglycol, or glycerin, a mixed solvent thereof, or the like, with methanol or ethanol being preferred. Examples of the transition metal catalyst include platinum oxide, platinum carbon, platinum black, palladium carbon, palladium black, palladium hydroxide carbon, palladium fibroin, or Raney nickel, with palladium fibroin being preferred. Usually, the reaction temperature is 0° C. to 80° C., preferably 20° C. to 50° C. The reaction pressure is, under a hydrogen atmosphere, normal pressure to increased pressure, preferably normal pressure. The reaction time is 3 hours to 100 hours, preferably 18 hours to 48 hours.

(Step 10-4)

The present step is an intramolecular cyclization reaction. A base can be allowed to act on compound (50) in a solvent inactive to the reaction to produce compound (51). Examples of the solvent include ethers such as diethylether, diisopropylether, tetrahydrofuran, dioxane, dimethoxyethane, or tert-butyl methylether, alcohols such as methanol, ethanol, n-propanol, isopropanol, n-butanol, isobutanol, tert-butanol, isoamyl alcohol, octanol, cyclohexanol, 2-methoxyethanol, diethyleneglycol, or glycerin, amides such as N,N-dimethylformamide, N,N-dimethylacetamide, N-methyl-2-pyrrolidinone, or hexamethylphosphorotriamide, a mixed solvent thereof, or the like, with tetrahydrofuran being preferred. Examples of the base include sodium tert-butoxide, potassium tert-butoxide, sodium methoxide, potassium methoxide, sodium carbonate, potassium carbonate, cesium carbonate, or the like, with potassium tert-butoxide being preferred. Usually, the reaction temperature is −50° C. to 100° C., preferably −20° C. to 30° C. The reaction time is 1 minute to 12 hours, preferably 10 minutes to 6 hours.

(Step 10-5)

The present step is an alkylation reaction. When $R^3$ and $R^4$ of compound (52) are both a hydrogen atom, this step is not carried out. A base and an electrophile can be allowed to act on compound (51) in a solvent inactive to the reaction to produce compound (52). Examples of the solvent include aromatic hydrocarbons such as benzene, toluene, or xylene, ethers such as diethylether, diisopropylether, tetrahydrofuran, dioxane, dimethoxyethane, or tert-butyl methylether, amides such as N,N-dimethylformamide, N,N-dimethylacetamide, N-methyl-2-pyrrolidinone, or hexamethylphosphorotriamide, a mixed solvent thereof, or the like, with tetrahydrofuran being preferred. Examples of the base include lithium hexamethyldisilazide, sodium hexamethyldisilazide, lithium diisopropylamide, sodium hydride, sodium tert-butoxide, potassium tert-butoxide, or the like, with lithium hexamethyldisilazide being preferred. Examples of the electrophile to be used include alkyl halide, methylsulfonic acid alkyl ester, p-toluenesulfonic acid alkyl ester, or the like (Such alkyl groups may be substituted by a halogen atom, an alkoxy group or a protected hydroxyl group. A protective group of a hydroxyl group can be deprotected as needed.). Usually, the reaction temperature is −100° C. to 80° C., preferably −78° C. to 50° C. The reaction time is 5 minutes to 24 hours, preferably 10 minutes to 12 hours.

(Step 10-6)

The present step is deprotection of a tert-butyloxycarbonyl group which is a protective group of an amine. Analogously to Step 8-8, compound (8b) can be produced from compound (52).

Production Method 11

Production Method 11 is a method for producing a compound in which $R^5$ is an amino group in the compound (I) of the present invention.

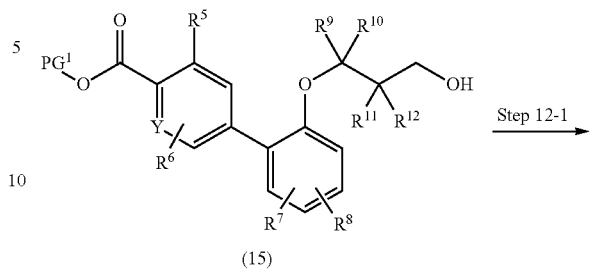

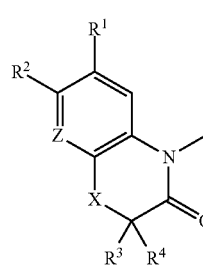

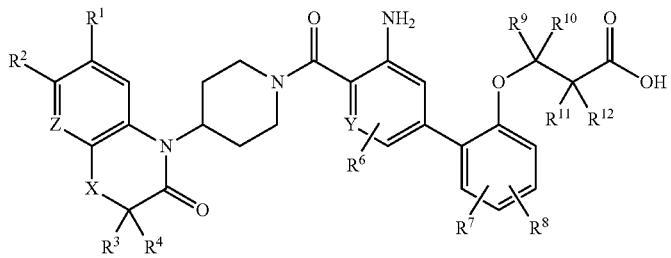

In the formulae, $R^1$, $R^2$, $R^3$, $R^4$, $R^6$, $R^7$, $R^8$, $R^9$, $R^{10}$, $R^{11}$, $R^{12}$, X, Y and Z have the same meanings as those mentioned above. Compound (Ia) is a compound in which $R^5$ of the compound (I) is defined by a nitro group. Compound (Ib) is a compound in which $R^5$ of the compound (I) is defined by an amino group.

(Step 11-1)

The present step is a reduction reaction of a nitro group. Analogously to Step 7-3, compound (Ib) can be produced from compound (Ia).

Production Method 12

Production Method 12 is an alternative method for producing compound (6) in Production Method 1 from compound (15) in Production Method 3.

-continued

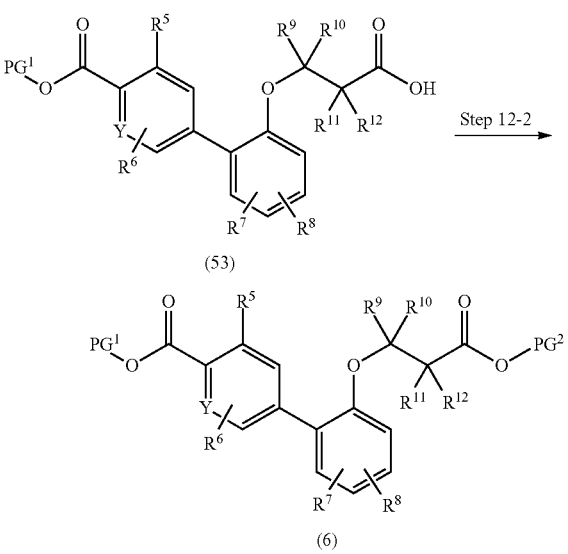

In the formulae, $R^5$, $R^6$, $R^7$, $R^8$, $R^9$, $R^{10}$, $R^{11}$, $R^{12}$, Y, $PG^1$ and $PG^2$ have the same meanings as those mentioned above.

(Step 12-1)

The present step is an oxidation reaction of an alcohol. Analogously to Step 2-5, compound (53) can be produced from compound (15).

(Step 12-2)

The present step is a step in which a protective group of a carboxyl group is introduced. When $PG^2$ is a tert-butyl group, a method for allowing a tert-butylating reagent to act on compound (53) in a solvent inactive to the reaction can be used to produce compound (6). Examples of the solvent include aromatic hydrocarbons such as benzene, toluene, or xylene, hydrocarbons such as pentane, hexane, or cyclohexane, ethers such as diethylether, diisopropylether, tetrahydrofuran, dioxane, dimethoxyethane, or tert-butyl methylether, or halogenated hydrocarbons such as dichloromethane, chloroform, carbon tetrachloride, 1,2-dichloroethane, chlorobenzene, or dichlorobenzene, with toluene being preferred. Examples of the tert-butylating reagent include tert-butyl N,N'-diisopropylimidocarbamate, N,N-dimethylformamide di-tert-butyl acetal, or tert-butyl 2,2,2-trichloroacetimidate, with tert-butyl N,N'-diisopropylimidocarbamate being preferred. Usually, the reaction temperature is 0° C. to 100° C., preferably 20° C. to 80° C. The reaction time is 1 hour to 24 hours, preferably 2 hours to 12 hours.

When $PG^2$ is a 2-trimethylsilylethyl group, a reagent for use in the Mitsunobu reaction can be allowed to act on compound (53) and 2-trimethylsilylethanol in a solvent inactive to the reaction to produce compound (6). Examples of the solvent include aromatic hydrocarbons such as benzene, toluene, or xylene, halogenated hydrocarbons such as dichloromethane, chloroform, carbon tetrachloride, 1,2-dichloroethane, chlorobenzene, or dichlorobenzene, ethers such as diethylether, diisopropylether, tetrahydrofuran, dioxane, dimethoxyethane, or tert-butyl-methylether, a mixed solvent thereof, or the like, with tetrahydrofuran being preferred. A reagent for use in the Mitsunobu reaction includes a combination of azodicarboxylic acid derivatives such as diethyl azodicarboxylate, di-tert-butyl azodicarboxylate, or azodicarboxylic acid dipiperidinamide, and phosphine compounds such as triphenylphosphine, tri(2-tolyl)phosphine, or tri-n-butylphosphine, with a combination of di-tert-butyl azodicarboxylate and triphenylphosphine being preferred. Usually, the reaction temperature is 0° C. to 100° C., preferably 20° C. to 70° C. The reaction time is 30 minutes to 48 hours, preferably 1 hour to 24 hours.

Production Method 13

Production Method 13 is a method for producing a compound in which X is an oxygen atom, and Z is a group represented by =CH— in compound (8).

[Chemical 18]

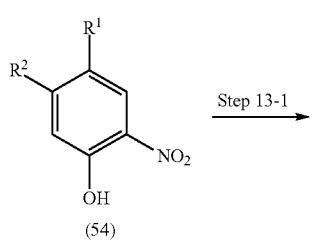

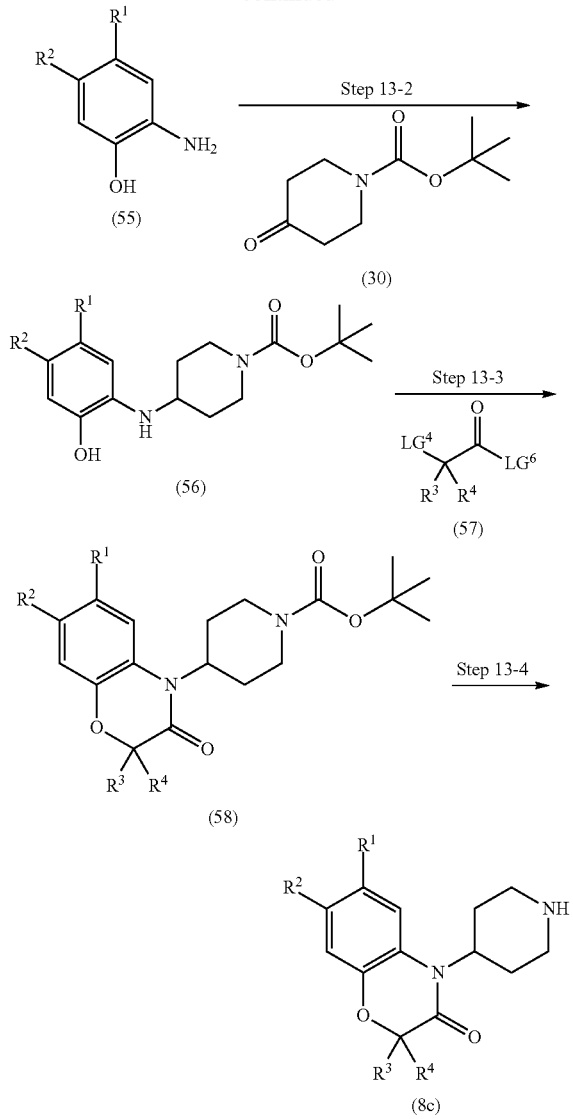

In the formulae, $R^1$, $R^2$, $R^3$, $R^4$, and $LG^4$ have the same meanings as those mentioned above. $LG^6$ is a methoxy group, an ethoxy group or a tert-butoxy group. Compound (8c) is a compound in which X is an oxygen atom, and Z is represented by =CH— in compound (8), and a free amine or an acid addition salt thereof can be used for the next step.

(Step 13-1)

The present step is a reduction reaction of a nitro group. Analogously to Step 7-3 or 8-5, compound (55) can be produced from compound (54).

(Step 13-2)

The present step is a reductive alkylation reaction. Analogously to Step 7-4, compound (56) can be produced from compound (30) and compound (55).

(Step 13-3)

The present step is an intermolecular cyclization reaction. A base can be allowed to act on compound (56) and compound (57) in a solvent inactive to the reaction to produce compound (58). Examples of the solvent include aromatic hydrocarbons such as benzene, toluene, or xylene, hydrocarbons such as pentane, hexane, or cyclohexane, halogenated hydrocarbons such as dichloromethane, chloroform, carbon tetrachloride, 1,2-dichloroethane, chlorobenzene, or dichlorobenzene, ethers such as diethylether, diisopropylether, tetrahydrofuran, dioxane, dimethoxyethane, or tert-butyl methylether, amides such as N,N-dimethylformamide, N,N-dimethylacetamide, N-methyl-2-pyrrolidinone, or hexamethylphosphorotriamide, sulfoxides such as dimethylsulfoxide or sulfolane, nitriles such as acetonitrile, a mixed solvent thereof, or the like, with N,N-dimethylformamide being preferred. Examples of the base include inorganic bases such as sodium carbonate, potassium carbonate, cesium carbonate, sodium tert-butoxide, or potassium tert-butoxide, or organic bases such as triethylamine, diisopropylethylamine, N-methylmorpholine, pyridine, or 2,6-lutidine, with cesium carbonate being preferred. Usually, the reaction temperature is 20° C. to 200° C., preferably 60° C. to 160° C. The reaction time is 30 minutes to 48 hours, preferably 1 hour to 24 hours.

(Step 13-4)

The present step is deprotection of a tert-butyloxycarbonyl group which is a protective group of an amine. Analogously to Step 8-8, compound (8c) can be produced from compound (58).

Production Method 14

Production Method 14 is a method for producing a compound in which X is a sulfur atom, and Z is a nitrogen atom in compound (8).

[Chemical 19]

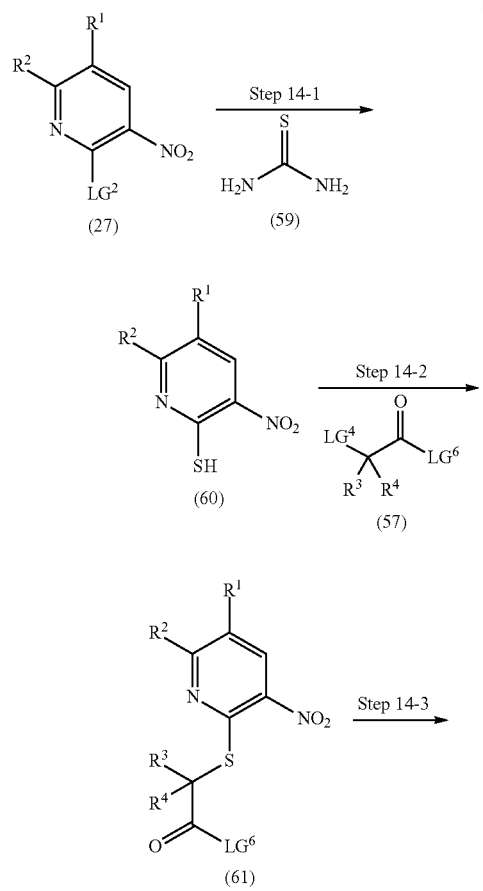

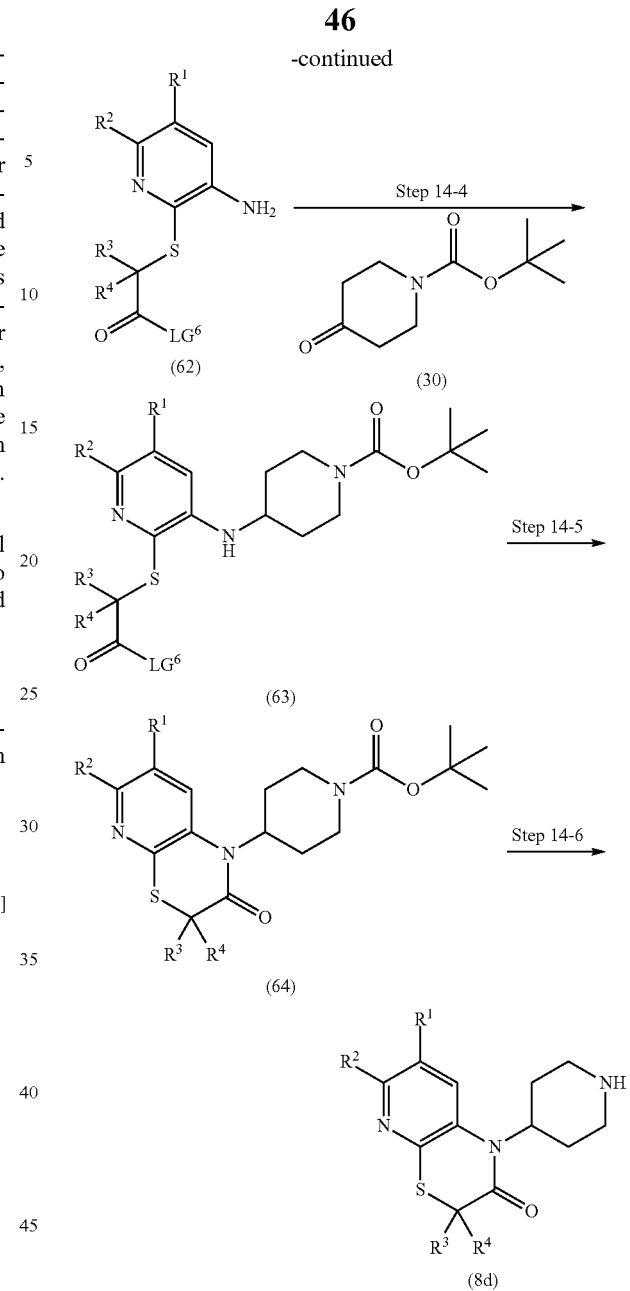

In the formulae, $R^1$, $R^2$, $R^3$, $R^4$, $LG^2$, $LG^4$, and $LG^6$ have the same meanings as those mentioned above. Compound (8d) is a compound in which X is a sulfur atom, and Z is a nitrogen atom in compound (8), and a free amine or an acid addition salt thereof can be used for the next step.

(Step 14-1)

The present step is a step for introducing a mercapto group. In a solvent inactive to the reaction, compound (27) is reacted with thiourea (59), and then a base can be allowed to act thereon to produce compound (60). Solvents for use in the reaction with thiourea (59) include alcohols such as methanol, ethanol, n-propanol, isopropanol, n-butanol, isobutanol, tert-butanol, isoamyl alcohol, octanol, cyclohexanol, 2-methoxyethanol, diethyleneglycol, or glycerin, with methanol or ethanol being preferred. Usually, the reaction temperature is 20° C. to 100° C., preferably 40° C. to 80° C. The reaction time is 1 hour to 24 hours, preferably 3 hours to 12 hours.

Examples of the solvent on which a base is allowed to act include alcohols such as methanol, ethanol, n-propanol, isopropanol, n-butanol, isobutanol, tert-butanol, isoamyl alcohol, octanol, cyclohexanol, 2-methoxyethanol, diethyleneglycol, or glycerin, water, a mixed solvent thereof, or the like, with a methanol-water mixed solvent, or an ethanol-water mixed solvent being preferred. Examples of the base include sodium carbonate, potassium carbonate, cesium carbonate, sodium hydroxide, or potassium hydroxide, with potassium hydroxide or sodium hydroxide being preferred. Usually, the reaction temperature is 0° C. to 80° C., preferably 0° C. to 40° C. The reaction time is 10 minutes to 12 hours, preferably 30 minutes to 6 hours.

(Step 14-2)

The present step is an alkylation reaction of a mercapto group. A base can be allowed to act on compound (57) and compound (60) in a solvent inactive to the reaction to produce compound (61). Examples of the solvent include aromatic hydrocarbons such as benzene, toluene, or xylene, hydrocarbons such as pentane, hexane, or cyclohexane, halogenated hydrocarbons such as dichloromethane, chloroform, carbon tetrachloride, 1,2-dichloroethane, chlorobenzene, or dichlorobenzene, ethers such as diethylether, diisopropylether, tetrahydrofuran, dioxane, dimethoxyethane, or tert-butyl methylether, amides such as N,N-dimethylformamide, N,N-dimethylacetamide, N-methyl-2-pyrrolidinone, or hexamethylphosphorotriamide, sulfoxides such as dimethylsulfoxide or sulfolane, nitriles such as acetonitrile, a mixed solvent thereof, or the like, with N,N-dimethylformamide being preferred. Examples of the base include inorganic bases such as sodium carbonate, potassium carbonate, cesium carbonate, sodium tert-butoxide, or potassium tert-butoxide, or organic bases such as triethylamine, diisopropylethylamine, N-methylmorpholine, pyridine, or 2,6-lutidine, with potassium carbonate being preferred. Usually, the reaction temperature is 0° C. to 100° C., preferably 20° C. to 80° C. The reaction time is 30 minutes to 48 hours, preferably 1 hour to 24 hours.

(Step 14-3)

The present step is a reduction reaction of a nitro group. Analogously to Step 7-3, compound (62) can be produced from compound (61).

(Step 14-4)

The present step is a reductive alkylation reaction. Analogously to Step 7-4, compound (63) can be produced from compound (30) and compound (62).

(Step 14-5)

The present step is an intramolecular cyclization reaction. A base can be allowed to act on compound (63) in a solvent inactive to the reaction to produce compound (64). Examples of the solvent include ethers such as diethylether, diisopropylether, tetrahydrofuran, dioxane, dimethoxyethane, or tert-butyl methylether, alcohols such as methanol, ethanol, n-propanol, isopropanol, n-butanol, isobutanol, tert-butanol, isoamyl alcohol, octanol, cyclohexanol, 2-methoxyethanol, diethyleneglycol, or glycerin, amides such as N,N-dimethylformamide, N,N-dimethylacetamide, N-methyl-2-pyrrolidinone, or hexamethylphosphorotriamide, a mixed solvent thereof, or the like, with N,N-dimethylformamide being preferred. Examples of the base include sodium tert-butoxide, potassium tert-butoxide, sodium methoxide, potassium methoxide, sodium carbonate, potassium carbonate, cesium carbonate, or the like, with cesium carbonate being preferred. Usually, the reaction temperature is 20° C. to 200° C., preferably 40° C. to 150° C. The reaction time is 2 hours to 48 hours, preferably 4 hours to 24 hours.

(Step 14-6)

The present step is deprotection of a tert-butyloxycarbonyl group which is a protective group of an amine. Analogously to Step 8-8, compound (8d) can be produced from compound (64).

Production Method 15

Production Method 15 is a method for producing a compound in which $R^3$ is a hydroxymethyl group in compound (8).

[Chemical 20]

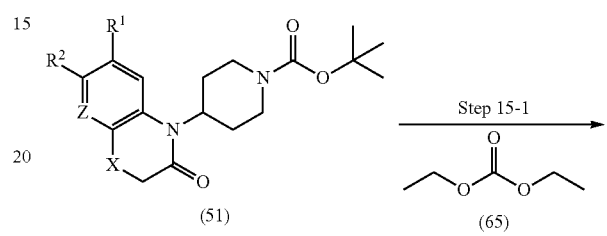

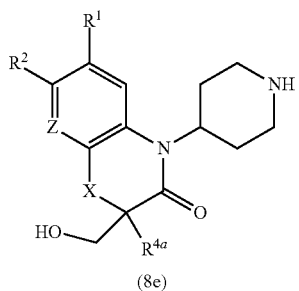

(8e)

In the formulae, $R^1$, $R^2$, X and Z have the same meanings as those mentioned above, and $R^{4a}$ represents a hydrogen atom, a $C_{1-4}$ alkyl group, a halogenated $C_{1-4}$ alkyl group, a $C_{1-4}$ alkoxy $C_{1-4}$ alkyl group, or a hydroxy $C_{1-4}$ alkyl group. Compound (8e) is a compound in which $R^3$ of compound (8) is defined by a hydroxymethyl group, and a free amine or an acid addition salt thereof can be used for the next step.

(Step 15-1)

The present step is a step for producing compound (66) by allowing a base to act on compound (51) and diethyl carbonate (65) in a solvent inactive to the reaction. Examples of the solvent include aromatic hydrocarbons such as benzene, toluene, or xylene, ethers such as diethylether, diisopropylether, tetrahydrofuran, dioxane, dimethoxyethane, or tert-butyl methylether, amides such as N,N-dimethylformamide, N,N-dimethylacetamide, N-methyl-2-pyrrolidinone, or hexamethylphosphorotriamide, a mixed solvent thereof, or the like, with tetrahydrofuran being preferred. Examples of the base include lithium hexamethyldisilazide, sodium hexamethyldisilazide, lithium diisopropylamide, sodium hydride, sodium tert-butoxide, potassium tert-butoxide, or the like, with sodium hydride or lithium hexamethyldisilazide being preferred. Usually, the reaction temperature is −100° C. to 120° C., preferably −78° C. to 80° C. The reaction time is 1 hour to 24 hours, preferably 3 hours to 12 hours.

(Step 15-2)

The present step is an alkylation reaction. When $R^{4a}$ of compound (67) is a hydrogen atom, this step is not carried out. A base and an electrophile can be allowed to act on compound (66) in a solvent inactive to the reaction to produce compound (67). Examples of the solvent include aromatic hydrocarbons such as benzene, toluene, or xylene, ethers such as diethylether, diisopropylether, tetrahydrofuran, dioxane, dimethoxyethane, or tert-butyl methylether, amides such as N,N-dimethylformamide, N,N-dimethylacetamide, N-methyl-2-pyrrolidinone, or hexamethylphosphorotriamide, a mixed solvent thereof, or the like, with tetrahydrofuran being preferred. Examples of the base include lithium hexamethyldisilazide, sodium hexamethyldisilazide, lithium diisopropylamide, sodium hydride, sodium tert-butoxide, potassium tert-butoxide, or the like, with sodium hydride or lithium hexamethyldisilazide being preferred. Examples of the electrophile to be used include alkyl halide, methylsulfonic acid alkyl ester, p-toluenesulfonic acid alkyl ester, or the like (Such alkyl groups may be substituted by a halogen atom, an alkoxy group or a protected hydroxyl group. A protective group of a hydroxyl group can be deprotected as needed.). Usually, the reaction temperature is −100° C. to 120° C., preferably −78° C. to 80° C. The reaction time is 2 hours to 48 hours, preferably 4 hours to 24 hours.

(Step 15-3)

The present step is a reduction reaction of an ester. A reducing agent can be allowed to act on compound (67) in a solvent inactive to the reaction in the presence of calcium chloride to produce compound (68). Examples of the solvent include ethers such as diethylether, diisopropylether, tetrahydrofuran, dioxane, dimethoxyethane, or tert-butyl methylether, alcohols such as methanol, ethanol, n-propanol, isopropanol, n-butanol, isobutanol, tert-butanol, isoamyl alcohol, octanol, cyclohexanol, 2-methoxyethanol, diethyleneglycol, or glycerin, a mixed solvent thereof, or the like, with methanol or ethanol being preferred. Sodium borohydride is preferred as the reducing agent. Usually, the reaction temperature is 0° C. to 100° C., preferably 0° C. to 50° C. The reaction time is 1 hour to 24 hours, preferably 2 hours to 12 hours.

(Step 15-4)

The present step is deprotection of a tert-butyloxycarbonyl group which is a protective group of an amine. Analogously to Step 8-8, compound (8e) can be produced from compound (68).

Production Method 16

Production Method 16 is a method for producing a compound in which X is a group represented by —CH(OH)— in the compound (1) of the present invention.

[Chemical 21]

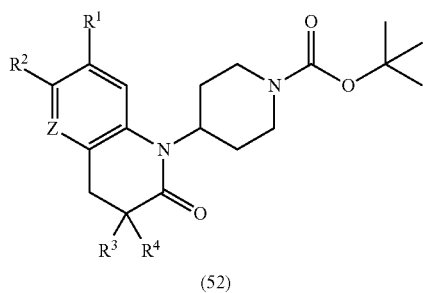

(52)

Step 16-1 →

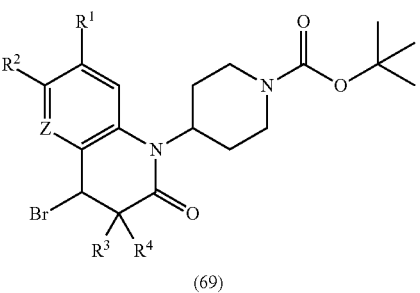

(69)

Step 16-2 →

-continued

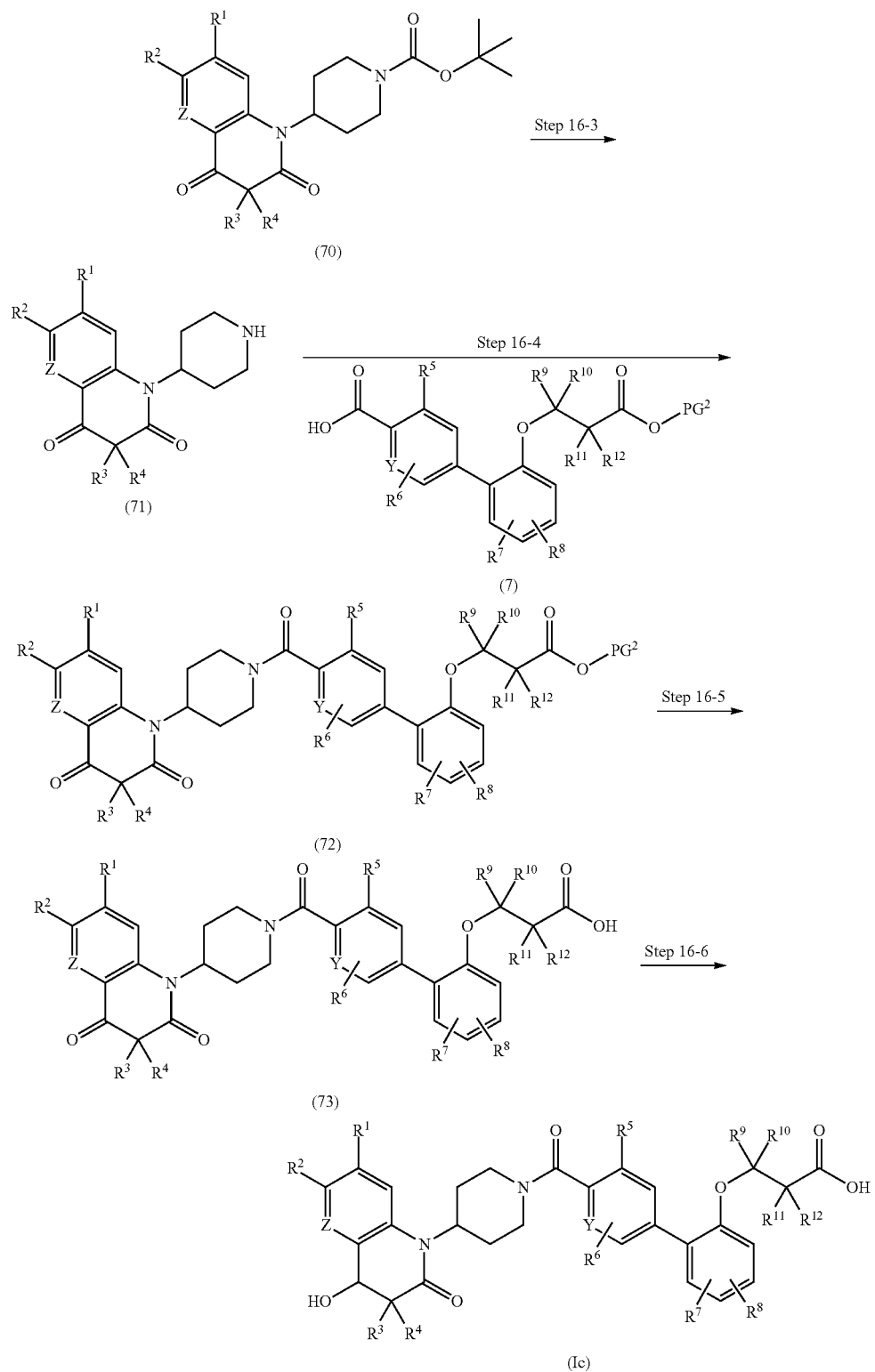

In the formulae, $R^1$, $R^2$, $R^3$, $R^4$, $R^5$, $R^6$, $R^7$, $R^8$, $R^9$, $R^{10}$, $R^{11}$, $R^{12}$, Y, Z, and $PG^2$ have the same meanings as those mentioned above. Compound (Ic) is a compound in which X of compound (I) is represented by —CH(OH)—.

(Step 16-1)

The present step is a step for producing compound (69) by allowing N-bromosuccinimide and 2,2'-azoisobutyronitrile to act on compound (52) in a solvent inactive to the reaction.

Carbon tetrachloride is preferred as the solvent. Usually, the reaction temperature is 20° C. to 80° C., preferably 50° C. to 80° C. The reaction time is 15 minutes to 12 hours, preferably 30 minutes to 6 hours.
(Step 16-2)

The present step is a step to produce compound (70), in which dimethylsulfoxide solvent is allowed to act on compound (69) in the presence of a base, and then an oxidizing agent is allowed to act in a solvent inactive to the reaction. When dimethylsulfoxide is allowed to act, examples of the base to be used include sodium hydrogen carbonate, sodium carbonate or potassium carbonate, with sodium hydrogen carbonate being preferred. Usually, the reaction temperature is 20° C. to 150° C., preferably 20° C. to 100° C. The reaction time is 1 hour to 24 hours, preferably 2 hours to 12 hours.

Examples of the solvent in which the oxidizing agent is allowed to act include halogenated hydrocarbons such as dichloromethane, chloroform, carbon tetrachloride, 1,2-dichloroethane, chlorobenzene, or dichlorobenzene, with dichloromethane being preferred. Usually, the reaction temperature is 0° C. to 100° C., preferably 20° C. to 40° C. The reaction time is 30 minutes to 8 hours, preferably 1 hour to 4 hours.
(Step 16-3)

The present step is deprotection of a tert-butyloxycarbonyl group which is a protective group of an amine. Analogously to Step 8-8, compound (71) can be produced from compound (70).
(Step 16-4)

The present step is an amidation reaction. Analogously to Step 1-5, compound (72) can be produced from compound (7) and compound (71).
(Step 16-5)

The present step is deprotection of PG2 of compound (72). Analogously to Step 1-6, compound (73) can be produced from compound (72).
(Step 16-6)

The present step is a reduction reaction of a ketone. A reducing agent can be allowed to act on compound (73) in a solvent inactive to the reaction to produce compound (Ic). Examples of the solvent include ethers such as diethylether, diisopropylether, tetrahydrofuran, dioxane, dimethoxyethane, or tert-butyl methylether, alcohols such as methanol, ethanol, n-propanol, isopropanol, n-butanol, isobutanol, tert-butanol, isoamyl alcohol, octanol, cyclohexanol, 2-methoxyethanol, diethyleneglycol, or glycerin, a mixed solvent thereof, or the like, with tetrahydrofuran, methanol, ethanol, or a mixed solvent thereof being preferred. Sodium borohydride is preferred as the reducing agent. Usually, the reaction temperature is 0° C. to 80° C., preferably 0° C. to 50° C. The reaction time is 30 minutes to 12 hours, preferably 1 hour to 12 hours.

Production Method 17

Further, several functional groups of the compound of the general formula (I) of the present invention may also be introduced by applying a step, which can usually be employed by a person skilled in the art, such as known substitution reactions, reduction reactions, oxidation reactions, or alkylation reactions, to a compound which is obtained in the final step or any of the intermediate steps of the aforementioned production methods.

For example, a bromine atom of $R^1$ can be converted to a cyano group, an ethyl group or a methoxy group. For the conversion to a cyano group, a method set forth in Tetrahedron Letters, 2000, 41(18), 3271-3273 can be used. Tris(dibenzylideneacetone)dipalladium and zinc cyanide can be allowed to act on a compound in which $R^1$ is a bromine atom in N,N-dimethylformamide to produce a compound in which $R^1$ is a cyano group. It is useful to use as an additive 1,1'-bis(diphenylphosphino)ferrocene and zinc, in order to allow the reaction to proceed smoothly. Usually, the reaction temperature is 100° C. to 150° C., preferably 120° C. to 140° C. The reaction time is 15 minutes to 12 hours, preferably 45 minutes to 6 hours.

A compound in which $R^1$ is an ethyl group can be produced by allowing [1,1'-bis(diphenylphosphino)ferrocene]dichloropalladium and diethyl zinc to act on a compound in which $R^1$ is a bromine atom in 1,4-dioxane. Usually, the reaction temperature is 0° C. to 100° C., preferably 20° C. to 80° C. The reaction time is 1 hour to 48 hours, preferably 3 hours to 24 hours.

A compound in which $R^1$ is a methoxy group can be produced by allowing a catalyst and a base to act on a compound in which $R^1$ is a bromine atom and methanol in toluene. Copper iodide can be used as the catalyst. Cesium carbonate can be used as the base. It is useful to add as an additive 3,4,7,8-tetramethyl-1,10-phenanthroline, in order to allow the reaction to proceed smoothly. Usually, the reaction temperature is 60° C. to the temperature at heating under reflux. The reaction time is 15 hours to 30 hours.

A product from each of the above steps can be isolated from the reaction mixture as needed after completion of the reaction, as a free compound or a salt thereof, by means of a conventional method, for example, (1) a method for concentrating the reaction solution as it stands, (2) a method for removing insolubles such as a catalyst by filtration to then concentrate the filtrate, (3) a method for adding to the reaction solution water and a solvent immiscible with water (e.g., dichloroethane, diethylether, ethyl acetate, toluene, or the like) to extract a product, (4) a method for collecting a crystallized or precipitated product by filtration, or the like. The isolated product can be purified as needed by means of a conventional method, for example, recrystallization, reprecipitation, various kinds of chromatography, or the like. Alternatively, a product from each step can also be used for the next step without isolation or purification.

The compound (I) of the present invention is isolated and purified as a free compound, a pharmacologically acceptable salt thereof, a hydrate, or a solvate. The pharmacologically acceptable salt of the compound (I) of the present invention can be produced by subjecting it to a salification reaction of the conventional type. Isolation and purification are carried out by applying a usual chemical operation such as extraction, concentration, distillation, crystallization, filtration, recrystallization, or various kinds of chromatography.

Various isomers can be isolated utilizing a difference in physicochemical properties among isomers. For example, a racemic mixture can be led to an optically pure isomer by means of fractional crystallization which leads it to a diastereomeric salt with an optically active base or acid, chromatography using a chiral column, or other means. Alternatively, a diastereomeric mixture can be separated by means of fractional crystallization, various kinds of chromatography, or other means. Alternatively, an optically active compound can also be produced by using a suitable optically active starting material.

Examples of the mode of administration of a compound having the general formula (I) or a pharmacologically acceptable salt thereof of the present invention include oral administration using tablets, granules, powders, capsules, syrups, or the like, or parenteral administration using injection solutions or suppositories, which can be administered systemically or topically.

Examples of the form of a medicament for oral administration of a compound having the general formula (I) or a pharmacologically acceptable salt thereof of the present invention include tablets, pills, granules, powders, capsules, solutions, suspensions, emulsions, syrups, elixirs, or the like. Examples of the form of a parenteral medicament include injection solutions, ointments, gels, creams, patches, nebulas, inhalants, sprays, eye drops, suppositories, or the like. Medicaments in these forms can be prepared according to the conventional methods using an additive selected appropriately, as needed, from pharmaceutically acceptable additives such as excipients, binders, diluents, stabilizers, preservatives, colorants, solubilizers, suspending agents, buffers, and wetting agents.

The dosage of a compound having the general formula (I) or a pharmacologically acceptable salt thereof of the present invention upon administration varies depending on symptoms, body weights, ages, modes of administration, or the like of a subject to be administered (warm-blooded animal, e.g., human). For example, in the case of oral administration, it is desirable to administer it with a lower limit of 0.001 mg/kg body weight (preferably, 0.01 mg/kg body weight), and with an upper limit of 500 mg/kg body weight (preferably, 50 mg/kg body weight) per dose, one to several times per day depending on symptoms. Further, in the case of intravenous administration, it is desirable to administer it with a lower limit of 0.0005 mg/kg body weight (preferably, 0.05 mg/kg body weight), and with an upper limit of 50 mg/kg body weight (preferably, 5 mg/kg body weight) per dose, one to several times per day depending on symptoms.

EXAMPLES

Hereinafter, the present invention will be explained in more detail with reference to reference examples, examples, formulation examples, and test examples; however, the scope of the present invention is not limited thereto.

Reference Example 1

7'-Chloro-1'-piperidin-4-ylspiro[cyclopropane-1,3'-pyrido[2,3-b][1,4]oxazine]-2'(1'H)-one trifluoroacetate

[Chemical 22]

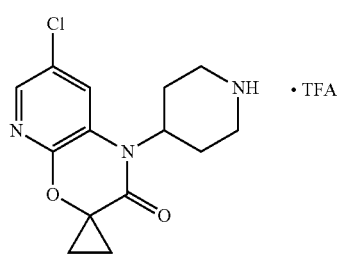

Reference Example 1-1

At room temperature under shielded light, to N,N'-diisopropylcarbodiimide (99.75 g) was added copper(I) chloride (1.57 g), and then tert-butanol (83 ml) was added dropwise over 20 minutes, followed by stirring for 4 days. The supernatant (48 ml) was added dropwise to a dichloromethane suspension (120 ml) of 1-hydroxycyclopropanecarboxylic acid (17.12 g) using an ice bath over 15 minutes. The temperature was brought back to room temperature, followed by stirring for 40 hours, and then acetic acid (11.5 ml) was added and stirred for 1 hour. The reaction suspension was filtered, and ice water and sodium hydrogen carbonate were added to the filtrate for neutralization. After the precipitate was filtered off, the organic layer separated from the filtrate was washed with saturated sodium hydrogen carbonate, dried over anhydrous sodium sulfate, and concentrated under reduced pressure. After pentane was added to the residue, insolubles were filtered off, and the filtrate was concentrated under reduced pressure to afford tert-butyl 1-hydroxycyclopropanecarboxylate (11.65 g).

$^1$H NMR (500 MHz, CDCl$_3$) δ: 1.09 (dd, 2H, J=8.3, 4.4 Hz), 1.21 (dd, 2H, J=8.3, 4.4 Hz), 1.47 (s, 9H), 2.99 (br s, 1H).

Reference Example 1-2

Under ice cooling, to a toluene suspension (60 ml) of 63% sodium hydride (2.81 g) was added dropwise a toluene solution (30 ml) of tert-butyl 1-hydroxycyclopropanecarboxylate (11.65 g) over 15 minutes, followed by stirring as it stood for 30 minutes, and further at room temperature for 2 hours. After cooling again using an ice bath, a toluene solution (30 ml) of 2,5-dichloro-3-nitropyridine (7.13 g) was added, and the temperature was brought back to room temperature, followed by stirring for 3 hours. After a 10% aqueous citric acid solution was added, the separated organic layer was washed with saturated sodium chloride solution, and the aqueous layer was extracted with ethyl acetate. The collected organic layer was dried over anhydrous sodium sulfate, and concentrated under reduced pressure. The residue was purified by silica gel column chromatography to afford tert-butyl 1-[(5-chloro-3-nitropyridin-2-yl)oxy]cyclopropanecarboxylate (9.61 g).

$^1$H NMR (500 MHz, CDCl$_3$) δ: 1.33 (dd, 2H, J=8.5, 5.6 Hz), 1.37 (s, 9H), 1.61 (dd, 2H, J=8.5, 5.6 Hz), 8.27 (d, 1H, J=2.4 Hz), 8.35 (d, 1H, J=2.4 Hz).

Reference Example 1-3

At room temperature, to an acetic acid solution (100 ml) of tert-butyl 1-[(5-chloro-3-nitropyridin-2-yl)oxy]cyclopropanecarboxylate (9.61 g) was added iron powder (13.6 g), and stirred for 7 hours, followed by concentration under reduced pressure. To the residue were added ethyl acetate and a saturated aqueous sodium hydrogen carbonate solution for neutralization, followed by filtration through Celite. The organic layer separated from the filtrate was washed with saturated sodium chloride solution, and the aqueous layer was collected and extracted with ethyl acetate. The collected organic layer was dried over anhydrous sodium sulfate, and concentrated under reduced pressure to afford tert-butyl 1-[(3-amino-5-chloropyridin-2-yl)oxy]cyclopropanecarboxylate (7.88 g).

$^1$H NMR (500 MHz, CDCl$_3$) δ: 1.23 (dd, 2H, J=8.3, 5.4 Hz), 1.38 (s, 9H), 1.55 (dd, 2H, J=8.3, 5.4 Hz), 3.85 (br s, 2H), 7.26 (d, 1H, J=2.0 Hz), 7.49 (d, 1H, J=2.0 Hz).

Reference Example 1-4

At room temperature, to a 1,2-dichloroethane solution (280 ml) of tert-butyl 1-[(3-amino-5-chloropyridin-2-yl)oxy]cyclopropanecarboxylate (7.88 g) were added tert-butyl 4-oxopiperidine-1-carboxylate (22.1 g) and sodium triacetoxyborohydride (23.5 g), and then temperature was raised to 75° C., followed by stirring for 20 hours. After the temperature was brought back to room temperature, a saturated aqueous sodium hydrogen carbonate solution was added, and extracted with dichloromethane. The collected organic layer was dried over anhydrous sodium sulfate, and concentrated under reduced pressure. The residue was purified by silica gel column chromatography to afford tert-butyl 4-[(2-{[1-(tert-butoxycarbonyl)cyclopropyl]oxy}-5-chloropyridin-3-yl)amino]piperidine-1-carboxylate (7.09 g).

¹H NMR (500 MHz, CDCl₃) δ: 1.23 (dd, 2H, J=8.1, 5.6 Hz), 1.36 (s, 9H), 1.47 (s, 9H), 1.55 (dd, 2H, J=8.1, 5.6 Hz), 2.00-2.02 (m, 2H), 2.91-2.96 (m, 2H), 3.17-3.22 (m, 0.4H), 3.31-3.38 (m, 1H), 3.71-3.75 (m, 0.4H), 4.05-4.15 (m, 3H), 6.69 (d, 1H, J=2.0 Hz), 7.39 (d, 1H, J=2.0 Hz).

Reference Example 1-5

A trifluoroacetic acid solution (70 ml) of tert-butyl 4-[(2-{[1-(tert-butoxycarbonyl)cyclopropyl]oxy}-5-chloropyridin-3-yl)amino]piperidine-1-carboxylate (7.09 g) was stirred at 70° C. for 28 hours. The temperature was brought back to room temperature, followed by concentration under reduced pressure, and toluene was further added and concentrated under reduced pressure. After ether was added to the residue, the suspension was stirred for 2 hours, and then the insolubles were collected by filtration to afford 7'-chloro-1'-piperidin-4-ylspiro[cyclopropane-1,3'-pyrido[2,3-b][1,4]oxazine]-2'(1'H)-one trifluoroacetate (5.37 g).

¹H NMR (500 MHz, DMSO-D₆) δ: 1.29-1.31 (m, 4H), 1.95-1.98 (m, 2H), 2.62-2.71 (m, 2H), 3.04-3.11 (m, 2H), 3.38-3.40 (m, 2H), 4.29-4.35 (m, 1H), 7.96 (d, 1H, J=2.0 Hz), 8.04 (d, 1H, J=2.0 Hz), 8.40 (br m, 1H), 8.74 (br m, 1H).

Reference Example 2

(3S)-7-Fluoro-3-methyl-1-piperidin-4-yl-1H-pyrido[2,3-b][1,4]oxazin-2(3H)-one

[Chemical 23]

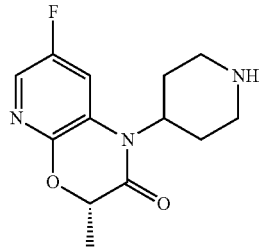

Reference Example 2-1

Under ice cooling, to 5-fluoropyridine-2-amine (10.36 g) was added concentrated sulfuric acid (48 ml), followed by stirring for 10 minutes, and then fuming nitric acid (3.83 ml) was added dropwise over 30 minutes. Stirring was carried out at room temperature for 1 hour, and further at 55° C. for 90 minutes. Ice was poured thereinto, and neutralized with a 10 N aqueous sodium hydroxide solution, followed by concentration under reduced pressure. The residue was dissolved in dichloromethane (600 ml), followed by stirring for 30 minutes, and then the insolubles were filtered off to concentrate the filtrate under reduced pressure. The residue was purified by silica gel column chromatography to afford 5-fluoro-3-nitropyridine-2-amine (2.66 g).

¹H NMR (500 MHz, CDCl₃) δ: 6.61 (br s, 2H), 8.17 (dd, 1H, J=7.6, 3.1 Hz), 8.31 (d, 1H, J=3.1 Hz).

Reference Example 2-2

5-Fluoro-3-nitropyridine-2-amine (2.66 g) suspended in concentrated hydrochloric acid (35 ml) was cooled to −15° C., and an aqueous solution (7 ml) of sodium nitrite (2.57 g) was added dropwise over 10 minutes. After stirring at −10° C. for 1 hour, and further stirring at room temperature for 1 hour, under ice cooling a 30% aqueous sodium hydroxide solution was added for neutralization. The insolubles were collected by filtration, washed with water, air-dried, and then redissolved in ethyl acetate, before the insolubles were filtered off. The filtrate was concentrated under reduced pressure to afford 2-chloro-5-fluoro-3-nitropyridine (1.41 g).

¹H NMR (400 MHz, CDCl₃) δ: 8.03 (dd, 1H, J=6.6, 2.7 Hz), 8.55 (d, 1H, J=2.7 Hz).

Reference Example 2-3

In accordance with the method of Reference Example 1-2, tert-butyl (2S)-2-hydroxypropionate (2.68 g) (The Journal of Organic Chemistry, 1995, 60(15), 4782-4785) was used instead of the compound of Reference Example 1-1, and the compound of Reference Example 2-2 was used instead of 2,5-dichloro-3-nitropyridine to afford tert-butyl (2S)-2-[(5-fluoro-3-nitropyridin-2-yl)oxy]propionate.

¹H NMR (400 MHz, CDCl₃) δ: 1.43 (s, 9H), 1.66 (d, 3H, J=7.0 Hz), 5.26 (q, 1H, J=7.0 Hz), 8.10 (dd, 1H, J=7.0, 2.7 Hz), 8.21 (d, 1H, J=2.7 Hz).

Reference Example 2-4

In accordance with the method of Reference Example 1-3, the compound of Reference Example 2-3 was used instead of the compound of Reference Example 1-2 to afford tert-butyl (2S)-2-[(3-amino-5-fluoropyridin-2-yl)oxy]propionate.

¹H NMR (400 MHz, CDCl₃) δ: 1.43 (s, 9H), 1.58 (d, 3H, J=7.0 Hz), 3.98 (br s, 2H), 5.17 (q, 1H, J=7.0 Hz), 6.67 (dd, 1H, J=9.0, 2.7 Hz), 7.30 (d, 1H, J=2.7 Hz).

Reference Example 2-5

In accordance with the method of Reference Example 1-4, the compound of Reference Example 2-4 was used instead of the compound of Reference Example 1-3 to afford tert-butyl 4-({2-[(1S)-2-tert-butoxy-1-methyl-2-oxoethoxy]-5-fluoropyridin-3-yl}amino)piperidine-1-carboxylate.

¹H NMR (400 MHz, CDCl₃) δ: 1.43 (s, 9H), 1.47 (s, 9H), 1.58 (d, 3H, J=7.0 Hz), 2.01-2.05 (m, 2H), 2.91-2.97 (m, 2H), 3.16-3.22 (m, 0.4H), 3.30-3.36 (m, 1H), 3.70-3.76 (m, 0.4H), 4.01-4.10 (m, 2H), 4.32-4.34 (m, 1H), 5.15 (q, 1H, J=7.0 Hz), 6.49 (dd, 1H, J=10.2, 2.7 Hz), 7.19 (d, 1H, J=2.7 Hz).

Reference Example 2-6

A trifluoroacetic acid solution (10 ml) of tert-butyl 4-({2-[(1S)-2-tert-butoxy-1-methyl-2-oxoethoxy]-5-fluoropyridin-3-yl}amino)piperidine-1-carboxylate (861 mg) was stirred at room temperature for 24 hours, and then concentrated under reduced pressure. To the residue were added dichloromethane and a saturated aqueous sodium hydrogen carbonate solution, and the solution was separated. The aqueous layer was saturated with salt, and then extracted with dichloromethane. The collected organic layer was dried over anhydrous sodium sulfate, and concentrated under reduced pressure to afford (3S)-7-fluoro-3-methyl-1-piperidin-4-yl-1H-pyrido[2,3-b][1,4]oxazin-2(3H)-one (434 mg).

¹H NMR (400 MHz, CDCl₃) δ: 1.60 (d, 3H, J=7.0 Hz), 1.69-1.82 (m, 2H), 2.39-2.50 (m, 2H), 2.74-2.81 (m, 2H), 3.27-3.31 (m, 2H), 4.48 (tt, 1H, J=12.5, 3.9 Hz), 4.70 (q, 1H, J=7.0 Hz), 7.41 (dd, 1H, J=9.0, 2.7 Hz), 7.79 (d, 1H, J=2.7 Hz).

Reference Example 3

7-Chloro-3,3-dimethyl-1-piperidin-4-yl-1H-pyrido[2,3-b][1,4]oxazin-2(3H)-one trifluoroacetate

[Chemical 24]

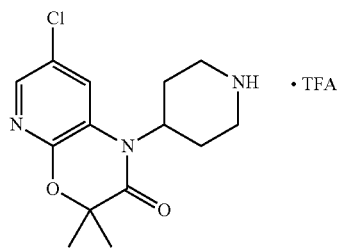

Reference Example 3-1

To an acetonitrile solution (400 ml) of 2,5-dichloropyridin-3-ol (20.0 g) (Synthesis, 1990, 6, 499-501) and tert-butyl 2-bromo-2-methylpropionate (54.4 g) was added at room temperature potassium carbonate (30.3 g), followed by stirring for 12 hours under heating at reflux. The insolubles were filtered off, and washed with ethyl acetate. The filtrate was concentrated under reduced pressure, and then the residue was purified by silica gel chromatography to afford tert-butyl 2-[(2,5-dichloropyridin-3-yl)oxy]-2-methylpropionate (31.1 g).
¹H NMR (400 MHz, CDCl₃) δ: 1.45 (s, 9H), 1.63 (s, 6H), 7.19 (d, 1H, J=2.2 Hz), 8.00 (d, 1H, J=2.2 Hz).

Reference Example 3-2

To a dichloromethane solution (157 ml) of tert-butyl 2-[(2,5-dichloropyridin-3-yl)oxy]-2-methylpropionate (79.1 g) was added at 0° C. trifluoroacetic acid (157 ml). The reaction solution was brought back to room temperature, stirred overnight, and then concentrated under reduced pressure. The residue was dissolved in ethyl acetate, washed sequentially with water and saturated sodium chloride solution, dried over anhydrous sodium sulfate, and concentrated under reduced pressure. The residue was azeotroped with toluene to afford 2-[(2,5-dichloropyridin-3-yl)oxy]-2-methylpropionic acid (81.1 g).
¹H NMR (400 MHz, CDCl₃) δ: 1.71 (s, 6H), 7.39 (d, 1H, J=2.2 Hz), 8.12 (d, 1H, J=2.2 Hz).

Reference Example 3-3

To a dichloromethane solution (1500 ml) of 2-[(2,5-dichloropyridin-3-yl)oxy]-2-methylpropionic acid (81.1 g) and tert-butyl 4-aminopiperidine-1-carboxylate (67.3 g) were added under ice cooling diisopropylethylamine (161 ml) and 2-(1H-benzotriazol-1-yl)-1,1,3,3-tetramethyluronium hexafluorophosphate (127 g). The reaction solution was brought back to room temperature and stirred overnight, then washed sequentially with water and saturated sodium chloride solution, dried over anhydrous sodium sulfate, and concentrated under reduced pressure. The residue was purified by silica gel chromatography, and then stirred under heating in a hexane-ethyl acetate mixed solvent, followed by filtration to collect tert-butyl 4-({2-[(2,5-dichloropyridin-3-yl)oxy]-2-methylpropanoyl}amino)piperidine-1-carboxylate (97.1 g).
¹H NMR (400 MHz, CDCl₃) δ: 1.32-1.44 (m, 2H), 1.46 (s, 9H), 1.62 (s, 6H), 1.89-1.99 (m, 2H), 2.84-2.98 (m, 2H), 3.90-4.17 (m, 3H), 6.91 (d, 1H, J=8.2 Hz), 7.37 (d, 1H, J=2.2 Hz), 8.13 (d, 1H, J=2.2 Hz).

Reference Example 3-4

At room temperature, to an N,N-dimethylformamide solution (1000 ml) of tert-butyl 4-({2-[(2,5-dichloropyridin-3-yl)oxy]-2-methylpropanoyl}amino)piperidine-1-carboxylate (97.1 g) was added cesium carbonate (146 g), followed by stirring at 100° C. for 4 hours. The reaction solution was poured into water, and extracted with ethyl acetate. The organic layer was washed sequentially with water and saturated sodium chloride solution, dried over anhydrous sodium sulfate, and concentrated under reduced pressure. The residue was purified by silica gel chromatography to afford tert-butyl 4-(7-chloro-3,3-dimethyl-2-oxo-2,3-dihydro-1H-pyrido[2,3-b][1,4]oxazin-1-yl)piperidine-1-carboxylate (74.2 g).
¹H NMR (400 MHz, CDCl₃) δ: 1.50 (s, 9H), 1.53 (s, 6H), 1.65-1.79 (m, 2H), 2.36-2.52 (m, 2H), 2.74-2.91 (m, 2H), 4.19-4.50 (m, 3H), 7.37 (d, 1H, J=2.2 Hz), 7.91 (d, 1H, J=2.2 Hz).

Reference Example 3-5

Under ice cooling, to a dichloromethane solution (145 ml) of tert-butyl 4-(7-chloro-3,3-dimethyl-2-oxo-2,3-dihydro-1H-pyrido[2,3-b][1,4]oxazin-1-yl)piperidine-1-carboxylate (74.2 g) was added trifluoroacetic acid (145 ml), followed by stirring at room temperature for 3 hours. After the reaction solution was concentrated under reduced pressure, ether was added to the residue, and the slurry was stirred overnight. The insolubles were collected by filtration to afford 7-chloro-3,3-dimethyl-1-piperidin-4-yl-1H-pyrido[2,3-b][1,4]oxazin-2(3H)-one trifluoroacetate (76.1 g).
¹H NMR (400 MHz, DMSO-D₆) δ: 1.42 (s, 6H), 1.84-1.96 (m, 2H), 2.61-2.75 (m, 2H), 3.00-3.15 (m, 2H), 3.33-3.45 (m, 2H), 4.32-4.44 (m, 1H), 7.97 (d, 1H, J=2.0 Hz), 8.05 (d, 1H, J=2.0 Hz), 8.45 (br m, 1H), 8.81 (br m, 1H).

Reference Example 4

(3S)-7-Chloro-3-methyl-1-piperidin-4-yl-1H-pyrido[2,3-b][1,4]oxazin-2(3H)-one trifluoroacetate

[Chemical 25]

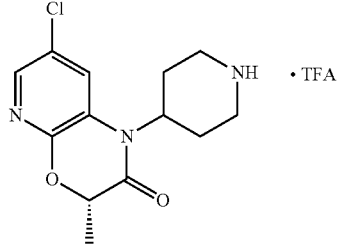

Reference Example 4-1

To a dichloromethane solution (1000 ml) of (2R)-2-(benzyloxy)propionic acid (51.7 g) and tert-butyl 4-aminopiperidine-1-carboxylate (63.2 g) were added at room temperature 1-ethyl-3-(3-dimethylaminopropyl)carbodiimide hydrochloride (60.5 g) and 1-hydroxybenzotriazole monohydrate (42.7 g), followed by stirring overnight. The reaction solution was poured into a 0.5 N aqueous hydrochloric acid solution, and extracted with dichloromethane. The organic layer was washed sequentially with water, a saturated aqueous sodium hydrogen carbonate solution, water and saturated sodium chloride solution, dried over anhydrous sodium sulfate, and concentrated under reduced pressure. The residue was purified by silica gel column chromatography to afford tert-butyl 4-{[(2R)-2-(benzyloxy)propanoyl]amino}piperidine-1-carboxylate (100 g).

$^1$H NMR (400 MHz, CDCl$_3$) δ: 1.24-1.37 (m, 2H), 1.41 (d, 3H, J=6.8 Hz), 1.45 (s, 9H), 1.86-1.87 (m, 2H), 2.85-2.88 (m, 2H), 3.86-4.11 (m, 4H), 4.50 (d, 1H, J=11.2 Hz), 4.59 (d, 1H, J=11.2 Hz), 6.53 (d, 1H, J=8.0 Hz), 7.32-7.40 (m, 5H).

Reference Example 4-2

At room temperature, to a methanol solution (200 ml) of tert-butyl 4-{[(2R)-2-(benzyloxy)propanoyl]amino}piperidine-1-carboxylate (6.90 g) was added 10% palladium carbon (2.03 g), followed by stirring overnight under a hydrogen atmosphere. The reaction solution was filtered through Celite, and then concentrated under reduced pressure to afford tert-butyl 4-{[(2R)-2-hydroxypropanoyl]amino}piperidine-1-carboxylate (5.19 g).

$^1$H NMR (400 MHz, CDCl$_3$) δ: 1.30-1.38 (m, 2H), 1.44 (d, 3H, J=6.8 Hz), 1.46 (s, 9H), 1.89-1.91 (m, 2H), 2.69 (br s, 1H), 2.86-2.89 (m, 2H), 3.87-3.97 (m, 1H), 4.09-4.13 (m, 2H), 4.19-4.26 (m, 1H), 6.47 (d, 1H, J=7.4 Hz).

Reference Example 4-3

To a tetrahydrofuran solution (148 ml) of tert-butyl 4-{[(2R)-2-hydroxypropanoyl]amino}piperidine-1-carboxylate (5.13 g), 2,5-dichloropyridin-3-ol (3.40 g) and triphenylphosphine (6.41 g) was added dropwise at room temperature a tetrahydrofuran solution (40 ml) of di-tert-butyl azodicarboxylate (5.63 g) over 10 minutes. The reaction solution was stirred at room temperature for 1 hour, then poured into water, and extracted with ethyl acetate. The organic layer was washed sequentially with water and saturated sodium chloride solution, dried over anhydrous sodium sulfate, and concentrated under reduced pressure. The residue was purified by silica gel column chromatography to afford tert-butyl 4-({(2S)-2-[(2,5-dichloropyridin-3-yl)oxy]propanoyl}amino)piperidine-1-carboxylate (6.40 g).

$^1$H NMR (400 MHz, CDCl$_3$) δ: 1.28-1.32 (m, 2H), 1.46 (s, 9H), 1.66 (d, 3H, J=6.8 Hz), 1.86-1.95 (m, 2H), 2.89-2.91 (m, 2H), 3.90-4.10 (m, 3H), 4.70 (q, 1H, J=6.8 Hz), 6.58 (d, 1H, J=8.0 Hz), 7.22 (d, 1H, J=1.6 Hz), 8.06 (d, 1H, J=1.6 Hz).

Reference Example 4-4

To a tetrahydrofuran solution (129 ml) of 63% sodium hydride (1.59 g) was added dropwise a tetrahydrofuran solution (80 ml) of tert-butyl 4-({(2S)-2-[(2,5-dichloropyridin-3-yl)oxy]propanoyl}amino)piperidine-1-carboxylate (8.74 g) at 8° C. over 15 minutes. The reaction solution was stirred at room temperature for 1 hour, then poured into ice water, and extracted with ethyl acetate. The organic layer was washed sequentially with water and saturated sodium chloride solution, dried over anhydrous sodium sulfate, and concentrated under reduced pressure. The residue was purified by silica gel column chromatography to afford tert-butyl 4-[(3S)-7-chloro-3-methyl-2-oxo-2,3-dihydro-1H-pyrido[2,3-b][1,4]oxazin-1-yl]piperidine-1-carboxylate (7.00 g).

$^1$H NMR (400 MHz, CDCl$_3$) δ: 1.49 (s, 9H), 1.60 (d, 3H, J=6.8 Hz), 1.70-1.75 (m, 2H), 2.40-2.45 (m, 2H), 2.80-2.83 (m, 2H), 4.33-4.40 (m, 3H), 4.71 (q, 1H, J=6.8 Hz), 7.39 (d, 1H, J=2.0 Hz), 7.90 (d, 1H, J=2.0 Hz).

Reference Example 4-5

In accordance with the method of Reference Example 3-5, the compound of Reference Example 4-4 was used instead of the compound of Reference Example 3-4 to afford (3S)-7-chloro-3-methyl-1-piperidin-4-yl-1H-pyrido[2,3-b][1,4]oxazin-2(3H)-one trifluoroacetate.

$^1$H NMR (400 MHz, DMSO-D$_6$) δ: 1.45 (d, 3H, J=6.8 Hz), 1.89-1.92 (m, 2H), 2.65-2.70 (m, 2H), 2.97-3.14 (m, 2H), 3.36-3.39 (m, 2H), 4.32-4.35 (m, 1H), 4.87 (q, 1H, J=6.8 Hz), 7.96 (d, 1H, J=2.0 Hz), 8.03 (d, 1H, J=2.0 Hz), 8.40 (br m, 1H), 8.71 (br m, 1H).

Reference Example 5

3,3,7-Trimethyl-1-piperidin-4-yl-1H-pyrido[2,3-b][1,4]oxazin-2(3H)-one trifluoroacetate

[Chemical 26]

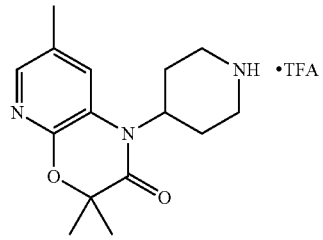

Reference Example 5-1

At room temperature, to a mixed solvent solution of 5-methyl-3-nitropyridin-2-ol (5.0 g) in tetrahydrofuran (200 ml) and methanol (200 ml) was added 10% palladium carbon (0.5 g), followed by stirring for 24 hours under a hydrogen atmosphere. The reaction solution was filtered through Celite, and then the filtrate was concentrated under reduced pressure to afford 3-amino-5-methylpyridin-2-ol (4.03 g).

$^1$H NMR (400 MHz, CDCl$_3$) δ: 2.03 (s, 3H), 4.11 (br s, 2H), 6.53 (s, 1H), 6.59 (s, 1H), 12.21 (br s, 1H).

Reference Example 5-2

At room temperature, to a mixed solvent solution of 3-amino-5-methylpyridin-2-ol (4.03 g) in tetrahydrofuran (50 ml) and 1,2-dichloroethane (50 ml) were added tert-butyl 4-oxopiperidine-1-carboxylate (13.04 g), sodium triacetoxyborohydride (13.87 g) and acetic acid (3.75 ml), followed by heating at reflux for 16 hours. After the temperature was brought back to room temperature, 1 N aqueous sodium hydroxide solution was added, and extracted with chloroform. The organic layer was washed with saturated sodium chloride solution, dried over anhydrous sodium sulfate, and concentrated under reduced pressure to afford tert-butyl 4-[(2-hydroxy-5-methylpyridin-3-yl)amino]piperidine-1-carboxylate (7.6 g).

¹H NMR (400 MHz, CDCl₃) δ: 1.40-1.50 (m, 2H), 1.47 (s, 9H), 1.98-2.10 (m, 2H), 2.06 (s, 3H), 2.92-3.02 (m, 2H), 3.32-3.41 (m, 1H), 3.95-4.10 (m, 2H), 4.78-4.83 (m, 1H), 6.16 (s, 1H), 6.48 (s, 1H), 11.5-11.8 (br m, 1H).

Reference Example 5-3

At room temperature, to a dichloromethane solution (15 ml) of tert-butyl 4-[(2-hydroxy-5-methylpyridin-3-yl)amino]piperidine-1-carboxylate (3.08 g) were added 2,6-lutidine (2.25 ml) and 2-bromoisobutyryl bromide (1.74 ml). After stirring at room temperature for 18 hours, N,N-dimethylformamide (15 ml) was added, and stirred at 70° C. for 1 hour. The reaction solution was concentrated under reduced pressure, and the residue was purified by silica gel column chromatography to afford tert-butyl 4-(3,3,7-trimethyl-2-oxo-2,3-dihydro-1H-pyrido[2,3-b][1,4]oxazin-1-yl)piperidine-1-carboxylate (1.04 g).

¹H NMR (400 MHz, CDCl₃) δ: 1.49 (s, 9H), 1.50 (s, 6H), 1.62-1.74 (m, 2H), 2.32 (s, 3H), 2.40-2.55 (m, 2H), 2.75-2.90 (m, 2H), 4.20-4.50 (m, 3H), 7.18 (s, 1H), 7.76 (s, 1H).

Reference Example 5-4

In accordance with the method of Reference Example 3-5, the compound of Reference Example 5-3 was used instead of the compound of Reference Example 3-4 to afford 3,3,7-trimethyl-1-piperidin-4-yl-1H-pyrido[2,3-b][1,4]oxazin-2(3H)-one trifluoroacetate.

¹H NMR (400 MHz, DMSO-D₆) δ: 1.38 (s, 6H), 1.85-1.88 (m, 2H), 2.30 (s, 3H), 2.65-2.75 (m, 2H), 3.02-3.11 (m, 2H), 3.38-3.41 (m, 2H), 4.34-4.42 (m, 1H), 7.69 (s, 1H), 7.74 (s, 1H), 8.42 (br m, 1H), 8.66 (br m, 1H).

Reference Example 6

3,3-Dimethyl-7-trifluoromethyl-1-piperidin-4-yl-1H-pyrido[2,3-b][1,4]oxazin-2(3H)-one trifluoroacetate

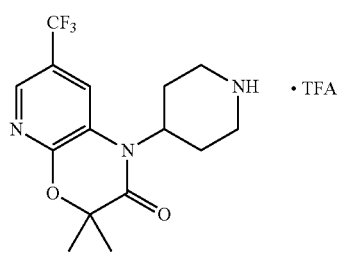

[Chemical 27]

In accordance with the method of Reference Example 5, 3-nitro-5-trifluoromethylpyridin-2-ol was used instead of 5-methyl-3-nitropyridin-2-ol to afford 3,3-dimethyl-7-trifluoromethyl-1-piperidin-4-yl-1H-pyrido[2,3-b][1,4]oxazin-2(3H)-one trifluoroacetate.

¹H NMR (400 MHz, DMSO-D₆) δ: 1.46 (s, 6H), 1.91-1.94 (m, 2H), 2.64-2.74 (m, 2H), 3.06-3.12 (m, 2H), 3.38-3.41 (m, 2H), 4.40-4.47 (m, 1H), 8.14 (s, 1H), 8.33 (s, 1H), 8.40 (br m, 1H), 8.70 (br m, 1H).

Reference Example 7

3,7-Dimethyl-1-piperidin-4-yl-1H-pyrido[2,3-b][1,4]oxazin-2(3H)-one trifluoroacetate

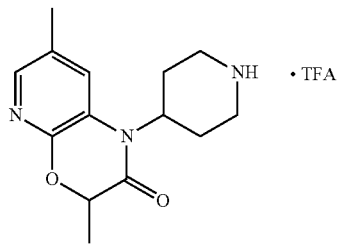

[Chemical 28]

In accordance with the method of Reference Example 5, 2-bromopropanoyl bromide was used instead of 2-bromoisobutyryl bromide to afford 3,7-dimethyl-1-piperidin-4-yl-1H-pyrido[2,3-b][1,4]oxazin-2(3H)-one trifluoroacetate.

¹H NMR (400 MHz, DMSO-D₆) δ: 1.42 (d, 3H, J=6.6 Hz), 1.85-1.91 (m, 2H), 2.30 (s, 3H), 2.62-2.79 (m, 2H), 2.98-3.13 (m, 2H), 3.37-3.41 (m, 2H), 4.32-4.38 (m, 1H), 4.75 (q, 1H, J=6.6 Hz), 7.69 (s, 1H), 7.73 (s, 1H), 8.39 (br m, 1H), 8.64 (br m, 1H).

Reference Example 8

7-Chloro-1-piperidin-4-yl-1H-pyrido[2,3-b][1,4]oxazin-2(3H)-one trifluoroacetate

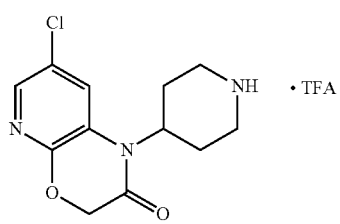

[Chemical 29]

Reference Example 8-1

To an 80% aqueous ethanol suspension (150 ml) of 5-chloro-3-nitropyridin-2-ol (15.0 g) and calcium chloride (9.54 g) was added iron powder (24.0 g), followed by stirring at room temperature for 30 minutes, and further under heating at reflux for 1 hour. After the temperature was brought back to room temperature, the reaction suspension was filtered through Celite. Water was added to the filtrate, and extracted 8 times with a methanol-dichloromethane (1:10) mixed solvent. The collected organic layer was dried over anhydrous sodium sulfate, and concentrated under reduced pressure to afford 3-amino-5-chloropyridin-2-ol (8.86 g).

¹H NMR (400 MHz, DMSO-D₆) δ: 5.43 (s, 2H), 6.38 (d, 1H, J=2.7 Hz), 6.72 (d, 1H, J=2.7 Hz), 11.52 (s, 1H).

Reference Example 8-2

To a 1,2-dichloroethane suspension (177 ml) of 3-amino-5-chloropyridin-2-ol (8.85 g) and tert-butyl 4-oxopiperidine- 1-carboxylate (24.4 g) was added sodium triacetoxyborohydride (26.0 g), followed by stirring under heating at reflux for 4 hours. Tert-butyl 4-oxopiperidine-1-carboxylate (12.4 g) and sodium triacetoxyborohydride (13.7 g) were further added, and stirred under heating at reflux for 2 hours. After the reaction solution was brought back to room temperature, water and dichloromethane were added, and the solution was separated. The organic layer was dried over anhydrous sodium sulfate, and concentrated under reduced pressure. The residue was purified by silica gel column chromatography to afford tert-butyl 4-[(5-chloro-2-hydroxypiperidin-3-yl)amino]piperidine-1-carboxylate (12.7 g).

$^1$H NMR (400 MHz, CDCl$_3$) δ: 1.43-1.50 (m, 2H), 1.47 (s, 9H), 2.00-2.03 (m, 2H), 2.95-3.01 (m, 2H), 3.32-3.35 (m, 1H), 4.03-4.06 (m, 2H), 4.98-5.00 (m, 1H), 6.25 (d, 1H, J=2.4 Hz), 6.71 (d, 1H, J=2.4 Hz), 12.37 (br s, 1H).

Reference Example 8-3

To an N,N-dimethylformamide suspension (60 ml) of tert-butyl 4-[(5-chloro-2-hydroxypiperidin-3-yl)amino]piperidine-1-carboxylate (3.00 g) and potassium carbonate (3.79 g) was added chloroacetyl chloride (1.09 ml), followed by stirring at room temperature for 30 minutes, and at 140° C. for 4 hours. After the reaction solution was brought back to room temperature, water and ethyl acetate were added, and the solution was separated. The organic layer was washed with water, dried over anhydrous sodium sulfate, and concentrated under reduced pressure. The residue was purified by silica gel column chromatography to afford tert-butyl 4-(7-chloro-2-oxo-2,3-dihydro-1H-pyrido[2,3-b][1,4]oxazin-1-yl)piperidine-1-carboxylate (1.33 g).

$^1$H NMR (400 MHz, CDCl$_3$) δ: 1.50 (s, 9H), 1.73-1.76 (m, 2H), 2.39-2.50 (m, 2H), 2.78-2.85 (m, 2H), 4.22-4.40 (br m, 3H), 4.71 (s, 2H), 7.39 (d, 1H, J=2.3 Hz), 7.90 (d, 1H, J=2.3 Hz).

Reference Example 8-4

In accordance with the method of Reference Example 3-5, the compound of Reference Example 8-3 was used instead of the compound of Reference Example 3-4 to afford 7-chloro-1-piperidin-4-yl-1H-pyrido[2,3-b][1,4]oxazin-2(3H)-one trifluoroacetate.

$^1$H NMR (500 MHz, DMSO-D$_6$) δ: 1.92-1.94 (m, 2H), 2.65-2.73 (m, 2H), 3.02-3.10 (m, 2H), 3.38-3.40 (m, 2H), 4.32 (tt, 1H, J=12.0, 3.4 Hz), 4.77 (s, 2H), 7.94 (d, 1H, J=2.4 Hz), 8.01 (d, 1H, J=2.4 Hz), 8.38 (br m, 1H), 8.70 (br m, 1H).

Reference Example 9

7-Chloro-1-piperidin-4-yl-3,4-dihydro-1,5-naphthyridin-2(1H)-one bis(trifluoroacetate)

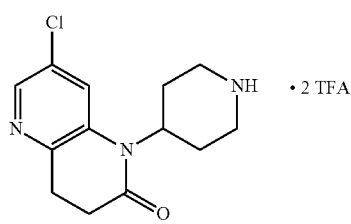

[Chemical 30]

Reference Example 9-1

A N,N-dimethylformamide suspension (406 ml) of 2,5-dichloropyridine-3-amine (81.2 g), palladium acetate (11.2 g), 1,4-bis(diphenylphosphino)butane (42.5 g), ethyl acrylate (109 ml), diisopropylethylamine (174 ml) and tetrabutylammonium bromide (161 g) was stirred at 140° C. for 30 hours. After the reaction solution was brought back to room temperature, ethyl acetate and water were added and the solution was separated, and the aqueous layer was extracted with ethyl acetate. The combined organic layer was dried over anhydrous sodium sulfate, and concentrated under reduced pressure. To the residue was added a 50% ethyl acetate-hexane mixed solvent, followed by stirring. The insolubles were filtered off, and washed with ethyl acetate, and the filtrate was concentrated under reduced pressure. The residue was purified by silica gel column chromatography to afford ethyl (2E)-3-(3-amino-5-chloropyridin-2-yl)acrylate (50.6 g).

$^1$H NMR (400 MHz, CDCl$_3$) δ: 1.33 (t, 3H, J=7.0 Hz), 4.04 (br s, 2H), 4.27 q, 2H, J=7.0 Hz), 6.90 (d, 1H, J=15.3 Hz), 7.01 (d, 1H, J=2.0 Hz), 7.71 (d, 1H, J=15.3 Hz), 8.00 (d, 1H, J=2.0 Hz).

Reference Example 9-2

To a dichloromethane (377 ml) solution of ethyl (2E)-3-(3-amino-5-chloropyridin-2-yl)acrylate (37.7 g) and trifluoroacetic acid (12.7 ml) was added tert-butyl 4-oxopiperidine-1-carboxylate (49.7 g). After stirring at room temperature for 15 minutes, sodium triacetoxyborohydride (70.5 g) was added, and stirred at 40° C. for 1.5 hours. After the reaction solution was brought back to room temperature, dichloromethane and a saturated aqueous sodium hydrogen carbonate solution were added and the solution was separated, and the aqueous layer was extracted with dichloromethane. The collected organic layer was dried over anhydrous sodium sulfate, and concentrated under reduced pressure. The resulting residue was dissolved in methanol (2 ml), and 1.7% palladium-fibroin (10 g) was added, followed by stirring at room temperature for 18 hours under a hydrogen atmosphere. The reaction solution was filtered, and the filtrate was concentrated under reduced pressure. The residue was purified by silica gel column chromatography to afford tert-butyl 4-{[5-chloro-2-(3-ethoxy-3-oxopropyl)pyridin-3-yl]amino}piperidine-1-carboxylate (55.3 g).

$^1$H NMR (400 MHz, CDCl$_3$) δ: 1.25 (t, 3H, J=7.0 Hz), 1.41-1.45 (m, 2H), 1.48 (s, 9H), 1.99-2.04 (m, 2H), 2.79-2.88 (m, 4H), 2.95-3.01 (m, 2H), 3.33-3.41 (m, 1H), 4.01-4.09 (m, 2H), 4.14 (q, 2H, J=7.0 Hz), 4.24 (d, 1H, J=7.0 Hz), 6.81 (d, 1H, J=2.0 Hz), 7.82 (d, 1H, J=2.0 Hz).

Reference Example 9-3

Under ice cooling, to a tetrahydrofuran solution (500 ml) of tert-butyl 4-{[5-chloro-2-(3-ethoxy-3-oxopropyl)pyridin-3-yl]amino}piperidine-1-carboxylate (54.7 g) was added dropwise a tetrahydrofuran solution (1 M, 159 ml) of potassium tert-butoxide over 15 minutes. After stirring for 15 minutes at the same temperature, water was added to the reaction solution, and extracted with dichloromethane. The organic layer was washed with saturated sodium chloride solution, dried over anhydrous sodium sulfate, and concentrated under reduced pressure. The resulting residue was purified by silica gel column chromatography to afford tert-butyl 4-(7-chloro-2-oxo-3,4-dihydro-1,5-naphthyridin-1(2H)-yl)piperidine-1-carboxylate (31.2 g).

$^1$H NMR (400 MHz, CDCl$_3$) δ: 1.49 (s, 9H), 1.68-1.72 (m, 2H), 2.38-2.48 (m, 2H), 2.67-2.71 (m, 2H), 2.78-2.84 (m, 2H), 3.02-3.06 (m, 2H), 4.26-4.37 (m, 3H), 7.35 (d, 1H, J=2.0 Hz), 8.16 (d, 1H, J=2.0 Hz).

Reference Example 9-4

In accordance with the method of Reference Example 3-5, the compound of Reference Example 9-3 was used instead of the compound of Reference Example 3-4 to afford 7-chloro-1-piperidin-4-yl-3,4-dihydro-1,5-naphthyridin-2(1H)-one bis(trifluoroacetate).

$^1$H NMR (400 MHz, DMSO-D$_6$) δ: 1.87-1.91 (m, 2H), 2.61 (m, 2H), 2.69-2.78 (m, 2H), 2.97 (m, 2H), 3.02-3.10 (m, 2H), 3.35-3.38 (m, 2H), 4.17-4.23 (m, 1H), 4.88 (br m, 1H), 7.86 (s, 1H), 8.21 (s, 1H), 8.35 (br m, 1H), 8.67 (br m, 1H).

Reference Example 10

7-Chloro-3,3-dimethyl-1-piperidin-4-yl-3,4-dihydro-1,5-naphthyridin-2(1H)-one trifluoroacetate

[Chemical 31]

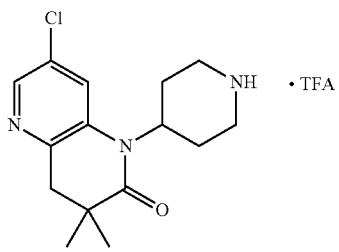

Reference Example 10-1

To a tetrahydrofuran solution (195 ml) of tert-butyl 4-(7-chloro-2-oxo-3,4-dihydro-1,5-naphthyridin-1(2H)-yl)piperidine-1-carboxylate (13.0 g) was added dropwise at –78° C. a tetrahydrofuran solution (1 M, 39.1 ml) of lithium hexamethyldisilazide. After stirring at the same temperature for 30 minutes, a tetrahydrofuran solution (65 ml) of methyl iodide (2.65 ml) was added dropwise. After stirring at the same temperature for 10 minutes and under ice cooling for 1 hour, ethyl acetate and water were added to the reaction solution, and the solution was separated. The organic layer was dried over anhydrous sodium sulfate, and concentrated under reduced pressure. The resulting residue was purified by silica gel column chromatography to afford tert-butyl 4-(7-chloro-3-methyl-2-oxo-3,4-dihydro-1,5-naphthyridin-1(2H)-yl)piperidine-1-carboxylate (12.2 g).

$^1$H NMR (400 MHz, CDCl$_3$) δ: 1.25 (d, 3H, J=7.0 Hz), 1.49 (s, 9H), 1.61-1.76 (m, 2H), 2.36-2.48 (m, 2H), 2.58-2.67 (m, 1H), 2.77-2.86 (m, 2H), 2.82 (dd, 1H, J=15.6, 11.7 Hz), 3.07 (dd, 1H, J=15.6, 5.5 Hz), 4.23-4.38 (m, 3H), 7.34 (d, 1H, J=2.0 Hz), 8.16 (d, 1H, J=2.0 Hz).

Reference Example 10-2

To a tetrahydrofuran solution (161 ml) of tert-butyl 4-(7-chloro-3-methyl-2-oxo-3,4-dihydro-1,5-naphthyridin-1(2H)-yl)piperidine-1-carboxylate (10.7 g) was added dropwise at –78° C. lithium hexamethyldisilazide (1.0 M tetrahydrofuran solution, 31.0 ml). After stirring at the same temperature for 15 minutes and under ice cooling for 20 minutes, a tetrahydrofuran solution (54 ml) of methyl iodide (2.10 ml) was added dropwise. After stirring at the same temperature for 10 minutes and at room temperature for 30 minutes, ethyl acetate and water were added to the reaction solution, and the solution was separated. The organic layer was dried over anhydrous sodium sulfate, and concentrated under reduced pressure. The resulting residue was purified by silica gel column chromatography to afford tert-butyl 4-(7-chloro-3,3-dimethyl-2-oxo-3,4-dihydro-1,5-naphthyridin-1(2H)-yl)piperidine-1-carboxylate (9.31 g).

$^1$H NMR (400 MHz, CDCl$_3$) δ: 1.13 (s, 6H), 1.49 (s, 9H), 1.65-1.68 (m, 2H), 2.38-2.49 (m, 2H), 2.78-2.84 (m, 2H), 2.91 (s, 2H), 4.27-4.39 (m, 3H), 7.33 (d, 1H, J=2.0 Hz), 8.17 (d, 1H, J=2.0 Hz).

Reference Example 10-3

In accordance with the method of Reference Example 3-5, the compound of Reference Example 10-2 was used instead of the compound of Reference Example 3-4 to afford 7-chloro-3,3-dimethyl-1-piperidin-4-yl-3,4-dihydro-1,5-naphthyridin-2(1H)-one trifluoroacetate.

$^1$H NMR (400 MHz, DMSO-D$_6$) δ: 1.03 (s, 6H), 1.83-1.86 (m, 2H), 2.66-2.77 (m, 2H), 2.91 (s, 2H), 3.03-3.12 (m, 2H), 3.35-3.38 (m, 2H), 4.22-4.30 (m, 1H), 7.87 (d, 1H, J=2.0 Hz), 8.23 (d, 1H, J=2.0 Hz), 8.39 (br m, 1H), 8.73 (br m, 1H).

Example 1

3-{[3'-Fluoro-4'-({4-[(3S)-7-fluoro-3-methyl-2-oxo-2,3-dihydro-1H-pyrido[2,3-b][1,4]oxazin-1-yl]piperidin-1-yl}carbonyl)biphenyl-2-yl]oxy}-2,2-dimethylpropanoic acid

[Chemical 32]

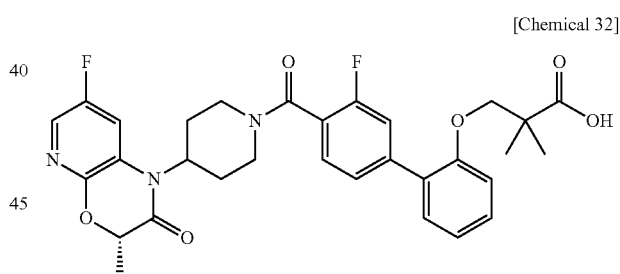

Example 1-1

At room temperature under shielded light, to N,N'-diisopropylcarbodiimide (99.75 g) was added copper(I) chloride (1.57 g), and then tert-butanol (83 ml) was added dropwise over 20 minutes, followed by stirring for 4 days. The supernatant (78 ml) was added dropwise to a dichloromethane suspension (270 ml) of 3-bromo-2,2-dimethylpropanoic acid (49.4 g) at room temperature over 30 minutes, followed by stirring for 18 hours. Acetic acid (18.8 ml) was added, and stirred for 1 hour. The reaction suspension was filtered, and ice water and sodium hydrogen carbonate were added to the filtrate for neutralization. After the precipitate was filtered off, the organic layer separated from the filtrate was washed with saturated sodium hydrogen carbonate, dried over anhydrous sodium sulfate, and concentrated under reduced pressure. After pentane was added to the residue, insolubles were filtered off, and the filtrate was concentrated under reduced pressure to afford tert-butyl 3-bromo-2,2-dimethylpropanoic acid (18.81 g).

$^1$H NMR (400 MHz, CDCl$_3$) δ: 1.27 (s, 6H), 1.46 (s, 9H), 3.47 (s, 2H).

Example 1-2

To an N,N-dimethylformamide solution (400 ml) of 4-bromo-2-fluorobenzoic acid (50.3 g) were added at room temperature potassium carbonate (63.5 g) and benzyl bromide (27.3 ml), followed by stirring at 60° C. for 3 hours. After the precipitate was filtered off, the filtrate was concentrated to 100 ml, and then diluted with ethyl acetate. This was washed sequentially with a saturated aqueous ammonium chloride solution, water and saturated sodium chloride solution, dried over anhydrous sodium sulfate, and concentrated under reduced pressure to afford benzyl 4-bromo-2-fluorobenzoate (70.5 g).

$^1$H NMR (400 MHz, CDCl$_3$) δ: 5.37 (s, 2H), 7.33-7.46 (m, 7H), 7.84 (t, 1H, J=8.4 Hz).

Example 1-3

To a mixed solvent solution of benzyl 4-bromo-2-fluorobenzoate (67.0 g) and 2-hydroxyphenylboronic acid (31.3 g) in 1,2-dimethoxyethane (750 ml) and water (250 ml) were added sodium carbonate (68.7 g) and tetrakis(triphenylphosphine)palladium (12.5 g), followed by stirring under heating at reflux for 5 hours. The reaction solution was brought back to room temperature, and then poured into ice water, followed by extraction with ethyl acetate. The organic layer was washed sequentially with water and saturated sodium chloride solution, dried over anhydrous sodium sulfate, and concentrated under reduced pressure. The resulting residue was purified by silica gel column chromatography, and further washed with hexane to afford benzyl 3-fluoro-2'-hydroxybiphenyl-4-carboxylate (62.5 g).

$^1$H NMR (500 MHz, CDCl$_3$) δ: 5.07 (s, 1H), 5.42 (s, 2H), 6.95 (d, 1H, J=8.0 Hz), 7.03 (td, 1H, J=7.6, 1.2 Hz), 7.28-7.32 (m, 2H), 7.34-7.42 (m, 5H), 7.48-7.49 (m, 2H), 8.06 (t, 1H, J=8.0 Hz).

Example 1-4

To an N,N-dimethylformamide solution (200 ml) of benzyl 3-fluoro-2'-hydroxybiphenyl-4-carboxylate (14.8 g) was added at room temperature cesium carbonate (37.5 g), followed by stirring for 30 minutes. To this was added an N,N-dimethylformamide solution (200 ml) of tert-butyl 3-bromo-2,2-dimethylpropanoate (27.2 g), followed by stirring at 60° C. for 3 days. After the reaction solution was concentrated under reduced pressure, water and ethyl acetate were added to the residue, and the solution was separated. The organic layer was washed with saturated sodium chloride solution, dried over anhydrous sodium sulfate, and concentrated under reduced pressure. The resulting residue was purified by silica gel column chromatography to afford benzyl 2'-(3-tert-butoxy-2,2-dimethyl-3-oxopropoxy)-3-fluorobiphenyl-4-carboxylate (15.0 g).

$^1$H NMR (400 MHz, CDCl$_3$) δ: 1.17 (s, 6H), 1.31 (s, 9H), 3.94 (s, 2H), 5.40 (s, 2H), 6.98 (d, 1H, J=8.0 Hz), 7.03 (td, 1H, J=7.4, 0.8 Hz), 7.31-7.42 (m, 7H), 7.47-7.49 (m, 2H), 7.96 (t, 1H, J=8.0 Hz).

Example 1-5

To a mixed solvent solution of benzyl 2'-(3-tert-butoxy-2, 2-dimethyl-3-oxopropoxy)-3-fluorobiphenyl-4-carboxylate (15.0 g) in water (75 ml) and tetrahydrofuran (300 ml) was added 10% palladium carbon (4.50 g), followed by stirring at room temperature for 7 hours under a hydrogen atmosphere. The reaction solution was filtered through Celite, and washed with methanol, and then the filtrate was concentrated under reduced pressure. The residue was dissolved in dichloromethane, dried over anhydrous sodium sulfate, and concentrated under reduced pressure to afford 2'-(3-tert-butoxy-2,2-dimethyl-3-oxopropoxy)-3-fluorobiphenyl-4-carboxylic acid (8.38 g).

$^1$H NMR (400 MHz, CDCl$_3$) δ: 1.19 (s, 6H), 1.34 (s, 9H), 3.96 (s, 2H), 7.00 (d, 1H, J=8.0 Hz), 7.05 (td, 1H, J=7.4, 0.8 Hz), 7.33-7.42 (m, 4H), 8.04 (t, 1H, J=8.0 Hz).

Example 1-6

At room temperature, to an N,N-dimethylformamide solution (10 ml) of (3S)-7-fluoro-3-methyl-1-piperidin-4-yl-1H-pyrido[2,3-b][1,4]oxazin-2(3H)-one (Reference Example 2) (434 mg) and 2'-(3-tert-butoxy-2,2-dimethyl-3-oxopropoxy)-3-fluorobiphenyl-4-carboxylic acid (636 mg) were added 2-(1H-benzotriazol-1-yl)-1,1,3,3-tetramethyluronium hexafluorophosphate (683 mg) and diisopropylethylamine (0.855 ml), followed by stirring for 24 hours. The reaction solution was poured into water (40 ml), and stirred for 6 hours. The precipitate was collected by filtration and dried to afford tert-butyl 3-{[3'-fluoro-4'-({4-[(3S)-7-fluoro-3-methyl-2-oxo-2,3-dihydro-1H-pyrido[2,3-b][1,4]oxazin-1-yl]piperidin-1-yl}carbonyl)biphenyl-2-yl]oxy}-2,2-dimethylpropanoate (940 mg).

$^1$H NMR (400 MHz, CDCl$_3$) δ: 1.15 (s, 6H), 1.31 (s, 9H), 1.60-1.95 (m, 5H), 2.50-2.59 (m, 2H), 2.80-3.36 (br m, 3H), 3.81-3.86 (m, 1H), 3.93 (s, 2H), 4.67-4.72 (m, 1H), 4.99-5.04 (m, 1H), 6.69-7.06 (m, 2H), 7.30-7.45 (m, 6H), 7.81-7.82 (m, 1H).

Example 1-7

A trifluoroacetic acid solution (10 ml) of tert-butyl 3-{[3'-fluoro-4'-({4-[(3S)-7-fluoro-3-methyl-2-oxo-2,3-dihydro-1H-pyrido[2,3-b][1,4]oxazin-1-yl]piperidin-1-yl}carbonyl)biphenyl-2-yl]oxy}-2,2-dimethylpropanoate (940 mg) was stirred at room temperature for 1 hour. After the reaction solution was concentrated under reduced pressure, the resulting residue was neutralized with a saturated aqueous sodium hydrogen carbonate solution, and then a 10% aqueous citric acid solution was added, followed by extraction with ethyl acetate. The organic layer was dried over anhydrous sodium sulfate, and concentrated under reduced pressure. Ethyl acetate-hexane was added to the residue to collect the precipitate by filtration. This was redissolved in ethanol, to which water was added, and the resulting precipitate was collected by filtration to afford 3-{[3'-fluoro-4'-({4-[(3S)-7-fluoro-3-methyl-2-oxo-2,3-dihydro-1H-pyrido[2,3-b][1,4]oxazin-1-yl]piperidin-1-yl}carbonyl)biphenyl-2-yl]oxy}-2, 2-dimethylpropanoic acid (668 mg).

$^1$H NMR (500 MHz, CDCl$_3$) δ: 1.21 (s, 6H), 1.60 (d, 3H, J=6.8 Hz), 1.70-1.79 (m, 1H), 1.86-1.94 (m, 1H), 2.53-2.61 (m, 2H), 2.83-2.89 (m, 1H), 3.09-3.18 (m, 2H), 3.80-3.82 (m, 1H), 3.97 (s, 2H), 4.33-4.63 (br m, 1H), 4.67-4.71 (m, 1H), 4.98-5.00 (m, 1H), 6.97 (d, 1H, J=8.3 Hz), 7.05 (t, 1H, J=7.3 Hz), 7.24-7.40 (m, 6H), 7.82 (d, 1H, J=2.0 Hz).

Example 2

3-{[4'-({4-[(3S)-7-Chloro-3-methyl-2-oxo-2,3-dihydro-1H-pyrido[2,3-b][1,4]oxazin-1-yl]piperidin-1-yl}carbonyl)-3'-fluorobiphenyl-2-yl]oxy}-2,2-dimethylpropanoic acid

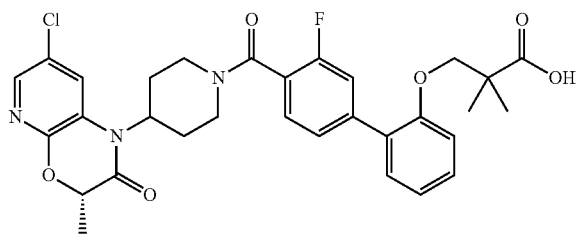

[Chemical 33]

In accordance with the method of Example 1, the compound of Reference Example 4 was used instead of the compound of Reference Example 2 in Example 1-6 to afford 3-{[4'-({4-[(3S)-7-chloro-3-methyl-2-oxo-2,3-dihydro-1H-pyrido[2,3-b][1,4]oxazin-1-yl]piperidin-1-yl}carbonyl)-3'-fluorobiphenyl-2-yl]oxy}-2,2-dimethylpropanoic acid.

$^1$H NMR (400 MHz, CDCl$_3$) δ: 1.21 (s, 6H), 1.60 (d, 3H, J=6.6 Hz), 1.69-1.77 (m, 1H), 1.87-1.94 (m, 1H), 2.54-2.64 (m, 2H), 2.82-2.89 (m, 1H), 3.13-3.23 (m, 1H), 3.78-3.82 (m, 1H), 3.97 (s, 2H), 4.33-4.63 (br m, 1H), 4.71 (q, 1H, J=6.6 Hz), 4.98-5.01 (m, 1H), 6.97 (d, 1H, J=8.2 Hz), 7.05 (t, 1H, J=7.4 Hz), 7.24-7.44 (m, 6H), 7.91 (d, 1H, J=2.0 Hz).

Example 3

3-{[4'-({4-[3,3-Dimethyl-2-oxo-7-(trifluoromethyl)-2,3-dihydro-1H-pyrido[2,3-b][1,4]oxazin-1-yl]piperidin-1-yl}carbonyl)-3'-fluorobiphenyl-2-yl]oxy}-2,2-dimethylpropanoic acid

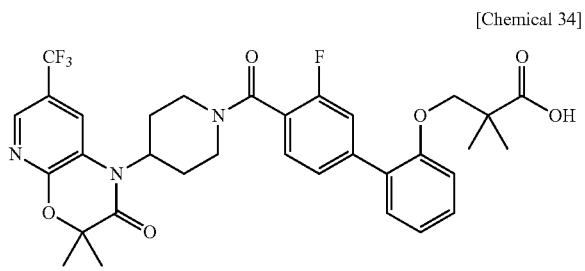 [SMILES: CC(C)(COc1ccccc1-c1ccc(C(=O)N2CCC(N3C(=O)C(C)(C)Oc4ncc(C(F)(F)F)cc43)CC2)c(F)c1)C(=O)O]

[Chemical 34]

In accordance with the method of Example 1, the compound of Reference Example 6 was used instead of the compound of Reference Example 2 in Example 1-6 to afford 3-{[4'-({4-[3,3-dimethyl-2-oxo-7-(trifluoromethyl)-2,3-dihydro-1H-pyrido[2,3-b][1,4]oxazin-1-yl]piperidin-1-yl}carbonyl)-3'-fluorobiphenyl-2-yl]oxy}-2,2-dimethylpropanoic acid.

$^1$H NMR (400 MHz, CD$_3$OD) δ: 1.19 (s, 6H), 1.52 (s, 3H), 1.53 (s, 3H), 1.78-1.82 (m, 1H), 1.93-1.96 (m, 1H), 2.60-2.80 (m, 2H), 3.00-3.10 (m, 1H), 3.34-3.40 (m, 1H), 3.73-3.76 (m, 1H), 4.01 (s, 2H), 4.40-4.55 (m, 1H), 7.01-7.10 (m, 2H), 7.33-7.42 (m, 5H), 8.02 (s, 1H), 8.23 (s, 1H).

Example 4

3-[(4'-{[4-(3,7-Dimethyl-2-oxo-2,3-dihydro-1H-pyrido[2,3-b][1,4]oxazin-1-yl)piperidin-1-yl]carbonyl}-3'-fluorobiphenyl-2-yl)oxy]-2,2-dimethylpropanoic acid

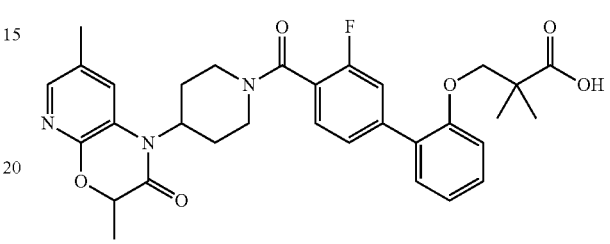

[Chemical 35]

In accordance with the method of Example 1, the compound of Reference Example 7 was used instead of the compound of Reference Example 2 in Example 1-6 to afford 3-[(4'-{[4-(3,7-dimethyl-2-oxo-2,3-dihydro-1H-pyrido[2,3-b][1,4]oxazin-1-yl)piperidin-1-yl]carbonyl}-3'-fluorobiphenyl-2-yl)oxy]-2,2-dimethylpropanoic acid.

$^1$H NMR (400 MHz, CDCl$_3$) δ: 1.21 (s, 6H), 1.58 (d, 3H, J=6.9 Hz), 1.66-1.75 (m, 1H), 1.85-1.94 (m, 1H), 2.34 (s, 3H), 2.54-2.61 (m, 2H), 2.83-2.89 (m, 1H), 3.15-3.21 (m, 1H), 3.76-3.79 (m, 1H), 3.96 (d, 1H, J=10.3 Hz), 3.99 (d, 1H, J=10.3 Hz), 4.36-4.83 (m, 1H), 4.67 (q, 1H, J=6.9 Hz), 4.97-5.00 (m, 1H), 6.97 (d, 1H, J=8.3 Hz), 7.04 (t, 1H, J=7.5 Hz), 7.25-7.41 (m, 6H), 7.77 (s, 1H).

Example 5

(3R)-3-[(4'-{[4-(7-Chloro-3,3-dimethyl-2-oxo-3,4-dihydro-1,5-naphthyridin-1(2H)-yl)piperidin-1-yl]carbonyl}-3'-fluorobiphenyl-2-yl)oxy]butanoic acid

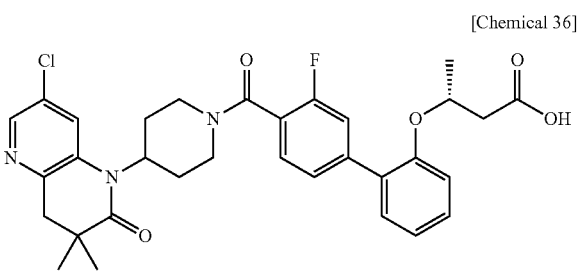 [SMILES: C[C@H](CC(=O)O)Oc1ccccc1-c1ccc(C(=O)N2CCC(N3C(=O)C(C)(C)Cc4ncc(Cl)cc43)CC2)c(F)c1]

[Chemical 36]

Example 5-1

Under ice cooling, to a dichloromethane solution (20.0 ml) of (S)-1,3-butanediol (519 mg) were added triethylamine (1.04 ml) and tert-butylchlorodiphenylsilane (1.63 ml), followed by stirring at room temperature overnight. The reaction solution was poured into a saturated aqueous ammonium chloride solution, and extracted with ethyl acetate. The organic layer was washed with saturated sodium chloride solution, dried over anhydrous sodium sulfate, and concentrated under reduced pressure. The resulting residue was purified by silica gel chromatography to afford (2S)-4-{[tert-butyl(diphenyl)silyl]oxy}butan-2-ol (1.69 g).

$^1$H NMR (400 MHz, CDCl$_3$) δ: 1.05 (9H, s), 1.22 (3H, d, J=6.3 Hz), 1.58-1.68 (1H, m), 1.69-1.81 (1H, m), 3.31 (1H, d, J=2.0 Hz), 3.80-3.91 (2H, m), 4.07-4.15 (1H, m), 7.37-7.50 (6H, m), 7.69 (4H, d, J=6.2 Hz).

Example 5-2

To a tetrahydrofuran solution (24 ml) of benzyl 3-fluoro-2'-hydroxybiphenyl-4-carboxylate (Example 1-3) (968 mg) were added at room temperature (2S)-4-{[tert-butyl(diphenyl)silyl]oxy}butan-2-ol (1.48 g), triphenylphosphine (1.18 g) and di-tert-butyl azodicarboxylate (1.04 g), followed by stirring overnight. The reaction solution was concentrated under reduced pressure, and the residue was purified by silica gel column chromatography to afford benzyl 2'-{[(1R)-3-{[tert-butyl(diphenyl)silyl]oxy}-1-methylpropyl]oxy}-3-fluorobiphenyl-4-carboxylate (2.25 g).

$^1$H NMR (500 MHz, CDCl$_3$) δ: 1.02 (s, 9H), 1.24 (d, 3H, J=6.3 Hz), 1.71-1.77 (m, 1H), 1.88-1.94 (m, 1H), 3.65-3.75 (m, 2H), 4.71-4.77 (m, 1H), 5.39 (s, 2H), 7.00-7.09 (m, 2H), 7.24-7.40 (m, 15H), 7.55-7.66 (m, 4H), 7.88-7.91 (m, 1H).

Example 5-3

Under a hydrogen atmosphere, a tetrahydrofuran suspension (45 ml) of benzyl 2'-{[(1R)-3-{[tert-butyl(diphenyl)silyl]oxy}-1-methylpropyl]oxy}-3-fluorobiphenyl-4-carboxylate (2.23 g) and 20% palladium hydroxide carbon (2.23 g) was stirred at room temperature overnight. The reaction solution was filtered through Celite, and washed with methanol, and the filtrate was concentrated under reduced pressure. The residue was dried to afford 2'-{[(1R)-3-{[tert-butyl(diphenyl)silyl]oxy}-1-methylpropyl]oxy}-3-fluorobiphenyl-4-carboxylic acid (1.31 g).

$^1$H NMR (500 MHz, CDCl$_3$) δ: 1.03 (s, 9H), 1.26 (d, 3H, J=5.9 Hz), 1.73-1.79 (m, 1H), 1.90-1.96 (m, 1H), 3.66-3.76 (m, 2H), 4.72-4.78 (m, 1H), 7.03 (t, 1H, J=7.3 Hz), 7.09 (d, 1H, J=7.8 Hz), 7.26-7.43 (m, 10H), 7.56-7.63 (m, 4H), 7.96 (t, 1H, J=7.8 Hz).

Example 5-4

To an N,N-dimethylformamide solution (6 ml) of 2'-{[(1R)-3-{[tert-butyl(diphenyl)silyl]oxy}-1-methylpropyl]oxy}-3-fluorobiphenyl-4-carboxylic acid (387 mg) were added at room temperature 7-chloro-3,3-dimethyl-1-piperidin-4-yl-3,4-dihydro-1,5-naphthyridin-2(1H)-one trifluoroacetate (Reference Example 10) (291 mg), diisopropylethylamine (0.497 ml) and 2-(1H-benzotriazol-1-yl)-1,1,3,3-tetramethyluronium hexafluorophosphate (298 mg), followed by stirring overnight. The reaction solution was diluted with ethyl acetate, washed sequentially with a 10% aqueous citric acid solution, a saturated aqueous sodium hydrogen carbonate solution and saturated sodium chloride solution, dried over anhydrous sodium sulfate, and concentrated under reduced pressure. The resulting residue was purified by silica gel column chromatography to afford 1-{1-[(2'-{[(1R)-3-{[tert-butyl(diphenyl)silyl]oxy}-1-methylpropyl]oxy}-3-fluorobiphenyl-4-yl)carbonyl]piperidin-4-yl}-7-chloro-3,3-dimethyl-3,4-dihydro-1,5-naphthyridin-2(1H)-one (530 mg).

$^1$H NMR (400 MHz, CDCl$_3$) δ: 1.03 (m, 9H), 1.14 (s, 6H), 1.26 (d, 3H, J=6.3 Hz), 1.64-1.97 (m, 4H), 2.54-2.61 (m, 2H), 2.83-2.96 (m, 3H), 3.13-3.19 (m, 1H), 3.67-3.81 (m, 3H), 4.15-4.71 (br m, 1H), 4.73-4.79 (m, 1H), 4.97-5.00 (m, 1H), 7.00-7.10 (m, 2H), 7.22-7.43 (m, 12H), 7.56-7.64 (m, 4H), 8.19 (d, 1H, J=2.0 Hz).

Example 5-5

To a tetrahydrofuran solution (11 ml) of 1-{1-[(2'-{[(1R)-3-{[tert-butyl(diphenyl)silyl]oxy}-1-methylpropyl]oxy}-3-fluorobiphenyl-4-yl)carbonyl]piperidin-4-yl}-7-chloro-3,3-dimethyl-3,4-dihydro-1,5-naphthyridin-2(1H)-one (525 mg) was added at room temperature a tetrahydrofuran solution (1 M, 1.28 ml) of tetrabutylammonium fluoride, followed by stirring for 3 hours. The reaction solution was diluted with ethyl acetate, washed sequentially with a saturated aqueous ammonium chloride solution and saturated sodium chloride solution, dried over anhydrous sodium sulfate, and concentrated under reduced pressure. The resulting residue was purified by silica gel column chromatography to afford 7-chloro-1-{1-[(3-fluoro-2'-{[(1R)-3-hydroxy-1-methylpropyl]oxy}biphenyl-4-yl)carbonyl]piperidin-4-yl}-3,3-dimethyl-3,4-dihydro-1,5-naphthyridin-2(1H)-one (301 mg).

$^1$H NMR (400 MHz, CDCl$_3$) δ: 1.14 (s, 3H), 1.15 (s, 3H), 1.29 (d, 3H, J=6.3 Hz), 1.69-1.73 (m, 1H), 1.78-1.94 (m, 3H), 2.58-2.62 (m, 2H), 2.85-2.92 (m, 3H), 3.17-3.25 (m, 1H), 3.65-3.73 (m, 2H), 3.81-3.85 (m, 1H), 4.23-4.67 (br m, 1H), 4.58-4.66 (m, 1H), 4.98-5.01 (m, 1H), 7.01-7.06 (m, 2H), 7.28-7.47 (m, 6H), 8.19 (d, 1H, J=2.0 Hz).

Example 5-6

Under ice cooling, to a mixed solvent solution of 7-chloro-1-{1-[(3-fluoro-2'-{[(1R)-3-hydroxy-1-methylpropyl]oxy}biphenyl-4-yl)carbonyl]piperidin-4-yl}-3,3-dimethyl-3,4-dihydro-1,5-naphthyridin-2(1H)-one (296 mg) in ethyl acetate (6 ml) and water (2 ml) were added 2,2,6,6-tetramethyl-1-piperidyloxy radical (4.0 mg) and potassium bromide (60.7 mg). To this was added dropwise a 5% aqueous sodium hypochlorite solution (0.812 ml), followed by stirring for 1 hour. 1 N hydrochloric acid was added to adjust the pH to around 4, and then 79% sodium chlorite (73.0 mg) was added, and stirred at room temperature for 3 hours. To the reaction solution were added water, a saturated aqueous sodium sulfite solution and a 10% aqueous citric acid solution, followed by extraction with dichloromethane. The organic layer was washed with saturated sodium chloride solution, dried over anhydrous sodium sulfate, and concentrated under reduced pressure. The resulting residue was purified by silica gel column chromatography to afford (3R)-3-[(4'-{[4-(7-chloro-3,3-dimethyl-2-oxo-3,4-dihydro-1,5-naphthyridin-1(2H)-yl)piperidin-1-yl]carbonyl}-3'-fluorobiphenyl-2-yl)oxy]butanoic acid (202 mg).

$^1$H NMR (400 MHz, CDCl$_3$) δ: 1.14 (s, 3H), 1.15 (s, 3H), 1.33 (d, 3H, J=6.3 Hz), 1.69-1.72 (m, 1H), 1.83-1.87 (m, 1H), 2.53 (dd, 1H, J=15.6, 5.5 Hz), 2.57-2.65 (m, 2H), 2.72 (dd, 1H, J=15.6, 7.0 Hz), 2.84-2.92 (m, 3H), 3.17-3.26 (m, 1H), 3.82-3.85 (m, 1H), 3.90-4.70 (br m, 1H), 4.75-4.81 (m, 1H), 4.96-5.00 (m, 1H), 7.02-7.07 (m, 2H), 7.26-7.43 (m, 6H), 8.19 (d, 1H, J=2.0 Hz).

Example 6

(3R)-3-[(4'-{[4-(7-Chloro-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]butanoic acid

[Chemical 37]

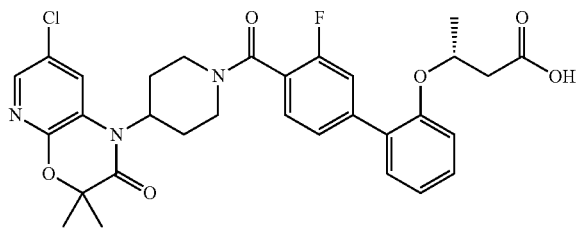

In accordance with the method of Example 5, the compound of Reference Example 3 was used instead of the compound of Reference Example 10 in Example 5-4 to afford (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]butanoic acid.

$^1$H NMR (500 MHz, CDCl$_3$) δ: 1.33 (d, 3H, J=5.9 Hz), 1.54 (s, 6H), 1.72-1.75 (m, 1H), 1.89-1.91 (m, 1H), 2.54 (dd, 1H, J=15.9, 5.6 Hz), 2.52-2.68 (br m, 2H), 2.74 (dd, 1H, J=15.9, 7.1 Hz), 2.86-2.92 (m, 1H), 3.17-3.28 (br m, 1H), 3.85-3.87 (m, 1H), 4.30-4.67 (br m, 1H), 4.76-4.80 (m, 1H), 5.00-5.03 (m, 1H), 7.04-7.07 (m, 2H), 7.26-7.35 (m, 4H), 7.38-7.45 (br, 2H), 7.92 (d, 1H, J=2.0 Hz).

Example 7

(3R)-3-[(4'-{[4-(7-Chloro-2-oxo-2,3-dihydro-1H-pyrido[2,3-b][1,4]oxazin-1-yl)piperidin-1-yl]carbonyl}-3'-fluorobiphenyl-2-yl)oxy]butanoic acid

[Chemical 38]

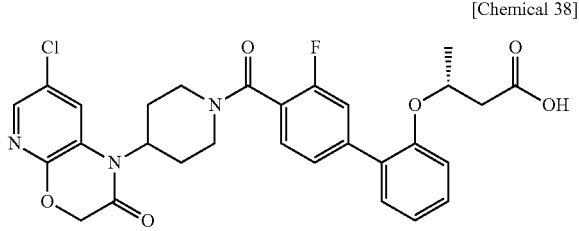 [SMILES: C[C@H](CC(=O)O)Oc1ccccc1-c1ccc(C(=O)N2CCC(N3C(=O)COc4ncc(Cl)cc43)CC2)c(F)c1]

In accordance with the method of Example 5, the compound of Reference Example 8 was used instead of the compound of Reference Example 10 in Example 5-4 to afford (3R)-3-[(4'-{[4-(7-chloro-2-oxo-2,3-dihydro-1H-pyrido[2,3-b][1,4]oxazin-1-yl)piperidin-1-yl]carbonyl}-3'-fluorobiphenyl-2-yl)oxy]butanoic acid.

$^1$H NMR (400 MHz, CDCl$_3$) δ: 1.33 (d, 3H, J=6.3 Hz), 1.75-1.78 (m, 1H), 1.92-1.95 (m, 1H), 2.53 (dd, 1H, J=15.8, 5.7 Hz), 2.56-2.65 (m, 2H), 2.73 (dd, 1H, J=15.8, 7.2 Hz), 2.85-2.92 (m, 1H), 3.15-3.26 (m, 1H), 3.84-3.87 (m, 1H), 4.00-4.71 (br m, 1H), 4.72 (s, 2H), 4.77-4.82 (m, 1H), 4.99-5.03 (m, 1H), 7.02-7.06 (m, 2H), 7.26-7.45 (m, 6H), 7.91 (d, 1H, J=2.0 Hz).

Example 8

(3R)-3-[(4'-{[4-(7-Chloro-2-oxo-3,4-dihydro-1,5-naphthyridin-1(2H)-yl)piperidin-1-yl]carbonyl}-3'-fluorobiphenyl-2-yl)oxy]butanoic acid

[Chemical 39]

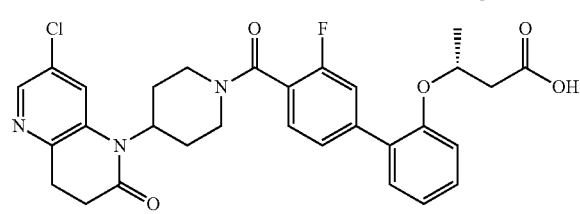

In accordance with the method of Example 5, the compound of Reference Example 9 was used instead of the compound of Reference Example 10 in Example 5-4 to afford (3R)-3-[(4'-{[4-(7-chloro-2-oxo-3,4-dihydro-1,5-naphthyridin-1(2H)-yl)piperidin-1-yl]carbonyl}-3'-fluorobiphenyl-2-yl)oxy]butanoic acid.

$^1$H NMR (400 MHz, CDCl$_3$) δ: 1.33 (d, 3H, J=6.3 Hz), 1.71-1.74 (m, 1H), 1.87-1.91 (m, 1H), 2.50-2.76 (m, 6H), 2.84-2.91 (m, 1H), 3.03-3.07 (m, 2H), 3.18-3.24 (m, 1H), 3.82-3.85 (m, 1H), 3.85-4.76 (br m, 1H), 4.76-4.84 (m, 1H), 4.97-5.00 (m, 1H), 7.02-7.07 (m, 2H), 7.26-7.40 (m, 6H), 8.18 (d, 1H, J=1.6 Hz).

Example 9

(2R,3R)-3-[(4'-{[4-(7-Chloro-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]-2-methylbutanoic acid

[Chemical 40]

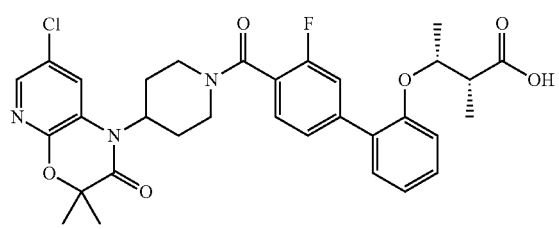

Example 9-1

In accordance with the methods of Examples 5-1, 5-2 and 1-5, (2S,3S)-2-methylbutan-1,3-diol (Tetrahedron Letters, 2006, 47(7), 1213-1215) was used instead of (S)-1,3-butanediol to afford 2'-{[(1R,2S)-3-{[tert-butyl(diphenyl)silyl]oxy}-1,2-dimethylpropyl]oxy}-3-fluorobiphenyl-4-carboxylic acid.

$^1$H NMR (500 MHz, CDCl$_3$) δ: 0.87 (d, 3H, J=7.3 Hz), 1.04 (s, 9H), 1.16 (d, 3H, J=5.9 Hz), 2.04-2.09 (m, 1H), 3.49

(dd, 1H, J=10.3, 6.6 Hz), 3.63 (dd, 1H, J=10.3, 4.9 Hz), 4.68-4.73 (m, 1H), 7.02 (td, 1H, J=7.3, 1.0 Hz), 7.08 (d, 1H, J=8.3 Hz), 7.27-7.42 (m, 10H), 7.56-7.63 (m, 4H), 7.96 (t, 1H, J=8.3 Hz).

Example 9-2

In accordance with the methods of Examples 5-4, 5-5 and 5-6, the compound of Example 9-1 was used instead of the compound of Example 5-3, and the compound of Reference Example 3 was used instead of the compound of Reference Example 10 to afford (2R,3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]-2-methylbutanoic acid.

$^1$H NMR (500 MHz, CDCl$_3$) δ: 1.13-1.15 (m, 3H), 1.25 (d, 3H, J=5.9 Hz), 1.53 (s, 6H), 1.71-1.74 (m, 1H), 1.88-1.91 (m, 1H), 2.57-2.64 (m, 2H), 2.75 (dq, 1H, J=11.2, 6.8 Hz), 2.86-2.91 (m, 1H), 3.16-3.25 (m, 1H), 3.82-3.85 (m, 1H), 4.31-4.66 (br m, 2H), 5.00-5.02 (m, 1H), 7.01-7.04 (m, 2H), 7.25-7.42 (m, 6H), 7.92 (d, 1H, J=2.0 Hz).

Example 10

(2S)-2-{[(4'-{[4-(7-Chloro-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]methyl}butanoic acid

[Chemical 41]

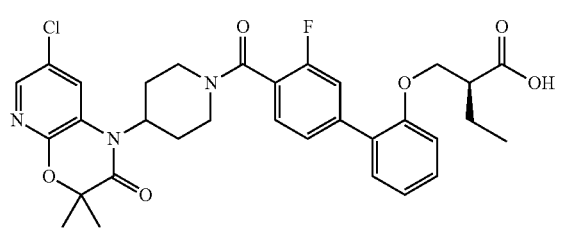

Example 10-1

In accordance with the methods of Examples 5-2 and 5-3, (2S)-2-({[tert-butyl(dimethyl)silyl]oxy}methyl)butan-1-ol (The Journal of Organic Chemistry, 1994, 59(18), 5317-5323) was used instead of the compound of Example 5-1 to afford 2'-{[(2S)-2-({[tert-butyl(dimethyl)silyl]oxy}methyl)butyl]oxy}-3-fluorobiphenyl-4-carboxylic acid.

$^1$H NMR (400 MHz, CDCl$_3$) δ: −0.04 (s, 6H), 0.84 (s, 9H), 0.91 (t, 3H, J=7.4 Hz), 1.32-1.44 (m, 2H), 1.76-1.85 (m, 1H), 3.53 (dd, 1H, J=9.8, 6.3 Hz), 3.59 (dd, 1H, J=9.8, 4.7 Hz), 4.00 (d, 2H, J=5.1 Hz), 7.02-7.06 (m, 2H), 7.33-7.42 (m, 4H), 8.07 (t, 1H, J=7.8 Hz).

Example 10-2

In accordance with the methods of Examples 5-4, 5-5 and 5-6, the compound of Reference Example 3 was used instead of the compound of Reference Example 10 to afford ((2S)-2-{[(4'-{[4-(7-chloro-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]methyl}butanoic acid.

$^1$H NMR (400 MHz, CDCl$_3$) δ: 0.95 (t, 3H, J=7.4 Hz), 1.53 (s, 6H), 1.57-1.74 (m, 3H), 1.87-1.90 (m, 1H), 2.58-2.61 (m, 2H), 2.72-2.78 (m, 1H), 2.83-2.90 (m, 1H), 3.15-3.23 (m, 1H), 3.81-3.85 (m, 1H), 4.08-4.46 (m, 3H), 4.97-5.00 (m, 1H), 6.98-7.06 (m, 2H), 7.26-7.42 (m, 6H), 7.92 (d, 1H, J=2.3 Hz).

Example 11

(2S)-3-[(4'-{[4-(7-Chloro-3,3-dimethyl-2-oxo-3,4-dihydro-1,5-naphthyridin-1(2H)-yl)piperidin-1-yl]carbonyl}-3'-fluorobiphenyl-2-yl)oxy]-2-methylpropanoic acid

[Chemical 42]

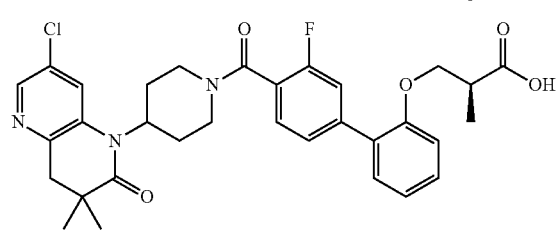

Example 11-1

To an N,N-dimethylformamide solution (50.0 ml) of (2R)-3-bromo-2-methyl-1-propanol (7.63 g) were added under ice cooling imidazole (7.13 g) and tert-butylchlorodiphenylsilane (14.8 ml), followed by stirring at room temperature for 5 hours. The reaction solution was poured into a saturated aqueous ammonium chloride solution, and extracted with ethyl acetate. The organic layer was washed with brine, dried over anhydrous sodium sulfate, and concentrated under reduced pressure. The resulting residue was purified by silica gel chromatography to afford {[(2R)-3-bromo-2-methylpropyl]oxy}(tert-butyl)diphenylsilane (19.2 g).

$^1$H NMR (400 MHz, CDCl$_3$) δ: 1.00 (d, 3H, J=6.7 Hz), 1.06 (s, 9H), 1.98-2.12 (m, 1H), 3.50-3.67 (m, 4H), 7.37-7.49 (m, 6H), 7.64-7.72 (m, 4H).

Example 11-2

To an N,N-dimethylformamide solution (30 ml) of benzyl 3-fluoro-2'-hydroxybiphenyl-4-carboxylate (Example 1-3) (1.0 g) and {[(2R)-3-bromo-2-methylpropyl]oxy}(tert-butyl)diphenylsilane (1.5 g) was added at room temperature cesium carbonate (2.4 g), followed by stirring at 60° C. for 1 hour. Ethyl acetate and water were added to the reaction solution, and the solution was separated. The organic layer was washed with saturated sodium chloride solution, dried over anhydrous sodium sulfate, and concentrated under reduced pressure. The resulting residue was purified by silica gel column chromatography to afford benzyl 2'-{[(2S)-3-{[tert-butyl(diphenyl)silyl]oxy}-2-methylpropyl]oxy}-3-fluorobiphenyl-4-carboxylate (1.5 g).

$^1$H NMR (400 MHz, CDCl$_3$) δ: 0.95 (d, 3H, J=7.0 Hz), 1.01 (s, 9H), 2.07-2.15 (m, 1H), 3.54-3.64 (m, 2H), 3.93 (dd, 1H, J=9.0, 5.5 Hz), 4.05 (dd, 1H, J=9.0, 5.9 Hz), 5.40 (s, 2H), 6.98-7.06 (m, 2H), 7.22-7.42 (m, 13H), 7.47-7.49 (m, 2H), 7.57-7.59 (m, 4H), 7.87 (t, 1H, J=8.0 Hz).

Example 11-3

In accordance with the method of Example 5-3, the compound of Example 11-2 was used instead of the compound of Example 5-2 to afford 2'-{[(2S)-3-{[tert-butyl(diphenyl)silyl]oxy}-2-methylpropyl]oxy}-3-fluorobiphenyl-4-carboxylic acid.

$^1$H NMR (400 MHz, CDCl$_3$) δ: 0.96 (d, 3H, J=6.8 Hz), 1.02 (s, 9H), 2.10-2.16 (m, 1H), 3.57 (dd, 1H, J=9.8, 6.3 Hz), 3.63 (dd, 1H, J=9.8, 4.9 Hz), 3.95 (dd, 1H, J=8.8, 5.4 Hz), 4.06 (dd, 1H, J=8.8, 5.9 Hz), 7.00 (d, 1H, J=8.3 Hz), 7.05 (t, 1H, J=7.3 Hz), 7.25-7.40 (m, 10H), 7.59 (m, 4H), 7.93 (t, 1H, J=8.1 Hz).

Example 11-4

In accordance with the methods of Examples 5-4, 5-5 and 5-6, the compound of Example 11-3 was used instead of the compound of Example 5-3 to afford (2S)-3-[(4'-{[4-(7-chloro-3,3-dimethyl-2-oxo-3,4-dihydro-1,5-naphthyridin-1(2H)-yl)piperidin-1-yl]carbonyl}-3'-fluorobiphenyl-2-yl)oxy]-2-methylpropanoic acid.

$^1$H NMR (400 MHz, CDCl$_3$) δ: 1.13-1.14 (m, 6H), 1.22 (d, 3H, J=7.0 Hz), 1.68-1.71 (m, 1H), 1.83-1.86 (m, 1H), 2.59-2.62 (m, 2H), 2.83-2.92 (m, 3H), 3.16-3.23 (m, 1H), 3.53-3.60 (m, 1H), 3.80-3.84 (m, 1H), 4.06-4.15 (m, 2H), 4.20-4.80 (m, 1H), 4.95-4.99 (m, 1H), 6.98-7.07 (m, 2H), 7.29-7.41 (m, 6H), 8.19 (d, 1H, J=2.0 Hz).

Example 12

(2S)-3-[(4'-{[4-(7-Chloro-2-oxo-3,4-dihydro-1,5-naphthyridin-1(2H)-yl)piperidin-1-yl]carbonyl}-3'-fluorobiphenyl-2-yl)oxy]-2-methylpropanoic acid

[Chemical 43]

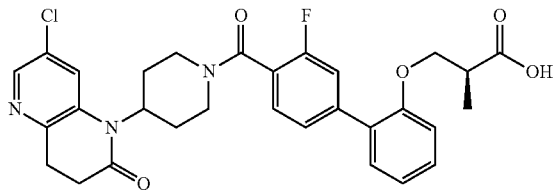

In accordance with the method of Example 11, the compound of Reference Example 9 was used instead of the compound of Reference Example 10 to afford (2S)-3-[(4'-{[4-(7-chloro-2-oxo-3,4-dihydro-1,5-naphthyridin-1(2H)-yl)piperidin-1-yl]carbonyl}-3'-fluorobiphenyl-2-yl)oxy]-2-methylpropanoic acid.

$^1$H NMR (400 MHz, CDCl$_3$) δ: 1.22 (d, 3H, J=7.4 Hz), 1.71-1.73 (m, 1H), 1.86-1.89 (m, 1H), 2.49-2.66 (m, 2H), 2.68-2.71 (m, 2H), 2.81-2.91 (m, 2H), 3.03-3.07 (m, 2H), 3.11-3.26 (m, 1H), 3.79-3.83 (m, 1H), 4.06-4.16 (m, 2H), 4.17-4.41 (m, 2H), 4.95-4.98 (m, 1H), 6.98-7.07 (m, 2H), 7.26-7.39 (m, 6H), 8.18 (d, 1H, J=2.0 Hz).

Example 13

(3R)-3-[(4'-{[4-(7-Chloro-3,3-dimethyl-2-oxo-2,3-dihydro-1H-pyrido[2,3-b][1,4]oxazin-1-yl)piperidin-1-yl]carbonyl}-3',5-difluorobiphenyl-2-yl)oxy]butanoic acid

[Chemical 44]

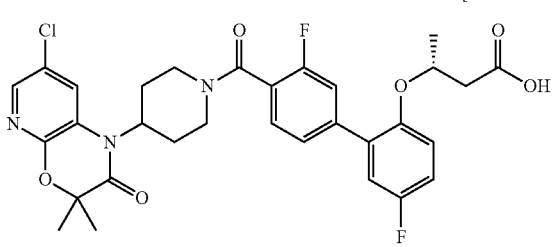

Example 13-1

In accordance with the method of Example 1-3, 5-fluoro-2-hydroxyphenylboronic acid was used instead of 2-hydroxyphenylboronic acid to afford benzyl 3,5'-difluoro-2'-hydroxybiphenyl-4-carboxylate.

$^1$H NMR (400 MHz, CDCl$_3$) δ: 4.96 (s, 1H), 5.41 (s, 2H), 6.89-6.90 (m, 1H), 6.98-7.00 (m, 2H), 7.32-7.42 (m, 5H), 7.47-7.48 (m, 2H), 8.06 (t, 1H, J=8.0 Hz).

Example 13-2

In accordance with the method of Example 5-2, the compound of Example 13-1 was used instead of the compound of Example 1-3 to afford benzyl 2'-{[(1R)-3-{[tert-butyl(diphenyl)silyl]oxy}-1-methylpropyl]oxy}-3,5'-difluorobiphenyl-4-carboxylate.

$^1$H NMR (400 MHz, CDCl$_3$) δ: 1.05 (s, 9H), 1.23 (d, 3H, J=6.3 Hz), 1.69-1.78 (m, 1H), 1.84-1.94 (m, 1H), 3.65-3.77 (m, 2H), 4.61-4.69 (m, 1H), 5.42 (s, 2H), 7.01-7.08 (m, 3H), 7.25-7.33 (m, 4H), 7.34-7.45 (m, 7H), 7.50 (d, 2H, J=7.8 Hz), 7.57-7.60 (m, 2H), 7.61-7.65 (m, 2H), 7.93 (t, 1H, J=7.8 Hz).

Example 13-3

In accordance with the method of Example 1-5, the compound of Example 13-2 was used instead of the compound of Example 1-4 to afford 2'-{[(1R)-3-{[tert-butyl(diphenyl)silyl]oxy}-1-methylpropyl]oxy}-3,5'-difluorobiphenyl-4-carboxylic acid.

$^1$H NMR (400 MHz, CDCl$_3$) δ: 1.01 (s, 9H), 1.19 (d, 3H, J=5.9 Hz), 1.65-1.78 (m, 1H), 1.81-1.94 (m, 1H), 3.60-3.76 (m, 2H), 4.56-4.68 (m, 1H), 6.97-7.06 (m, 3H), 7.23-7.44 (m, 8H), 7.52-7.66 (m, 4H), 7.95 (t, 1H, J=8.0 Hz).

Example 13-4

At room temperature, to a dichloromethane solution (10 ml) of 2'-{[(1R)-3-{[tert-butyl(diphenyl)silyl]oxy}-1-methylpropyl]oxy}-3,5'-difluorobiphenyl-4-carboxylic acid (180 mg) were added 7-chloro-3,3-dimethyl-1-piperidin-4-yl-1H-pyrido[2,3-b][1,4]oxazin-2(3H)-one trifluoroacetate (Reference Example 3) (132 mg), diisopropylethylamine (0.280 ml) and 2-(1H-benzotriazol-1-yl)-1,1,3,3-tetramethyluronium hexafluorophosphate (183 mg), followed by stirring overnight. The reaction solution was diluted with dichloromethane, washed sequentially with a 10% aqueous citric acid solution, a saturated aqueous sodium hydrogen carbonate solution and saturated sodium chloride solution, dried over anhydrous sodium sulfate, and concentrated under reduced pressure. The resulting residue was purified by silica gel column chromatography to afford 1-{1-[(2'-{[(1R)-3-{[tert-butyl(diphenyl)silyl]oxy}-1-methylpropyl]oxy}-3,5'-difluorobiphenyl-4-yl)carbonyl]piperidin-4-yl}-7-chloro-3,3-dimethyl-1H-pyrido[2,3-b][1,4]oxazin-2(3H)-one (256 mg).

$^1$H NMR (400 MHz, CDCl$_3$) δ: 1.02 (s, 9H), 1.20 (d, 3H, J=6.3 Hz), 1.53 (s, 6H), 1.60-1.76 (m, 2H), 1.81-1.94 (m, 2H), 2.46-2.65 (m, 2H), 2.79-2.91 (m, 1H), 3.05-3.24 (m, 1H), 3.61-3.82 (m, 3H), 4.20-5.04 (br m, 3H), 6.95-7.04 (m, 3H), 7.18-7.43 (m, 10H), 7.52-7.64 (m, 4H), 7.87-7.92 (m, 1H).

Example 13-5

In accordance with the method of Example 5-5, the compound of Example 13-4 was used instead of the compound of Example 5-4 to afford 7-chloro-1-{1-[(3,5'-difluoro-2'-{[(1R)-3-hydroxy-1-methylpropyl]oxy}biphenyl-4-yl)carbonyl]piperidin-4-yl}-3,3-dimethyl-1H-pyrido[2,3-b][1,4]oxazin-2(3H)-one.

$^1$H NMR (400 MHz, CDCl$_3$) δ: 1.22 (d, 3H, J=5.9 Hz), 1.53 (s, 6H), 1.56-1.94 (m, 4H), 2.48-2.68 (m, 2H), 2.80-2.94 (m, 1H), 3.10-3.29 (m, 1H), 3.60-3.74 (m, 2H), 3.75-3.87 (br m, 1H), 4.20-4.80 (m, 2H), 4.93-5.05 (br m, 1H), 6.95-7.05 (m, 3H), 7.24-7.50 (m, 4H), 7.91 (d, 1H, J=1.2 Hz).

Example 13-6

In accordance with the method of Example 5-6, the compound of Example 13-5 was used instead of the compound of Example 5-5 to afford (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3',5-difluorobiphenyl-2-yl)oxy]butanoic acid.

$^1$H NMR (400 MHz, CDCl$_3$) δ: 1.25 (d, 3H, J=5.9 Hz), 1.52 (s, 6H), 1.66-1.77 (m, 1H), 1.83-1.94 (m, 1H), 2.43-2.72 (m, 4H), 2.80-2.94 (m, 1H), 3.11-3.29 (br m, 1H), 3.75-3.87 (m, 1H), 4.25-4.72 (br m, 2H), 4.94-5.05 (m, 1H), 6.97-7.04 (m, 3H), 7.22-7.47 (m, 4H), 7.91 (s, 1H).

Example 14

(3R)-3-[(4'-{[4-(7-Chloro-3,3-dimethyl-2-oxo-3,4-dihydro-1,5-naphthyridin-1(2H)-yl)piperidin-1-yl]carbonyl}-3',5-difluorobiphenyl-2-yl)oxy]butanoic acid

[Chemical 45]

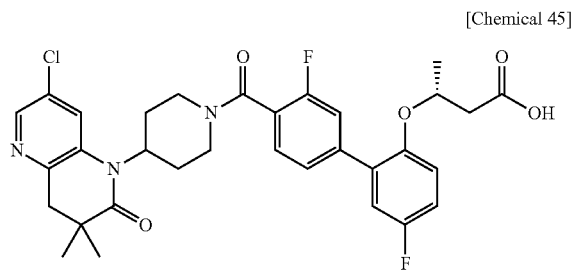 [SMILES: C[C@H](CC(=O)O)Oc1ccc(F)cc1-c1ccc(C(=O)N2CCC(N3C(=O)C(C)(C)Cc4ncc(Cl)cc43)CC2)c(F)c1]

In accordance with the method of Example 13, the compound of Reference Example 10 was used instead of the compound of Reference Example 3 to afford (3R)-3-[(4'-{[4-(7-chloro-3,3-dimethyl-2-oxo-3,4-dihydro-1,5-naphthyridin-1(2H)-yl)piperidin-1-yl]carbonyl}-3',5-difluorobiphenyl-2-yl)oxy]butanoic acid.

$^1$H NMR (400 MHz, CDCl$_3$) δ: 1.14 (m, 6H), 1.27 (d, 3H, J=6.3 Hz), 1.69-1.72 (m, 1H), 1.84-1.88 (m, 1H), 2.47-2.71 (m, 4H), 2.85-2.92 (m, 3H), 3.19-3.25 (m, 1H), 3.79-3.82 (m, 1H), 3.40-4.60 (br m, 1H), 4.62-4.68 (m, 1H), 4.96-5.00 (m, 1H), 7.00-7.03 (m, 3H), 7.26-7.44 (m, 4H), 8.20 (d, 1H, J=1.6 Hz).

Example 15

3-[(4'-{[4-(7'-Chloro-2'-oxospiro[cyclopropane-1,3'-pyrido[2,3-b][1,4]oxazin]-1'(2'H)-yl)piperidin-1-yl]carbonyl}-3'-methylbiphenyl-2-yl)oxy]-2,2-dimethylpropanoic acid

[Chemical 46]

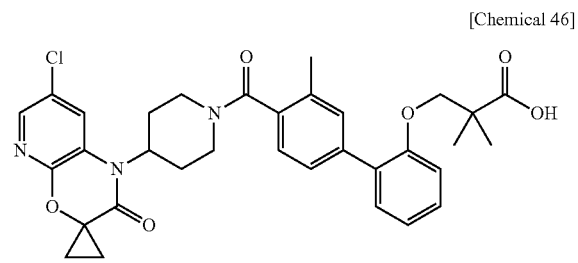 [SMILES: Cc1cc(-c2ccccc2OCC(C)(C)C(=O)O)ccc1C(=O)N1CCC(N2C(=O)C3(CC3)Oc3ncc(Cl)cc32)CC1]

Example 15-1

In accordance with the method of Example 1-2, 4-bromo-2-methylbenzoic acid was used instead of 4-bromo-2-fluorobenzoic acid to afford benzyl 4-bromo-2-methylbenzoate.

$^1$H NMR (400 MHz, CDCl$_3$) δ: 2.58 (s, 3H), 5.33 (s, 2H), 7.32-7.45 (m, 7H), 7.82 (d, 1H, J=8.2 Hz).

Example 15-2

To a 1,4-dioxane solution (99 ml) of benzyl 4-bromo-2-methylbenzoate (6.63 g) were added at room temperature 2-(4,4,5,5-tetramethyl-1,3,2-dioxaborolane-2-yl)phenol (4.86 ml), tripotassium phosphate hydrate (16.8 g), a [1,1'-bis(diphenylphosphino)ferrocene]dichloropalladium-dichloromethane complex (860 mg) and 1,1'-bis(diphenylphosphino)ferrocene (584 mg), followed by stirring at 80° C. for 8 hours. After the reaction solution was brought back to room temperature, a 10% aqueous citric acid solution and dichloromethane were added, and the solution was separated. The organic layer was dried over anhydrous sodium sulfate, and concentrated under reduced pressure. The resulting residue was purified by silica gel column chromatography to afford benzyl 2'-hydroxy-3-methylbiphenyl-4-carboxylate (6.01 g).

$^1$H NMR (400 MHz, CDCl$_3$) δ: 2.66 (s, 3H), 5.26 (s, 1H), 5.36 (s, 2H), 6.95-7.02 (m, 2H), 7.23-7.47 (m, 9H), 8.06 (d, 1H, J=8.6 Hz).

Example 15-3

In accordance with the methods of Examples 1-4 and 1-5, the compound of Example 15-2 was used instead of the compound of Example 1-3 to afford 2'-(3-tert-butoxy-2,2-dimethyl-3-oxopropoxy)-3-methylbiphenyl-4-carboxylic acid.

¹H NMR (500 MHz, DMSO-D₆) δ: 1.13 (s, 6H), 1.21 (s, 9H), 2.56 (s, 3H), 3.95 (s, 2H), 7.03-7.11 (m, 2H), 7.34-7.42 (m, 4H), 7.82 (d, 1H, J=7.8 Hz), 12.79 (br s, 1H).

Example 15-4

In accordance with the method of Example 5-4, the compound of Reference Example 1 was used instead of the compound of Reference Example 10, and the compound of Example 15-3 was used instead of the compound of Example 5-3 to afford tert-butyl 3-[(4'-{[4-(7'-chloro-2'-oxospiro[cyclopropane-1,3'-pyrido[2,3-b][1,4]oxazin]-1'(2'H)-yl)piperidin-1-yl]carbonyl}-3'-methylbiphenyl-2-yl)oxy]-2,2-dimethylpropanoate.

¹H NMR (400 MHz, CDCl₃) δ: 1.15 (s, 6H), 1.29 (s, 9H), 1.32-1.46 (m, 4H), 1.71-1.75 (m, 1H), 1.95-1.98 (m, 1H), 2.33 & 2.48 (s, total 3H), 2.53-2.67 (m, 2H), 2.84-2.89 (m, 1H), 3.08-3.15 (m, 1H), 3.73-3.79 (m, 1H), 3.92 (s, 2H), 4.29-4.33 (m, 1H), 5.05-5.08 (m, 1H), 6.94-7.05 (m, 2H), 7.26-7.41 (m, 6H), 7.87 (d, 1H, J=1.6 Hz).

Example 15-5

To a dichloromethane solution (13 ml) of tert-butyl 3-[(4'-{[4-(7'-Chloro-2'-oxospiro[cyclopropane-1,3'-pyrido[2,3-b][1,4]oxazin]-1'(2'H)-yl)piperidin-1-yl]carbonyl}-3'-methylbiphenyl-2-yl)oxy]-2,2-dimethylpropanoate (642 mg) was added at room temperature trifluoroacetic acid (6.5 ml), followed by stirring overnight. After the reaction solution was concentrated under reduced pressure, a saturated aqueous sodium hydrogen carbonate solution was added to the residue for neutralization, and then a 10% aqueous citric acid solution was added, and extracted with dichloromethane. The organic layer was washed with saturated sodium chloride solution, dried over anhydrous sodium sulfate, and concentrated under reduced pressure. The resulting residue was purified by silica gel column chromatography to afford 3-[(4'-{[4-(7'-chloro-2'-oxospiro[cyclopropane-1,3'-pyrido[2,3-b][1,4]oxazin]-1'(2'H)-yl)piperidin-1-yl]carbonyl}-3'-methylbiphenyl-2-yl)oxy]-2,2-dimethylpropanoic acid (440 mg).

¹H NMR (400 MHz, CDCl₃) δ: 1.20 (s, 6H), 1.31-1.45 (m, 4H), 1.69-1.72 (m, 1H), 1.93-1.96 (m, 1H), 2.26 & 2.44 (s, total 3H), 2.48-2.67 (m, 2H), 2.80-2.86 (m, 1H), 3.04-3.10 (m, 1H), 3.68-3.73 (m, 1H), 3.92-3.97 (m, 2H), 4.24-4.27 (m, 1H), 5.01-5.04 (m, 1H), 6.95-7.12 (m, 2H), 7.26-7.37 (m, 6H), 7.87-7.88 (m, 1H).

Example 16

(3R)-3-[(4'-{[4-(7-Chloro-3,3-dimethyl-2-oxo-2,3-dihydro-1H-pyrido[2,3-b][1,4]oxazin-1-yl)piperidin-1-yl]carbonyl}-3'-methylbiphenyl-2-yl)oxy]butanoic acid

[Chemical 47]

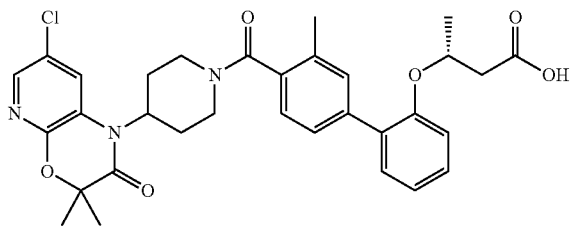

Example 16-1

In accordance with the methods of Examples 5-2 and 5-3, the compound of Example 15-2 was used instead of the compound of Example 1-3 to afford 2'-{[(1R)-3-{[tert-butyl(diphenyl)silyl]oxy}-1-methylpropyl]oxy}-3-methylbiphenyl-4-carboxylic acid.

¹H NMR (400 MHz, CDCl₃) δ: 1.03 (s, 9H), 1.25 (d, 3H, J=5.9 Hz), 1.72-1.79 (m, 1H), 1.89-1.97 (m, 1H), 2.62 (s, 3H), 3.66-3.78 (m, 2H), 4.70-4.75 (m, 1H), 7.03 (t, 1H, J=7.4 Hz), 7.08 (d, 1H, J=8.2 Hz), 7.25-7.43 (m, 10H), 7.57-7.64 (m, 4H), 8.00 (d, 1H, J=7.8 Hz).

Example 16-2

In accordance with the methods of Examples 13-4, 5-5 and 5-6, the compound of Example 16-1 was used instead of the compound of Example 13-3 to afford (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3'-methylbiphenyl-2-yl)oxy]butanoic acid.

¹H NMR (500 MHz, CDCl₃) δ: 1.31 (d, 3H, J=5.9 Hz), 1.53 (s, 6H), 1.67-1.71 (m, 1H), 1.90-1.93 (m, 1H), 2.32 & 2.49 (s, total 3H), 2.51-2.71 (m, 4H), 2.84-2.91 (m, 1H), 3.11-3.16 (m, 1H), 3.75-3.84 (br m, 1H), 4.33-4.45 (m, 1H), 4.68-4.72 (m, 1H), 5.03-5.07 (m, 1H), 7.03-7.07 (m, 2H), 7.26-7.38 (m, 6H), 7.91-7.92 (m, 1H).

Example 17

(3R)-3-[(4'-{[4-(7-Chloro-3,3-dimethyl-2-oxo-2,3-dihydro-1H-pyrido[2,3-b][1,4]oxazin-1-yl)piperidin-1-yl]carbonyl}-5-fluoro-3'-methylbiphenyl-2-yl)oxy]butanoic acid

[Chemical 48]

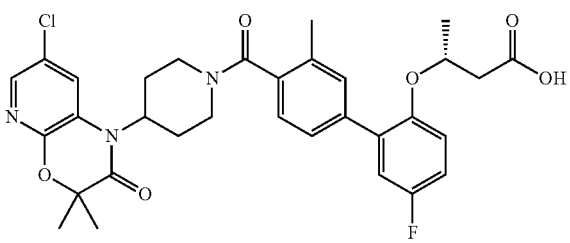

Example 17-1

In accordance with the method of Example 1-3, the compound of Example 15-1 was used instead of the compound of Example 1-2, and 5-fluoro-2-hydroxyphenylboronic acid was used instead of 2-hydroxyphenylboronic acid to afford benzyl 5'-fluoro-2'-hydroxy-3-methylbiphenyl-4-carboxylate.

¹H NMR (400 MHz, CDCl₃) δ: 2.66 (s, 3H), 5.13 (br s, 1H), 5.38 (s, 2H), 7.02-7.31 (m, 3H), 7.31-7.50 (m, 7H), 8.07 (d, 1H, J=8.6 Hz).

Example 17-2

In accordance with the methods of Examples 5-2 and 5-3, the compound of Example 17-1 was used instead of the compound of Example 1-3 to afford 2'-{[(1R)-3-{[tert-butyl (diphenyl)silyl]oxy}-1-methylpropyl]oxy}-5'-fluoro-3-methylbiphenyl-4-carboxylic acid.

$^1$H NMR (500 MHz, CDCl$_3$) δ: 1.03 (s, 9H), 1.20 (d, 3H, J=5.9 Hz), 1.69-1.75 (m, 1H), 1.85-1.91 (m, 1H), 2.62 (s, 3H), 3.65-3.75 (m, 2H), 4.56-4.63 (m, 1H), 6.98-7.00 (m, 1H), 7.04-7.06 (m, 1H), 7.28-7.43 (m, 9H), 7.57-7.63 (m, 4H), 8.00 (d, 1H, J=8.3 Hz).

Example 17-3

In accordance with the methods of Examples 13-4, 5-5 and 5-6, the compound of Example 17-2 was used instead of the compound of Example 13-3 to afford (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-5'-fluoro-3'-methylbiphenyl-2-yl)oxy]butanoic acid.

$^1$H NMR (400 MHz, CDCl$_3$) δ: 1.24 (d, 3H, J=6.3 Hz), 1.53 (s, 6H), 1.67-1.72 (m, 1H), 1.90-1.94 (m, 1H), 2.32 & 2.49 (s, total 3H), 2.45-2.67 (m, 4H), 2.85-2.91 (m, 1H), 3.10-3.18 (m, 1H), 3.71-3.84 (m, 1H), 4.30-4.46 (m, 1H), 4.50-4.58 (m, 1H), 5.03-5.07 (m, 1H), 6.99-7.04 (m, 3H), 7.28-7.37 (m, 4H), 7.93 (d, 1H, J=2.0 Hz).

Example 18

3-[(3'-Chloro-4'-{[4-(7'-chloro-2'-oxospiro[cyclopropane-1,3'-pyrido[2,3-b][1,4]oxazin]-1'(2'H)-yl)piperidin-1-yl]carbonyl}biphenyl-2-yl)oxy]-2,2-dimethylpropanoic acid

[Chemical 49]

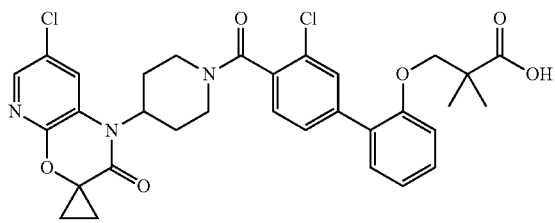

Example 18-1

In accordance with the methods of Examples 1-2 and 15-2, 4-bromo-2-chlorobenzoic acid was used instead of 4-bromo-2-fluorobenzoic acid to afford benzyl 3-chloro-2'-hydroxybiphenyl-4-carboxylate.

$^1$H NMR (400 MHz, CDCl$_3$) δ: 4.70 (s, 1H), 5.40 (s, 2H), 6.93 (d, 1H, J=7.4 Hz), 6.99-7.03 (m, 1H), 7.24-7.48 (m, 8H), 7.64 (d, 1H, J=1.6 Hz), 7.95 (d, 1H, J=7.8 Hz).

Example 18-2

In accordance with the method of Example 1-4, the compound of Example 18-1 was used instead of the compound of Example 1-3 to afford benzyl 2'-(3-tert-butoxy-2,2-dimethyl-3-oxopropoxy)-3-chlorobiphenyl-4-carboxylate.

$^1$H NMR (500 MHz, CDCl$_3$) δ: 1.18 (s, 6H), 1.29 (s, 9H), 3.94 (s, 2H), 5.39 (s, 2H), 6.98 (d, 1H, J=8.3 Hz), 7.02-7.05 (m, 1H), 7.26-7.49 (m, 8H), 7.65 (s, 1H), 7.89 (d, 1H, J=8.3 Hz).

Example 18-3

To a tetrahydrofuran (48 ml) and water (24 ml) mixed solvent suspension of benzyl 2'-(3-tert-butoxy-2,2-dimethyl-3-oxopropoxy)-3-chlorobiphenyl-4-carboxylate (2.40 g) was added lithium hydroxide monohydrate (224 mg). After the reaction solution was stirred at 60° C. for 17 hours, lithium hydroxide monohydrate (112 mg) was further added, and stirred at 60° C. for 6 hours. Tetrahydrofuran (40 ml) was further added, and stirred at 60° C. for 1 hour. After the reaction solution was brought back to room temperature, an aqueous ammonium chloride solution and dichloromethane were added, and the solution was separated. The organic layer was dried over anhydrous sodium sulfate, and concentrated under reduced pressure. Methanol was added to the resulting residue, and diluted with a large amount of water. The precipitated solid was collected by filtration and dried to afford 2'-(3-tert-butoxy-2,2-dimethyl-3-oxopropoxy)-3-chlorobiphenyl-4-carboxylic acid (1.69 g).

$^1$H NMR (400 MHz, DMSO-D$_6$) δ: 1.15 (s, 6H), 1.20 (s, 9H), 3.97 (s, 2H), 7.05-7.09 (m, 1H), 7.13-7.15 (m, 1H), 7.38-7.42 (m, 2H), 7.49-7.52 (m, 1H), 7.65-7.66 (m, 1H), 7.82 (d, 1H, J=7.8 Hz), 13.35 (br s, 1H).

Example 18-4

In accordance with the methods of Examples 5-4 and 15-5, the compound of Reference Example 1 was used instead of the compound of Reference Example 10, and the compound of Example 18-3 was used instead of the compound of Example 5-3 to afford 3-[(3'-chloro-4'-{[4-(7'-chloro-2'-oxospiro[cyclopropane-1,3'-pyrido[2,3-b][1,4]oxazin]-1'(2'H)-yl)piperidin-1-yl]carbonyl}biphenyl-2-yl)oxy]-2,2-dimethylpropanoic acid.

$^1$H NMR (400 MHz, CDCl$_3$) δ: 1.21 (s, 6H), 1.31-1.36 (m, 2H), 1.40-1.47 (m, 2H), 1.71-1.74 (m, 1H), 1.92-1.97 (m, 1H), 2.50-2.71 (m, 2H), 2.82-2.92 (m, 1H), 3.08-3.26 (m, 1H), 3.63-3.67 (m, 1H), 3.94-3.99 (m, 2H), 4.16-4.23 (m, 0.5H), 4.66-4.72 (m, 0.5H), 4.98-5.05 (m, 1H), 6.97 (d, 1H, J=8.2 Hz), 7.03-7.07 (m, 1H), 7.22-7.42 (m, 4H), 7.49-7.50 (m, 1H), 7.56-7.58 (m, 1H), 7.86-7.88 (m, 1H).

Example 19

(3R)-3-[(3'-Chloro-4'-{[4-(7-chloro-3,3-dimethyl-2-oxo-2,3-dihydro-1H-pyrido[2,3-b][1,4]oxazin-1-yl)piperidin-1-yl]carbonyl}biphenyl-2-yl)oxy]butanoic acid

[Chemical 50]

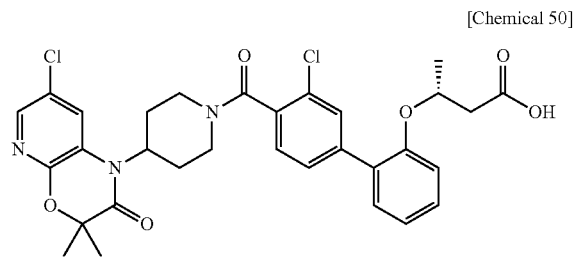 [SMILES: C[C@H](CC(=O)O)Oc1ccccc1-c1ccc(C(=O)N2CCC(N3C(=O)C(C)(C)Oc4ncc(Cl)cc43)CC2)c(Cl)c1]

Example 19-1

To a methanol solution (25 ml) of 4-bromo-2-chlorobenzoic acid (5.0 g) was added hydrochloric acid/a 1,4-dioxane solution (4 N, 25 ml), followed by heating at reflux for 90 minutes. The reaction solution was brought back to room temperature, and concentrated under reduced pressure. Dichloromethane and a saturated aqueous sodium hydrogen carbonate solution were added to the residue, and the solution was separated. The organic layer was washed with saturated sodium chloride solution, dried over anhydrous sodium sulfate, and concentrated under reduced pressure to afford methyl 4-bromo-2-chlorobenzoate (5.3 g).

$^1$H NMR (400 MHz, CDCl$_3$) δ: 3.93 (s, 3H), 7.46 (dd, 1H, J=8.2, 2.0 Hz), 7.64 (d, 1H, J=2.0 Hz), 7.73 (d, 1H, J=8.2 Hz).

Example 19-2

In accordance with the method of Example 15-2, the compound of Example 19-1 was used instead of the compound of Example 15-1 to afford methyl 3-chloro-2'-hydroxybiphenyl-4-carboxylate.

$^1$H NMR (400 MHz, CDCl$_3$) δ: 3.96 (s, 3H), 5.03 (s, 1H), 6.95 (d, 1H, J=7.8 Hz), 7.03 (t, 1H, J=7.3 Hz), 7.26-7.31 (m, 2H), 7.49 (dd, 1H, J=8.3, 1.5 Hz), 7.65 (d, 1H, J=1.5 Hz), 7.94 (d, 1H, J=8.3 Hz).

Example 19-3

In accordance with the method of Example 5-2, the compound of Example 19-2 was used instead of the compound of Example 1-3 to afford methyl 2'-{[(1R)-3-{[tert-butyl(diphenyl)silyl]oxy}-1-methylpropyl]oxy}-3-chlorobiphenyl-4-carboxylate.

$^1$H NMR (400 MHz, CDCl$_3$) δ: 1.01 (s, 9H), 1.23 (d, 3H, J=6.3 Hz), 1.69-1.80 (m, 1H), 1.83-1.96 (m, 1H), 3.60-3.78 (m, 2H), 3.91 (s, 3H), 4.67-4.80 (m, 1H), 7.00 (t, 1H, J=7.4 Hz), 7.06 (d, 1H, J=8.2 Hz), 7.21-7.43 (m, 9H), 7.51-7.64 (m, 5H), 7.76 (d, 1H, J=8.2 Hz).

Example 19-4

To a solution in tetrahydrofuran (5.0 ml), ethanol (5.0 ml) and water (5.0 ml) of methyl 2'-{[(1R)-3-{[tert-butyl(diphenyl)silyl]oxy}-1-methylpropyl]oxy}-3-chlorobiphenyl-4-carboxylate (565 mg) was added 1 N aqueous sodium hydroxide solution (1.48 ml), followed by stirring at 60° C. for 8 hours. After the reaction solution was concentrated under reduced pressure, a 10% aqueous citric acid solution and dichloromethane were added to the residue, and the solution was separated. The organic layer was washed with saturated sodium chloride solution, dried over anhydrous sodium sulfate, and concentrated under reduced pressure to afford 2'-{[(1R)-3-{[tert-butyl(diphenyl)silyl]oxy}-1-methylpropyl]oxy}-3-chlorobiphenyl-4-carboxylic acid.

$^1$H NMR (500 MHz, CDCl$_3$) δ: 1.06 (s, 9H), 1.29 (d, 3H, J=5.9 Hz), 1.75-1.84 (m, 1H), 1.90-2.00 (m, 1H), 3.69-3.81 (m, 2H), 4.75-4.83 (m, 1H), 7.06 (t, 1H, J=7.6 Hz), 7.12 (d, 1H, J=8.3 Hz), 7.27-7.47 (m, 9H), 7.58-7.68 (m, 5H), 8.00 (d, 1H, J=8.3 Hz).

Example 19-5

In accordance with the methods of Examples 13-4, 5-5 and 5-6, the compound of Example 19-4 was used instead of the compound of Example 13-3 to afford (3R)-3-[(3'-chloro-4'-{[4-(7-chloro-3,3-dimethyl-2-oxo-2,3-dihydro-1H-pyrido[2,3-b][1,4]oxazin-1-yl)piperidin-1-yl]carbonyl}biphenyl-2-yl)oxy]butanoic acid.

$^1$H NMR (500 MHz, CDCl$_3$) δ: 1.35 (d, 3H, J=5.9 Hz), 1.54-1.59 (m, 6H), 1.67-1.76 (m, 1H), 1.89-1.98 (m, 1H), 2.50-2.73 (m, 2H), 2.56 (dd, 1H, J=15.6, 5.4 Hz), 2.76 (dd, 1H, J=15.6, 7.3 Hz), 2.86-2.99 (m, 1H), 3.13-3.29 (m, 1H), 3.69-3.79 (m, 1H), 4.25-4.35 (m, 0.5H), 4.75-4.90 (m, 1.5H), 5.00-5.12 (m, 1H), 7.05-7.10 (m, 2H), 7.27-7.64 (m, 6H), 7.92-7.97 (m, 1H).

Example 20

3-{[4'-({4-[(3S)-7-Chloro-3-methyl-2-oxo-2,3-dihydro-1H-pyrido[2,3-b][1,4]oxazin-1-yl]piperidin-1-yl}carbonyl)biphenyl-2-yl]oxy}-2,2-dimethylpropanoic acid

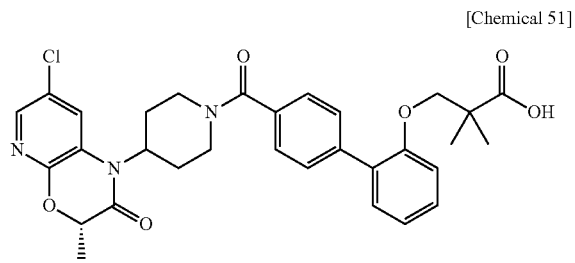 [SMILES: C[C@@H]1Oc2ncc(Cl)cc2N(C2CCN(C(=O)c3ccc(-c4ccccc4OCC(C)(C)C(=O)O)cc3)CC2)C1=O]

[Chemical 51]

Example 20-1

In accordance with the methods of Examples 1-3, 1-4 and 1-5, benzyl 4-iodobenzoate (The Journal of Organic Chemistry, 1994, 59(23), 7096-7098) was used instead of the compound of Example 1-2 to afford 2'-(3-tert-butoxy-2,2-dimethyl-3-oxopropoxy)biphenyl-4-carboxylic acid.

$^1$H NMR (400 MHz, CDCl$_3$) δ: 1.16 (s, 6H), 1.30 (s, 9H), 3.93 (s, 2H), 6.93-7.07 (m, 2H), 7.29-7.37 (m, 2H), 7.58-7.65 (m, 2H), 8.07-8.14 (m, 2H).

Example 20-2

In accordance with the methods of Examples 13-4 and 15-5, the compound of Reference Example 4 was used instead of the compound of Reference Example 3, and the compound of Example 20-1 was used instead of the compound of Example 13-3 to afford 3-{[4'-({4-[(3S)-7-chloro-3-methyl-2-oxo-2,3-dihydro-1H-pyrido[2,3-b][1,4]oxazin-1-yl]piperidin-1-yl}carbonyl)biphenyl-2-yl]oxy}-2,2-dimethylpropanoic acid.

$^1$H NMR (400 MHz, CDCl$_3$) δ: 1.18 (s, 6H), 1.58 (d, 3H, J=6.6 Hz), 1.62-1.99 (br m, 2H), 2.40-3.26 (br m, 5H), 3.78-5.07 (br m, 2H), 3.94 (s, 2H), 4.68 (q, 1H, J=6.6 Hz), 6.96 (d, 1H, J=8.6 Hz), 7.03 (t, 1H, J=7.4 Hz), 7.27-7.33 (m, 2H), 7.37-7.45 (m, 3H), 7.49 (d, 2H, J=8.2 Hz), 7.90 (d, 1H, J=2.3 Hz).

Example 21

3-[(4'-{[4-(7-Chloro-3,3-dimethyl-2-oxo-2,3-dihydro-1H-pyrido[2,3-b][1,4]oxazin-1-yl)piperidin-1-yl]carbonyl}-3'-hydroxybiphenyl-2-yl)oxy]-2,2-dimethylpropanoic acid

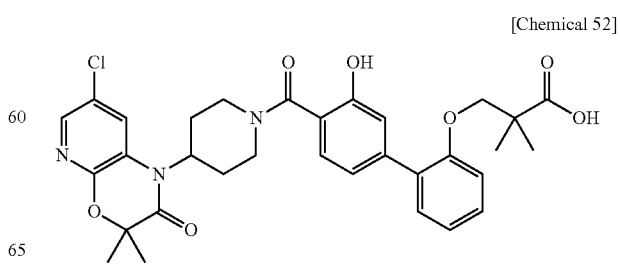

[Chemical 52]

Example 21-1

In accordance with the methods of Examples 15-2, 1-4 and 1-5, benzyl 2-(benzyloxy)-4-bromobenzoate (European Journal of Medicinal Chemistry, 2004, 39(1), 11-26) was used instead of the compound of Example 15-1 to afford 2'-(3-tert-butoxy-2,2-dimethyl-3-oxopropoxy)-3-hydroxybiphenyl-4-carboxylic acid.

$^1$H NMR (400 MHz, CDCl$_3$) δ: 1.18 (s, 6H), 1.31 (s, 9H), 3.93 (s, 2H), 6.96 (d, 1H, J=8.6 Hz), 7.01 (t, 1H, J=7.8 Hz), 7.10 (d, 1H, J=7.8 Hz), 7.14 (s, 1H), 7.29-7.40 (m, 2H), 7.89 (d, 1H, J=8.2 Hz).

Example 21-2

In accordance with the methods of Examples 13-4 and 15-5, the compound of Example 21-1 was used instead of the compound of Example 13-3 to afford 3-[(4'-{[4-(7-chloro-3,3-dimethyl-2-oxo-2,3-dihydro-1H-pyrido[2,3-b][1,4]oxazin-1-yl)piperidin-1-yl]carbonyl}-3'-hydroxybiphenyl-2-yl)oxy]-2,2-dimethylpropanoic acid.

$^1$H NMR (500 MHz, CDCl$_3$) δ: 1.26 (s, 6H), 1.56 (s, 6H), 1.82-1.90 (br m, 2H), 2.64-2.76 (br m, 2H), 3.00-3.11 (br m, 2H), 4.01 (s, 2H), 4.35-4.46 (br m, 1H), 4.54-4.66 (br m, 2H), 6.99 (d, 1H, J=8.3 Hz), 7.02 (dd, 1H, J=7.8, 1.5 Hz), 7.06 (t, 1H, J=7.6 Hz), 7.16 (s, 1H), 7.26-7.37 (br m, 3H), 7.44 (d, 1H, J=2.4 Hz), 7.95 (d, 1H, J=2.0 Hz).

Example 22

3-[(4'-{[4-(7-Chloro-3,3-dimethyl-2-oxo-2,3-dihydro-1H-pyrido[2,3-b][1,4]oxazin-1-yl)piperidin-1-yl]carbonyl}-3'-nitrobiphenyl-2-yl)oxy]-2,2-dimethylpropanoic acid

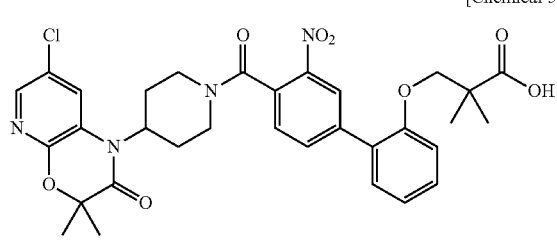

[Chemical 53]

Example 22-1

To a methanol solution (50 ml) of 4-bromo-2-nitrobenzoic acid (2.54 g) was added concentrated sulfuric acid (1.0 ml), followed by heating at reflux for 4 hours. The reaction solution was concentrated under reduced pressure, and water (20 ml) was added to the residue. Under ice cooling, 5 N aqueous sodium hydroxide solution (2.0 ml) and a saturated aqueous sodium hydrogen carbonate solution were added, and extracted with dichloromethane. The organic layer was washed with saturated sodium chloride solution, dried over anhydrous sodium sulfate, and concentrated under reduced pressure. The resulting residue was purified by silica gel column chromatography to afford methyl 4-bromo-2-nitrobenzoate (619 mg).

$^1$H NMR (500 MHz, CDCl$_3$) δ: 3.95 (s, 3H), 7.69 (d, 1H, J=8.3 Hz), 7.84 (dd, 1H, J=8.3, 2.0 Hz), 8.05 (d, 1H, J=2.0 Hz).

Example 22-2

In accordance with the methods of Examples 15-2, 1-4 and 19-4, the compound of Example 22-1 was used instead of the compound of Example 15-1 to afford 2'-(3-tert-butoxy-2,2-dimethyl-3-oxopropoxy)-3-nitrobiphenyl-4-carboxylic acid.

$^1$H NMR (500 MHz, CDCl$_3$) δ: 1.23 (s, 6H), 1.34 (s, 9H), 4.01 (s, 2H), 7.05 (dd, 1H, J=8.3, 1.0 Hz), 7.11 (ddd, 1H, J=7.3, 7.3, 1.0 Hz), 7.39 (dd, 1H, J=7.3, 2.0 Hz), 7.44 (ddd, 1H, J=8.3, 7.3, 2.0 Hz), 7.87 (dd, 1H, J=8.1, 2.0 Hz), 7.96 (d, 1H, J=8.1 Hz), 8.04 (d, 1H, J=2.0 Hz).

Example 22-3

In accordance with the methods of Example 13-4 and Example 15-5, the compound of Example 22-2 was used instead of the compound of Example 13-3 to afford 3-[(4'-{[4-(7-chloro-3,3-dimethyl-2-oxo-2,3-dihydro-1H-pyrido[2,3-b][1,4]oxazin-1-yl)piperidin-1-yl]carbonyl}-3'-nitrobiphenyl-2-yl)oxy]-2,2-dimethylpropanoic acid.

$^1$H NMR (400 MHz, CDCl$_3$) δ: 1.18 (s, 6H), 1.50 (s, 3H), 1.52 (s, 3H), 1.57-1.72 (br m, 1H), 1.74-1.99 (br m, 1H), 2.27-2.80 (br m, 2H), 2.80-3.02 (br m, 1H), 3.03-3.32 (br m, 1H), 3.48-3.70 (br m, 1H), 3.96 (d, 1H, J=10.6 Hz), 3.98 (d, 1H, J=10.6 Hz), 4.00-5.10 (br m, 2H), 6.99 (d, 1H, J=8.6 Hz), 7.07 (t, 1H, J=7.4 Hz), 7.23-7.27 (m, 1H), 7.29-7.83 (m, 4H), 7.90 (s, 1H), 8.32 (br s, 1H).

Example 23

1-{[(4'-{[4-(7-Chloro-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]methyl}cyclopropanecarboxylic acid

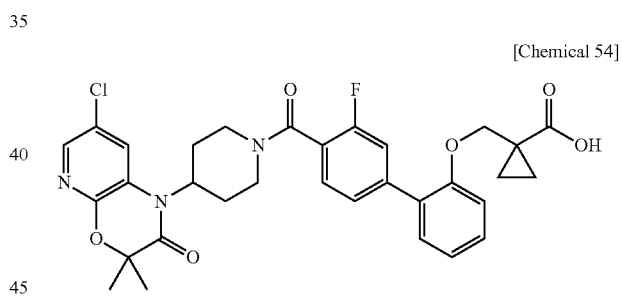

[Chemical 54]

Example 23-1

To an ethanol solution (93 ml) of diethyl cyclopropane-1,1-dicarboxylate (9.31 g) was added 1 N aqueous sodium hydroxide solution (50 ml), followed by stirring at room temperature for 9 hours. Ethanol was distilled off under reduced pressure, and the remaining aqueous solution was washed with dichloromethane. Under ice cooling, 5 N hydrochloric acid was added to the aqueous layer, and extracted with dichloromethane. The organic layer was washed with water and saturated sodium chloride solution, dried over anhydrous sodium sulfate, and concentrated under reduced pressure to afford 1-(ethoxycarbonyl)cyclopropanecarboxylic acid (6.38 g).

$^1$H NMR (400 MHz, CDCl$_3$) δ: 1.27 (t, 3H, J=7.0 Hz), 1.72-1.77 (m, 2H), 1.81-1.86 (m, 2H), 4.24 (q, 2H, J=7.0 Hz).

Example 23-2

At room temperature under shielded light, to N,N'-diisopropylcarbodiimide (99.75 g) was added copper(I) chloride (1.57 g), and then tert-butanol (83 ml) was added dropwise over 20 minutes, followed by stirring for 4 days. The supernatant (12.7 ml) was added to a dichloromethane solution (40 ml) of 1-(ethoxycarbonyl)cyclopropanecarboxylic acid (6.37 g), and heated at reflux for 3 hours. Hexane (50 ml) was added to the reaction solution, and the precipitate was filtered off. After the filtrate was concentrated under reduced pressure, a saturated aqueous sodium hydrogen carbonate solution was added to the residue, and extracted with dichloromethane. The organic layer was washed with saturated sodium chloride solution, dried over anhydrous sodium sulfate, and concentrated under reduced pressure. After hexane was added to the resulting residue, the precipitate was filtered off, and the filtrate was concentrated. The resulting residue was dissolved in tetrahydrofuran (25 ml), and 1 N aqueous sodium hydroxide solution (25 ml) was added, and stirred at room temperature overnight. After the reaction solution was concentrated under reduced pressure, 1 N aqueous sodium hydroxide solution (15 ml) was added to the residue, and washed with dichloromethane. A 10% aqueous citric acid solution was added to the aqueous layer to render it acidic, and extracted with dichloromethane. The organic layer was washed with saturated sodium chloride solution, dried over anhydrous sodium sulfate, and concentrated under reduced pressure to afford 1-(tert-butoxycarbonyl)cyclopropanecarboxylic acid (1.80 g).

$^1$H NMR (400 MHz, CDCl$_3$) δ: 1.46 (s, 9H), 1.60-1.66 (m, 2H), 1.73-1.80 (m, 2H).

Example 23-3

Under ice cooling, to a tetrahydrofuran solution (20 ml) of 1-(tert-butoxycarbonyl)cyclopropanecarboxylic acid (1.79 g) and triethylamine (1.48 ml) was added dropwise isobutyl chlorocarbonate (1.37 ml), followed by stirring for 1 hour. Under ice cooling, the supernatant was added dropwise to a mixed solvent solution of sodium borohydride (1.09 g) in tetrahydrofuran (20 ml) and water (5 ml), and stirred for 30 minutes. A 10% aqueous citric acid solution was added, and extracted with ethyl acetate. The organic layer was washed sequentially with a saturated aqueous sodium hydrogen carbonate solution and saturated sodium chloride solution, dried over anhydrous sodium sulfate, and concentrated under reduced pressure to afford tert-butyl 1-(hydroxymethyl)cyclopropanecarboxylate (1.28 g).

$^1$H NMR (400 MHz, CDCl$_3$) δ: 0.75-1.21 (m, 4H), 1.43 (s, 9H), 2.66 (br s, 1H), 3.56 (br s, 2H).

Example 23-4

In accordance with the methods of Example 5-2 and Example 1-5, the compound of Example 23-3 was used instead of the compound of Example 5-1 to afford 2'-{[1-(tert-butoxycarbonyl)cyclopropyl]methoxy}-3-fluorobiphenyl-4-carboxylic acid.

$^1$H NMR (400 MHz, CDCl$_3$) δ: 0.81-0.87 (m, 2H), 1.18-1.25 (m, 2H), 1.37 (s, 9H), 4.10 (s, 2H), 6.97 (d, 1H, J=8.2 Hz), 7.03 (t, 1H, J=7.2 Hz), 7.30-7.37 (m, 2H), 7.37-7.45 (m, 2H), 8.00 (t, 1H, J=7.2 Hz).

Example 23-5

In accordance with the methods of Example 13-4 and Example 15-5, the compound of Example 23-4 was used instead of the compound of Example 13-3 to afford 1-{[(4'-{[4-(7-chloro-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]methyl}cyclopropanecarboxylic acid.

$^1$H NMR (400 MHz, CDCl$_3$) δ: 0.92-0.98 (m, 2H), 1.29-1.35 (m, 2H), 1.52 (s, 6H), 1.66-1.76 (m, 1H), 1.83-1.93 (m, 1H), 2.49-2.68 (m, 2H), 2.80-2.92 (m, 1H), 3.11-3.27 (m, 1H), 3.34-4.72 (br m, 2H), 4.13 (s, 2H), 4.92-5.05 (m, 1H), 6.99 (d, 1H, J=7.8 Hz), 7.04 (t, 1H, J=7.4 Hz), 7.28-7.46 (m, 6H), 7.90 (d, 1H, J=2.0 Hz).

Example 24

(2S)-3-{[4'-({4-[(3S)-7-Chloro-3-methyl-2-oxo-2,3-dihydro-1H-pyrido[2,3-b][1,4]oxazin-1-yl]piperidin-1-yl}carbonyl)-3'-fluorobiphenyl-2-yl]oxy}-2-methylpropanoic acid

[Chemical 55]

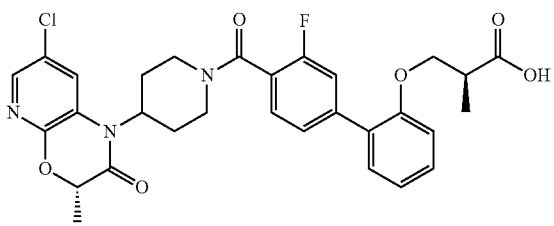

Example 24-1

In accordance with the method of Example 13-4, the compound of Reference Example 4 was used instead of the compound of Reference Example 3, and the compound of Example 11-3 was used instead of the compound of Example 13-3 to afford (3S)-1-{[1-[(2'-{[(2S)-3-{[tert-butyl(diphenyl)silyl]oxy}-2-methylpropyl]oxy}-3-fluorobiphenyl-4-yl)carbonyl]piperidin-4-yl}-7-chloro-3-methyl-1H-pyrido[2,3-b][1,4]oxazin-2(3H)-one.

$^1$H NMR (400 MHz, CDCl$_3$) δ: 0.94-0.97 (m, 3H), 1.02 (s, 9H), 1.61 (d, 3H, J=6.7 Hz), 1.63-1.69 (m, 1H), 1.86-1.95 (m, 1H), 2.09-2.15 (m, 1H), 2.47-2.62 (m, 2H), 2.83-2.92 (m, 1H), 3.05-3.22 (br m, 1H), 3.55-3.68 (m, 2H), 3.73-3.77 (m, 1H), 3.90-3.94 (m, 1H), 4.07-4.15 (m, 1H), 4.33-4.66 (br m, 1H), 4.72 (q, 1H, J=6.7 Hz), 4.99-5.03 (m, 1H), 6.99-7.06 (m, 2H), 7.22-7.41 (m, 12H), 7.58-7.61 (m, 4H), 7.90-7.92 (br s, 1H).

Example 24-2

To a tetrahydrofuran solution (20 ml) of (3S)-1-{1-[(2'-{[(2S)-3-{[tert-butyl(diphenyl)silyl]oxy}-2-methylpropyl]oxy}-3-fluorobiphenyl-4-yl)carbonyl]piperidin-4-yl}-7-chloro-3-methyl-1H-pyrido[2,3-b][1,4]oxazin-2(3H)-one (1.52 g) were added at room temperature acetic acid (0.22 ml) and a tetrahydrofuran solution (1 M, 3.76 ml) of tetrabutylammonium fluoride, followed by stirring overnight. The reaction solution was concentrated under reduced pressure, and the resulting residue was purified by silica gel column chromatography to afford (3S)-7-chloro-1-{[1-[(3-fluoro-2'-{[(2R)-3-hydroxy-2-methylpropyl]oxy}biphenyl-4-yl)carbonyl]piperidin-4-yl}-3-methyl-1H-pyrido[2,3-b][1,4]oxazin-2(3H)-one (920 mg).

$^1$H NMR (400 MHz, CDCl$_3$) δ: 0.96-0.98 (m, 3H), 1.61 (d, 3H, J=6.7 Hz), 1.67-1.78 (m, 1H), 1.87-1.97 (m, 1H), 2.11-2.16 (m, 1H), 2.54-2.63 (m, 2H), 2.85-2.92 (m, 1H), 3.16-

3.27 (br m, 1H), 3.51-3.59 (m, 2H), 3.82-3.86 (m, 1H), 3.92-4.03 (m, 2H), 4.32-4.63 (br m, 1H), 4.72 (q, 1H, J=6.7 Hz), 4.99-5.05 (m, 1H), 7.00-7.07 (m, 2H), 7.27-7.47 (m, 6H), 7.92 (d, 1H, J=2.0 Hz).

Example 24-3

To a mixed solvent solution of (3S)-7-chloro-1-{1-[(3-fluoro-2'-{[(2R)-3-hydroxy-2-methylpropyl]oxy}biphenyl-4-yl)carbonyl]piperidin-4-yl}-3-methyl-1H-pyrido[2,3-b][1,4]oxazin-2(3H)-one (920 mg) in acetonitrile (10 ml) and a neutral phosphate pH standard solution (pH 6.86) (8 ml) were added at room temperature 2,2,6,6-tetramethyl-1-piperidyloxy radical (25.3 mg), 79% sodium chlorite (371 mg) and a 5% aqueous sodium hypochlorite solution (0.041 ml). After the reaction solution was stirred at 50° C. overnight, 2,2,6,6-tetramethyl-1-piperidyloxy radical (25.3 mg) and a 5% aqueous sodium hypochlorite solution (0.041 ml) were added, and further stirred for 4 hours. The reaction solution was brought back to room temperature, and an aqueous sodium sulfite solution and a 10% aqueous citric acid solution were added, and extracted with dichloromethane. The organic layer was washed with saturated sodium chloride solution, dried over anhydrous sodium sulfate, and concentrated under reduced pressure. The resulting residue was purified by silica gel column chromatography to afford (2S)-3-{[4'-({4-[(3S)-7-chloro-3-methyl-2-oxo-2,3-dihydro-1H-pyrido[2,3-b][1,4]oxazin-1-yl]piperidin-1-yl}carbonyl)-3'-fluorobiphenyl-2-yl]oxy}-2-methylpropanoic acid (701 mg).
¹H NMR (500 MHz, CDCl₃) δ: 1.23 (d, 3H, J=7.3 Hz), 1.61 (d, 3H, J=6.8 Hz), 1.70-1.77 (m, 1H), 1.87-1.95 (m, 1H), 2.52-2.67 (br m, 2H), 2.85-2.93 (m, 2H), 2.94-3.32 (br m, 2H), 3.83-3.85 (m, 1H), 4.06-4.15 (m, 2H), 4.71 (q, 1H, J=6.8 Hz), 4.99-5.03 (m, 1H), 7.00 (d, 1H, J=8.3 Hz), 7.06 (t, 1H, J=7.3 Hz), 7.25-7.46 (m, 6H), 7.92 (d, 1H, J=2.0 Hz).

Example 25

(2S)-3-[(4'-{[4-(7-Chloro-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]-2-methylpropanoic acid

[Chemical 56]

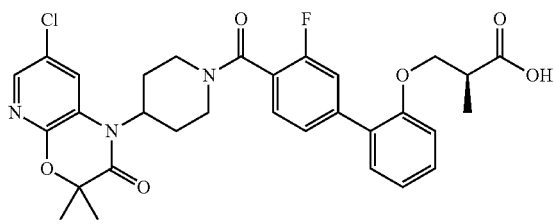

In accordance with the method of Example 24, the compound of Reference Example 3 was used instead of the compound of Reference Example 4 to afford (2S)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]-2-methylpropanoic acid.
¹H NMR (400 MHz, CDCl₃) δ: 1.23 (d, 3H, J=7.0 Hz), 1.53 (s, 6H), 1.71-1.73 (m, 1H), 1.87-1.91 (m, 1H), 2.54-2.66 (m, 2H), 2.84-2.93 (m, 2H), 3.12-3.28 (br m, 1H), 3.82-3.86 (m, 1H), 4.06-4.16 (m, 2H), 4.30-4.66 (br m, 1H), 4.98-5.01 (m, 1H), 7.00 (d, 1H, J=8.2 Hz), 7.06 (t, 1H, J=7.4 Hz), 7.26-7.47 (m, 6H), 7.92 (d, 1H, J=2.0 Hz).

Example 26

(2S)-3-{[4'-({4-[(3S)-7-Chloro-3-methyl-2-oxo-2,3-dihydro-1H-pyrido[2,3-b][1,4]oxazin-1-yl]piperidin-1-yl}carbonyl)-3',5-difluorobiphenyl-2-yl]oxy}-2-methylpropanoic acid

[Chemical 57]

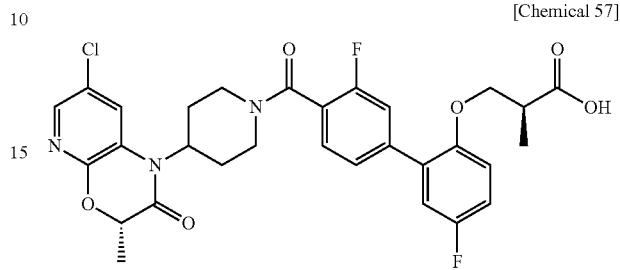

Example 26-1

In accordance with the methods of Examples 11-1, 11-2 and 11-3, the compound of Example 13-1 was used instead of the compound of Example 1-3 to afford 2'-{[(2S)-3-{[tert-butyl(diphenyl)silyl]oxy}-2-methylpropyl]oxy}-3,5'-difluorobiphenyl-4-carboxylic acid.
¹H NMR (400 MHz, CDCl₃) δ: 0.95 (d, 3H, J=7.0 Hz), 1.02 (s, 9H), 2.08-2.14 (m, 1H), 3.55 (dd, 2H, J=10.0, 6.6 Hz), 3.62 (dd, 2H, J=10.0, 4.7 Hz), 3.91 (dd, 2H, J=8.6, 5.5 Hz), 4.00 (dd, 2H, J=8.6, 5.9 Hz), 6.91-6.95 (m, 1H), 7.04-7.07 (m, 2H), 7.22-7.42 (m, 7H), 7.52-7.54 (m, 1H), 7.58-7.60 (m, 4H), 7.94 (t, 1H, J=8.0 Hz).

Example 26-2

In accordance with the method of Example 24, the compound of Example 26-1 was used instead of the compound of Example 11-3 to afford (2S)-3-{[4'-({4-[(3S)-7-chloro-3-methyl-2-oxo-2,3-dihydro-1H-pyrido[2,3-b][1,4]oxazin-1-yl]piperidin-1-yl}carbonyl)-3',5-difluorobiphenyl-2-yl]oxy}-2-methylpropanoic acid.
¹H NMR (400 MHz, CDCl₃) δ: 1.21 (d, 3H, J=7.4 Hz), 1.61 (d, 3H, J=6.7 Hz), 1.70-1.80 (m, 1H), 1.88-1.96 (m, 1H), 2.52-2.67 (m, 2H), 2.85-2.91 (m, 2H), 3.16-3.28 (br m, 1H), 3.80-3.84 (m, 1H), 4.00-4.10 (m, 2H), 4.25-4.67 (br m, 1H), 4.72 (q, 1H, J=6.7 Hz), 4.98-5.02 (m, 1H), 6.92-6.96 (m, 1H), 7.00-7.05 (m, 2H), 7.25-7.50 (m, 4H), 7.93 (d, 1H, J=2.4 Hz).

Example 27

(2S)-3-[(4'-{[4-(7-Chloro-3,3-dimethyl-2-oxo-2,3-dihydro-1H-pyrido[2,3-b][1,4]oxazin-1-yl)piperidin-1-yl]carbonyl}-3',5-difluorobiphenyl-2-yl)oxy]-2-methylpropanoic acid

[Chemical 58]

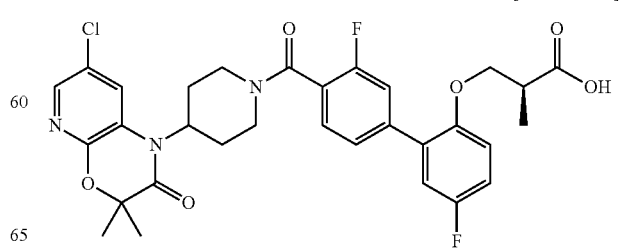

In accordance with the method of Example 24, the compound of Reference Example 3 was used instead of the compound of Reference Example 4, and the compound of Example 26-1 was used instead of the compound of Example 11-3 to afford (2S)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3',5-difluorobiphenyl-2-yl)oxy]-2-methylpropanoic acid.

$^1$H NMR (400 MHz, CDCl$_3$) δ: 1.22 (d, 3H, J=7.0 Hz), 1.53 (s, 6H), 1.71-1.75 (m, 1H), 1.88-1.92 (m, 1H), 2.55-2.67 (m, 2H), 2.84-2.92 (m, 2H), 3.17-3.27 (br m, 1H), 3.80-3.84 (m, 1H), 4.01-4.10 (m, 2H), 4.18-4.80 (br m, 1H), 4.98-5.02 (m, 1H), 6.92-6.95 (m, 1H), 7.00-7.05 (m, 2H), 7.29-7.45 (m, 4H), 7.92 (d, 1H, J=2.0 Hz).

Example 28

(3R)-3-{[4'-({4-[(3S)-7-Chloro-3-methyl-2-oxo-2,3-dihydro-1H-pyrido[2,3-b][1,4]oxazin-1-yl]piperidin-1-yl}carbonyl)-3'-fluorobiphenyl-2-yl]oxy}butanoic acid

[Chemical 59]

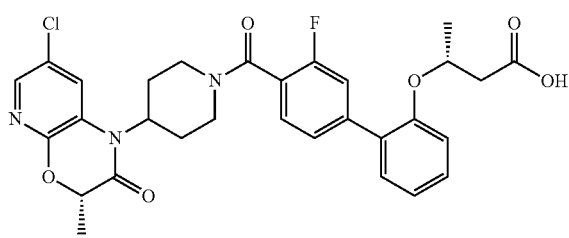

In accordance with the method of Example 24, the compound of Example 5-3 was used instead of the compound of Example 11-3 to afford (3R)-3-{[4'-({4-[(3S)-7-chloro-3-methyl-2-oxo-2,3-dihydro-1H-pyrido[2,3-b][1,4]oxazin-1-yl]piperidin-1-yl}carbonyl)-3'-fluorobiphenyl-2-yl]oxy}butanoic acid.

$^1$H NMR (500 MHz, CDCl$_3$) δ: 1.33 (d, 3H, J=5.9 Hz), 1.61 (d, 3H, J=6.9 Hz), 1.70-1.79 (m, 1H), 1.88-1.96 (m, 1H), 2.51-2.61 (m, 3H), 2.73 (dd, 1H, J=15.6, 7.3 Hz), 2.85-2.92 (m, 1H), 3.15-3.28 (m, 1H), 3.84-3.87 (m, 1H), 4.26-4.80 (br m, 1H), 4.70-4.80 (m, 2H), 4.99-5.03 (m, 1H), 7.04-7.07 (m, 2H), 7.26-7.35 (m, 4H), 7.39-7.46 (m, 2H), 7.91-7.93 (m, 1H).

Example 29

(3R)-3-{[4'-({4-[(3S)-7-Chloro-3-methyl-2-oxo-2,3-dihydro-1H-pyrido[2,3-b][1,4]oxazin-1-yl]piperidin-1-yl}carbonyl)-3',5-difluorobiphenyl-2-yl]oxy}butanoic acid

[Chemical 60]

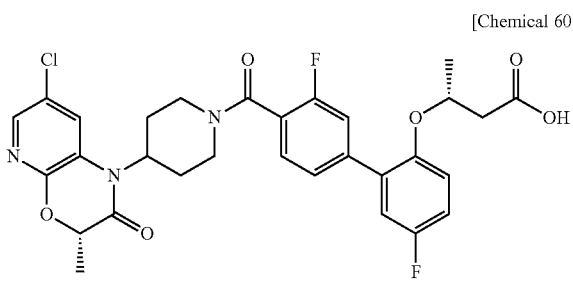

In accordance with the method of Example 24, the compound of Example 13-3 was used instead of the compound of Example 11-3 to afford (3R)-3-{[4'-({4-[(3S)-7-chloro-3-methyl-2-oxo-2,3-dihydro-1H-pyrido[2,3-b][1,4]oxazin-1-yl]piperidin-1-yl}carbonyl)-3',5-difluorobiphenyl-2-yl]oxy}butanoic acid.

$^1$H NMR (400 MHz, CDCl$_3$) δ: 1.27 (d, 3H, J=6.3 Hz), 1.61 (d, 3H, J=6.6 Hz), 1.71-1.80 (m, 1H), 1.88-1.96 (m, 1H), 2.46-2.70 (m, 4H), 2.85-2.92 (m, 1H), 3.13-3.30 (m, 1H), 3.85-4.70 (br m, 1H), 3.81-3.85 (m, 1H), 4.61-4.67 (m, 1H), 4.72 (q, 1H, J=6.6 Hz), 4.98-5.03 (m, 1H), 7.01-7.03 (m, 3H), 7.27-7.47 (m, 4H), 7.93 (d, 1H, J=2.0 Hz).

Example 30

(3R)-3-[(4'-{[4-(3,3,7-Trimethyl-2-oxo-2,3-dihydro-1H-pyrido[2,3-b][1,4]oxazin-1-yl)piperidin-1-yl]carbonyl}-3'-fluorobiphenyl-2-yl)oxy]butanoic acid

[Chemical 61]

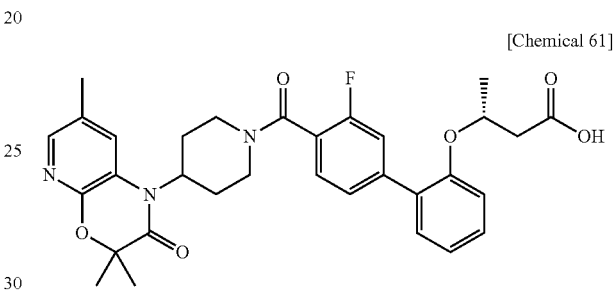

In accordance with the methods of Examples 13-4, 5-5 and 24-3, the compound of Reference Example 5 was used instead of the compound of Reference Example 3, and the compound of Example 5-3 was used instead of the compound of Example 13-3 to afford (3R)-3-[(4'-{[4-(3,3,7-trimethyl-2-oxo-2,3-dihydro-1H-pyrido[2,3-b][1,4]oxazin-1-yl)piperidin-1-yl]carbonyl}-3'-fluorobiphenyl-2-yl)oxy]butanoic acid.

$^1$H NMR (400 MHz, CDCl$_3$) δ: 1.32 (d, 3H, J=6.3 Hz), 1.51 (s, 6H), 1.71-1.74 (m, 1H), 1.88-1.91 (m, 1H), 2.35 (s, 3H), 2.53 (dd, 1H, J=15.6, 5.5 Hz), 2.55-2.65 (m, 2H), 2.73 (dd, 1H, J=15.6, 7.0 Hz), 2.86-2.92 (m, 1H), 3.18-3.26 (m, 1H), 3.82-3.85 (m, 1H), 4.34-4.88 (br m, 1H), 4.75-4.83 (m, 1H), 4.98-5.01 (m, 1H), 7.03-7.07 (m, 2H), 7.26-7.43 (m, 6H), 7.78 (s, 1H).

Example 31

(3R)-3-[(4'-{[4-(7-Chloro-2-oxo-2,3-dihydro-1H-pyrido[2,3-b][1,4]oxazin-1-yl)piperidin-1-yl]carbonyl}-3',5-difluorobiphenyl-2-yl)oxy]butanoic acid

[Chemical 62]

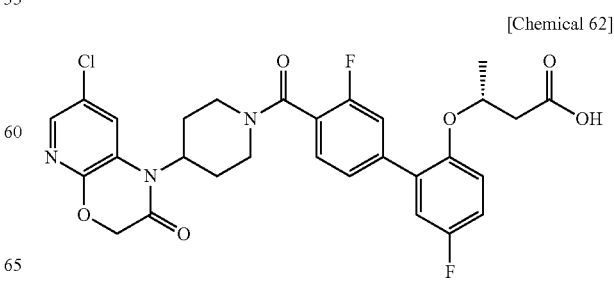

In accordance with the methods of Examples 13-4, 5-5 and 24-3, the compound of Reference Example 8 was used instead of the compound of Reference Example 3 to afford (3R)-3-[(4'-{[4-(7-chloro-2-oxo-2,3-dihydro-1H-pyrido[2,3-b][1,4]oxazin-1-yl)piperidin-1-yl]carbonyl}-3',5-difluorobiphenyl-2-yl)oxy]butanoic acid.

$^1$H NMR (400 MHz, CDCl$_3$) δ: 1.28 (d, 3H, J=6.3 Hz), 1.75-1.81 (m, 1H), 1.93-1.98 (m, 1H), 2.51 (dd, 1H, J=16.0, 5.1 Hz), 2.56-2.72 (m, 3H), 2.86-2.94 (m, 1H), 3.17-3.30 (br m, 1H), 3.82-3.87 (m, 1H), 4.31-4.69 (br m, 1H), 4.61-4.68 (m, 1H), 4.73 (s, 2H), 4.99-5.04 (m, 1H), 7.02-7.04 (m, 3H), 7.28-7.49 (m, 4H), 7.92 (d, 1H, J=2.4 Hz).

Example 32

(3R)-3-[(4'-{[4-(7-Chloro-2-oxo-3,4-dihydro-1,5-naphthyridin-1(2H)-yl)piperidin-1-yl]carbonyl}-3',5-difluorobiphenyl-2-yl)oxy]butanoic acid

[Chemical 63]

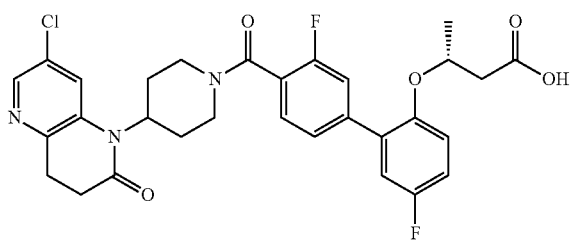

In accordance with the methods of Examples 13-4, 5-5 and 24-3, the compound of Reference Example 9 was used instead of the compound of Reference Example 3 to afford (3R)-3-[(4'-{[4-(7-chloro-2-oxo-3,4-dihydro-1,5-naphthyridin-1(2H)-yl)piperidin-1-yl]carbonyl}-3',5-difluorobiphenyl-2-yl)oxy]butanoic acid.

$^1$H NMR (400 MHz, CDCl$_3$) δ: 1.29 (d, 3H, J=6.3 Hz), 1.72-2.00 (m, 2H), 2.47-2.72 (m, 6H), 2.86-2.93 (m, 1H), 3.04-3.08 (m, 2H), 3.17-3.29 (br m, 1H), 3.80-3.84 (m, 1H), 4.20-4.64 (br m, 1H), 4.57-4.64 (m, 1H), 4.97-5.01 (m, 1H), 7.00-7.04 (m, 3H), 7.29-7.47 (m, 4H), 8.19 (d, 1H, J=1.6 Hz).

Example 33

(2S,3R)-3-[(4'-{[4-(7-Chloro-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]-2-methylbutanoic acid

[Chemical 64]

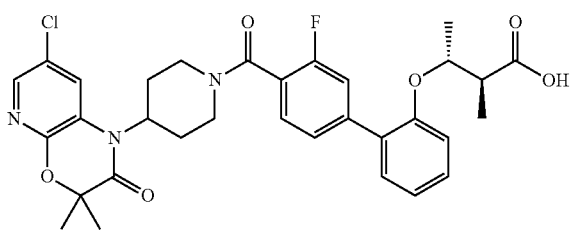

Example 33-1

Under ice cooling, a tetrahydrofuran solution (5 ml) of (1R,2R)-1-{[(4-methylphenyl)sulfonyl]amino}-2,3-dihydro-1H-inden-2-yl (2S,3S)-3-hydroxy-2-methylbutanoate (Journal of the American Chemical Society, 1996, 118, 2527-2528)(579 mg) was added dropwise to a tetrahydrofuran suspension (15 ml) of lithium aluminum hydride (136 mg). After stirring at room temperature for 1 and a half hours, sodium sulfate decahydrate, ethyl acetate, and water were added, and further stirred for 1 hour. The reaction solution was filtered through Celite, and the filtrate was concentrated under reduced pressure. The resulting residue was purified by silica gel column chromatography to afford (2R,3S)-2-methylbutan-1,3-diol (85.3 mg).

$^1$H NMR (400 MHz, CDCl$_3$) δ: 0.86 (d, 3H, J=7.0 Hz), 1.25 (d, 3H, J=6.3 Hz), 1.64-1.73 (m, 1H), 2.54-2.61 (br s, 1H), 2.61-2.69 (br s, 1H), 3.61-3.66 (m, 1H), 3.71-3.77 (m, 2H).

Example 33-2

In accordance with the methods of Examples 5-1, 5-2 and Example 5-3, the compound of Example 33-1 was used instead of (S)-1,3-butanediol to afford 2'-{[(1R,2R)-3-{[tert-butyl(diphenyl)silyl]oxy}-1,2-dimethylpropyl]oxy}-3-fluorobiphenyl-4-carboxylic acid.

$^1$H NMR (400 MHz, CDCl$_3$) δ: 0.82 (d, 3H, J=7.0 Hz), 1.00 (s, 9H), 1.25 (d, 3H, J=6.3 Hz), 1.84-1.91 (m, 1H), 3.47-3.49 (m, 2H), 4.82-4.88 (m, 1H), 7.00-7.08 (m, 2H), 7.20-7.38 (m, 10H), 7.49-7.60 (m, 4H), 7.94 (t, 1H, J=8.2 Hz).

Example 33-3

In accordance with the methods of Examples 13-4, 5-5 and Example 24-3, the compound of Example 33-2 was used instead of the compound of Example 13-3 to afford (2S,3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]-2-methylbutanoic acid.

$^1$H NMR (400 MHz, CDCl$_3$) δ: 1.17 (d, 3H, J=7.4 Hz), 1.27 (d, 3H, J=6.3 Hz), 1.54 (s, 6H), 1.70-1.76 (m, 1H), 1.87-1.93 (m, 1H), 2.55-2.72 (m, 3H), 2.85-2.93 (m, 1H), 3.16-3.28 (br m, 1H), 3.82-3.87 (m, 1H), 4.32-4.73 (br m, 1H), 4.68-4.73 (m, 1H), 4.99-5.03 (m, 1H), 7.03-7.06 (m, 2H), 7.25-7.43 (m, 6H), 7.92 (d, 1H, J=2.4 Hz).

Example 34

(3R)-3-[(4'-{[4-(7-Chloro-3,3-dimethyl-2-oxo-2,3-dihydro-1H-pyrido[2,3-b][1,4]oxazin-1-yl)piperidin-1-yl]carbonyl}-2',5'-difluorobiphenyl-2-yl)oxy]butanoic acid

[Chemical 65]

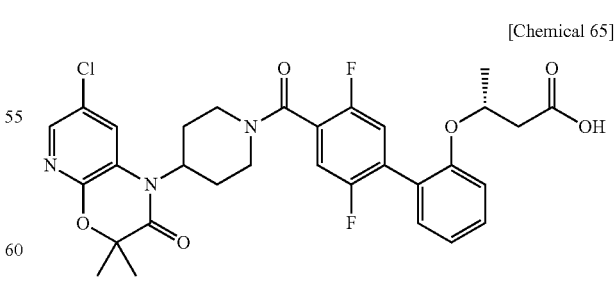

Example 34-1

In accordance with the methods of Examples 1-2, 1-3, 5-2 and 1-5, 4-chloro-2,5-difluorobenzoic acid was used instead of 4-bromo-2-fluorobenzoic acid to afford 2'-{[(1R)-3-{[tert-butyl(diphenyl)silyl]oxy}-1-methylpropyl]oxy}-2,5-difluorobiphenyl-4-carboxylic acid.

$^1$H NMR (400 MHz, CDCl$_3$) δ: 1.04 (s, 9H), 1.24 (d, 3H, J=5.8 Hz), 1.67-1.79 (m, 1H), 1.82-1.97 (m, 1H), 3.62-3.74 (m, 2H), 4.72-4.81 (m, 1H), 6.99-7.14 (m, 3H), 7.23-7.45 (m, 8H), 7.55-7.74 (m, 5H).

Example 34-2

In accordance with the methods of Examples 13-4, 5-5 and 24-3, the compound of Example 34-1 was used instead of the compound of Example 13-3 to afford (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-2',5'-difluorobiphenyl-2-yl)oxy]butanoic acid.

$^1$H NMR (400 MHz, CDCl$_3$) δ: 1.35 (d, 3H, J=5.8 Hz), 1.54 (s, 6H), 1.70-1.94 (m, 2H), 2.47-2.73 (m, 4H), 2.83-2.97 (m, 1H), 3.18-3.33 (m, 1H), 3.81-3.93 (m, 1H), 4.29-4.58 (br m, 1H), 4.76-4.84 (m, 1H), 4.95-5.03 (m, 1H), 7.02-7.20 (m, 4H), 7.24-7.29 (m, 1H), 7.36-7.43 (m, 2H), 7.93 (d, 1H, J=1.9 Hz).

Example 35

(3R)-3-[(4'-{[4-(7-Chloro-3,3-dimethyl-2-oxo-2,3-dihydro-1H-pyrido[2,3-b][1,4]oxazin-1-yl)piperidin-1-yl]carbonyl}-3',4-difluorobiphenyl-2-yl)oxy]butanoic acid

[Chemical 66]

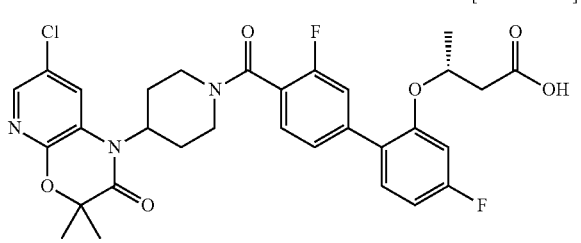

Example 35-1

In accordance with the methods of Examples 1-3, 5-2 and 1-5, 4-fluoro-2-hydroxyphenylboronic acid was used instead of 2-hydroxyphenylboronic acid to afford 2'-{[(1R)-3-{[tert-butyl(diphenyl)silyl]oxy}-1-methylpropyl]oxy}-3,4'-difluorobiphenyl-4-carboxylic acid.

$^1$H NMR (400 MHz, CDCl$_3$) δ: 1.04 (s, 9H), 1.28 (d, 3H, J=5.9 Hz), 1.72-1.84 (m, 1H), 1.84-2.01 (m, 1H), 3.64-3.80 (m, 2H), 4.65-4.79 (m, 1H), 6.74 (td, 1H, J=8.2, 2.3 Hz), 6.82 (dd, 1H, J=11.0, 2.3 Hz), 7.19-7.46 (m, 9H), 7.56-7.66 (m, 4H), 7.96 (t, 1H, J=8.2 Hz).

Example 35-2

In accordance with the methods of Examples 13-4, 5-5 and 24-3, the compound of Example 35-1 was used instead of the compound of Example 13-3 to afford (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3',4-difluorobiphenyl-2-yl)oxy]butanoic acid.

$^1$H NMR (400 MHz, CDCl$_3$) δ: 1.36 (d, 3H, J=6.2 Hz), 1.54 (s, 6H), 1.66-1.79 (m, 1H), 1.85-1.95 (m, 1H), 2.52-2.74 (m, 4H), 2.83-2.96 (m, 1H), 3.14-3.33 (m, 1H), 3.79-3.91 (m, 1H), 4.04-4.65 (br m, 1H), 4.69-4.84 (m, 1H), 4.96-5.05 (m, 1H), 6.71-6.83 (m, 2H), 7.18-7.34 (m, 3H), 7.37-7.48 (m, 2H), 7.93 (d, 1H, J=2.4 Hz).

Example 36

(3R)-3-[(4'-{[4-(7-Chloro-3,3-dimethyl-2-oxo-3,4-dihydro-1,5-naphthyridin-1(2H)-yl)piperidin-1-yl]carbonyl}-3'-methylbiphenyl-2-yl)oxy]butanoic acid

[Chemical 67]

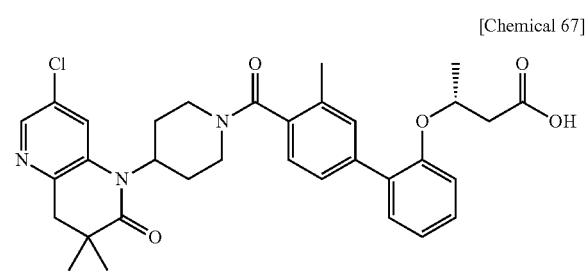 [SMILES: Cc1cc(-c2ccccc2O[C@H](C)CC(=O)O)ccc1C(=O)N1CCC(N2C(=O)C(C)(C)Cc3ncc(Cl)cc32)CC1]

In accordance with the methods of Examples 5-4, 5-5 and Example 24-3, Example 16-1 was used instead of the compound of Example 5-3 to afford (3R)-3-[(4'-{[4-(7-chloro-3,3-dimethyl-2-oxo-3,4-dihydro-1,5-naphthyridin-1(2H)-yl)piperidin-1-yl]carbonyl}-3'-methylbiphenyl-2-yl)oxy]butanoic acid.

$^1$H NMR (400 MHz, CDCl$_3$) δ: 1.14 (s, 6H), 1.31 (d, 3H, J=5.9 Hz), 1.64-1.68 (m, 1H), 1.86-1.89 (m, 1H), 2.31 & 2.49 (s, total 3H), 2.48-2.69 (m, 4H), 2.83-2.89 (m, 1H), 2.92 (s, 2H), 3.09-3.15 (m, 1H), 3.73-3.82 (m, 1H), 4.22-4.42 (br m, 1H), 4.65-4.72 (m, 1H), 5.00-5.04 (m, 1H), 7.03-7.07 (m, 2H), 7.28-7.36 (m, 6H), 8.19 (d, 1H, J=1.2 Hz).

Example 37

3-[(4'-{[4-(7-Chloro-3,3-dimethyl-2-oxo-3,4-dihydro-1,5-naphthyridin-1(2H)-yl)piperidin-1-yl]carbonyl}-3',5-difluorobiphenyl-2-yl)oxy]propanoic acid

[Chemical 68]

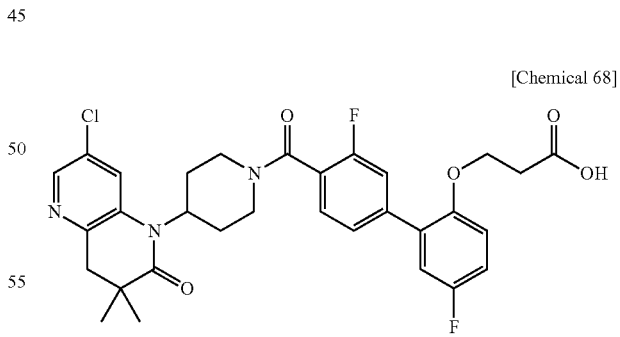

Example 37-1

In accordance with the methods of Examples 11-2 and 1-5, 2-(3-bromopropoxy)tetrahydro-2H-pyran was used instead of the compound of Example 11-1, and the compound of Example 13-1 was used instead of the compound of Example 1-3 to afford 3,5'-difluoro-2'-[3-(tetrahydro-2H-pyran-2-yloxy)propoxy]biphenyl-4-carboxylic acid.

¹H NMR (400 MHz, CDCl₃) δ: 1.40-1.85 (m, 6H), 1.95-2.04 (m, 2H), 3.41-3.51 (m, 2H), 3.75-3.86 (m, 2H), 4.05 (t, 2H, J=6.1 Hz), 4.51-4.54 (m, 1H), 6.94 (dd, 1H, J=8.4, 4.5 Hz), 6.99-7.09 (m, 2H), 7.34-7.41 (m, 2H), 8.03 (t, 1H, J=7.8 Hz).

Example 37-2

In accordance with the method of Example 5-4, the compound of Example 37-1 was used instead of the compound of Example 5-3 to afford 7-chloro-1-[1-({3,5'-difluoro-2'-[3-(tetrahydro-2H-pyran-2-yloxy)propoxy]biphenyl-4-yl}carbonyl)piperidin-4-yl]-3,3-dimethyl-3,4-dihydro-1,5-naphthyridin-2(1H)-one.

¹H NMR (400 MHz, CDCl₃) δ: 1.13 (s, 6H), 1.41-1.88 (m, 8H), 1.95-2.03 (m, 2H), 2.49-2.67 (br m, 2H), 2.79-2.92 (br m, 1H), 2.91 (s, 2H), 3.13-3.26 (br m, 1H), 3.40-3.50 (m, 2H), 3.68-3.86 (m, 3H), 4.05 (t, 2H, J=6.3 Hz), 4.18-4.63 (m, 2H), 4.93-5.02 (br m, 1H), 6.93 (dd, 1H, J=8.6, 4.3 Hz), 6.97-7.05 (m, 2H), 7.29-7.48 (m, 4H), 8.17 (d, 1H, J=2.0 Hz).

Example 37-3

To a methanol solution (10 ml) of 7-chloro-1-[1-({3,5'-difluoro-2'-[3-(tetrahydro-2H-pyran-2-yloxy)propoxy]biphenyl-4-yl}carbonyl)piperidin-4-yl]-3,3-dimethyl-3,4-dihydro-1,5-naphthyridin-2(1H)-one (300 mg) was added at room temperature p-toluenesulfonic acid monohydrate (8.7 mg), followed by stirring for 4 hours. After the reaction solution was concentrated under reduced pressure, a saturated aqueous sodium hydrogen carbonate solution and dichloromethane were added, and the solution was separated. The organic layer was washed with saturated sodium chloride solution, dried over anhydrous sodium sulfate, and concentrated under reduced pressure. The resulting residue was purified by silica gel column chromatography to afford 7-chloro-1-(1-{[3,5'-difluoro-2'-(3-hydroxypropoxy)biphenyl-4-yl]carbonyl}piperidin-4-yl)-3,3-dimethyl-3,4-dihydro-1,5-naphthyridin-2(1H)-one (231 mg).

¹H NMR (400 MHz, CDCl₃) δ: 1.13 (s, 6H), 1.64-1.73 (br m, 1H), 1.79-1.88 (br m, 1H), 1.91-1.99 (m, 2H), 2.50-2.67 (br m, 2H), 2.79-2.94 (br m, 1H), 2.90 (s, 2H), 3.11-3.27 (br m, 1H), 3.70 (t, 2H, J=5.9 Hz), 3.74-3.83 (br m, 1H), 4.07 (t, 2H, J=6.1 Hz), 4.17-4.64 (br m, 1H), 4.92-5.02 (br m, 1H), 6.94 (dd, 1H, J=9.8, 4.7 Hz), 6.98-7.05 (m, 2H), 7.24-7.37 (m, 3H), 7.40-7.50 (br m, 1H), 8.17 (d, 1H, J=2.0 Hz).

Example 37-4

In accordance with the method of Example 24-3, the compound of Example 37-3 was used instead of the compound of Example 24-2 to afford 3-[(4'-{[4-(7-chloro-3,3-dimethyl-2-oxo-3,4-dihydro-1,5-naphthyridin-1(2H)-yl)piperidin-1-yl]carbonyl}-3',5-difluorobiphenyl-2-yl)oxy]propanoic acid.

¹H NMR (500 MHz, CDCl₃) δ: 1.16 (s, 3H), 1.17 (s, 3H), 1.69-1.78 (m, 1H), 1.84-1.93 (m, 1H), 2.58-2.72 (m, 2H), 2.73 (t, 2H, J=5.9 Hz), 2.86-2.96 (br m, 1H), 2.95 (s, 2H), 3.15-3.32 (br m, 1H), 3.46-4.62 (br m, 2H), 4.23 (t, 2H, J=5.9 Hz), 4.95-5.04 (br m, 1H), 6.96-7.02 (m, 1H), 7.02-7.09 (m, 2H), 7.26-7.51 (m, 4H), 8.22 (d, 1H, J=1.5 Hz).

Example 38

(3R)-3-[2-(6-{[4-(7-Chloro-3,3-dimethyl-2-oxo-3,4-dihydro-1,5-naphthyridin-1(2H)-yl)piperidin-1-yl]carbonyl}-5-fluoropyridin-3-yl)phenoxy]butanoic acid

[Chemical 69]

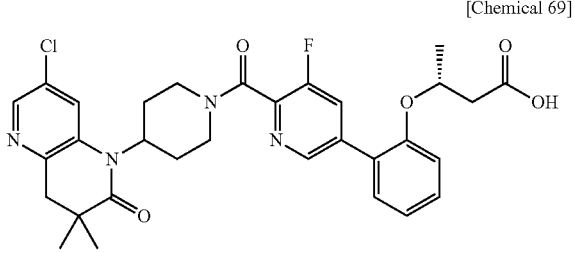 [SMILES: C[C@H](CC(=O)O)Oc1ccccc1-c1cnc(C(=O)N2CCC(N3C(=O)C(C)(C)Cc4ncc(Cl)cc43)CC2)c(F)c1]

Example 38-1

At room temperature, to a tetrahydrofuran solution (60 ml) of 5-bromo-3-nitropyridine-2-carbonitrile (6.00 g) was added a tetrahydrofuran solution (1 M, 52.8 ml) of tetrabutylammonium fluoride, followed by stirring for 1 hour. The reaction solution was poured into ice water, and extracted with ethyl acetate. The organic layer was washed sequentially with water and saturated sodium chloride solution, dried over anhydrous sodium sulfate, and concentrated under reduced pressure. The resulting residue was purified by silica gel column chromatography to afford 5-bromo-3-fluoropyridine-2-carbonitrile. To a mixed solvent solution of this in 1,2-dimethoxyethane (120 ml) and water (30 ml) were added 2-hydroxyphenylboronic acid (4.37 g), sodium carbonate (8.39 g) and tetrakis(triphenylphosphine)palladium (1.52 g), followed by stirring under heating at reflux for 2 hours. The reaction solution was brought back to room temperature, poured into ice water, and extracted with ethyl acetate. The organic layer was washed sequentially with water and saturated sodium chloride solution, dried over anhydrous sodium sulfate, and concentrated under reduced pressure. The resulting residue was purified by silica gel column chromatography to afford 3-fluoro-5-(2-hydroxyphenyl)pyridine-2-carbonitrile (2.73 g).

¹H NMR (400 MHz, CDCl₃) δ: 5.12 (br s, 1H), 6.91 (d, 1H, J=8.0 Hz), 7.00 (t, 1H, J=8.0 Hz), 7.27-7.39 (m, 2H), 7.85 (dd, 1H, J=11.2, 1.6 Hz), 8.77 (t, 1H, J=1.6 Hz).

Example 38-2

Under ice cooling, to an aqueous solution (40 ml) of 3-fluoro-5-(2-hydroxyphenyl)pyridine-2-carbonitrile (2.73 g) was added concentrated sulfuric acid (40 ml), followed by stirring under heating at reflux for 4 hours. Under ice cooling, ice water was added dropwise to the reaction solution, and the precipitate was collected by filtration, and dried. To this methanol solution (60 ml) was added a catalytic amount of concentrated sulfuric acid, followed by stirring under heating at reflux for 2 hours. The reaction solution was brought back to room temperature, and concentrated under reduced pressure. The resulting residue was recrystallized from hexane/ethyl acetate to afford methyl 3-fluoro-5-(2-hydroxyphenyl)pyridine-2-carboxylate (2.80 g).

¹H NMR (500 MHz, CDCl₃) δ: 4.01 (s, 3H), 5.74 (br s, 1H), 6.93 (d, 1H, J=8.0 Hz), 7.05 (t, 1H, J=8.0 Hz), 7.29-7.36 (m, 2H), 7.84 (dd, 1H, J=11.2, 1.6 Hz), 8.75 (t, 1H, J=1.6 Hz).

Example 38-3

In accordance with the method of Example 5-2, the compound of Example 38-2 was used instead of the compound of Example 1-3 to afford methyl 5-(2-{[(1R)-3-{[tert-butyl(diphenyl)silyl]oxy}-1-methylpropyl]oxy}phenyl)-3-fluoropyridine-2-carboxylate.

$^1$H NMR (400 MHz, CDCl$_3$) δ: 1.03 (s, 9H), 1.27 (d, 3H, J=5.9 Hz), 1.71-1.79 (m, 1H), 1.89-1.97 (m, 1H), 3.64-3.75 (m, 2H), 4.02 (s, 3H), 4.78-4.86 (m, 1H), 7.05-7.14 (m, 2H), 7.24-7.27 (m, 2H), 7.32-7.42 (m, 6H), 7.54-7.56 (m, 2H), 7.60-7.64 (m, 3H), 8.67 (t, 1H, J=1.6 Hz).

Example 38-4

To a tetrahydrofuran solution (96 ml) of methyl 5-(2-{[(1R)-3-{[tert-butyl(diphenyl)silyl]oxy}-1-methylpropyl]oxy}phenyl)-3-fluoropyridine-2-carboxylate (4.79 g) was added at room temperature an aqueous solution (48 ml) of lithium hydroxide monohydrate (192 mg), followed by stirring for 90 minutes. To the reaction solution was added 1 N hydrochloric acid for neutralization, followed by extraction with dichloromethane. The organic layer was washed with water, dried over anhydrous sodium sulfate, and concentrated under reduced pressure. The resulting residue was purified by silica gel column chromatography to afford 5-(2-{[(1R)-3-{[tert-butyl(diphenyl)silyl]oxy}-1-methylpropyl]oxy}phenyl)-3-fluoropyridine-2-carboxylic acid (3.27 g).

$^1$H NMR (400 MHz, CDCl$_3$) δ: 1.03 (s, 9H), 1.29 (d, 3H, J=6.3 Hz), 1.74-1.82 (m, 1H), 1.89-1.97 (m, 1H), 3.68-3.71 (m, 2H), 4.79-4.86 (m, 1H), 7.06-7.15 (m, 2H), 7.24-7.27 (m, 2H), 7.33-7.43 (m, 6H), 7.52-7.71 (m, 5H), 8.51 (s, 1H).

Example 38-5

In accordance with the methods of Examples 5-4, 5-5 and 24-3, the compound of Example 38-4 was used instead of the compound of Example 5-3 to afford (3R)-3-[2-(6-{[4-(7-chloro-3,3-dimethyl-2-oxo-3,4-dihydro-1,5-naphthyridin-1(2H)-yl)piperidin-1-yl]carbonyl}-5-fluoropyridin-3-yl)phenoxy]butanoic acid.

$^1$H NMR (400 MHz, CDCl$_3$) δ: 1.13 (s, 3H), 1.14 (s, 3H), 1.38 (d, 3H, J=5.9 Hz), 1.69-1.73 (m, 1H), 1.84-1.88 (m, 1H), 2.53-2.74 (m, 4H), 2.88-2.95 (m, 3H), 3.21-3.28 (m, 1H), 3.77-3.81 (m, 1H), 4.46-4.54 (m, 1H), 4.80-4.88 (m, 1H), 4.96-4.99 (m, 1H), 7.05-7.09 (m, 2H), 7.31 (dd, 1H, J=7.4, 1.6 Hz), 7.36-7.42 (m, 2H), 7.68 (ddd, 1H, J=10.2, 2.7, 1.6 Hz), 8.19 (d, 1H, J=1.6 Hz), 8.57 (d, 1H, J=1.6 Hz).

Example 39

(3R)-3-[2-(6-{[4-(7-Chloro-3,3-dimethyl-2-oxo-2,3-dihydro-1H-pyrido[2,3-b][1,4]oxazin-1-yl)piperidin-1-yl]carbonyl}-5-fluoropyridin-3-yl)phenoxy]butanoic acid

[Chemical 70]

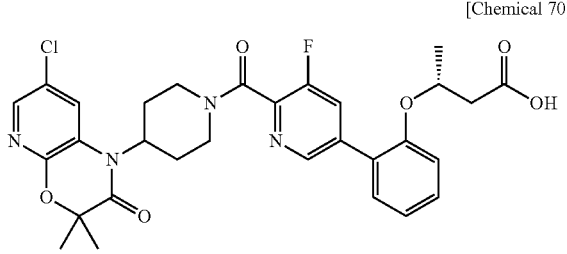

In accordance with the method of Example 38, the compound of Reference Example 3 was used instead of the compound of Reference Example 10 to afford (3R)-3-[2-(6-{[4-(7-chloro-3,3-dimethyl-2-oxo-2,3-dihydro-1H-pyrido[2,3-b][1,4]oxazin-1-yl)piperidin-1-yl]carbonyl}-5-fluoropyridin-3-yl)phenoxy]butanoic acid.

$^1$H NMR (400 MHz, CDCl$_3$) δ: 1.38 (d, 3H, J=6.3 Hz), 1.53 (s, 6H), 1.71-1.75 (m, 1H), 1.89-1.92 (m, 1H), 2.53-2.74 (m, 4H), 2.89-2.96 (m, 1H), 3.21-3.28 (m, 1H), 3.79-3.83 (m, 1H), 4.51-4.61 (m, 1H), 4.80-4.89 (m, 1H), 4.98-5.02 (m, 1H), 7.05-7.09 (m, 2H), 7.31 (dd, 1H, J=7.8, 1.6 Hz), 7.37-7.41 (m, 1H), 7.47 (d, 1H, J=2.0 Hz), 7.68 (ddd, 1H, J=10.2, 3.1, 1.6 Hz), 7.91 (d, 1H, J=2.0 Hz), 8.56-8.57 (m, 1H).

Example 40

(3R)-3-{2-[6-({4-[(3S)-7-Chloro-3-methyl-2-oxo-2,3-dihydro-1H-pyrido[2,3-b][1,4]oxazin-1-yl]piperidin-1-yl}carbonyl)-5-fluoropyridin-3-yl]phenoxy}butanoic acid

[Chemical 71]

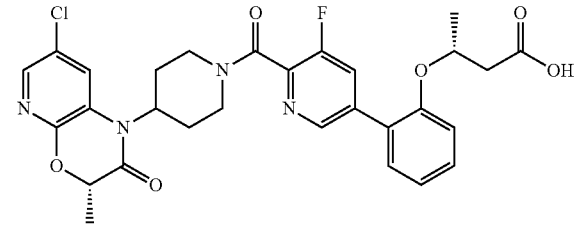

In accordance with the method of Example 38, the compound of Reference Example 4 was used instead of the compound of Reference Example 10 to afford (3R)-3-{2-[6-({4-[(3S)-7-chloro-3-methyl-2-oxo-2,3-dihydro-1H-pyrido[2,3-b][1,4]oxazin-1-yl]piperidin-1-yl}carbonyl)-5-fluoropyridin-3-yl]phenoxy}butanoic acid.

$^1$H NMR (400 MHz, CDCl$_3$) δ: 1.38 (d, 3H, J=5.9 Hz), 1.60 (d, 3H, J=6.7 Hz), 1.70-1.78 (m, 1H), 1.88-1.96 (m, 1H), 2.53-2.74 (m, 4H), 2.89-2.95 (m, 1H), 3.21-3.28 (m, 1H), 3.79-3.83 (m, 1H), 4.51-4.58 (m, 1H), 4.69-4.74 (m, 1H), 4.82-4.88 (m, 1H), 4.98-5.02 (m, 1H), 7.05-7.09 (m, 2H), 7.31 (dd, 1H, J=7.8, 1.6 Hz), 7.37-7.41 (m, 1H), 7.50 (dd, 1H, J=2.0, 1.6 Hz), 7.68 (ddd, 1H, J=10.2, 2.7, 1.6 Hz), 7.91 (dd, 1H, J=2.0, 1.6 Hz), 8.55-8.57 (m, 1H).

Example 41

(3R)-3-[2-(6-{[4-(7-Chloro-3,3-dimethyl-2-oxo-2,3-dihydro-1H-pyrido[2,3-b][1,4]oxazin-1-yl)piperidin-1-yl]carbonyl}-5-fluoropyridin-3-yl)phenoxy]pentanoic acid

[Chemical 72]

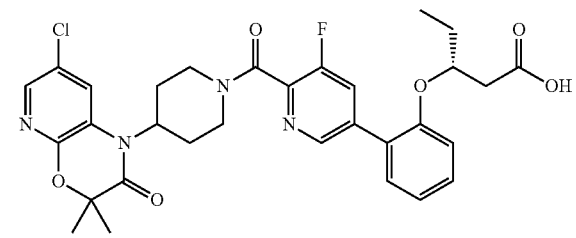

Example 41-1

In accordance with the method of Example 5-2, the compound of Example 38-2 was used instead of the compound of Example 1-3, and (3S)-1-{[tert-butyl(diphenyl)silyl]oxy}pentane-3-ol (Tetrahedron Letters, 2006, 47(7), 1213-1215) was used instead of the compound of Example 5-1 to afford methyl 5-(2-{[(1R)-3-{[tert-butyl(diphenyl)silyl]oxy}-1-ethylpropyl]oxy}phenyl)-3-fluoropyridine-2-carboxylate.

$^1$H NMR (400 MHz, CDCl$_3$) δ: 0.86 (t, 3H, J=7.4 Hz), 1.04 (s, 9H), 1.61-1.67 (m, 2H), 1.74-1.91 (m, 2H), 3.65-3.72 (m, 2H), 4.02 (s, 3H), 4.62-4.67 (m, 1H), 7.05 (t, 1H, J=7.4 Hz), 7.15 (d, 1H, J=8.2 Hz), 7.25-7.43 (m, 8H), 7.54-7.66 (m, 5H), 8.67-8.68 (m, 1H).

Example 41-2

To a tetrahydrofuran solution (7.0 ml) of methyl 5-(2-{[(1R)-3-{[tert-butyl(diphenyl)silyl]oxy}-1-ethylpropyl]oxy}phenyl)-3-fluoropyridine-2-carboxylate (440 mg) was added at room temperature 1 N aqueous sodium hydroxide solution (1.69 ml), followed by stirring for 2 hours. The reaction solution was poured into a 10% aqueous citric acid solution, and extracted with dichloromethane. The organic layer was dried over anhydrous sodium sulfate, and concentrated under reduced pressure to afford 5-(2-{[(1R)-3-{[tert-butyl(diphenyl)silyl]oxy}-1-ethylpropyl]oxy}phenyl)-3-fluoropyridine-2-carboxylic acid (429 mg).

$^1$H NMR (400 MHz, CDCl$_3$) δ: 0.88 (t, 3H, J=7.4 Hz), 1.04 (s, 9H), 1.61-1.68 (m, 2H), 1.78-1.90 (m, 2H), 3.73-3.76 (m, 2H), 4.62-4.68 (m, 1H), 7.07 (t, 1H, J=7.4 Hz), 7.17 (d, 1H, J=8.2 Hz), 7.26-7.44 (m, 8H), 7.55-7.62 (m, 4H), 7.72 (dd, 1H, J=10.9, 1.6 Hz), 8.52 (dd, 1H, J=1.6, 1.2 Hz).

Example 41-3

In accordance with the methods of Examples 13-4, 5-5 and 24-3, the compound of Example 41-2 was used instead of the compound of Example 13-3 to afford (3R)-3-[2-(6-{[4-(7-chloro-3,3-dimethyl-2-oxo-2,3-dihydro-1H-pyrido[2,3-b][1,4]oxazin-1-yl)piperidin-1-yl]carbonyl}-5-fluoropyridin-3-yl)phenoxy]pentanoic acid.

$^1$H NMR (400 MHz, CDCl$_3$) δ: 0.93 (t, 3H, J=7.4 Hz), 1.53 (s, 6H), 1.68-1.81 (m, 3H), 1.89-1.92 (m, 1H), 2.55-2.96 (m, 5H), 3.22-3.28 (m, 1H), 3.79-3.82 (m, 1H), 4.51-4.62 (m, 1H), 4.66-4.73 (m, 1H), 4.99-5.02 (m, 1H), 7.05-7.10 (m, 2H), 7.32 (d, 1H, J=7.4 Hz), 7.39 (t, 1H, J=7.6 Hz), 7.47 (d, 1H, J=1.2 Hz), 7.70 (dd, 1H, J=10.2, 1.2 Hz), 7.92 (d, 1H, J=1.6 Hz), 8.57 (s, 1H).

Example 42

(3R)-3-[2-(6-{[4-(7-Chloro-3,3-dimethyl-2-oxo-2,3-dihydro-1H-pyrido[2,3-b][1,4]oxazin-1-yl)piperidin-1-yl]carbonyl}-5-fluoropyridin-3-yl)-4-fluorophenoxy]butanoic acid

[Chemical 73]

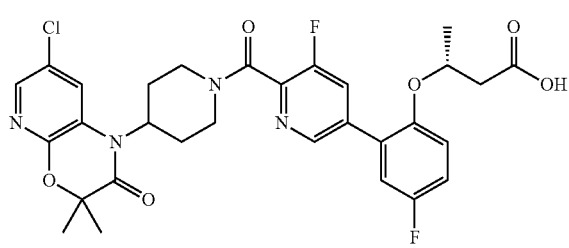

Example 42-1

In accordance with the methods of Examples 38-1 and 38-2, 5-fluoro-2-hydroxyphenylboronic acid was used instead of 2-hydroxyphenylboronic acid to afford methyl 3-fluoro-5-(5-fluoro-2-hydroxyphenyl)pyridine-2-carboxylate.

$^1$H NMR (500 MHz, CDCl$_3$) δ: 4.05 (s, 3H), 6.93 (dd, 1H, J=8.4, 4.4 Hz), 7.04-7.08 (m, 2H), 7.86 (dd, 1H, J=11.2, 1.6 Hz), 8.80 (s, 1H).

Example 42-2

In accordance with the methods of Examples 5-2, 41-2, 13-4, 5-5 and 24-3, the compound of Example 42-1 was used instead of the compound of Example 1-3 to afford (3R)-3-[2-(6-{[4-(7-chloro-3,3-dimethyl-2-oxo-2,3-dihydro-1H-pyrido[2,3-b][1,4]oxazin-1-yl)piperidin-1-yl]carbonyl}-5-fluoropyridin-3-yl)-4-fluorophenoxy]butanoic acid.

$^1$H NMR (400 MHz, CDCl$_3$) δ: 1.33 (d, 3H, J=5.9 Hz), 1.54 (s, 6H), 1.72-1.76 (m, 1H), 1.90-1.94 (m, 1H), 2.51-2.73 (m, 4H), 2.90-2.97 (m, 1H), 3.22-3.30 (m, 1H), 3.79-3.82 (m, 1H), 4.51-4.61 (m, 1H), 4.68-4.77 (m, 1H), 4.99-5.03 (m, 1H), 7.03-7.12 (m, 3H), 7.45 (d, 1H, J=1.2 Hz), 7.68 (ddd, 1H, J=10.2, 2.7, 1.6 Hz), 7.92 (d, 1H, J=1.6 Hz), 8.55-8.56 (m, 1H).

Example 43

(3R)-3-{2-[6-({4-[(3S)-7-Chloro-3-methyl-2-oxo-2,3-dihydro-1H-pyrido[2,3-b][1,4]oxazin-1-yl]piperidin-1-yl}carbonyl)-5-fluoropyridin-3-yl]-4-fluorophenoxy}butanoic acid

[Chemical 74]

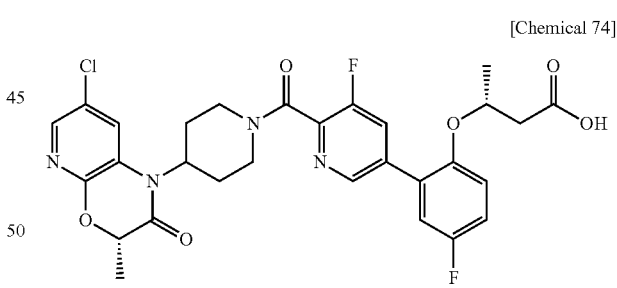

In accordance with the method of Example 42, the compound of Example 4 was used instead of the compound of Example 3 to afford (3R)-3-{2-[6-({4-[(3S)-7-chloro-3-methyl-2-oxo-2,3-dihydro-1H-pyrido[2,3-b][1,4]oxazin-1-yl]piperidin-1-yl}carbonyl)-5-fluoropyridin-3-yl]-4-fluorophenoxy}butanoic acid.

$^1$H NMR (400 MHz, CDCl$_3$) δ: 1.32 (d, 3H, J=6.3 Hz), 1.60 (d, 3H, J=6.6 Hz), 1.73-1.77 (m, 1H), 1.90-1.94 (m, 1H), 2.51-2.71 (m, 4H), 2.91-2.94 (m, 1H), 3.24-3.27 (m, 1H), 3.77-3.80 (m, 1H), 4.50-4.58 (m, 1H), 4.70-4.72 (m, 2H), 4.97-5.01 (m, 1H), 7.04-7.09 (m, 3H), 7.49 (dd, 1H, J=3.5, 2.0 Hz), 7.68 (dt, 1H, J=10.2, 1.6 Hz), 7.91 (dd, 1H, J=2.0, 1.2 Hz), 8.55-8.56 (m, 1H).

Example 44

(3R)-3-[2-(6-{[4-(7-Chloro-3,3-dimethyl-2-oxo-3,4-dihydro-1,5-naphthyridin-1(2H)-yl)piperidin-1-yl]carbonyl}-5-fluoropyridin-3-yl)-4-fluorophenoxy]butanoic acid

[Chemical 75]

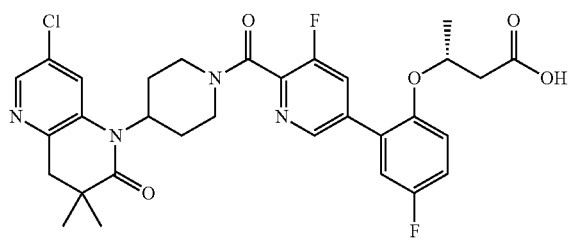

In accordance with the method of Example 42, the compound of Example 10 was used instead of the compound of Example 3 to afford (3R)-3-[2-(6-{[4-(7-chloro-3,3-dimethyl-2-oxo-3,4-dihydro-1,5-naphthyridin-1(2H)-yl)piperidin-1-yl]carbonyl}-5-fluoropyridin-3-yl)-4-fluorophenoxy]butanoic acid.

$^1$H NMR (400 MHz, CDCl$_3$) δ: 1.13 (s, 3H), 1.15 (s, 3H), 1.33 (d, 3H, J=6.3 Hz), 1.70-1.73 (m, 1H), 1.86-1.89 (m, 1H), 2.50-2.71 (m, 4H), 2.89-2.96 (m, 3H), 3.22-3.29 (m, 1H), 3.77-3.80 (m, 1H), 4.47-4.53 (m, 1H), 4.68-4.74 (m, 1H), 4.97-5.00 (m, 1H), 7.03-7.09 (m, 3H), 7.41 (d, 1H, J=1.6 Hz), 7.67 (d, 1H, J=9.8 Hz), 8.19 (d, 1H, J=2.0 Hz), 8.56 (s, 1H).

Example 45

(3R)-3-[(4'-{[4-(7-Chloro-3,3-dimethyl-2-oxo-3,4-dihydro-1,5-naphthyridin-1(2H)-yl)piperidin-1-yl]carbonyl}-5-fluoro-3'-methylbiphenyl-2-yl)oxy]butanoic acid

[Chemical 76]

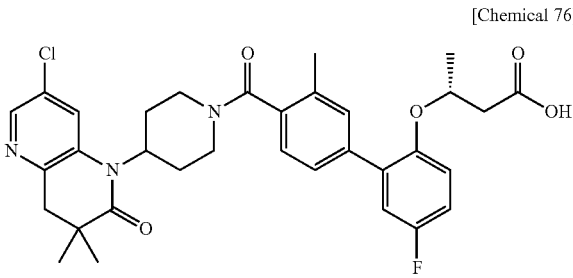

Example 45-1

In accordance with the method of Example 5-2, the compound of Example 17-1 was used instead of the compound of Example 1-3 to afford benzyl 2'-{[(1R)-3-{[tert-butyl(diphenyl)silyl]oxy}-1-methylpropyl]oxy}-5'-fluoro-3-methylbiphenyl-4-carboxylate.

$^1$H NMR (400 MHz, CDCl$_3$) δ: 1.02 (s, 9H), 1.18 (d, 3H, J=5.9 Hz), 1.66-1.74 (m, 1H), 1.82-1.90 (m, 1H), 2.59 (s, 3H), 3.63-3.75 (m, 2H), 4.54-4.61 (m, 1H), 5.35 (s, 2H), 6.96-7.04 (m, 3H), 7.28-7.41 (m, 11H), 7.45-7.47 (m, 2H), 7.55-7.62 (m, 4H), 7.92 (d, 1H, J=7.8 Hz).

Example 45-2

In accordance with the method of Example 5-5, the compound of Example 45-1 was used instead of the compound of Example 5-4 to afford benzyl 5'-fluoro-2'-{[(1R)-3-hydroxy-1-methylpropyl]oxy}-3-methylbiphenyl-4-carboxylate.

$^1$H NMR (400 MHz, CDCl$_3$) δ: 1.19 (d, 3H, J=5.9 Hz), 1.74-1.88 (m, 2H), 2.65 (s, 3H), 3.63-3.74 (m, 2H), 4.39-4.47 (m, 1H), 5.36 (s, 2H), 6.97-7.04 (m, 3H), 7.33-7.48 (m, 7H), 8.00 (dd, 1H, J=6.6, 2.0 Hz).

Example 45-3

In accordance with the method of Example 1-5, the compound of Example 45-2 was used instead of the compound of Example 1-4 to afford 5'-fluoro-2'-{[(1R)-3-hydroxy-1-methylpropyl]oxy}-3-methylbiphenyl-4-carboxylic acid.

$^1$H NMR (400 MHz, CDCl$_3$) δ: 1.22 (d, 3H, J=5.9 Hz), 1.77-1.90 (m, 2H), 2.69 (s, 3H), 3.65-3.76 (m, 2H), 4.41-4.48 (m, 1H), 6.97-7.06 (m, 3H), 7.39-7.42 (m, 2H), 8.08 (d, 1H, J=7.8 Hz).

Example 45-4

To a methanol-tetrahydrofuran (1:1) mixed solvent solution (20.0 ml) of 5'-fluoro-2'-{[(1R)-3-hydroxy-1-methylpropyl]oxy}-3-methylbiphenyl-4-carboxylic acid (637 mg) and 7-chloro-3,3-dimethyl-1-piperidin-4-yl-3,4-dihydro-1,5-naphthyridin-2(1H)-one trifluoroacetate (Reference Example 10) (876 mg) were added at room temperature N-methylmorpholine (0.660 ml) and 4-(4,6-dimethoxy-1,3,5-triazin-2-yl)-4-methylmorpholinium chloride (940 mg), followed by stirring for 1 hour. The reaction solution was diluted with methylene chloride, then washed sequentially with water and saturated sodium chloride solution, dried over anhydrous sodium sulfate, and concentrated under reduced pressure. The resulting residue was purified by silica gel chromatography to afford 7-chloro-1-{1-[(5'-fluoro-2'-{[(1R)-3-hydroxy-1-methylpropyl]oxy}-3-methylbiphenyl-4-yl)carbonyl]piperidin-4-yl}-3,3-dimethyl-3,4-dihydro-1,5-naphthyridin-2(1H)-one (820 mg).

$^1$H NMR (400 MHz, CDCl$_3$) δ: 1.14 (s, 6H), 1.21 (d, 3H, J=6.3 Hz), 1.53-1.71 (m, 1H), 1.77-1.89 (m, 3H), 2.34-2.69 (br m, 5H), 2.83-2.90 (m, 1H), 2.92 (s, 2H), 3.08-3.15 (m, 1H), 3.59-3.76 (m, 3H), 4.24-4.44 (m, 2H), 4.47-4.99 (m, 1H), 6.97-7.03 (m, 3H), 7.33-7.46 (m, 4H), 8.19 (s, 1H).

Example 45-5

In accordance with the method of Example 24-3, the compound of Example 45-4 was used instead of the compound of Example 24-2 to afford (3R)-3-[(4'-{[4-(7-chloro-3,3-dimethyl-2-oxo-3,4-dihydro-1,5-naphthyridin-1(2H)-yl)piperidin-1-yl]carbonyl}-5-fluoro-3'-methylbiphenyl-2-yl)oxy]butanoic acid.

$^1$H NMR (400 MHz, CDCl$_3$) δ: 1.14 (s, 6H), 1.24 (d, 3H, J=5.9 Hz), 1.62-1.71 (m, 1H), 1.83-1.92 (m, 1H), 2.31 & 2.49 (s, total 3H), 2.22-2.73 (m, 4H), 2.81-2.96 (m, 1H), 2.92 (s, 2H), 3.07-3.19 (m, 1H), 3.69-3.81 (m, 1H), 4.21-4.44 (m, 1H), 4.49-4.61 (m, 1H), 4.97-5.08 (m, 1H), 6.94-7.06 (m, 3H), 7.12-7.41 (m, 4H), 8.20 (s, 1H).

Example 46

(2S)-3-[2-(6-{[4-(7-Chloro-3,3-dimethyl-2-oxo-3,4-dihydro-1,5-naphthyridin-1(2H)-yl)piperidin-1-yl]carbonyl}-5-fluoropyridin-3-yl)phenoxy]-2-methylpropanoic acid

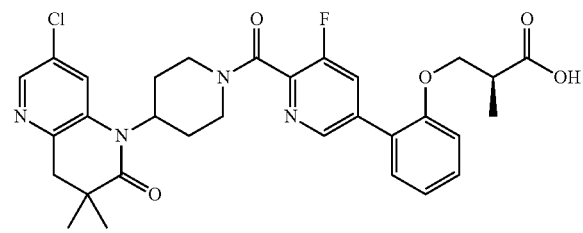

[Chemical 77]

Example 46-1

In accordance with the methods of Examples 11-2, 5-5 and 41-2, the compound of Example 38-2 was used instead of the compound of Example 1-3 to afford 3-fluoro-5-(2-{[(2R)-3-hydroxy-2-methylpropyl]oxy}phenyl)pyridine-2-carboxylic acid.

$^1$H NMR (400 MHz, CDCl$_3$) δ: 1.00 (d, 3H, J=6.7 Hz), 2.10-2.17 (m, 1H), 3.55-3.64 (m, 2H), 3.99-4.07 (m, 2H), 7.06-7.12 (m, 2H), 7.35 (d, 1H, J=7.4 Hz), 7.44 (t, 1H, J=7.8 Hz), 7.85 (d, 1H, J=11.3 Hz), 8.64 (s, 1H).

Example 46-2

In accordance with the methods of Examples 45-4 and 24-3, the compound of Example 46-1 was used instead of the compound of Example 45-3 to afford (2S)-3-[2-(6-{[4-(7-chloro-3,3-dimethyl-2-oxo-3,4-dihydro-1,5-naphthyridin-1(2H)-yl)piperidin-1-yl]carbonyl}-5-fluoropyridin-3-yl)phenoxy]-2-methylpropanoic acid.

$^1$H NMR (400 MHz, CDCl$_3$) δ: 1.13 (s, 3H), 1.15 (s, 3H), 1.22 & 1.23 (d, total 3H, J=7.0 Hz), 1.70-1.74 (m, 1H), 1.85-1.88 (m, 1H), 2.58-2.90 (m, 4H), 2.92 (s, 2H), 3.20-3.27 (m, 1H), 3.76-3.80 (m, 1H), 4.09-4.17 (m, 2H), 4.41-4.51 (m, 1H), 4.95-4.99 (m, 1H), 7.03 (d, 1H, J=8.2 Hz), 7.09 (t, 1H, J=7.2 Hz), 7.32-7.42 (m, 3H), 7.68 (dd, 1H, J=10.0, 1.6 Hz), 8.20 (d, 1H, J=1.6 Hz), 8.58 (s, 1H).

Example 47

(2S)-3-[2-(6-{[4-(7-Chloro-3,3-dimethyl-2-oxo-2,3-dihydro-1H-pyrido[2,3-b][1,4]oxazin-1-yl)piperidin-1-yl]carbonyl}-5-fluoropyridin-3-yl)phenoxy]-2-methylpropanoic acid

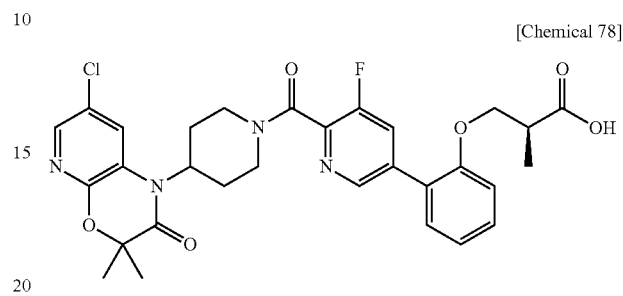

[Chemical 78]

In accordance with the method of Example 46, the compound of Reference Example 3 was used instead of the compound of Reference Example 10 to afford (2S)-3-[2-(6-{[4-(7-chloro-3,3-dimethyl-2-oxo-2,3-dihydro-1H-pyrido[2,3-b][1,4]oxazin-1-yl)piperidin-1-yl]carbonyl}-5-fluoropyridin-3-yl)phenoxy]-2-methylpropanoic acid.

$^1$H NMR (400 MHz, CDCl$_3$) δ: 1.21 & 1.23 (d, total 3H, J=7.0 Hz), 1.53 (s, 3H), 1.54 (s, 3H), 1.72-1.76 (m, 1H), 1.89-1.93 (m, 1H), 2.57-2.75 (m, 2H), 2.86-2.96 (m, 2H), 3.21-3.28 (m, 1H), 3.79-3.82 (m, 1H), 4.08-4.17 (m, 2H), 4.47-4.60 (m, 1H), 4.98-5.02 (m, 1H), 7.03 (d, 1H, J=8.2 Hz), 7.09 (t, 1H, J=7.4 Hz), 7.33 (dd, 1H, J=7.4, 1.2 Hz), 7.38-7.43 (m, 1H), 7.47 (dd, 1H, J=5.1, 2.3 Hz), 7.69 (dd, 1H, J=10.2, 1.6 Hz), 7.92 (d, 1H, J=2.0 Hz), 8.58 (s, 1H).

Example 48

(2S)-3-[2-(6-{[4-(7-Chloro-3,3-dimethyl-2-oxo-3,4-dihydro-1,5-naphthyridin-1(2H)-yl)piperidin-1-yl]carbonyl}-5-fluoropyridin-3-yl)-4-fluorophenoxy]-2-methylpropanoic acid

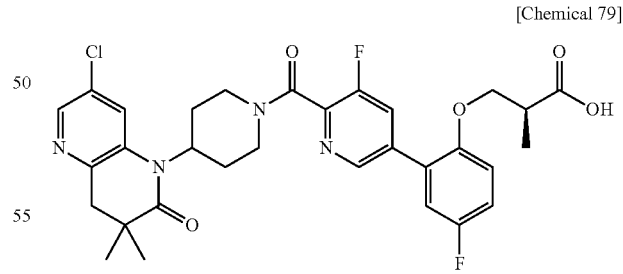

[Chemical 79]

Example 48-1

In accordance with the methods of Examples 11-2, 5-5 and 41-2, the compound of Example 42-1 was used instead of the compound of Example 1-3 to afford 3-fluoro-5-(5-fluoro-2-{[(2R)-3-hydroxy-2-methylpropyl]oxy}phenyl)pyridine-2-carboxylic acid.

¹H NMR (400 MHz, DMSO-d6) δ: 0.87 (d, 3H, J=7.0 Hz), 1.89-1.97 (m, 1H), 3.31-3.32 (m, 2H), 3.91 (dd, 1H, J=9.0, 5.9 Hz), 3.97 (dd, 1H, J=9.4, 5.5 Hz), 4.58 (t, 1H, J=5.1 Hz), 7.20 (dd, 1H, J=9.4, 4.7 Hz), 7.29 (ddd, 1H, J=9.0, 8.2, 3.1 Hz), 7.44 (dd, 1H, J=9.4, 3.1 Hz), 8.06 (dd, 1H, J=11.7, 1.6 Hz), 8.71 (t, 1H, J=1.6 Hz), 13.61 (br s, 1H).

Example 48-2

In accordance with the methods of Examples 45-4 and 24-3, the compound of Example 48-1 was used instead of the compound of Example 45-3 to afford (2S)-3-[2-(6-{[4-(7-chloro-3,3-dimethyl-2-oxo-3,4-dihydro-1,5-naphthyridin-1(2H)-yl)piperidin-1-yl]carbonyl}-5-fluoropyridin-3-yl)-4-fluorophenoxy]-2-methylpropanoic acid.

¹H NMR (400 MHz, CDCl₃) δ: 1.13 (s, 3H), 1.15 (s, 3H), 1.20 & 1.22 (d, total 3H, J=7.0 Hz), 1.70-1.74 (m, 1H), 1.85-1.88 (m, 1H), 2.59-2.73 (m, 2H), 2.83-2.96 (m, 4H), 3.21-3.27 (m, 1H), 3.74-3.78 (m, 1H), 4.04-4.12 (m, 2H), 4.42-4.48 (m, 1H), 4.95-4.99 (m, 1H), 6.98 (dd, 1H, J=8.8, 4.5 Hz), 7.05-7.12 (m, 2H), 7.41 (d, 1H, J=1.6 Hz), 7.68 (dd, 1H, J=9.8, 1.6 Hz), 8.19 (d, 1H, J=1.6 Hz), 8.56 (s, 1H).

Example 49

(2S)-3-[2-(6-{[4-(7-Chloro-3,3-dimethyl-2-oxo-2,3-dihydro-1H-pyrido[2,3-b][1,4]oxazin-1-yl)piperidin-1-yl]carbonyl}-5-fluoropyridin-3-yl)-4-fluorophenoxy]-2-methylpropanoic acid

[Chemical 80]

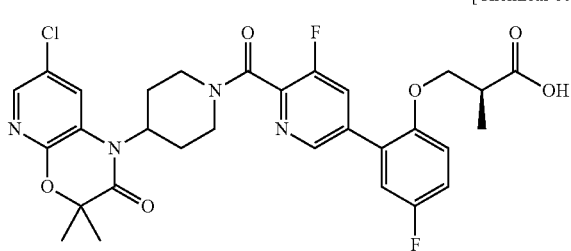

In accordance with the method of Example 48, the compound of Reference Example 3 was used instead of the compound of Reference Example 10 to afford (2S)-3-[2-(6-{[4-(7-chloro-3,3-dimethyl-2-oxo-2,3-dihydro-1H-pyrido[2,3-b][1,4]oxazin-1-yl)piperidin-1-yl]carbonyl}-5-fluoropyridin-3-yl)-4-fluorophenoxy]-2-methylpropanoic acid.

¹H NMR (400 MHz, CDCl₃) δ: 1.20 & 1.22 (d, total 3H, J=7.0 Hz), 1.53 (s, 3H), 1.54 (s, 3H), 1.72-1.76 (m, 1H), 1.89-1.93 (m, 1H), 2.59-2.73 (m, 2H), 2.82-2.97 (m, 2H), 3.22-3.29 (m, 1H), 3.77-3.81 (m, 1H), 4.02-4.12 (m, 2H), 4.49-4.58 (m, 1H), 4.97-5.01 (m, 1H), 6.98 (dd, 1H, J=9.0, 4.3 Hz), 7.05-7.12 (m, 2H), 7.47 (d, 1H, J=2.3 Hz), 7.68 (dt, 1H, J=10.2, 1.6 Hz), 7.92 (d, 1H, J=2.3 Hz), 8.56 (s, 1H).

Example 50

(3R)-3-[(3'-Amino-4'-{[4-(7-chloro-3,3-dimethyl-2-oxo-2,3-dihydro-1H-pyrido[2,3-b][1,4]oxazin-1-yl)piperidin-1-yl]carbonyl}biphenyl-2-yl)oxy]butanoic acid

[Chemical 81]

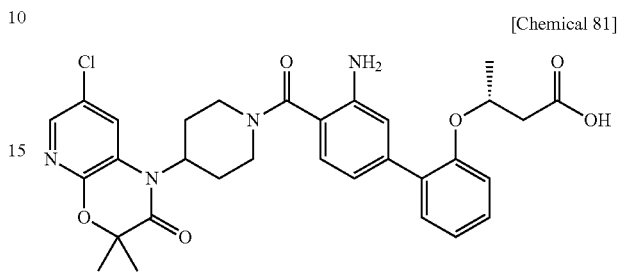

Example 50-1

In accordance with the methods of Examples 15-2, 5-2 and 5-5, the compound of Example 22-1 was used instead of the compound of Example 15-1 to afford methyl 2'-{[(1R)-3-hydroxy-1-methylpropyl]oxy}-3-nitrobiphenyl-4-carboxylate.

¹H NMR (400 MHz, CDCl₃) δ: 1.30 (d, 3H, J=6.3 Hz), 1.79-1.97 (m, 2H), 3.74 (t, 2H, J=5.9 Hz), 3.94 (s, 3H), 4.65-4.73 (m, 1H), 7.04-7.09 (m, 2H), 7.33-7.40 (m, 2H), 7.76-7.82 (m, 2H), 8.12 (s, 1H).

Example 50-2

To a tetrahydrofuran solution (20.0 ml) of methyl 2'-{[(1R)-3-hydroxy-1-methylpropyl]oxy}-3-nitrobiphenyl-4-carboxylate (793 mg) was added at room temperature potassium trimethylsilanolate (982 mg), followed by stirring for 7 hours. A 10% aqueous citric acid solution was added to the reaction solution, and extracted with ethyl acetate. The organic layer was washed with brine, dried over anhydrous sodium sulfate, and concentrated under reduced pressure to afford 2'-{[(1R)-3-hydroxy-1-methylpropyl]oxy}-3-nitrobiphenyl-4-carboxylic acid (761 mg).

¹H NMR (400 MHz, CDCl₃) δ: 1.33 (d, 3H, J=6.3 Hz), 1.85-2.01 (m, 2H), 3.73-3.83 (m, 2H), 4.66-4.73 (m, 1H), 4.89 (br s, 1H), 7.05-7.09 (m, 2H), 7.33-7.41 (m, 2H), 7.80 (dd, 1H, J=7.8, 1.6 Hz), 7.91 (d, 1H, J=7.8 Hz), 8.03 (d, 1H, J=1.6 Hz).

Example 50-3

In accordance with the methods of Examples 45-4 and 24-3, the compound of Example 50-2 was used instead of the compound of Example 45-3 to afford (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3'-nitrobiphenyl-2-yl)oxy]butanoic acid.

¹H NMR (500 MHz, CDCl₃) δ: 1.33-1.44 (m, 3H), 1.53 (s, 6H), 1.61-1.78 (m, 1H), 1.82-2.03 (m, 1H), 2.06-2.82 (m, 4H), 2.89-3.06 (m, 1H), 3.11-3.39 (m, 1H), 3.61-3.79 (m, 1H), 4.78-4.90 (m, 1H), 4.92-5.18 (m, 2H), 7.05-7.15 (m, 2H), 7.25-7.46 (m, 4H), 7.80-7.88 (m, 1H), 7.92 (s, 1H), 8.38 (s, 1H).

Example 50-4

To an 80% aqueous ethanol solution (7.50 ml) of (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}3'-nitrobiphenyl-2-yl)oxy]butanoic acid (132 mg) were added at room temperature ammonium chloride (11.3 mg) and iron powder (59.0 mg), followed by stirring under heating at reflux for 1 hour. Water was added to the reaction solution, and extracted with ethyl acetate. The organic layer was washed with brine, dried over anhydrous sodium sulfate, and concentrated under reduced pressure. The resulting residue was purified by silica gel chromatography to afford (3R)-3-[(3'-amino-4'-{[4-(7-chloro-3,3-dimethyl-2-oxo-2,3-dihydro-1H-pyrido[2,3-b][1,4]oxazin-1-yl)piperidin-1-yl]carbonyl}biphenyl-2-yl)oxy]butanoic acid (40.5 mg).

$^1$H NMR (400 MHz, CDCl$_3$) δ: 1.32 (d, 3H, J=6.1 Hz), 1.53 (s, 6H), 1.75-1.85 (m, 2H), 2.00-2.70 (m, 7H), 2.90-3.10 (m, 2H), 4.41-4.52 (m, 2H), 4.64-4.74 (m, 1H), 6.87 (dd, 1H, J=7.8, 1.5 Hz), 6.93 (d, 1H, J=1.5 Hz), 6.99-7.07 (m, 2H), 7.14 (d, 1H, J=7.8 Hz), 7.25-7.32 (m, 2H), 7.44 (d, 1H, J=2.2 Hz), 7.92 (d, 1H, J=2.2 Hz).

Example 51

(3R)-3-[(4'-{[4-(7-Chloro-3,3-dimethyl-2-oxo-2,3-dihydro-1H-pyrido[2,3-b][1,4]oxazin-1-yl)piperidin-1-yl]carbonyl}-3',5'-difluorobiphenyl-2-yl)oxy]butanoic acid

[Chemical 82]

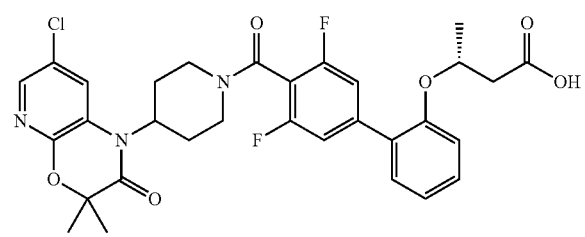

In accordance with the method of Example 34, 4-bromo-2,6-difluorobenzoic acid was used instead of 4-chloro-2,5-difluorobenzoic acid to afford (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-3',5'-difluorobiphenyl-2-yl)oxy]butanoic acid.

$^1$H NMR (400 MHz, CDCl$_3$) δ: 1.356 & 1.359 (d, total 3H, J=5.6 Hz), 1.54 (s, 6H), 1.71-1.81 (m, 1H), 1.86-1.95 (m, 1H), 2.50-2.66 (m, 3H), 2.74 (dd, 1H, J=15.6, 7.4 Hz), 2.85-2.98 (m, 1H), 3.20-3.33 (m, 1H), 3.79-3.89 (m, 1H), 4.55-4.69 (m, 1H), 4.75-4.87 (m, 1H), 4.98-5.08 (m, 1H), 7.02-7.18 (m, 4H), 7.25-7.31 (m, 1H), 7.33-7.40 (m, 1H), 7.42 (d, 1H, J=2.0 Hz), 7.93 (d, 1H, J=2.0 Hz).

Example 52

(3R)-3-[(4'-{[4-(7-Cyano-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]butanoic acid

[Chemical 83]

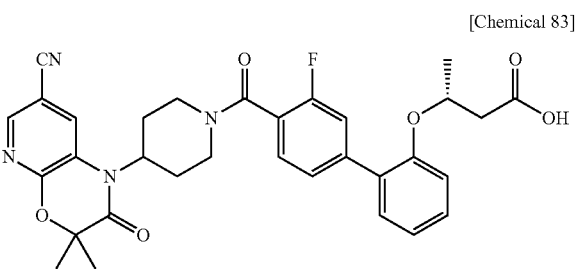 [SMILES: C[C@H](CC(=O)O)Oc1ccccc1-c1ccc(C(=O)N2CCC(N3C(=O)C(C)(C)Oc4ncc(C#N)cc43)CC2)c(F)c1]

Example 52-1

In accordance with the method of Reference Example 3, 5-bromo-2-chloropyridin-3-ol was used instead of 2,5-dichloropyridin-3-ol to afford tert-butyl 4-(7-bromo-3,3-dimethyl-2-oxo-2,3-dihydro-1H-pyrido[2,3-b][1,4]oxazin-1-yl)piperidine-1-carboxylate.

$^1$H NMR (400 MHz, CDCl$_3$) δ: 1.50 (s, 9H), 1.53 (s, 6H), 1.69-1.71 (m, 2H), 2.38-2.48 (m, 2H), 2.78-2.85 (m, 2H), 4.21-4.43 (br m, 3H), 7.47 (d, 1H, J=2.0 Hz), 7.99 (d, 1H, J=2.0 Hz).

Example 52-2

In accordance with the method of Reference Example 3-5, the compound of Example 52-1 was used instead of the compound of Reference Example 3-4 to afford 7-bromo-3,3-dimethyl-1-piperidin-4-yl-1H-pyrido[2,3-b][1,4]oxazin-2(3H)-one trifluoroacetate.

$^1$H NMR (400 MHz, DMSO-D$_6$) δ: 1.54 (s, 6H), 1.98-2.02 (m, 2H), 2.88-2.99 (m, 2H), 3.11-3.20 (m, 2H), 3.68-3.72 (m, 2H), 4.55-4.62 (m, 1H), 7.67 (s, 1H), 8.06 (s, 1H), 8.63 (br m, 1H), 9.25 (br m, 1H).

Example 52-3

In accordance with the methods of Examples 13-4 and 5-5, the compound of Example 5-3 was used instead of the compound of Example 13-3, and the compound of Example 52-2 was used instead of the compound of Reference Example 3 to afford 7-bromo-1-{1-[(3-fluoro-2'-{[(1R)-3-hydroxy-1-methylpropyl]oxy}biphenyl-4-yl)carbonyl]piperidin-4-yl}-3,3-dimethyl-1H-pyrido[2,3-b][1,4]oxazin-2(3H)-one.

$^1$H NMR (400 MHz, CDCl$_3$) δ: 1.29 (d, 3H, J=6.3 Hz), 1.54 (s, 6H), 1.71-1.74 (m, 1H), 1.79-1.94 (m, 3H), 2.55-2.65 (m, 2H), 2.85-2.92 (m, 1H), 3.18-3.26 (m, 1H), 3.65-3.75 (m, 2H), 3.83-3.88 (m, 1H), 4.39-4.66 (br m, 2H), 4.99-5.04 (m, 1H), 7.02-7.06 (m, 2H), 7.29-7.38 (m, 4H), 7.43-7.53 (m, 2H), 8.01 (d, 1H, J=2.0 Hz).

Example 52-4

To an N,N-dimethylformamide solution (3.0 ml) of 7-bromo-1-{1-[(3-fluoro-2'-{[(1R)-3-hydroxy-1-methylpropyl]oxy}biphenyl-4-yl)carbonyl]piperidin-4-yl}-3,3-dimethyl-1H-pyrido[2,3-b][1,4]oxazin-2(3H)-one (135 mg)

were added at room temperature 1,1'-bis(diphenylphosphino)ferrocene (239 mg), zinc powder (1.7 mg), zinc cyanide (15.5 mg) and tris(dibenzylideneacetone)dipalladium (19.8 mg), followed by stirring at 130° C. for 3 hours. The reaction solution was poured into a saturated aqueous sodium hydrogen carbonate solution, and extracted with ethyl acetate. The organic layer was washed sequentially with water and saturated sodium chloride solution, dried over anhydrous sodium sulfate, and concentrated under reduced pressure. The resulting residue was purified by silica gel column chromatography to afford 1-{1-[(3-fluoro-2'-{[(1R)-3-hydroxy-1-methylpropyl]oxy}biphenyl-4-yl)carbonyl]piperidin-4-yl}-3,3-dimethyl-2-oxo-2,3-dihydro-1H-pyrido[2,3-b][1,4]oxazine-7-carbonitrile (111 mg).

¹H NMR (400 MHz, CDCl₃) δ: 1.29 & 1.30 (d, total 3H, J=6.3 Hz), 1.58 (s, 6H), 1.72-1.76 (m, 1H), 1.80-1.95 (m, 3H), 2.56-2.67 (m, 2H), 2.86-2.92 (m, 1H), 3.18-3.27 (m, 1H), 3.67-3.72 (br m, 2H), 3.85-3.90 (m, 1H), 4.41-4.66 (br m, 2H), 5.00-5.06 (m, 1H), 7.02-7.06 (m, 2H), 7.27-7.49 (m, 5H), 7.64 (br s, 1H), 8.28 (d, 1H, J=2.0 Hz).

Example 52-5

In accordance with the method of Example 24-3, the compound of Example 52-4 was used instead of the compound of Example 24-2 to afford (3R)-3-[(4'-{[4-(7-cyano-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]butanoic acid.

¹H NMR (400 MHz, CDCl₃) δ: 1.33 & 1.34 (d, total 3H, J=6.2 Hz), 1.57-1.58 (m, 6H), 1.67-1.76 (m, 1H), 1.87-1.95 (br m, 1H), 2.53-2.76 (m, 4H), 2.86-2.93 (m, 1H), 3.17-3.31 (br m, 1H), 3.83-3.90 (m, 1H), 4.30-4.71 (br m, 1H), 4.75-4.87 (m, 1H), 5.00-5.05 (m, 1H), 7.01-7.06 (m, 2H), 7.27-7.45 (m, 5H), 7.66-7.71 (m, 1H), 8.28 (d, 1H, J=2.0 Hz).

Example 53

(3R)-3-[(4'-{[4-(7-Ethyl-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]butanoic acid

[Chemical 84]

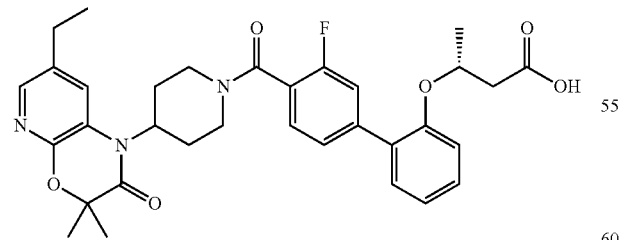

Example 53-1

At room temperature, to a 1,4-dioxane solution (10.0 ml) of tert-butyl 4-(7-bromo-3,3-dimethyl-2-oxo-2,3-dihydro-1H-pyrido[2,3-b][1,4]oxazin-1-yl)piperidine-1-carboxylate (Example 52-1) (150 mg) was added a [1,1'-bis(diphenylphosphino)ferrocene]dichloropalladium-dichloromethane complex (69.5 mg), and then a hexane solution (1 M, 0.681 ml) of diethyl zinc was added dropwise, followed by stirring overnight. The reaction solution was poured into water, and extracted with ethyl acetate. The organic layer was washed with saturated sodium chloride solution, dried over anhydrous sodium sulfate, and concentrated under reduced pressure. The resulting residue was purified by silica gel column chromatography to afford tert-butyl 4-(7-ethyl-3,3-dimethyl-2-oxo-2,3-dihydro-1H-pyrido[2,3-b][1,4]oxazin-1-yl)piperidine-1-carboxylate (84.8 mg).

¹H NMR (400 MHz, CDCl₃) δ: 1.26 (t, 3H, J=7.4 Hz), 1.49 (s, 9H), 1.51 (s, 6H), 1.68-1.74 (m, 2H), 2.39-2.50 (m, 2H), 2.63 (q, 2H, J=7.4 Hz), 2.78-2.85 (m, 2H), 4.23-4.34 (br m, 2H), 4.42-4.50 (m, 1H), 7.19 (d, 1H, J=1.6 Hz), 7.78 (d, 1H, J=1.6 Hz).

Example 53-2

At room temperature, to a dichloromethane solution (1.5 ml) of tert-butyl 4-(7-ethyl-3,3-dimethyl-2-oxo-2,3-dihydro-1H-pyrido[2,3-b][1,4]oxazin-1-yl)piperidine-1-carboxylate (71.4 mg) was added trifluoroacetic acid (0.7 ml), followed by stirring for 2 hours. Toluene was added to the reaction solution, and concentrated under reduced pressure. To the resulting residue were added dichloromethane (2.0 ml), 2'-{[(1R)-3-{[tert-butyl(diphenyl)silyl]oxy}-1-methylpropyl]oxy}-3-fluorobiphenyl-4-carboxylic acid (Example 5-3) (99.5 mg), diisopropylethylamine (0.096 ml) and 2-(1H-benzotriazol-1-yl)-1,1,3,3-tetramethyluronium hexafluorophosphate (83.5 mg), followed by stirring at room temperature overnight. The reaction solution was diluted with dichloromethane, washed with saturated sodium chloride solution, dried over anhydrous sodium sulfate, and concentrated under reduced pressure. The resulting residue was purified by silica gel column chromatography to afford 1-{1-[(2'-{[(1R)-3-{[tert-butyl(diphenyl)silyl]oxy}-1-methylpropyl]oxy}-3-fluorobiphenyl-4-yl)carbonyl]piperidin-4-yl}-7-ethyl-3,3-dimethyl-1H-pyrido[2,3-b][1,4]oxazin-2(3H)-one (41.7 mg).

¹H NMR (400 MHz, CDCl₃) δ: 1.03 (s, 9H), 1.25-1.29 (m, 6H), 1.52 (s, 6H), 1.66-1.79 (m, 2H), 1.88-1.98 (m, 2H), 2.52-2.68 (m, 4H), 2.85-2.91 (m, 1H), 3.14-3.21 (m, 1H), 3.65-3.81 (m, 4H), 4.71-4.81 (m, 1H), 4.98-5.02 (m, 1H), 7.00-7.05 (m, 1H), 7.09 (d, 1H, J=8.2 Hz), 7.22-7.43 (m, 12H), 7.56-7.59 (m, 2H), 7.61-7.64 (m, 2H), 7.81 (d, 1H, J=2.0 Hz).

Example 53-3

In accordance with the methods of Examples 5-5 and 24-3, the compound of Example 53-2 was used instead of the compound of Example 5-4 to afford (3R)-3-[(4'-{[4-(7-ethyl-3,3-dimethyl-2-oxo-2,3-dihydro-1H-pyrido[2,3-b][1,4]oxazin-1-yl)piperidin-1-yl]carbonyl}-3'-fluorobiphenyl-2-yl)oxy]butanoic acid.

¹H NMR (400 MHz, CDCl₃) δ: 1.29 (t, 3H, J=7.6 Hz), 1.32 (d, 3H, J=5.9 Hz), 1.52 (s, 6H), 1.69-1.78 (m, 1H), 1.86-1.96 (m, 1H), 2.66 (q, 2H, J=7.6 Hz), 2.48-2.79 (m, 4H), 2.83-2.96 (m, 1H), 3.15-3.30 (m, 1H), 3.80-3.89 (m, 1H), 4.76-4.86 (m, 1H), 4.86-4.95 (m, 1H), 5.09-5.62 (br m, 1H), 7.01-7.12 (m, 2H), 7.23-7.46 (m, 6H), 7.81 (d, 1H, J=1.6 Hz).

Example 54

(3R)-3-[(4'-{[4-(7-Chloro-3,3-dimethyl-2-oxo-2,3-dihydro-1H-pyrido[2,3-b][1,4]oxazin-1-yl)piperidin-1-yl]carbonyl}-2',5'-dimethylbiphenyl-2-yl)oxy]butanoic acid

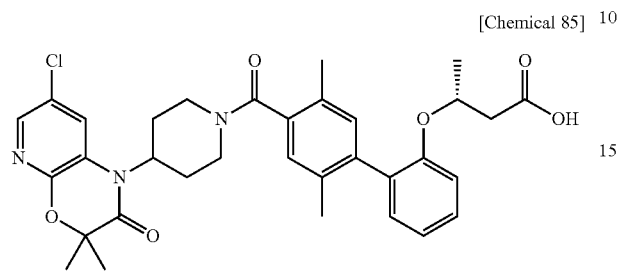

[Chemical 85]

Example 54-1

Under ice cooling, to a dichloromethane solution (27.0 ml) of 2,5-dimethyl-4-methoxybenzoic acid (1.65 g) was added dropwise a dichloromethane solution (1 M, 27.0 ml) of boron tribromide over 15 minutes, followed by stirring for 6 hours, which was then left at rest at room temperature overnight. To the reaction solution was added methanol (1.82 ml), followed by stirring for 1 hour, and then ethyl acetate and water were added, and the solution was separated. After the aqueous layer was extracted with ethyl acetate, the collected organic layer was dried over anhydrous sodium sulfate, and concentrated under reduced pressure. To the residue were added dichloromethane and hexane, and the precipitate was collected by filtration. To a methanol solution (5.0 ml) of this precipitate (500 mg) was added dropwise at room temperature thionyl chloride (0.66 ml). The reaction solution was stirred overnight, and then concentrated under reduced pressure. To a dichloromethane solution (5.0 ml) of methyl 2,5-dimethyl-4-hydroxybenzoate (441 mg) that had been purified by silica gel column chromatography from the resulting residue were added under ice cooling pyridine (0.238 ml) and trifluoromethanesulfonic acid anhydride (0.453 ml), followed by stirring for 6 hours, which was then left at rest at room temperature overnight. A saturated aqueous sodium hydrogen carbonate solution was added to the reaction solution, and extracted with dichloromethane. The organic layer was dried over anhydrous sodium sulfate, and concentrated under reduced pressure. The resulting residue was purified by silica gel column chromatography to afford methyl 2,5-dimethyl-4-{[(trifluoromethyl)sulfonyl]oxy}benzoate (692 mg).

$^1$H NMR (400 MHz, CDCl$_3$) δ: 2.37 (s, 3H), 2.59 (s, 3H), 3.90 (s, 3H), 7.12 (s, 1H), 7.87 (s, 1H).

Example 54-2

In accordance with the methods of Examples 1-3, 5-2, 5-5, 19-4, 45-4 and 24-3, the compound of Example 54-1 was used instead of the compound of Example 1-2, and the compound of Reference Example 3 was used instead of the compound of Reference Example 10 to afford (3R)-3-[(4'-{[4-(7-chloro-3,3-dimethyl-2-oxo-2,3-dihydro-1H-pyrido[2,3-b][1,4]oxazin-1-yl)piperidin-1-yl]carbonyl}-2',5'-dimethylbiphenyl-2-yl)oxy]butanoic acid.

$^1$H NMR (500 MHz, CDCl$_3$) δ: 1.20-1.35 (br m, 3H), 1.56 (s, 6H), 1.70-1.78 (m, 1H), 1.91-1.97 (m, 1H), 2.12 (s, 3H), 2.27 & 2.45 (s, total 3H), 2.35-2.70 (m, 4H), 2.87-2.93 (m, 1H), 3.12-3.22 (br m, 1H), 3.43-4.77 (br m, 3H), 5.03-5.12 (br m, 1H), 7.01-7.14 (m, 5H), 7.33-7.37 (m, 1H), 7.41 (s, 1H), 7.94 (s, 1H).

Example 55

(3R)-3-[(4'-{[4-(7-Chloro-3,3-dimethyl-2-oxo-2,3-dihydro-1H-pyrido[2,3-b][1,4]oxazin-1-yl)piperidin-1-yl]carbonyl}-3'-fluoro-4-methylbiphenyl-2-yl)oxy]butanoic acid

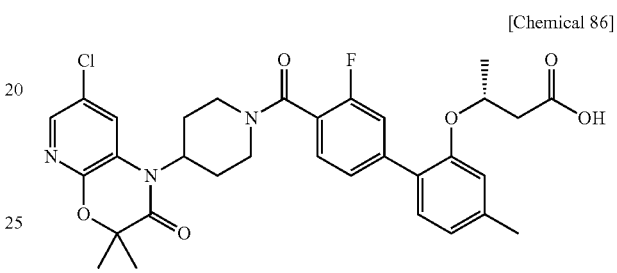

[Chemical 86]

Example 55-1

At room temperature, to an N,N-dimethylformamide solution (30.0 ml) of 2-methoxy-4-methylphenyltrifluoromethane sulfonate (Tetrahedron Letters, 2002, 43(39), 7077-7078)(2.70 g) were added 4-carboxy-3-fluorophenylboronic acid (1.84 g), potassium carbonate (4.15 g) and tetrakis(triphenylphosphine)palladium (1.16 g), followed by stirring at 100° C. for 10 hours. A 10% aqueous citric acid solution was added to the reaction solution, and extracted with dichloromethane. The organic layer was dried over anhydrous sodium sulfate, and concentrated under reduced pressure. To the resulting residue were added methanol (40.0 ml) and ethyl acetate (4.0 ml). Under ice cooling, a hexane solution (2 M, 20.7 ml) of trimethylsilyldiazomethane was added dropwise, and stirred at room temperature for 40 minutes. The reaction solution that had been diluted with ethyl acetate was washed sequentially with water and saturated sodium chloride solution, dried over anhydrous sodium sulfate, and concentrated under reduced pressure. The resulting residue was purified by silica gel column chromatography to afford methyl 3-fluoro-2'-methoxy-4'-methylbiphenyl-4-carboxylate (1.73 g).

$^1$H NMR (400 MHz, CDCl$_3$) δ: 2.41 (s, 3H), 3.82 (s, 3H), 3.94 (s, 3H), 6.81 (s, 1H), 6.86 (dd, 1H, J=7.8, 0.8 Hz), 7.22 (d, 1H, J=7.8 Hz), 7.34 (d, 1H, J=4.7 Hz), 7.37 (d, 1H, J=0.8 Hz), 7.94 (t, 1H, J=7.8 Hz).

Example 55-2

Under ice cooling, to a dichloromethane solution (10.0 ml) of methyl 3-fluoro-2'-methoxy-4'-methylbiphenyl-4-carboxylate (910 mg) was added a dichloromethane solution (1 M, 9.95 ml) of boron tribromide, followed by stirring at room temperature overnight. The reaction solution was poured into water, and extracted with dichloromethane. The organic layer was dried over anhydrous sodium sulfate, and concentrated under reduced pressure. To the resulting residue were added methanol (30.0 ml) and ethyl acetate (3.0 ml). Under ice cooling, a hexane solution (2 M, 8.30 ml) of trimethylsilyl-diazomethane was added dropwise, and stirred at room temperature overnight. The reaction solution was concentrated under reduced pressure, and the resulting residue was purified by silica gel column chromatography to afford methyl 3-fluoro-2'-hydroxy-4'-methylbiphenyl-4-carboxylate (137 mg).

$^1$H NMR (400 MHz, CDCl$_3$) δ: 2.35 (s, 3H), 3.95 (s, 3H), 6.77 (s, 1H), 6.84 (d, 1H, J=8.2 Hz), 7.18 (d, 1H, J=7.8 Hz), 7.34 (dd, 1H, J=11.7, 1.6 Hz), 7.37 (dd, 1H, J=8.2, 1.6 Hz), 8.00 (t, 1H, J=7.4 Hz).

Example 55-3

In accordance with the methods of Examples 5-2, 5-5, 41-2, 45-4 and 24-3, the compound of Example 55-2 was used instead of the compound of Example 1-3, and the compound of Reference Example 3 was used instead of the compound of Reference Example 10 to afford (3R)-3-[(4'-{[4-(7-chloro-3,3-dimethyl-2-oxo-2,3-dihydro-1H-pyrido[2,3-b][1,4]oxazin-1-yl]piperidin-1-yl]carbonyl}-3'-fluoro-4-methylbiphenyl-2-yl)oxy]butanoic acid.

$^1$H NMR (400 MHz, CDCl$_3$) δ: 1.32 (d, 3H, J=5.9 Hz), 1.53 (s, 6H), 1.71-1.74 (m, 1H), 1.87-1.91 (m, 1H), 2.38 (s, 3H), 2.52 (dd, 1H, J=15.6, 5.5 Hz), 2.54-2.64 (m, 2H), 2.73 (dd, 1H, J=15.6, 7.0 Hz), 2.85-2.91 (m, 1H), 3.17-3.25 (m, 1H), 3.83-3.86 (m, 1H), 4.31-4.68 (br m, 1H), 4.75-4.83 (m, 1H), 4.98-5.01 (m, 1H), 6.85-6.87 (m, 2H), 7.18 (d, 1H, J=7.4 Hz), 7.26 (d, 1H, J=10.9 Hz), 7.32 (d, 1H, J=7.8 Hz), 7.38-7.42 (m, 2H), 7.92 (d, 1H, J=2.0 Hz).

Example 56

(3R)-3-{[4'-({4-[7-Chloro-2-oxo-3-(2,2,2-trifluoroethyl)-3,4-dihydro-1,5-naphthyridin-1(2H)-yl]piperidin-1-yl}carbonyl)-3'-fluorobiphenyl-2-yl]oxy}butanoic acid

[Chemical 87]

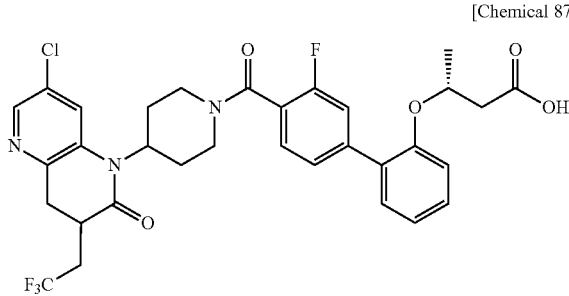

Example 56-1

In accordance with the method of Reference Example 10-1, 1,1,1-trifluoro-2-iodoethane was used instead of methyl iodide to afford tert-butyl 4-[7-chloro-2-oxo-3-(2,2,2-trifluoroethyl)-3,4-dihydro-1,5-naphthyridin-1(2H)-yl]piperidine-1-carboxylate.

$^1$H NMR (400 MHz, CDCl$_3$) δ: 1.49 (s, 9H), 1.60-1.63 (m, 1H), 1.76-1.79 (m, 1H), 2.14-2.28 (m, 1H), 2.33-2.49 (m, 2H), 2.75-3.12 (m, 5H), 3.32 (dd, 1H, J=15.3, 4.7 Hz), 4.30-4.36 (m, 3H), 7.38 (d, 1H, J=2.0 Hz), 8.21 (d, 1H, J=2.0 Hz).

Example 56-2

In accordance with the methods of Examples 53-2, 5-5 and 24-3, the compound of Example 56-1 was used instead of the compound of Example 53-1 to afford (3R)-3-{[4'-({4-[7-chloro-2-oxo-3-(2,2,2-trifluoroethyl)-3,4-dihydro-1,5-naphthyridin-1(2H)-yl]piperidin-1-yl}carbonyl)-3'-fluorobiphenyl-2-yl]oxy}butanoic acid.

$^1$H NMR (400 MHz, CDCl$_3$) δ: 1.33 (d, 3H, J=6.3 Hz), 1.65-1.97 (m, 2H), 2.15-2.29 (m, 1H), 2.50-2.75 (m, 4H), 2.80-3.36 (m, 6H), 3.82-3.87 (m, 1H), 4.33-4.53 (br m, 1H), 4.77-4.82 (m, 1H), 4.96-5.03 (m, 1H), 7.02-7.07 (m, 2H), 7.27-7.42 (m, 6H), 8.22-8.23 (m, 1H).

Example 57

(3R)-3-{[4'-({4-[7-Chloro-3-(2-methoxyethyl)-2-oxo-3,4-dihydro-1,5-naphthyridin-1(2H)-yl]piperidin-1-yl}carbonyl)-3'-fluorobiphenyl-2-yl]oxy}butanoic acid

[Chemical 88]

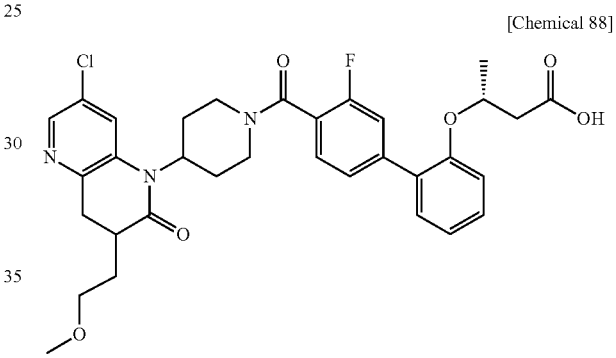

Example 57-1

In accordance with the method of Reference Example 10-1, 1-bromo-2-methoxyethane was used instead of methyl iodide to afford tert-butyl 4-[7-chloro-3-(2-methoxyethyl)-2-oxo-3,4-dihydro-1,5-naphthyridin-1(2H)-yl]piperidine-1-carboxylate.

$^1$H NMR (400 MHz, CDCl$_3$) δ: 1.49 (s, 9H), 1.61-1.74 (m, 3H), 2.12 (dq, 1H, J=14.5, 6.3 Hz), 2.35-2.47 (m, 2H), 2.67-2.88 (m, 4H), 3.15 (dd, 1H, J=15.7, 5.1 Hz), 3.30 (s, 3H), 3.49 (t, 2H, J=6.3 Hz), 4.21-4.40 (m, 3H), 7.33 (d, 1H, J=2.0 Hz), 8.16 (d, 1H, J=2.0 Hz).

Example 57-2

In accordance with the methods of Examples 53-2, 5-5 and 24-3, the compound of Example 57-1 was used instead of the compound of Example 53-1 to afford (3R)-3-{[4'-({4-[7-chloro-3-(2-methoxyethyl)-2-oxo-3,4-dihydro-1,5-naphthyridin-1(2H)-yl]piperidin-1-yl}carbonyl)-3'-fluorobiphenyl-2-yl]oxy}butanoic acid.

$^1$H NMR (400 MHz, CDCl$_3$) δ: 1.32 (d, 3H, J=6.3 Hz), 1.57-1.92 (m, 3H), 2.09-2.18 (m, 1H), 2.48-2.64 (m, 3H), 2.71-2.76 (m, 2H), 2.83-2.92 (m, 2H), 3.14-3.25 (m, 2H), 3.30 (s, 3H), 3.50 (t, 2H, J=6.3 Hz), 3.82-3.85 (m, 1H), 4.22-4.69 (br m, 1H), 4.78-4.83 (m, 1H), 4.97-5.00 (m, 1H), 7.02-7.08 (m, 2H), 7.27-7.45 (m, 6H), 8.18 (s, 1H).

Example 58

(3R)-3-[(3'-Fluoro-4'-{[4-(7-methoxy-3,3-dimethyl-2-oxo-2,3-dihydro-1H-pyrido[2,3-b][1,4]oxazin-1-yl)piperidin-1-yl]carbonyl}biphenyl-2-yl)oxy]butanoic acid

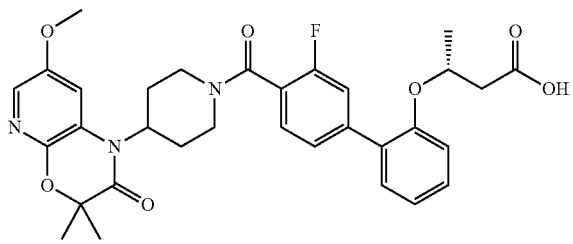

[Chemical 89]

Example 58-1

To a toluene suspension (5.6 ml) of tert-butyl 4-(7-bromo-3,3-dimethyl-2-oxo-2,3-dihydro-1H-pyrido[2,3-b][1,4]oxazin-1-yl)piperidine-1-carboxylate (Example 52-1) (1.11 g), copper iodide (24.0 mg), 3,4,7,8-tetramethyl-1,10-phenanthroline (59.6 mg) and cesium carbonate (1.23 g) was added methanol (0.204 ml), followed by stirring at 80° C. for 21 hours. After the reaction solution was brought back to room temperature, water was added, and extracted with ethyl acetate. The organic layer was dried over anhydrous sodium sulfate, and concentrated under reduced pressure. The resulting residue was purified by silica gel column chromatography to afford tert-butyl 4-(7-methoxy-3,3-dimethyl-2-oxo-2,3-dihydro-1H-pyrido[2,3-b][1,4]oxazin-1-yl)piperidine-1-carboxylate (246 mg).

$^1$H NMR (400 MHz, CDCl$_3$) δ: 1.49 (s, 9H), 1.50 (s, 6H), 1.68-1.71 (m, 2H), 2.39-2.50 (m, 2H), 2.77-2.82 (m, 2H), 3.87 (s, 3H), 4.28-4.45 (m, 3H), 7.01 (d, 1H, J=2.7 Hz), 7.58 (d, 1H, J=2.7 Hz).

Example 58-2

In accordance with the methods of Examples 53-2, 5-5 and 24-3, the compound of Example 58-1 was used instead of the compound of Example 53-1 to afford (3R)-3-[(3'-fluoro-4'-{[4-(7-methoxy-3,3-dimethyl-2-oxo-2,3-dihydro-1H-pyrido[2,3-b][1,4]oxazin-1-yl)piperidin-1-yl]carbonyl}biphenyl-2-yl)oxy]butanoic acid.

$^1$H NMR (500 MHz, CDCl$_3$) δ: 1.32 (d, 3H, J=5.9 Hz), 1.50 (s, 3H), 1.51 (s, 3H), 1.72-1.75 (m, 1H), 1.87-1.90 (m, 1H), 2.52 (dd, 1H, J=15.6, 5.9 Hz), 2.53-2.66 (br m, 2H), 2.73 (dd, 1H, J=15.6, 6.8 Hz), 2.84-2.89 (m, 1H), 3.17-3.22 (m, 1H), 3.82-3.85 (m, 1H), 3.88 (s, 3H), 4.47-4.69 (br m, 1H), 4.76-4.82 (m, 1H), 4.98-5.00 (m, 1H), 7.03-7.06 (m, 3H), 7.25-7.35 (m, 4H), 7.39-7.42 (m, 1H), 7.60 (d, 1H, J=2.4 Hz).

Example 59

(3R)-3-[(4'-{[4-(7-Chloro-3,3-dimethyl-2-oxo-3,4-dihydroquinoline-1(2H)-yl)piperidin-1-yl]carbonyl}-3'-fluorobiphenyl-2-yl)oxy]butanoic acid

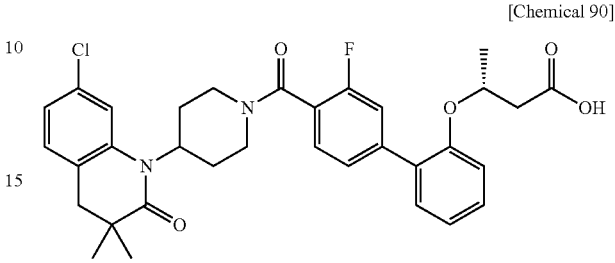

[Chemical 90]

Example 59-1

In accordance with the methods of References Examples 9-2, 9-3, 10-1 and 10-2, ethyl (2E)-3-(2-amino-4-chlorophenyl)acrylate (Journal of Organic Chemistry, 2003, 68(10), 4104-4107) was used instead of the compound of Reference Example 9-1 to afford tert-butyl 4-(7-chloro-3,3-dimethyl-2-oxo-3,4-dihydroquinoline-1(2H)-yl)piperidine-1-carboxylate.

$^1$H NMR (400 MHz, CDCl$_3$) δ: 1.09 (s, 6H), 1.49 (s, 9H), 1.65-1.68 (m, 2H), 2.48-2.58 (m, 2H), 2.66 (s, 2H), 2.73-2.85 (br m, 2H), 4.14-4.42 (br m, 2H), 4.28 (tt, 1H, J=12.1, 3.9 Hz), 6.99 (dd, 1H, J=7.8, 2.0 Hz), 7.04 (d, 1H, J=2.0 Hz), 7.06 (d, 1H, J=7.8 Hz).

Example 59-2

In accordance with the methods of Examples 53-2, 5-5 and 24-3, the compound of Example 59-1 was used instead of the compound of Example 53-1 to afford (3R)-3-[(4'-{[4-(7-chloro-3,3-dimethyl-2-oxo-3,4-dihydroquinoline-1(2H)-yl)piperidin-1-yl]carbonyl}-3'-fluorobiphenyl-2-yl)oxy]butanoic acid.

$^1$H NMR (400 MHz, CDCl$_3$) δ: 1.09 (s, 6H), 1.32 (d, 3H, J=5.9 Hz), 1.69-1.72 (m, 1H), 1.84-1.87 (m, 1H), 2.50-2.55 (m, 1H), 2.64-2.76 (m, 3H), 2.67 (s, 2H), 2.84-2.90 (m, 1H), 3.13-3.27 (br m, 1H), 3.80-3.83 (m, 1H), 3.89-4.49 (br m, 1H), 4.73-4.82 (m, 1H), 4.95-4.98 (m, 1H), 6.99-7.08 (m, 5H), 7.24-7.35 (m, 4H), 7.40-7.44 (m, 1H).

Example 60

(3R)-3-[(4'-{[4-(6-Chloro-2,2-dimethyl-3-oxo-2,3-dihydro-4H-1,4-benzoxazin-4-yl)piperidin-1-yl]carbonyl}-3'-fluorobiphenyl-2-yl)oxy]butanoic acid

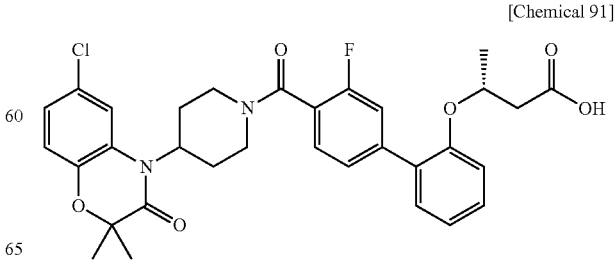

[Chemical 91]

Example 60-1

In accordance with the method of Reference Example 5-2, 2-amino-4-chlorophenol was used instead of the compound of Reference Example 5-1, and trifluoroacetic acid was used instead of acetic acid to afford tert-butyl 4-[(5-chloro-2-hydroxyphenyl)amino]piperidine-1-carboxylate.

$^1$H NMR (400 MHz, DMSO-D$_6$) δ: 1.22-1.32 (m, 2H), 1.40 (s, 9H), 1.83-1.87 (m, 2H), 2.76-2.98 (br m, 2H), 3.36-3.46 (m, 1H), 3.88-3.91 (m, 2H), 4.62 (d, 1H, J=8.6 Hz), 6.39 (dd, 1H, J=8.2, 2.7 Hz), 6.54 (d, 1H, J=2.7 Hz), 6.62 (d, 1H, J=8.2 Hz), 9.52 (s, 1H).

Example 60-2

To a N,N-dimethylformamide solution (23 ml) of tert-butyl 4-[(5-chloro-2-hydroxyphenyl)amino]piperidine-1-carboxylate (1.15 g) were added at room temperature cesium carbonate (5.73 g) and methyl 2-bromo-2-methylpropanoate (1.27 g), followed by stirring at 140° C. for 2 hours. After the reaction solution was cooled to room temperature, water was added, and extracted with ethyl acetate. The organic layer was washed with saturated sodium chloride solution, dried over anhydrous sodium sulfate, and concentrated under reduced pressure. The resulting residue was purified by silica gel column chromatography to afford tert-butyl 4-(6-chloro-2,2-dimethyl-3-oxo-2,3-dihydro-4H-1,4-benzoxazin-4-yl)piperidine-1-carboxylate.

$^1$H NMR (400 MHz, CDCl$_3$) δ: 1.44 (s, 6H), 1.49 (s, 9H), 1.68-1.71 (m, 2H), 2.46-2.56 (m, 2H), 2.77-2.83 (m, 2H), 4.18-4.39 (br m, 1H), 4.34 (tt, 1H, J=12.3, 3.9 Hz), 6.90 (d, 1H, J=8.6 Hz), 6.96 (dd, 1H, J=8.6, 2.3 Hz), 7.05 (d, 1H, J=2.3 Hz).

Example 60-3

In accordance with the methods of Examples 53-2, 5-5 and 24-3, the compound of Example 60-2 was used instead of the compound of Example 53-1 to afford (3R)-3-[(4'-{[4-(6-chloro-2,2-dimethyl-3-oxo-2,3-dihydro-4H-1,4-benzoxazin-4-yl)piperidin-1-yl]carbonyl}-3'-fluorobiphenyl-2-yl)oxy]butanoic acid.

$^1$H NMR (500 MHz, CDCl$_3$) δ: 1.32 (d, 3H, J=5.9 Hz), 1.44 (s, 6H), 1.71-1.74 (m, 1H), 1.88-1.90 (m, 1H), 2.52 (dd, 1H, J=15.6, 5.4 Hz), 2.63-2.76 (m, 3H), 2.85-2.90 (m, 1H), 3.13-3.28 (br m, 1H), 3.82-3.84 (m, 1H), 4.25-4.60 (br m, 1H), 4.75-4.81 (m, 1H), 4.98-5.00 (m, 1H), 6.91 (d, 1H, J=8.3 Hz), 6.98 (dd, 1H, J=8.3, 2.2 Hz), 7.03-7.09 (m, 3H), 7.25-7.34 (m, 4H), 7.41-7.43 (m, 1H).

Example 61

(3R)-3-{[4'-({4-[7-Chloro-3-(2-hydroxyethyl)-2-oxo-3,4-dihydroxy-1,5-naphthyridin-1(2H)-yl]piperidin-1-yl}carbonyl)-3'-fluorobiphenyl-2-yl]oxy}butanoic acid

[Chemical 92]

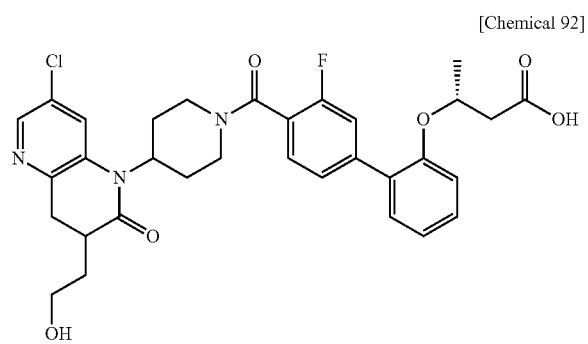 [SMILES: C[C@H](CC(=O)O)Oc1ccccc1-c1ccc(C(=O)N2CCC(N3C(=O)C(CCO)Cc4ncc(Cl)cc43)CC2)c(F)c1]

Example 61-1

In accordance with the method of Example 5-5, the compound of Example 5-2 was used instead of the compound of Example 5-4 to afford benzyl 3-fluoro-2'-{[(1R)-3-hydroxy-1-methylpropyl]oxy}biphenyl-4-carboxylate.

$^1$H NMR (400 MHz, CDCl$_3$) δ: 1.27 (d, 3H, J=6.3 Hz), 1.78-1.93 (m, 2H), 3.66-3.74 (m, 2H), 4.56-4.68 (m, 1H), 5.40 (s, 2H), 7.03 (dd, 1H, J=7.8, 6.8 Hz), 7.05 (d, 1H, J=7.3 Hz), 7.28-7.43 (m, 7H), 7.48 (d, 2H, J=7.8 Hz), 7.98 (t, 1H, J=7.8 Hz).

Example 61-2

To a mixed solvent solution of benzyl 3-fluoro-2'-{[(1R)-3-hydroxy-1-methylpropyl]oxy}biphenyl-4-carboxylate (13.4 g) in acetonitrile (252 ml) and a neutral phosphate pH standard solution (pH 6.86) (198 ml) were added at room temperature a 2,2,6,6-tetramethyl-1-piperidyloxy radical (533 mg), 79% sodium chlorite (7.83 g) and a 5% aqueous sodium hypochlorite solution (2.0 ml). The reaction solution was stirred at 50° C. for 4.5 hours. After the reaction solution was cooled to room temperature, an aqueous sodium sulfite solution and a 10% aqueous citric acid solution were added, and extracted with dichloromethane. The organic layer was washed with saturated sodium chloride solution, dried over anhydrous sodium sulfate, and concentrated under reduced pressure. To a toluene solution (80 ml) of the resulting residue (11.0 g) was added at room temperature a supernatant (34 ml) containing tert-butyl N,N'-diisopropylimidocarbamate prepared in the method described in Example 1-1, followed by stirring at 60° C. for 4.5 hours. The reaction solution was poured into ice water, and then filtered through Celite. After the filtrate was separated, the aqueous layer was extracted with ethyl acetate. The collected organic layer was washed with saturated sodium chloride solution, dried over anhydrous sodium sulfate, and concentrated under reduced pressure. The resulting residue was purified by silica gel column chromatography to afford benzyl 2'-{[(1R)-3-tert-butoxy-1-methyl-3-oxopropyl]oxy}-3-fluorobiphenyl-4-carboxylate (12.8 g).

$^1$H NMR (400 MHz, CDCl$_3$) δ: 1.27 (d, 3H, J=6.3 Hz), 1.39 (s, 9H), 2.38 (dd, 1H, J=15.4, 5.9 Hz), 2.65 (dd, 1H, J=15.4, 7.1 Hz), 4.81 (dq, 1H, J=12.7, 6.3 Hz), 5.40 (s, 2H), 7.03 (t, 1H, J=7.3 Hz), 7.06 (d, 1H, J=8.3 Hz), 7.30-7.41 (m, 7H), 7.48 (d, 2H, J=6.8 Hz), 7.96 (t, 1H, J=7.8 Hz).

Example 61-3

To an ethanol solution (80 ml) of benzyl 2'-{[(1R)-3-tert-butoxy-1-methyl-3-oxopropyl]oxy}-3-fluorobiphenyl-4-carboxylate (12.8 g) was added 10% palladium carbon (2.54 g), followed by stirring at room temperature for 7 hours under a hydrogen atmosphere. The reaction solution was filtered through Celite, and the filtrate was concentrated under reduced pressure. The resulting residue was purified by silica gel column chromatography to afford 2'-{[(1R)-3-tert-butoxy-1-methyl-3-oxopropyl]oxy}-3-fluorobiphenyl-4-carboxylic acid (9.87 g).

$^1$H NMR (400 MHz, CDCl$_3$) δ: 1.30 (d, 3H, J=6.3 Hz), 1.40 (s, 9H), 2.41 (dd, 1H, J=15.6, 5.6 Hz), 2.67 (dd, 1H, J=15.6, 7.3 Hz), 4.84 (dq, 1H, J=12.7, 5.9 Hz), 7.04 (dd, 1H, J=8.3, 7.3 Hz), 7.07 (d, 1H, J=8.3 Hz), 7.35-7.40 (m, 4H), 8.04 (t, 1H, J=8.3 Hz).

Example 61-4

To a tetrahydrofuran solution (2 ml) of tert-butyl 4-(7-chloro-2-oxo-3,4-dihydro-1,5-naphthyridin-1(2H)-yl)piperidine-1-carboxylate (Reference Example 9-3) (438 mg) was added dropwise at −20° C. a hexane solution (1.0 M, 1.32 ml) of lithium hexamethyldisilazide over 10 minutes. After the reaction solution was stirred for 30 minutes, was added dropwise a tetrahydrofuran solution of 1-(2-bromoethoxymethyl)-4-methoxybenzene (Journal of Medicinal Chemistry, 2007, 50(26), 6580-6595)(324 mg) and 1,3-dimethyltetrahydropyrimidin-2(1H)-one (315 mg). The reaction solution was brought to 0° C. over 30 minutes, and then stirred for 90 minutes. Water was added to the reaction solution, and extracted with ethyl acetate. The organic layer was washed with saturated sodium chloride solution, dried over anhydrous sodium sulfate, and concentrated under reduced pressure. The resulting residue was purified by silica gel column chromatography to afford tert-butyl 4-[7-chloro-3-{2-[(4-methoxybenzyl)oxy]ethyl}-2-oxo-3,4-dihydro-1,5-naphthyridin-1(2H)-yl]piperidine-1-carboxylate (189 mg).

$^1$H NMR (400 MHz, CDCl$_3$) δ: 1.49 (s, 9H), 1.60-1.70 (m, 3H), 2.15 (td, 1H, J=13.4, 6.9 Hz), 2.31-2.47 (m, 2H), 2.67-2.89 (m, 2H), 2.83 (dd, 2H, J=15.3, 11.0 Hz), 3.14 (dd, 1H, J=15.3, 5.1 Hz), 3.57 (t, 2H, J=6.3 Hz), 3.79 (s, 3H), 4.14-4.41 (m, 3H), 4.40 (s, 2H), 6.85 (d, 2H, J=8.6 Hz), 7.22 (d, 2H, J=8.6 Hz), 7.32 (d, 1H, J=2.0 Hz), 8.16 (d, 1H, J=2.0 Hz).

Example 61-5

To a dichloromethane solution (1 ml) of tert-butyl 4-[7-chloro-3-{2-[(4-methoxybenzyl)oxy]ethyl}-2-oxo-3,4-dihydro-1,5-naphthyridin-1(2H)-yl]piperidine-1-carboxylate (29.2 mg) was added at −78° C. a dichloromethane solution (0.5 ml) of trifluoromethanesulfonic acid trimethylsilyl ester (35.2 mg). The reaction solution was raised to 0° C., and stirred for 1 hour, and then methanol, water and a 2N aqueous sodium hydroxide solution were sequentially added, and extracted with dichloromethane. The collected organic layer was washed with saturated sodium chloride solution, and concentrated under reduced pressure. The resulting residue was dissolved in a mixed solvent of tetrahydrofuran (1.0 ml) and methanol (0.5 ml), followed by addition of 2'-{[(1R)-3-tert-butoxy-1-methyl-3-oxopropyl]oxy}-3-fluorobiphenyl-4-carboxylic acid (20.1 mg), N-methylmorpholine (18.0 mg) and 4-(4,6-dimethoxy-1,3,5-triazin-2-yl)-4-methylmorpholinium chloride (18.3 mg). After the reaction solution was stirred at room temperature for 5 hours, 1 N hydrochloric acid was added, and extracted with ethyl acetate. The collected organic layer was washed sequentially with 1 N hydrochloric acid and saturated sodium chloride solution, dried over anhydrous sodium sulfate, and concentrated under reduced pressure. The resulting residue was purified by silica gel thin layer chromatography to afford tert-butyl (3R)-3-{[4'-({4-[7-chloro-3-(2-hydroxyethyl)-2-oxo-3,4-dihydroxy-1,5-naphthyridin-1(2H)-yl]piperidin-1-yl}carbonyl)-3'-fluorobiphenyl-2-yl]oxy}butanoic acid (18.9 mg).

$^1$H NMR (400 MHz, CDCl$_3$) δ: 1.24-1.40 (m, 3H), 1.40 (s, 9H), 1.68-2.04 (m, 6H), 2.40 (dd, 1H, J=15.6, 5.9 Hz), 2.59 (br s, 1H), 2.67 (dd, 1H, J=15.6, 7.3 Hz), 2.78-2.95 (m, 3H), 3.08-3.32 (m, 2H), 3.72-3.86 (m, 3H), 4.19-4.74 (m, 1H), 4.75-5.10 (m, 2H), 6.97-7.11 (m, 2H), 7.28-7.50 (m, 6H), 8.16-8.22 (m, 1H).

Example 61-6

To a dichloromethane solution (1 ml) of tert-butyl (3R)-3-{[4'-({4-[7-chloro-3-(2-hydroxyethyl)-2-oxo-3,4-dihydroxy-1,5-naphthyridin-1(2H)-yl]piperidin-1-yl}carbonyl)-3'-fluorobiphenyl-2-yl]oxy}butanoic acid (28.3 mg) were added at room temperature triethylsilane (20.2 mg) and trifluoroacetic acid (0.5 ml). The reaction solution was stirred for 6 hours, and then concentrated under reduced pressure. The resulting residue was purified by silica gel thin layer chromatography to afford (3R)-3-{[4'-({4-[7-chloro-3-(2-hydroxyethyl)-2-oxo-3,4-dihydroxy-1,5-naphthyridin-1(2H)-yl]piperidin-1-yl}carbonyl)-3'-fluorobiphenyl-2-yl]oxy}butanoic acid (25.0 mg).

$^1$H NMR (400 MHz, CDCl$_3$) δ: 1.33 (d, 3H, J=6.3 Hz), 1.67-2.05 (m, 4H), 2.51-3.19 (m, 11H), 3.70-3.84 (m, 3H), 4.40 (br s, 1H), 4.74-4.81 (m, 1H), 4.95-4.99 (m, 1H), 7.00-7.08 (m, 2H), 7.23-7.50 (m, 5H), 8.19 (s, 1H).

Example 62

(3R)-3-{[4'-({4-[7-Chloro-3-(hydroxymethyl)-3-methyl-2-oxo-3,4-dihydro-1,5-naphthyridin-1(2H)-yl]piperidin-1-yl}carbonyl)-3'-fluorobiphenyl-2-yl]oxy}butanoic acid

[Chemical 93]

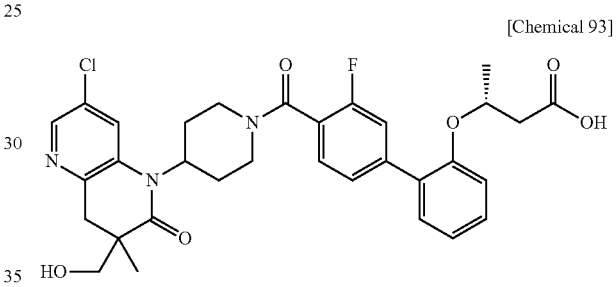

Example 62-1

To a tetrahydrofuran solution (10 ml) of tert-butyl 4-(7-chloro-2-oxo-3,4-dihydro-1,5-naphthyridin-1(2H)-yl)piperidine-1-carboxylate (Reference Example 9-3) (500 mg) were added at 0° C. sodium hydride (161 mg) and diethyl carbonate (0.66 ml). After the reaction solution was stirred at 70° C. for 4 hours, methyl iodide (0.171 ml) was added at 0° C., and stirred at room temperature for 6 hours. Water was added to the reaction solution at 0° C., and extracted with ethyl acetate. The collected organic layer was washed with saturated sodium chloride solution, dried over anhydrous sodium sulfate, and concentrated under reduced pressure. The resulting residue was purified by silica gel column chromatography to afford ethyl 1-[1-(tert-butoxycarbonyl)piperidin-4-yl]-7-chloro-3-methyl-2-oxo-1,2,3,4-tetrahydro-1,5-naphthyridine-3-carboxylate (286 mg).

$^1$H NMR (400 MHz, CDCl$_3$) δ: 1.06 (t, 3H, J=7.1 Hz), 1.49 (s, 9H), 1.52 (s, 3H), 1.64 (d, 1H, J=12.2 Hz), 1.79 (d, 1H, J=12.2 Hz), 2.36-2.54 (m, 2H), 2.82 (br s, 2H), 3.00 (d, 1H, J=16.1 Hz), 3.49 (d, 1H, J=16.1 Hz), 3.96-4.08 (m, 2H), 4.16-4.47 (m, 3H), 7.35 (d, 1H, J=2.0 Hz), 8.18 (d, 1H, J=2.0 Hz).

Example 62-2

To a methanol solution (4 ml) of ethyl 1-[1-(tert-butoxycarbonyl)piperidin-4-yl]-7-chloro-3-methyl-2-oxo-1,2,3,4-tetrahydro-1,5-naphthyridine-3-carboxylate (163 mg) was added at 0° C. calcium chloride (162 mg), followed by stirring for 15 minutes. Then, sodium borohydride (115 mg) was added, and stirred for 2 hours. Water was added to the reaction solution, and extracted with ethyl acetate. The collected organic layer was washed with saturated sodium chloride solution, dried over anhydrous sodium sulfate, and concentrated under reduced pressure. The resulting residue was purified by silica gel thin layer chromatography to afford tert-butyl 4-[7-chloro-3-(hydroxymethyl)-3-methyl-2-oxo-3,4-dihydro-1,5-naphthyridin-1(2H)-yl]piperidine-1-carboxylate (30.8 mg).

$^1$H NMR (400 MHz, CDCl$_3$) δ: 0.97 (s, 3H), 1.50 (s, 9H), 1.63 (d, 1H, J=12.2 Hz), 1.77 (d, 1H, J=12.7 Hz), 2.40 (dq, 1H, J=4.4, 12.2 Hz), 2.48 (dq, 1H, J=4.4, 12.7 Hz), 2.65 (d, 1H, J=16.1 Hz), 2.72-2.93 (m, 3H), 3.31 (d, 1H, J=16.1 Hz), 3.58 (dd, 1H, J=11.2, 6.3 Hz), 3.83 (dd, 1H, J=11.2, 6.8 Hz), 4.33 (s, 3H), 7.35 (d, 1H, J=2.0 Hz), 8.20 (d, 1H, J=2.0 Hz).

Example 62-3

To a dichloromethane solution (2 ml) of tert-butyl 4-[7-chloro-3-(hydroxymethyl)-3-methyl-2-oxo-3,4-dihydro-1,5-naphthyridin-1(2H)-yl]piperidine-1-carboxylate (39.1 mg) was added at room temperature trifluoroacetic acid (1 ml), followed by stirring for 30 minutes. The reaction solution was concentrated under reduced pressure, and then azeotroped sequentially with dichloromethane, methanol and toluene. The resulting residue was dissolved in a mixed solvent of tetrahydrofuran (1 ml) and methanol (0.5 ml), followed by addition of 2'-{[(1R)-3-tert-butoxy-1-methyl-3-oxopropyl]oxy}-3-fluorobiphenyl-4-carboxylic acid (35.7 mg), N-methylmorpholine (0.042 ml) and 4-(4,6-dimethoxy-1,3,5-triazin-2-yl)-4-methylmorpholinium chloride (29.0 mg) at room temperature. After the reaction solution had been stirring for 1 hour, 1 N hydrochloric acid was added, and extracted with ethyl acetate. The collected organic layer was washed sequentially with 1 N hydrochloric acid and saturated sodium chloride solution, dried over anhydrous sodium sulfate, and concentrated under reduced pressure. The resulting residue was purified by silica gel column chromatography to afford tert-butyl (3R)-3-{[4'-({4-[7-chloro-3-(hydroxymethyl)-3-methyl-2-oxo-3,4-dihydro-1,5-naphthyridin-1(2H)-yl]piperidin-1-yl}carbonyl)-3'-fluorobiphenyl-2-yl]oxy}butanoic acid (59.3 mg).

$^1$H NMR (400 MHz, CDCl$_3$) δ: 0.98 (s, 3H), 1.29 (d, 3H, J=6.3 Hz), 1.40 (s, 9H), 1.65 (d, 0.5H, J=12.1 Hz), 1.80 (d, 1H, J=11.0 Hz), 1.95 (d, 0.5H, J=12.5 Hz), 2.40 (dd, 1H, J=15.3, 5.9 Hz), 2.46-2.75 (m, 5H), 2.81-2.96 (m, 1H), 3.11-3.27 (m, 1H), 3.32 (d, 1H, J=16.0 Hz), 3.59 (d, 1H, J=11.0 Hz), 3.85 (dd, 2H, J=11.0, 4.5 Hz), 4.46 (br s, 1H), 4.83 (m, 1H), 5.00 (t, 1H, J=12.5 Hz), 6.98-7.09 (m, 2H), 7.29-7.46 (m, 6H), 8.22 (s, 1H).

Example 62-4

In accordance with the method of Example 61-6, the compound of Example 62-3 was used instead of the compound of Example 61-5 to afford (3R)-3-{[4'-({4-[7-chloro-3-(hydroxymethyl)-3-methyl-2-oxo-3,4-dihydro-1,5-naphthyridin-1(2H)-yl]piperidin-1-yl}carbonyl)-3'-fluorobiphenyl-2-yl]oxy}butanoic acid (46.8 mg).

$^1$H NMR (400 MHz, CDCl$_3$) δ: 0.96 (s, 3H), 1.32 (d, 3H, J=5.9 Hz), 1.64-1.93 (m, 2H), 2.50-2.75 (m, 6H), 2.82-2.92 (m, 1H), 3.06-3.29 (m, 1H), 3.33 (d, 1H, J=16.1 Hz), 3.54 (dd, 1H, J=11.2, 4.9 Hz), 3.80-3.87 (m, 2H), 4.40 (br s, 1H), 4.76-4.85 (m, 1H), 4.97 (t, 1H, J=14.6 Hz), 6.98-7.08 (m, 2H), 7.23-7.46 (m, 6H), 8.22 (s, 1H).

Example 63

(3R)-3-[(4'-{[4-(7-Chloro-3,3-dimethyl-2-oxo-2,3-dihydro-1H-pyrido[2,3-b][1,4]thiazin-1-yl)piperidin-1-yl]carbonyl}-3'-fluorobiphenyl-2-yl)oxy]butanoic acid

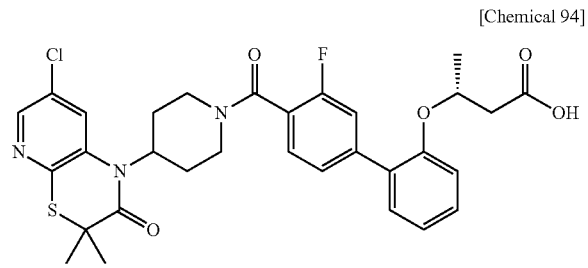

[Chemical 94]

Example 63-1

An ethanol solution (10 ml) of 2,5-dichloro-3-nitropyridine (1.11 g) and thiourea (916 mg) was heated at reflux for 5 hours. After the reaction solution was cooled to 0° C., a 2N aqueous sodium hydroxide solution (8 ml) was added, and stirred for 30 minutes. 2N hydrochloric acid was added to the reaction solution, and extracted with dichloromethane. The collected organic layer was washed with saturated sodium chloride solution, dried over anhydrous sodium sulfate, and concentrated under reduced pressure. The resulting residue (972 mg) was dissolved in N,N-dimethylformamide (10 ml), and potassium carbonate (1.25 g) and tert-butyl 2-bromo-2-methylpropanoate (0.774 ml) were added at room temperature. After the reaction solution was stirred for 5 hours, tert-butyl 2-bromo-2-methylpropanoate (0.774 ml) was added, and further stirred overnight. Water was added to the reaction solution, and extracted with ethyl acetate. The collected organic layer was washed with saturated sodium chloride solution, dried over anhydrous sodium sulfate, and concentrated under reduced pressure. The resulting residue was purified by silica gel column chromatography to afford tert-butyl 2-[(5-chloro-3-nitropyridin-2-yl)thio]-2-methylpropanoate (489 mg).

$^1$H NMR (400 MHz, CDCl$_3$) δ: 1.40 (s, 9H), 1.66 (s, 6H), 8.48 (dd, 1H, J=2.3, 0.8 Hz), 8.56 (dd, 1H, J=2.3, 0.8 Hz).

Example 63-2

To an ethanol solution (6 ml) of tert-butyl 2-[(5-chloro-3-nitropyridin-2-yl)thio]-2-methylpropanoate (442 mg) were added at room temperature acetic acid (6 ml) and iron powder (418 mg), followed by stirring for 4.5 hours. The reaction solution was diluted with ethyl acetate, followed by filtration through Celite, and the filtrate was concentrated under reduced pressure. To the resulting residue were added saturated sodium hydrogen carbonate and ethyl acetate, followed by filtration through Celite, and then the solution was separated. The organic layer was washed with saturated sodium chloride solution, dried over anhydrous sodium sulfate, and concentrated under reduced pressure. The resulting residue was purified by silica gel column chromatography to afford tert-butyl 2-[(3-amino-5-chloropyridin-2-yl)thio]-2-methylpropanoate (342 mg).

$^1$H NMR (400 MHz, CDCl$_3$) δ: 1.40 (s, 9H), 1.59 (s, 6H), 4.25 (br s, 2H), 6.92 (d, 1H, J=2.4 Hz), 7.88 (d, 1H, J=2.4 Hz).

Example 63-3

To a 1,2-dichloroethane solution (2 ml) of tert-butyl 2-[(3-amino-5-chloropyridin-2-yl)thio]-2-methylpropanoate (334 mg) and tert-butyl 4-oxopiperidine-1-carboxylate (272 mg) was added at room temperature trifluoroacetic acid (0.084 ml), followed by stirring for 15 minutes. Sodium triacetoxyborohydride (356 mg) was added to the reaction solution, and stirred at 45° C. overnight. Cooling to room temperature, tert-butyl 4-oxopiperidine-1-carboxylate (264 mg) and trifluoroacetic acid (0.084 ml) were added. After the reaction solution was stirred for 10 minutes, sodium triacetoxyborohydride (345 mg) was added, and further stirred at 45° C. overnight. After the reaction solution was cooled to room temperature, 1 N aqueous sodium hydroxide solution was added, and extracted with dichloromethane. The collected organic layer was washed with saturated sodium chloride solution, dried over anhydrous sodium sulfate, and concentrated under reduced pressure. The resulting residue was purified by silica gel column chromatography to afford tert-butyl 4-({2-[(2-tert-butoxy-1,1-dimethyl-2-oxoethyl)thio]-5-chloropyridin-3-yl}amino)piperidine-1-carboxylate (478 mg).

$^1$H NMR (400 MHz, CDCl$_3$) δ: 1.40 (s, 9H), 1.41-1.47 (br m, 2H), 1.47 (s, 9H), 1.57 (s, 6H), 1.93-2.04 (br m, 2H), 2.92-3.05 (br m, 2H), 3.28-3.43 (m, 1H), 4.03 (br s, 2H), 4.73 (d, 1H, J=7.3 Hz), 6.76 (d, 1H, J=2.0 Hz), 7.79 (d, 1H, J=2.0 Hz).

Example 63-4

To a N,N-dimethylformamide solution (5 ml) of tert-butyl 4-({2-[(2-tert-butoxy-1,1-dimethyl-2-oxoethyl)thio]-5-chloropyridin-3-yl}amino)piperidine-1-carboxylate (415 mg) was added at room temperature cesium carbonate (835 mg), followed by stirring at 110° C. overnight. The reaction solution was cooled to 0° C., water was added, and extracted with ethyl acetate. The collected organic layer was washed with saturated sodium chloride solution, dried over anhydrous sodium sulfate, and concentrated under reduced pressure. The resulting residue was purified by silica gel column chromatography to afford tert-butyl 4-(7-chloro-3,3-dimethyl-2-oxo-2,3-dihydroxy-1H-pyrido[2,3-b][1,4]thiazin-1-yl)piperidine-1-carboxylate (208 mg).

$^1$H NMR (400 MHz, CDCl$_3$) δ: 1.42 (s, 6H), 1.49 (s, 9H), 1.64-1.78 (br m, 2H), 2.37 (tdd, 2H, J=12.2, 12.7, 4.4 Hz), 2.80 (br s, 2H), 4.27-4.38 (m, 3H), 7.41 (d, 1H, J=2.0 Hz), 8.20 (d, 1H, J=2.0 Hz).

Example 63-5

In accordance with the methods of Reference Example 3-5, and Examples 5-4 and 15-5, the compound of Example 63-4 was used instead of the compound of Reference Example 3-4, and the compound of Example 61-3 was used instead of the compound of Example 5-3 to afford (3R)-3-[(4'-{[4-(7-chloro-3,3-dimethyl-2-oxo-2,3-dihydro-1H-pyrido[2,3-b][1,4]thiazin-1-yl)piperidin-1-yl]carbonyl}-3'-fluorobiphenyl-2-yl)oxy]butanoic acid.

$^1$H NMR (400 MHz, CDCl$_3$) δ: 1.32 (d, 3H, J=5.9 Hz), 1.43 (s, 6H), 1.73 (d, 1H, J=11.7 Hz), 1.90 (d, 1H, J=11.7 Hz), 2.52 (dd, 2H, J=15.6, 5.4 Hz), 2.47-2.62 (br m, 1H), 2.73 (dd, 1H, J=15.6, 7.3 Hz), 2.87 (t, 1H, J=12.9 Hz), 3.12-3.28 (br m, 1H), 3.82 (d, 1H, J=12.7 Hz), 4.44 (br s, 1H), 4.74-4.85 (m, 1H), 4.98 (d, 1H, J=12.7 Hz), 5.63 (br s, 1H), 7.04 (dd, 1H, J=7.8, 7.3 Hz), 7.05 (d, 1H, J=8.3 Hz), 7.21-7.52 (m, 6H), 8.21 (d, 1H, J=2.0 Hz).

Example 64

(3R)-3-[(4'-{[4-(7-Chloro-4-hydroxy-3,3-dimethyl-2-oxo-3,4-dihydro-1,5-naphthyridin-1(2H)-yl)piperidin-1-yl]carbonyl}-3'-fluorobiphenyl-2-yl)oxy]butanoic acid

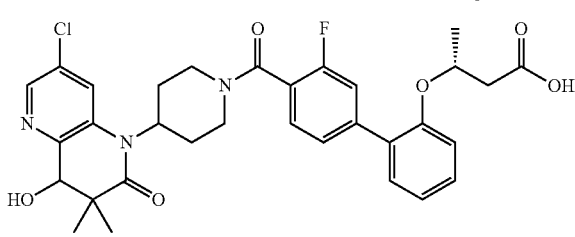

[Chemical 95]

Example 64-1

A carbon tetrachloride solution (25 ml) of tert-butyl 4-(7-chloro-3,3-dimethyl-2-oxo-3,4-dihydro-1,5-naphthyridin-1(2H)-yl)piperidine-1-carboxylate (Reference Example 10-2) (1.0 g), N-bromosuccinimide (903 mg) and 2,2'-azobisisobutyronitrile (43.2 mg) was heated at reflux for 40 minutes. After the reaction solution was cooled to 0° C., diethylether was added, and filtered through Celite. The filtrate was concentrated under reduced pressure, and the resulting residue was purified by silica gel column chromatography to afford tert-butyl 4-(4-bromo-7-chloro-3,3-dimethyl-2-oxo-3,4-dihydro-1,5-naphthyridin-1(2H)-yl)piperidine-1-carboxylate (492 mg).

$^1$H NMR (400 MHz, CDCl$_3$) δ: 1.49 (s, 9H), 1.50 (s, 6H), 1.60-1.71 (m, 1H), 1.77-1.91 (m, 1H), 2.31-2.59 (m, 2H), 2.71-2.93 (m, 2H), 4.30 (br s, 3H), 4.96 (s, 1H), 7.43 (d, 1H, J=2.0 Hz), 8.22 (d, 1H, J=2.0 Hz).

Example 64-2

To a dimethylsulfoxide solution (8 ml) of tert-butyl 4-(4-bromo-7-chloro-3,3-dimethyl-2-oxo-3,4-dihydro-1,5-naphthyridin-1(2H)-yl)piperidine-1-carboxylate (375 mg) was added sodium hydrogen carbonate (871 mg), followed by stirring at 100° C. for 6 hours. Water was added to the reaction solution, and extracted with ethyl acetate. The collected organic layer was washed sequentially with water and saturated sodium chloride solution, dried over anhydrous sodium sulfate, and concentrated under reduced pressure. After the resulting residue was dissolved in dichloromethane (14 ml), manganese dioxide (684 mg) was added and stirred for 50 minutes, and further manganese dioxide (690 mg) was added and stirred for 1 hour. The reaction mixture was filtered through Celite, and the filtrate was concentrated under reduced pressure. The resulting residue was purified by silica gel column chromatography to afford tert-butyl 4-(7-chloro-3,3-dimethyl-2,4-dioxo-3,4-dihydro-1,5-naphthyridin-1(2H)-yl)piperidine-1-carboxylate (270 mg).

$^1$H NMR (400 MHz, CDCl$_3$) δ: 1.496 (s, 6H), 1.499 (s, 9H), 1.65-1.75 (m, 2H), 2.53 (dq, 2H, J=4.4, 12.7 Hz), 2.72-2.99 (m, 2H), 4.15-4.58 (m, 3H), 7.64 (d, 1H, J=2.0 Hz), 8.46 (d, 1H, J=2.0 Hz).

Example 64-3

To a dichloromethane solution (1 ml) of tert-butyl 4-(7-chloro-3,3-dimethyl-2,4-dioxo-3,4-dihydro-1,5-naphthyridin-1(2H)-yl)piperidine-1-carboxylate (32.0 mg) was added at room temperature trifluoroacetic acid (0.5 ml), followed by stirring for 90 minutes. The reaction solution was concentrated under reduced pressure, and then azeotroped sequentially with dichloromethane, methanol and toluene. The resulting residue was dissolved in N,N-dimethylformamide (1.0 ml), and 2'-{[(1R)-3-tert-butoxy-1-methyl-3-oxopropyl]oxy}-3-fluorobiphenyl-4-carboxylic acid (29.3 mg), diisopropylethylamine (0.0546 ml) and 2-(1H-benzotriazol-1-yl)-1,1,3,3-tetramethyluronium hexafluorophosphate (37.7 mg) were added, followed by stirring overnight. Water was added to the reaction solution, and extracted with ethyl acetate. The organic layer was washed with saturated sodium chloride solution, dried over anhydrous sodium sulfate, and concentrated under reduced pressure. The resulting residue was purified by silica gel column chromatography to collect a solution containing the desired compound, followed by concentration under reduced pressure. The resulting residue (49.1 mg) was dissolved in dichloromethane (1 ml), and trifluoroacetic acid (0.5 ml) was added at room temperature, followed by stirring for 2 hours. After the reaction solution was neutralized with a saturated aqueous sodium hydrogen carbonate solution, 10% citric acid was added, and extracted with dichloromethane. The collected organic layer was washed with saturated sodium chloride solution, dried over anhydrous sodium sulfate, and concentrated under reduced pressure. The resulting residue was dissolved in a mixed solvent of methanol (1 ml) and tetrahydrofuran (1 ml), and sodium borohydride (4.5 mg) was added at 0° C., followed by stirring for 2 hours. A saturated aqueous ammonium chloride solution was added to the reaction solution, and extracted with dichloromethane. The collected organic layer was washed with saturated sodium chloride solution, dried over anhydrous sodium sulfate, and concentrated under reduced pressure. The resulting residue was purified twice by silica gel thin layer chromatography to afford (3R)-3-[(4'-{[4-(7-chloro-4-hydroxy-3,3-dimethyl-2-oxo-3,4-dihydro-1,5-naphthyridin-1(2H)-yl)piperidin-1-yl]carbonyl}-3'-fluorobiphenyl-2-yl)oxy]butanoic acid (29.8 mg).

$^1$H NMR (400 MHz, CDCl$_3$) δ: 0.86 (d, 3H, J=5.9 Hz), 1.31 (s, 1.5H), 1.33 (s, 1.5H), 1.36 (s, 3H), 1.58-1.97 (m, 2H), 2.46-2.95 (m, 5H), 3.11-3.30 (br m, 1H), 3.83 (d, 1H, J=14.5 Hz), 4.47 (br s, 2H), 4.54 (s, 1H), 4.73-4.85 (m, 1H), 4.91-5.05 (m, 1H), 7.02-7.06 (m, 2H), 7.20-7.48 (m, 6H), 8.23 (s, 1H).

Preparation Example 1

Powder 5 g of the compound of the present invention, 895 g of lactose and 100 g of corn starch can be mixed with a blender to obtain powders.

Preparation Example 2

Tablet 5 g of the compound of the present invention, 90 g of lactose, 34 g of corn starch, 20 g of crystalline cellulose and 1 g of magnesium stearate can be mixed with a blender, followed by tableting with a tablet-making machine to obtain tablets.

Preparation Example 3

Granule 5 g of the compound of the present invention, 895 g of lactose and 100 g of low-substituted hydroxypropylcellulose are mixed with a blender, followed by addition of 300 g of a 10% aqueous hydroxypropylcellulose solution for kneading. This can be granulated with an extruding granulator and dried to obtain granules.

Preparation Example 4

Injection Solution 1.5% by weight of the compound of the present invention is stirred in 10% by volume of propyleneglycol, then adjusted to a fixed volume with water for injection, and sterilized, which subsequently can be filled into a syringe to obtain an injection solution.

Test Example 1

Method for Measuring Human Platelet Aggregation Inhibitory Activity

A blood collecting syringe containing 1/10 volume of a 3.8% sodium citrate solution was used to collect blood from radial vein of a healthy person. The collected blood was centrifuged at 180×g at room temperature for 10 minutes to separate the supernatant (platelet-rich plasma; PRP). After PRP was separately collected, the remaining blood was centrifuged at 1,600×g for 10 minutes to separately collect platelet-poor plasma (PPP) of the upper layer. PRP was left at rest at 16° C. for 30 minutes, and subsequently used for measurement.

200 μL of the separately collected PRP was dispensed into a cuvette for the aggregation test, and 1 μL of dimethylsulfoxide (control) or a test compound solution diluted with dimethylsulfoxide was added, followed by incubation at 37° C. for 2 minutes. Subsequently, 2 μL of 2 mM ADP was added (final concentration 20 μM) to induce platelet aggregation.

Platelet aggregation was measured for 8 minutes using an aggregometer (MCM HEMA TRACER 313M; MC MEDICAL, INC.). With the light transmittance rate of PPP being set as an aggregation value of 100%, the maximum aggregation rate was determined for each concentration of the test compounds to calculate IC$_{50}$ values.

TABLE 1

| Test Compounds | IC$_{50}$ (μM) |
|---|---|
| Example 1 | 15 |
| Example 2 | 3.5 |
| Example 3 | 3.8 |
| Example 4 | 4 |
| Example 5 | 3.4 |
| Example 6 | 2.4 |
| Example 7 | 7.9 |
| Example 8 | 14 |
| Example 9 | 2.1 |
| Example 10 | 8.4 |
| Example 11 | 6.1 |
| Example 12 | 16 |
| Example 13 | 4.1 |
| Example 14 | 3.4 |
| Example 15 | 5.8 |
| Example 16 | 6.5 |
| Example 17 | 9.8 |

TABLE 1-continued

| Test Compounds | IC$_{50}$ (μM) |
|---|---|
| Example 18 | 10 |
| Example 19 | 7.5 |
| Example 20 | 2.8 |
| Example 21 | 8.7 |
| Example 22 | 5.7 |
| Example 23 | 5.2 |
| Example 24 | 3.1 |
| Example 25 | 5.1 |
| Example 26 | 7.3 |
| Example 27 | 6.5 |
| Example 28 | 1.8 |
| Example 29 | 4.3 |
| Example 30 | 2 |
| Example 31 | 18 |
| Example 32 | 17 |
| Example 33 | 16 |
| Example 34 | 2.3 |
| Example 35 | 3.6 |
| Example 36 | 5.2 |
| Example 37 | 6.6 |
| Example 38 | 2 |
| Example 39 | 1 |
| Example 40 | 1.1 |
| Example 41 | 5.7 |
| Example 42 | 1.4 |
| Example 43 | 2.6 |
| Example 44 | 3.4 |
| Example 45 | 11 |
| Example 46 | 1.8 |
| Example 47 | 2 |
| Example 48 | 3.7 |
| Example 49 | 1.7 |
| Example 50 | 0.87 |
| Example 51 | 7.7 |
| Example 52 | 2.3 |
| Example 53 | 6.4 |
| Example 54 | 11.4 |
| Example 55 | 8.4 |

Test Example 2

Method for Measuring Platelet Aggregation Inhibitory Activity During Oral Administration in a Rat 1 mg/10 ml/kg of the test compound was orally administered by gavage to male rats (Slc: Wistar, age 8 to 9 weeks) that had been fasted overnight. 4 hours after administration, a syringe containing 1/10 volume of a 3.13% sodium citrate solution was used to collect blood from the abdominal aorta of a rat under anesthesia. From the collected blood, platelet-rich plasma (PRP) and platelet-poor plasma (PPP) were prepared according to the method described in the method for measuring human platelet aggregation inhibitory activity. PRP was left at rest at 16° C. for 30 minutes, and subsequently used for measurement.

200 μL of the separately collected PRP was dispensed into a cuvette for the aggregation test, followed by incubation at 37° C. for 2 minutes, and subsequently 2 μL of 0.3 mM ADP was added (final concentration 3 μM) to induce platelet aggregation.

Platelet aggregation was measured for 8 minutes using an aggregometer (MCM HEMA TRACER 313M; MC MEDICAL, INC.). With the light transmittance rate of PPP being set as an aggregation value of 100%, the maximum aggregation rate of PRP was determined, and compared with the maximum aggregation rate of control PRP (rat administered only with a solvent) to calculate inhibition rates.

TABLE 2

| Test Compounds | Inhibition Rates (%) |
|---|---|
| Example 2 | 66 |
| Example 5 | 70 |
| Example 6 | 54 |
| Example 9 | 52 |
| Example 10 | 47 |
| Example 11 | 45 |
| Example 13 | 63 |
| Example 14 | 79 |
| Example 16 | 40 |
| Example 17 | 52 |
| Example 19 | 64 |
| Example 24 | 44 |
| Example 25 | 46 |
| Example 26 | 55 |
| Example 27 | 36 |
| Example 28 | 74 |
| Example 29 | 75 |
| Example 34 | 55 |
| Example 35 | 96 |
| Example 36 | 47 |
| Example 38 | 52 |
| Example 41 | 56 |
| Example 42 | 54 |
| Example 44 | 55 |
| Example 45 | 51 |
| Example 46 | 31 |
| Example 50 | 53 |
| Example 51 | 75 |
| Example 52 | 71 |
| Example 53 | 44 |
| Example 55 | 68 |

INDUSTRIAL APPLICABILITY

The compound (I) or pharmacologically acceptable salt thereof of the present invention has an excellent suppressive action on platelet aggregation. Therefore, the present invention is useful, as it can provide a novel preventive and/or therapeutic agent for thromboembolic diseases such as ischemic cerebrovascular diseases or acute coronary syndrome.

The invention claimed is:
1. A compound of formula (I):

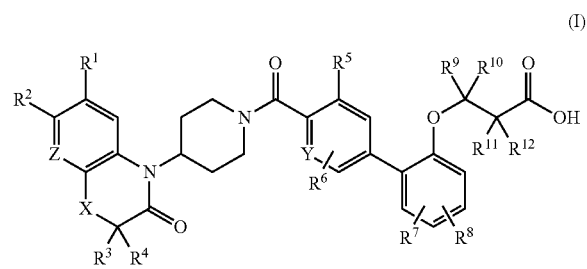

wherein,
$R^1$ represents a halogen atom, a cyano group, an amino group, a $C_{1-4}$ alkyl group, a halogenated $C_{1-4}$ alkyl group or a $C_{1-4}$ alkoxy group,
$R^2$ represents a hydrogen atom, a halogen atom, a cyano group, or a $C_{1-4}$ alkyl group,
$R^3$ and $R^4$, each independently, represent a hydrogen atom, a $C_{1-4}$ alkyl group, a halogenated $C_{1-4}$ alkyl group, a C1-4 alkoxy $C_{1-4}$ alkyl group, or a hydroxy $C_{1-4}$ alkyl group,
$R^5$ represents a hydrogen atom, a halogen atom, a hydroxy group, a nitro group, a $C_{1-4}$ alkyl group, or an amino group, R⁶ represents a hydrogen atom, a halogen atom, or a $C_{1-4}$ alkyl group, R⁷ and R⁸, each independently, represent a hydrogen atom, a halogen atom, or a $C_{1-4}$ alkyl group, R⁹ and R¹⁰, each independently, represent a hydrogen atom, or a $C_{1-4}$ alkyl group, R¹¹ and R¹², each independently, represent a hydrogen atom, or a $C_{1-4}$ alkyl group, or R¹¹ and R¹², together with the carbon atom to which they are attached, represent a group forming $C_{3-5}$ cycloalkyl, X represents a group represented by —CH(Rc)—, Rc represents a hydrogen atom, or a hydroxy group, Y represents a nitrogen atom, or a group represented by =C(Ra)—, Ra represents a hydrogen atom, a halogen atom, or a $C_{1-4}$ alkyl group, and Z represents a nitrogen atom, or a pharmacologically acceptable salt thereof.

2. The compound or pharmacologically acceptable salt thereof according to claim 1, wherein R¹ represents a fluorine atom, a chlorine atom, a cyano group, a methyl group, an ethyl group, or a trifluoromethyl group.

3. The compound or pharmacologically acceptable salt thereof according to claim 1, wherein R¹ represents a chlorine atom.

4. The compound or pharmacologically acceptable salt thereof according to claim 1, wherein R² represents a hydrogen atom, a chlorine atom, or a methyl group.

5. The compound or pharmacologically acceptable salt thereof according to claim 1, wherein R² represents a hydrogen atom.

6. The compound or pharmacologically acceptable salt thereof according to claim 1, wherein R³ and R⁴, each independently, represent a hydrogen atom, or a methyl group.

7. The compound or pharmacologically acceptable salt thereof according to claim 1, wherein R³ represents a methyl group, and R⁴ represents a hydrogen atom or a methyl group.

8. The compound or pharmacologically acceptable salt thereof according to claim 1, wherein R⁵ represents a hydrogen atom, a chlorine atom, a fluorine atom, a hydroxy group, a nitro group, a methyl group, or an amino group.

9. The compound or pharmacologically acceptable salt thereof according to claim 1, wherein R⁵ represents a fluorine atom, a methyl group, or an amino group.

10. The compound or pharmacologically acceptable salt thereof according to claim 1, wherein R⁶ represents a hydrogen atom, a fluorine atom, a chlorine atom, or a methyl group.

11. The compound or pharmacologically acceptable salt thereof according to claim 1, wherein R⁶ represents a hydrogen atom, or a fluorine atom.

12. The compound or pharmacologically acceptable salt thereof according to claim 1, wherein R⁷ and R⁸, each independently, represent a hydrogen atom, a fluorine atom, a chlorine atom, or a methyl group.

13. The compound or pharmacologically acceptable salt thereof according to claim 1, wherein R⁷ and R⁸, each independently, represent a hydrogen atom, or a fluorine atom.

14. The compound or pharmacologically acceptable salt thereof according to claim 1, wherein R⁹ and R¹⁰, each independently, represent a hydrogen atom, a methyl group, an ethyl group, or an n-propyl group.

15. The compound or pharmacologically acceptable salt thereof according to claim 1, wherein R⁹ represents a hydrogen atom, and R¹⁰ represents a hydrogen atom, a methyl group, or an ethyl group.

16. The compound or pharmacologically acceptable salt thereof according to claim 1, wherein R¹¹ and R¹², each independently, represent a hydrogen atom, a methyl group, or an ethyl group, or R¹¹ and R¹², together with the carbon atom to which they are attached, represent a group forming cyclopropyl.

17. The compound or pharmacologically acceptable salt thereof according to claim 1, wherein X represents a group represented by —CH₂—.

18. The compound or pharmacologically acceptable salt thereof according to claim 1, wherein Y represents a nitrogen atom, or a group represented by =C(Ra)—, and Ra represents a hydrogen atom.

19. The compound or pharmacologically acceptable salt thereof according to claim 1, selected from the following:

(3R)-3-[(4'-{[4-(7-chloro-3,3-dimethyl-2-oxo-3,4-dihydro-1,5-naphthyridin-1(2H)-yl)piperidin-1-yl]carbonyl}-3'-fluorobiphenyl-2-yl)oxy]butanoic acid, (2S)-3-[(4'-{[4-(7-chloro-3,3-dimethyl-2-oxo-3,4-dihydro-1,5-naphthyridin-1(2H)-yl)piperidin-1-yl]carbonyl}-3'-fluorobiphenyl-2-yl)oxy]-2-methylpropanoic acid, (3R)-3-[(4'-{[4-(7-chloro-3,3-dimethyl-2-oxo-3,4-dihydro-1,5-naphthyridin-1(2H)-yl)piperidin-1-yl]carbonyl}-3',5-difluorobiphenyl-2-yl)oxy]butanoic acid, (3R)-3-[(4'-{[4-(7-chloro-3,3-dimethyl-2-oxo-3,4-dihydro-1,5-naphthyridin-1(2H)-yl)piperidin-1-yl]carbonyl}-3'-methylbiphenyl-2-yl)oxy]butanoic acid, (3R)-3-[2-(6-{[4-(7-chloro-3,3-dimethyl-2-oxo-3,4-dihydro-1,5-naphthyridin-1(2H)-yl)piperidin-1-yl]carbonyl}-5-fluoropyridin-3-yl)phenoxy]butanoic acid, (3R)-3-[2-(6-{[4-(7-chloro-3,3-dimethyl-2-oxo-3,4-dihydro-1,5-naphthyridin-1(2H)-yl)piperidin-1-yl]carbonyl}-5-fluoropyridin-3-yl)-4-fluorophenoxy]butanoic acid, (3R)-3-[(4'-{[4-(7-chloro-3,3-dimethyl-2-oxo-3,4-dihydro-1,5-naphthyridin-1(2H)-yl)piperidin-1-yl]carbonyl}-5-fluoro-3'-methylbiphenyl-2-yl)oxy]butanoic acid, and (2S)-3-[2-(6-{[4-(7-chloro-3,3-dimethyl-2-oxo-3,4-dihydro-1,5-naphthyridin-1(2H)-yl)piperidin-1-yl]carbonyl}-5-fluoropyridin-3-yl)phenoxy]-2-methylpropanoic acid.

20. A medicament comprising as an active ingredient the compound or pharmacologically acceptable salt thereof according to claim 1, and further comprising a pharmacologically acceptable carrier, adjuvant and/or excipient.

21. A method for measuring platelet aggregation inhibitory activity, comprising administering to a mammal an effective amount of the compound or pharmacologically acceptable salt thereof according to claim 1.

22. A method for measuring platelet aggregation inhibitory activity, comprising administering to a human an effective amount of the compound or pharmacologically acceptable salt thereof according to claim 1.

23. The compound (3R)-3-[(4'-{[4-(7-Chloro-3,3-dimethyl-2-oxo-3,4-dihydro-1,5-naphthyridin-1(2H)-yl)piperidin-1-yl]carbonyl}-3'-fluorobiphenyl-2-yl)oxy]butanoic acid or a pharmacologically acceptable salt thereof.

24. The compound (3R)-3-[(4'-{[4-(7-Chloro-3,3-dimethyl-2-oxo-3,4-dihydro-1,5-naphthyridin-1(2H)-yl)piperidin-1-yl]carbonyl}-3',5-difluorobiphenyl-2-yl)oxy]butanoic acid or a pharmacologically acceptable salt thereof.

* * * * *